United States Patent
Ohmoto et al.

(10) Patent No.: US 6,900,207 B2
(45) Date of Patent: May 31, 2005

(54) N-CONTAINING FIVE-MEMBERED RING COMPOUNDS AND PHARMACEUTICAL AGENTS COMPRISING THE SAME AS ACTIVE INGREDIENT

(75) Inventors: Kazuyuki Ohmoto, Osaka (JP); Iori Itagaki, Nagano (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 52 days.

(21) Appl. No.: 10/181,799

(22) PCT Filed: Jan. 25, 2001

(86) PCT No.: PCT/JP01/00474

§ 371 (c)(1),
(2), (4) Date: Jul. 23, 2002

(87) PCT Pub. No.: WO01/55123

PCT Pub. Date: Aug. 2, 2001

(65) Prior Publication Data

US 2003/0153508 A1 Aug. 14, 2003

(30) Foreign Application Priority Data

Jan. 26, 2000 (JP) ......................................... 2000-017100

(51) Int. Cl.$^7$ .................... A61K 31/535; A61K 31/445; A61K 31/44; A61K 31/41
(52) U.S. Cl. .................... 514/236.2; 514/326; 514/340; 514/381; 544/132; 546/210; 546/268.4; 548/251; 548/253
(58) Field of Search ............................. 514/236.2, 326, 514/340, 381; 544/132; 546/210, 268.4; 548/251, 253

(56) References Cited

FOREIGN PATENT DOCUMENTS

EP 0 761 680 A2 3/1997
EP 0 900 791 A1 3/1999
JP 06192199 A * 7/1994

OTHER PUBLICATIONS

Derwent Acc. No. 1994–260477, 1994. Abstract of JP 06192199 A, 1994.*

* cited by examiner

Primary Examiner—Peter O'Sullivan
(74) Attorney, Agent, or Firm—Sughrue Mion, PLLC

(57) ABSTRACT

An N-containing five-membered ring compound of formula (I)

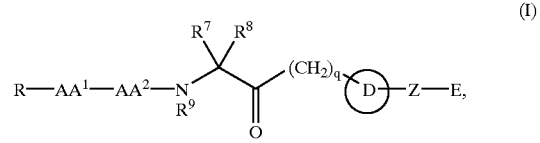

wherein all symbols are the same as described in the specification, and a non-toxic salt thereof.

The compound of formula (I) has an inhibitory activity against cysteine protease and therefore it is useful as an agent for the prophylaxis and/or treatment of inflammatory diseases, diseases induced by apoptosis, diseases induced by disorders of immune responses, autoimmune diseases, diseases induced by decomposition of proteins which compose organism, shock, circulatory system disorders, blood coagulation systems disorders, malignant tumors, acquired immune deficiency syndrome (AIDS) and AIDS-related complex (ARC), parasitic diseases, nerve degeneration diseases, pulmonary disorders, bone resorption diseases, endocrinesthenia, etc.

13 Claims, No Drawings

N-CONTAINING FIVE-MEMBERED RING COMPOUNDS AND PHARMACEUTICAL AGENTS COMPRISING THE SAME AS ACTIVE INGREDIENT

TECHNICAL FIELD

The present invention relates to an N-containing five-membered ring compound.

Particularly, the present invention relates to 1) an N-containing five-membered ring compound of formula (I)

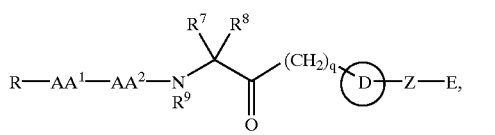

wherein all symbols have the same meanings as hereafter, and a non-toxic salt thereof,
2) a method for the preparation thereof and
3) a pharmaceutical agent comprising the N-containing five-membered ring compound and non-toxic salt thereof as active ingredient.

BACKGROUND OF THE INVENTION

Cysteine protease is a generic name of proteases which have a cysteine residue in the activity center and catalyze protein degradation thereat. In animal cells, a large number of cysteine proteases are known; for example, cathepsin family, calpain family, caspase-1, etc. Cysteine protease exists in various kinds of cells extensively and plays a basic and essential role in the homeostasis, such as conversion (processing) of precursor protein into its active form and degradation of proteins which have become out of use, etc. Until now, its physiological effects are being vigorously studied, and as the studies progress and characteristics of the enzymes are revealed, cysteine protease came to be taken as a cause of really various kinds of diseases.

It is revealed that cathepsin S (See J. Immunol., 161, 2731 (1998)) and cathepsin L (See J. Exp. Med., 183, 1331 (1996)) play a role in processing of major histocompatibility antigen class-II in antigen presenting cells which play an important role in the early stage of immune responses. In an experimental inflammatory response model induced by antigens, a specific inhibitor of cathepsin S showed an inhibitory effect (see J. Clin. Invest., 101, 2351 (1998)). It is also reported that in a leishmania-infected immune response model cathepsin B inhibitor inhibited an immune response and by means of this effect it inhibited the proliferation of protozoans (See J. Immunol., 161, 2120 (1998)). In vitro, a result is given that a calpain inhibitor and a cysteine protease inhibitor E-64 inhibited apoptosis which is induced by stimuli on T cell receptors (see J. Exp. Med., 178, 1693 (1993)). Therefore, it is conceivable that cysteine protease is much concerned with the progress of immune responses.

It is speculated that caspase-1 or a cysteine protease similar thereto occupies an important position in the mechanism of cell death including apoptosis. Therefore it is expected for a cysteine protease inhibitor to be used as an agent for the prophylaxis and/or treatment of those diseases concerning apoptosis, such as infectious diseases, deterioration or sthenia of immune function and brain function, tumors, etc. Diseases concerning apoptosis are, acquired immune deficiency syndrome (AIDS), AIDS-related complex (ARC), adult T cell leukemia, hairy cell leukemia, spondylopathy, respiratory apparatus disorder, arthitis, HIV or HTLV-1 related diseases such as uveitis, virus-related diseases such as hepatitis C, cancer, collagenosis (systemic lupus erythematosus, rheumatoid arthritis, etc.), autoimmune diseases (ulcerative colitis, Sjögren's syndrome, primary biliary cirrhosis, spontaneous thrombocytopenic purpura, autoimmune hemolytic anemia, myasthenia gravis, insulin dependent (type I) diabetes, etc.), diseases accompanied by thrombocytopenia (osteomyelodysplasia syndrome, periodic thrombocytopenia, aplastic anemia, spontaneous thrombocytopenia, disseminated intravascular coagulation (DIC), etc.), hepatic diseases such as viral hepatitis (type C, A, B, F, etc.) or hepatitis medicamentosus and cirrhosis, dementia (Alzheimer's diseases, Alzheimer's senile dementia, etc.), cerebrovascular injury, nerve degeneration diseases, adult acute respiratory distress syndrome, infectious diseases, prostatomegaly, hysteromyoma, bronchial asthma, arteriosclerosis, all kinds of lusus naturae, nephropathy, senile cataract, chronic fatigue syndrome, myodystrophy, peripheral neuropathy, etc.

Moreover, caspase-1 is concerned with various inflammatory diseases and those diseases caused by immune disorders, by means of interleukin-1β (IL-1β) production. A lot of diseases are shown to be involved with caspase-1 including inflammatory diseases and autoimmune diseases listed below; inflammatory bowel diseases such as ulcerative colitis, insulin-dependent (type-I) diabetes, autoimmune thyroid diseases, infectious diseases, rejection of an organ transplantation, graft versus host diseases, psoriasis, periodontitis (above, see N. Eng. J. Med., 328, 106 (1993)), pancreatitis (see J. Interferon Cytokine Res., 17, 113 (1997)), hepatitis (see J. Leuko. Biol., 58, 90 (1995)), glomerulonephritis (see Kidney Int., 47, 1303 (1995)), endocarditis (see Infect. Immun., 64, 1638 (1996)), myocarditis (see Br. Heart J., 72, 561 (1995)), systemic lupus erythematosus (see Br. J. Rheumatol., 34, 107 (1995)), Hashimoto's diseases (see Autoimmunity, 16, 141 (1993)), etc.), etc. Experimentally, it is reported that in liver injury model induced by lipopolysaccharide and D-galactosamine, a caspase-1 inhibitor depressed the symptoms, and it is expected that a caspase inhibitor shows an effect in sepsis, ischemic reperfusion and hepatitis gravis (see Am. J. Respir. Crit. Care Med., 159, 1308 (1999)).

It is also shown that cysteine protease is concerned with rheumatoid arthritis. IL-1β is shown to be concerned with this disease (see Arthritis Rheum., 39, 1092 (1996)), and in addition, as autoantibody toward calpastatin (endogenous calpain inhibitor) was found in the serum of the patients, it is considered that increase of calpain activity leads to the cause of diseases.

It is also known that cysteine protease causes a disease symptom by decomposing various proteins which compose the organism.

It is reported that cathepsin B plays a role in decomposing muscular protein in the chronic phase of sepsis (see J. Clin. Invest., 97, 1610 (1996)), and in decomposing muscular protein in myodystrophy model (see Biochem. J., 288, 643 (1992)). And it is also reported that calpain decomposes the myocyte cells protein of myodystrophy patients (see J. Biol. Chem., 270, 10909 (1995)).

In the ischemic reperfusion model, a result is given that calpain causes degeneration of brain tissues by means of degradation of protein kinase C-β (see J. Neurochem., 72, 2556 (1999)) and that a cathepsin B inhibitor inhibits nerve injury (see Eur. J. Neurosci., 10, 1723 (1998)).

In the brain ischemic model, it is known that the degradation of spectrin by calpain causes a damage and function disorder in the neurocyte (see Brain Res., 790, 1(1998)) and it is reported that an IL-1β receptor antagonist relieved the symptoms (see Brain Res. Bull., 29, 243 (1992)).

In myocardial ischemic model it is confirmed that cathepsin B activity increases in the lesion (see Biochem. Med. Metab. Biol., 45, 6 (1991)).

In the experiment utilizing ischemic liver injury model, it proved that necrosis and apoptosis of hepacyte were induced by means of protein-decomposing activity of calpain (see Gastroenterology, 116, 168 (1999)).

Besides, it is known that calpain causes cornea turbid in cataract by means of degradation of crystalline (see Biol. Chem., 268, 137 (1993)) and that in the lesion of contracted gut mucosa model it was confirmed that the activity of cathepsin B, H and L increased (see JPEN. J. Parenter. Enteral. Nutr., 19, 187 (1995)) and it is shown that cysteine protease is a cause of the diseases resulting from such protein degradation.

It has been revealed that cysteine protease is concerned with systemic disorders of organs and tissues by shock.

It is shown that IL-1β is concerned with septic shock and systemic inflammatory response syndrome (see Igakuno Ayumi, 169, 850 (1994)) and besides, it is reported that in endotoxin shock model induced by lipopolysaccharide, a calpain inhibitor prevented circulatory system disorder, disorders of liver and pancreas and acidosis by means of inhibitory effect of activation of nuclear factor κB (see Br. J. Pharmacol., 121, 695 (1997)).

Since it is reported that calpain is concerned with platelet coagulation process and a calpain inhibitor prevented the coagulation of platelets (see Am. J. Physiol., 259, C862 (1990)), it is conceivable that a cysteine protease inhibitor is useful for the disorder by blood coagulation. From the fact that calpain activity increased in the serum of the patients of purpura (thrombocytopenia) resulting from marrow transplantation, it is conceivable that calpain is concerned with the actual disease symptoms (see Bone Marrow Transplant., 24, 641 (1999)). Caspase-1 inhibitor inhibited the apoptosis of blood vessel endothelial cells, which is seen in the early phase of purpura (thrombocytopenia) and is thought to be important for the progression of the pathology afterwards (see Am. J. Hematol., 59, 279 (1998)), so it is expected that a cysteine protease inhibitor makes effect on purpura and hemolytic uremic syndrome.

The effect of cysteine protease and its inhibitor is being investigated in the field of cancer and metastasis of cancer.

Since the proliferations of pancreas cancer cells (see Cancer Res., 59, 4551 (1999)) and acute myeloid leukemia cells (see Clin. Lab. Haematol., 21, 173 (1999)) were inhibited by an inhibitor or receptor antagonist of caspase-1, it is expected that caspase-1 activity is essential for the process of proliferation of tumor cells, and that an inhibitor thereof is effective for these cancers. Cathepsin B activity increased in colon cancer metastasis model (see Clin. Exp. Metastasis, 16, 159 (1998)). Cathepsin K protein expression was recognized in human breast cancer cells and the relationship of cathepsin K and bone metastasis is shown (Cancer Res., 57, 5386 (1997)). Also, a calpain inhibitor inhibited migration of the cells and it implied the possibility that calpain inhibition may inhibit metastasis of cancer (J. Biochem., 272, 32719 (1997)). From these, a cysteine protease inhibitor is presumed to show an inhibitory effect on the metastasis of various malignant tumors.

As to AIDS (see AIDS, 10, 1349 (1996)) and AIDS-related complex (ARC) (see Arch. Immunol. Ther. Exp. (Warsz), 41, 147 (1993)), it is shown that IL-1 is concerned with the progress of symptoms, so it is conceivable that cysteine protease inhibition leads to an effective therapy of AIDS and its complication.

Some parasites have cysteine protease activity in their body. Cysteine protease in the phagosome of malaria protozoan is an essential enzyme for supplying nutrition of the parasites. A result is given that the inhibitor of cysteine protease shows an inhibitory effect of the proliferation of the protozoan (see Blood, 87, 4448 (1996)). Thus, it is possible to apply the inhibitor of cysteine protease to malaria.

In Alzheimer-type dementia, it is said that adhesion of non-physiological protein called amyloid to brain is deeply involved with nervous function disorders. Cysteine protease has an activity of generating amyloid by decomposing its precursor protein. Clinically, it is shown that cathepsin B is an enzyme that possesses a processing activity of amyloid proteins in the brains of Alzheimer-type dementia patients (see Biochem. Biophys. Res. Commun., 177, 377 (1991)). Also, expressions of cathepsin B protein (see Virchows Arch. A. Pathol. Anat. Histpathol., 423, 185 (1993)), cathepsin S protein (see Am. J. Pathol., 146, 848 (1995)) and calpain protein (see Proc. Natl. Acad. Sci. USA, 90, 2628 (1993)) and increase of caspase-1 activity (see J. Neuropathol. Exp. Neurol., 58, 582 (1999)) were confirmed in the brain lesions. Besides, by the fact that calpain is concerned with the formation of paired helical filaments which accumulate in Alzheimer dementia patients and production of protein kinase C which stabilizes the protein by phosphorylation (see J. Neurochem., 66, 1539 (1996)) and by the knowledge that caspase is concerned with neurocyte death by β amyloid protein adhesion (see Exp. Cell Res., 234, 507 (1997)), it is implied that cysteine protease is concerned with the disease symptoms.

As to Huntington's chorea, cathepsin H activity increased in the patient's brain (see J. Neurol. Sci., 131, 65 (1995)), and the ratio of activated form of calpain increased (see J. Neurosci., 48, 181 (1997)). In Parkinson's diseases, the increase of expression of m-calpain was recognized in the mesencephalon of the patients (see Neuroscience, 73, 979 (1996)) and IL-1β protein was expressed in brain (see Neurosci. Let., 202, 17 (1995)). Therefore, it is speculated that cysteine protease is concerned with the genesis and progress of these diseases.

Besides, in the central nervous system, spectrin degradation by calpain is found in the process of injury on neurocyte observed in the traumatic brain injury model (see J. Neuropathol. Exp. Neurol., 58, 365 (1999)).

In spinal cord injured model it was recognized that in glia cells calpain messenger RNA increased and its activity increased in the lesion and the possibility was shown that calpain had much to do with the degeneration of myelin and actin after injury (see Brain Res., 816, 375 (1999)). And IL-1β was shown to be concerned with the genesis of multiple sclerosis (see Immunol. Today, 14, 260 (1993)). Therefore, it is conceivable that a cysteine protease inhibitor is promising as an agent for the treatment of these nerve-injuring diseases.

Normally, cathepsin S and cathepsin K do not exist in human arterial walls but it was confirmed that they expressed in arterial sclerosis lesion and they had an decomposing activity of alveolus elastica (see J. Clin. Invest., 102, 576 (1998)) and a calpain inhibitor and antisense of m-calpain inhibited the proliferation of human blood vessel smooth muscle cells and it is shown that m-calpain is concerned with the proliferation of smooth muscle (see Arteioscler. Thromb. Vssc. Biol., 18, 493 (1998)), so it is conceivable that a cysteine protease inhibitor is promising for the treatment of blood vessel lesion such as arteriosclerosis, restenosis after percutaneous transluminal coronary angioplasty (PTCA), etc.

It is reported that in liver, cathepsin B is activated in the process of injuring hepatocyte by bile acid (see J. Clin. Invest., 103, 137 (1999)) and so it is expected that a cysteine protease inhibitor is effective for cholestatic cirrhosis.

In lungs and respiratory system, it is shown that cathepsin S is an enzyme that plays a role in elastin degradation by alveolus macrophages (see J. Biol. Chem., 269, 11530 (1994)), so it is probable that cysteine protease is a cause of pulmonary emphysema. And it is also shown that lung injury (see J. Clin. Invest., 97, 963 (1996)), lung fibrosis (see Cytokine, 5, 57 (1993)) and bronchial asthma (see J. Immunol., 149, 3078 (1992)) are caused by production of IL-1β by caspase-1.

It is pointed out that cysteine protease is also concerned with diseases concerning bones and cartilages. Cathepsin K is specifically recognized in osteoclast and it has a decomposing activity against bone matrix (see J. Biol. Chem., 271, 12517 (1996)), so its inhibitor is expected to show an effect against osteoporosis, arthritis, rheumatoid arthritis, osteoarthritis, hypercalcemia and osteometastasis of cancer, where pathologic bone resorption is recognized. And since IL-1β is shown to be concerned with bone resorption and cartilage degradation, and a caspase-1 inhibitor and IL-1β receptor antagonist inhibit the bone resorption and symptoms of arthritis, a caspase-1 inhibitor and IL-1β receptor antagonist are expected to be effective for arthritis (see Cytokine, 8, 377 (1996)) and osteoporosis (J. Clin. Invest., 93, 1959 (1994)). And it is reported that IL-1β is also concerned with osteoarthritis (see Life Sci., 41, 1187 (1987)).

Cysteine protease is involved with production of various hormones. Since increase of messenger RNA of cathepsin S was recognized by stimuli of thytropin on thyroid epitheliocyte strains (see J. Biol. Chem., 267, 26038 (1992)), it is conceivable that a cysteine protease inhibitor is effective for hyperthyrodism.

Since quantity and activity of cathepsin B protein increased in the gingival sulcus liquid of periodontitis patients (see J. Clin. Periodontol.,25, 34 (1998)), it is pointed out that cysteine protease is concerned with periodontitis.

Therefore, it is expected that the compound that possesses the inhibitory activity of cysteine protease is useful as an agent for the prophylaxis and/or treatment of inflammatory diseases (periodontitis, arthritis, inflammatory bowel diseases, infectious diseases, pancreatitis, hepatitis, glomerulonephritis, endocarditis, myocarditis, etc.), diseases induced by apoptosis (graft versus host diseases, rejection of an organ transplantation, acquired immune deficiency syndrome (AIDS), AIDS-related complex (ARC), adult T cell leukemia, hairy cells leukemia, spondylopathy, disorders of respiratory apparatus, arthritis, HIV or HTLV-1 related diseases such as uveitis, virus-related diseases such as hepatitis C, cancer, collagenosis (systemic lupus erythematosus, rheumatoid arthritis, etc.), ulcerative colitis, Sjögren's syndrome, primary biliary cirrhosis, spontaneous thrombocytopenic purpura, autoimmune hemolytic anemia, myasthenia gravis, autoimmune diseases such as insulin dependent (type I) diabetes, diseases accompanying thrombocytopenia (osteomyelodysplasia syndrome, periodic thrombocytopenia, aplastic anemia, spontaneous thrombocytopenia, disseminated intravascular coagulation (DIC), etc.), hepatic diseases such as viral hepatitis (type A, B, C, F, etc.) or hepatitis medicamentosus and cirrhosis, dementia such as Alzheimer's diseases and Alzheimer's senile dementia, cerebrovascular injury, nerve degeneration diseases, adult acute respiratory distress syndrome, infectious diseases, prostatomegaly, hysteromyoma, bronchial asthma, arteriosclerosis, all kinds of lusus naturae, nephropathy, senile cataract, chronic fatigue syndrome, myodystrophy, peripheral neuropathy, etc.), diseases induced by disorders of immune response (graft versus host diseases, rejection of an organ transplantation, allergic diseases (bronchial asthma, atopic dermatitis, allergic rhinitis, pollinosis, diseases induced by house dusts, irritable pneumonia, food allergy, etc.), psoriasis, rheumatoid arthritis, etc.), autoimmune diseases (insulin-dependent (type I) diabetes, systemic lupus erythematosus, Hashimoto's diseases, multiple sclerosis, etc.), disease by degradation various proteins which compose the organism (myodystrophy, cataract, periodontitis, hepatocyte disease by bile acid such as cholestatic cirrhosis, etc.), decomposition of alveolus elastica such as pulmonary emphysema, ischemic diseases (brain ischemia, brain disorders (encephalopathy) by ischemic reperfusion, myocardial infarction, ischemic hepatopathy, etc.), shock (septic shock, systemic inflammatory response syndrome, endotoxin shock, acidosis, etc.), circulatory system disorders (arteriosclerosis, restenosis after percutaneous transluminal coronary angioplasty (PTCA), etc.)), blood coagulation disorders (thrombocytopenic purpura, hemolytic uremic syndrome, etc.), malignant tumor, acquired immune deficiency syndrome (AIDS) and AIDS-related complex (ARC), parasitic diseases such as malaria, nerve degenerative diseases (Alzheimer-type dementia, Huntington's chorea, Parkinson's diseases, multiple sclerosis, traumatic encephalopathy, traumatic spondylopathy, etc.), pulmopathy such as lung fibrosis, bone resorption diseases (osteoporosis, rheumatoid arthritis, arthritis, osteoarthritis, hypercalcemia, osteometastasis of cancer, etc.), endocrinesthenia such as hyperthyroidism.

On the other hand, what is the most important for inhibitors in inhibiting the activity of proteases is, the special reaction site which interacts with the amino acid residue that is the activity center of proteases. The surrounding structure of the reaction sites are represented by - - - P3P2P1-P1'P2'P3' - - - , centering peptide binding (P1-P1') of the reaction site, and at P1 site there exist amino acid residues fitting the substance specificity of proteases which the inhibitors aim. Some reaction sites against cysteine proteases are known, for Example, in the specification of WO99/54317, the followings are described;

P1 position against calpain I, II (norvaline, phenylalanine, etc.),

P1 position against calpain I (arginine, lysine, tyrosine, valine, etc.),

P1 position against papain (homophenylalanine, arginine, etc.),

P1 position against cathepsin B (homophenylalanine, phenylalanine, tyrosine, etc.), P1 position against cathepsin S (valine, norleucine, phenylalanine, etc.), P1 position against cathepsin L (homophenylalanine, lysine, etc.), P1 position against cathepsin K (arginine, homophenylalanine, leucine, etc.), P1 position against caspase (aspartic acid).

On the other hand, in the specification of JP-A-H6-192199, it is disclosed that a ketone derivative of formula (V) is useful as a thiol protease inhibitor

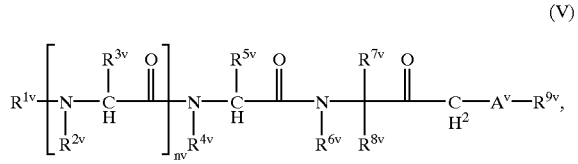
(V)

wherein $R^{1V}$ is hydrogen atom, $R^{10V}$—CO—, $R^{10V}$—OCO—, $R^{10V}$—SO$_2$— or $R^{10V}$—NHCO—, (1) when $A^V$ is —S—, —SO—, —SO$_2$—, $R^{9V}$ is C6–14 aryl which may have a substituent, or —(CH$_2$)$_{mv}$—X$^V$, where in $X^V$ is hydrogen atom, hydroxy, heteroring optionally having a substituent, etc., mv is an integer of 0 or 1 to 15, and (2) when $A^V$ is —O—, $R^{9V}$ is hydrogen atom or —(CH$_2$)$_{1V}$—X$^V$, wherein 1V is an integer of 1 to 15, (3) when $A^V$ is —NR$^{11V}$—, $R^{9V}$ is C6–14 aryl optionally having a substituent, or —(CH$_2$)$_{mv}$—X$^V$, $R^{9V}$ and $R^{11V}$ may be taken together to form a N-containing heteroring optionally having a substituent.

Also, in the specification of WO 93/09135, it is disclosed that the compound of formula (W)

$$R_W\text{—}[A_{1W}\text{—}A_{2W}]_{nw}\text{—}A_{3W}\text{—}A_{4W}\text{—}X_W\text{—}A_{5W}$$ (W)

wherein $R_W$ is hydrogen atom, a protected amino, etc., nw is 0 or 1, $A_{1W}$ is Val, Leu, Ala, Ile or trimethylsilyl-Ala, $A_{2W}$ is Phe or Tyr, $A_{3W}$ is a single bond, Val, Leu, Ala, Ile, trimethylsilyl-Ala, etc., $A_{4W}$ is a single bond or —NR$_{1W}$—CH (Y$_{1W}$) —CO—, $X_W$ is

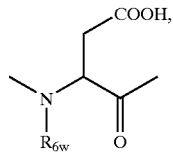

$A_{5W}$ is hydrogen, CF$_3$, —CH$_2$—Y$_{3W}$, wherein Y$_{3W}$ is heteroaryl, etc., is effective as an interleukin-1β releasing inhibitor.

Also, in the specifications of JP-A-H9-136878, WO 97/24339 and JP-A-H10-251295, it is disclosed that tetrazole compounds represented by formula (X), (Y) and (Z) respectively are effective as interleukin-1β converting enzyme inhibitors.

$$R^X\text{—}AA^{1x}\text{—}AA^{2x}\text{—}\underset{H}{N}\text{—}Y^x,$$ (X)

wherein $R^X$ is

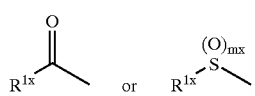

and $Y^X$ is

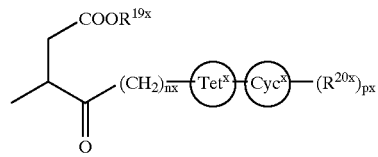

nx is an integer of 1 to 4,

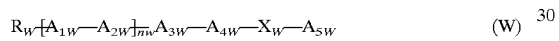

is a carboring or heteroring, and $R^{20X}$ is hydrogen atom, C1–4 alkyl, halogen atom, etc., $$R^Y\text{—}AA^{1Y}\text{—}AA^{2Y}\text{—}\underset{H}{N}\text{—}Y^Y,$$ (Y)

wherein $R^Y$ is

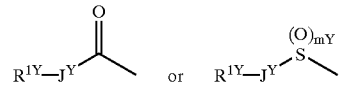

and $Y^Y$ is

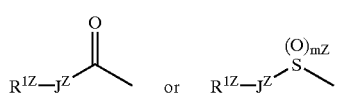

$Z^Y$ is C1–6 alkylene, C2–6 alkenylene, O, S, etc., and $E^Y$ is hydrogen, halogen, C1–4 alkyl, etc., $$R^Z\text{—}AA^{1Z}\text{—}AA^{2Z}\text{—}\underset{H}{N}\text{—}Y^Z,$$ (Z)

wherein $R^2$ is $Y^Z$ is

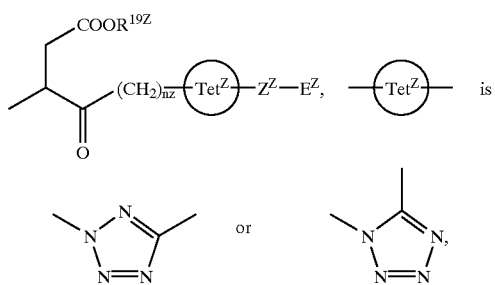

$Z^Z$ is a single bond, C1–6 alkylene, C2–6 alkenylene, O, S, etc. and $E^Z$ is hydrogen atom, halogen atom, $CF_3$, etc.

DISCLOSURE OF THE INVENTION

The present inventors have energetically investigated to find out such compounds that have cysteine protease inhibitory activity, and found out that the five-membered ring compound of formula (I) accomplishes the purpose.

The N-containing five-membered ring compound of formula (I) of the present invention is not known as a cysteine protease inhibitor at all.

The present invention relates to 1) a N-containing five-membered ring compound of formula (I) or a non-toxic salt thereof

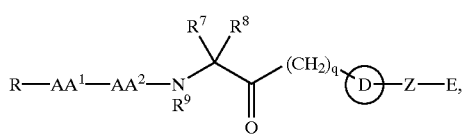

(I)

wherein R is (i) hydrogen,
(ii) C1–8 alkyl,
(iii) CycA,
(iv) C1–8 alkyl substituted with a group selected from halogen atom, CycA, nitro, $CF_3$ and cyano,

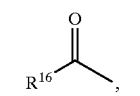 (v)

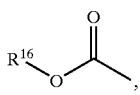 (vi)

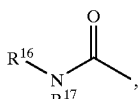 (vii)

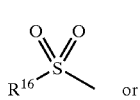 (viii) or

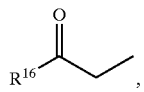 (ix)

CycA is a C3–15 mono-, bi- or tri-cyclic carboring or a mono-, bi- or tri-cyclic 3–15 membered heteroring comprising 1–4 of nitrogen, 1–2 of oxygen and/or 1 of sulfur;

$R^{16}$ is
(1) C1–8 alkyl,
(2) C2–8 alkenyl,
(3) C2–8 alkynyl,
(4) CycA or
(5) C1–8 alkyl, C2–8 alkenyl or C2–8 alkynyl substituted with a group selected from halogen atom, nitro, $CF_3$, cyano, CycA, $NR^{18}R^{19}$ and —NHC(O)-CycA;

$R^{17}$, $R^{18}$ and $R^{19}$ each independently represents hydrogen or C1–4 alkyl, $AA^1$ is
(i) a single bond, or

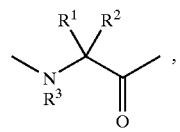 (ii)

wherein $R^1$ and $R^2$ are the same or different to represent
(i) hydrogen,
(ii) C1–8 alkyl,
(iii) CycA or
(iv) C1–8 alkyl substituted with 1–5 of group selected from the following (1) to (8):
(1) —$NR^{21}R^{22}$,
(2) —$OR^{23}$,
(3) —$SR^{24}$,
(4) —$COR^{25}$,
(5) —$NR^{26}CONR^{21}R^{22}$,
(6) guanidino,
(7) CycA,
(8) —$NR^{26}SO_2R^{21}$; or $R^1$ and $R^2$ are taken together to form C2–8 alkylene (wherein one carbon atom may be replaced by oxygen, sulfur or —$NR^{20}$— and the alkylene may be substituted with —$NR^{21}R^{22}$ or —$OR^{23}$, $R^{20}$ is hydrogen, C1–4 alkyl, —COO—(C1–4 alkyl), phenyl or C1–4 alkyl substituted with phenyl, $R^{21}$, $R^{22}$, $R^{23}$, $R^{24}$ and $R^{26}$ are the same or different to represent hydrogen, C1–4 alkyl, phenyl or C1–4 alkyl substituted with phenyl, $R^{25}$ is C1–4 alkyl, phenyl, —$NR^{21}R^{22}$, wherein all symbols have the same meaning as above, —$OR^{23}$, wherein $R^{23}$ is the same meaning as above, or C1–4 alkyl substituted with phenyl, $R^3$ is hydrogen, C1–8 alkyl, phenyl or C1–8 alkyl substituted with phenyl or $R^3$ is taken together with $R^1$ to form C2–6 alkylene, wherein one carbon atom may be replaced by oxygen, sulfur or —$NR^{20}$— and the alkylene may be substituted with —$NR^{21}R^{22}$ or —$OR^{23}$, or when $AA^1$ is

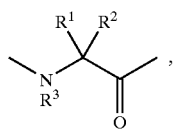

AA$^1$ and R may be taken together to form

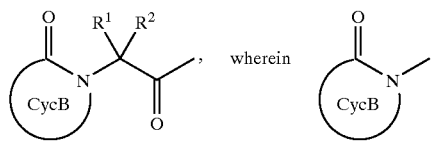, wherein is a 5–12 membered mono- or bi-cyclic heteroring and the other symbols are the same meanings as above, AA$^2$ is
(i) a single bond,

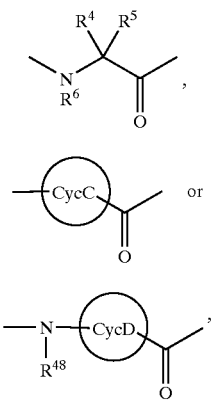

wherein R$^4$ and R$^5$ are the same or different to represent
(1) hydrogen,
(2) C1–8 alkyl,
(3) CycA or
(4) C1–8 alkyl substituted with 1–5 of group selected from the following (a) to (h):
(a) —NR$^{41}$R$^{42}$,
(b) —OR$^{43}$,
(c) —SR$^{44}$,
(d) —COR$^{45}$,
(e) —NR$^{46}$CONR$^{41}$R$^{42}$,
(f) guanidino,
(g) CycA,
(h) —NR46SO$_2$R$^{41}$; or R$^4$ and R$^5$ are taken together to form C2–8 alkylene, wherein one carbon atom may be replaced by oxygen, sulfur or —NR$^{40}$— and the alkylene may be substituted with —NR$^{41}$R$^{42}$ or —OR$^{43}$, R$^{40}$ is hydrogen, C1–4 alkyl, —COO—(C1–4 alkyl), phenyl or C1–4 alkyl substituted with phenyl, R$^{41}$, R$^{42}$, R$^{43}$, R$^{44}$ and R$^{46}$ are the same or different to represent hydrogen, C1–4 alkyl, phenyl or C1–4 alkyl substituted with phenyl, R$^{45}$ is C1–4 alkyl, phenyl, —NR$^{41}$R$^{42}$, wherein all symbols are the same meaning as above, —OR$^{43}$, wherein R$^{43}$ is the same meaning as above, or C1–4 alkyl substituted with phenyl, R$^6$ is hydrogen, C1–8 alkyl, phenyl or C1–8 alkyl substituted with phenyl or R$^6$ is taken together with R$^4$ to form C2–6 alkylene, wherein one carbon atom may be replaced by oxygen, sulfur or —NR$^{40}$— and the alkylene may be substituted with —NR$^{41}$R$^{42}$ or —OR$^{43}$, R$^{48}$ is hydrogen, C1–4 alkyl, phenyl or C1–4 alkyl substituted with phenyl or when AA$^1$ is a single bond, R$^{48}$ and R may be taken together to form C2–6 alkylene, wherein one carbon atom may be replaced by oxygen, sulfur or —NR$^{47}$, wherein R$^{47}$ is hydrogen or C1–4 alkyl, CycC is a 3–17 membered mono- or bi-cyclic heteroring, CycD is a C3–14 mono- or bi-cyclic carboring or a 3–14 membered mono- or bi-cyclic heteroring, or AA$^2$ and AA$^1$ are taken together to form

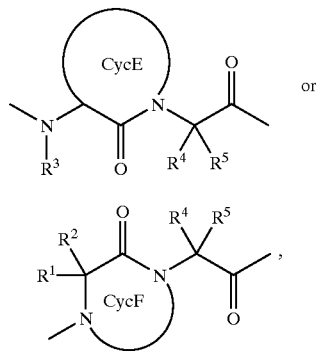

wherein CycE is a 4–18 membered mono- or bi-cyclic heteroring, CycF is a 5–8 membered monocyclic heteroring, and the other symbols have the same meanings as above, R$^7$ and R$^8$ are the same or different to represent
(i) hydrogen,
(ii) C1–8 alkyl,
(iii) CycA or
(iv) C1–8 alkyl substituted with 1–5 of group selected from the following (1) to (8);
(1) —NR$^{61}$R$^{62}$,
(2) —OR$^{63}$,
(3) —SR$^{64}$,
(4) —COR$^{65}$,
(5) —NR$^{66}$CONR$^{61}$R$^{62}$,
(6) guanidino,
(7) CycA,
(8) —NR$^{66}$SO$_2$R$^{61}$, or R$^7$ and R$^8$ are taken together to form C2–8 alkylene, wherein one carbon atom may be replaced by oxygen, sulfur or —NR$^{60}$— and the alkylene may be substituted with —NR$^{61}$R$^{62}$ or —OR$^{63}$, R$^{60}$ is hydrogen, C1–4 alkyl, —COO—(C1–4 alkyl), phenyl or C1–4 alkyl substituted with phenyl, R$^{61}$, R$^{62}$, R$^{63}$, R$^{64}$ and R$^{66}$ are the same or different to represent hydrogen, C1–4 alkyl, phenyl or C1–4 alkyl substituted with phenyl, R$^{65}$ is C1–4 alkyl, phenyl, —NR$^{61}$R$^{62}$, wherein all symbols are the same meanings as above, —OR$^{63}$, wherein R$^{63}$ is the same meaning as above, or C1–4 alkyl substituted with phenyl, R$^9$ is hydrogen, C1–8 alkyl, phenyl or C1–8 alkyl substituted with phenyl or R$^9$ is taken together with R$^7$ to form C2–6 alkylene, wherein one carbon atom may be replaced by oxygen, sulfur or —NR$^{60}$— and the alkylene may be substituted with —NR$^{61}$R$^{62}$ or —OR$^{63}$, q is an integer of 1 to 4,

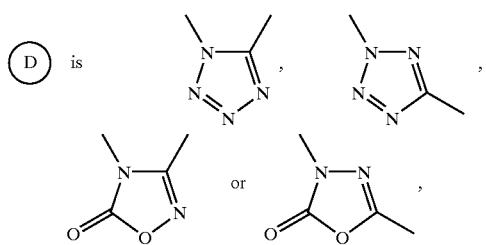

Z is a single bond, C1–6 alkylene, C2–6 alkenylene, C2–6 alkynylene, —O—, —S—, —CO—, —SO—, —SO$_2$—, —NR$^{10}$—, or C1–6 alkylene whose one carbon atom is replaced by —O—, —S—, —CO—, —SO—, —SO$_2$— or —NR$^{10}$—, R$^{10}$ is hydrogen atom, C1–4 alkyl, phenyl, or C1–4 alkyl substituted with phenyl, E is hydrogen atom, halogen atom, CF$_3$, diphenyl(C1–4) alkyl, tri(C1–4 alkyl) silyl, C1–4 alkyl, —COOR$^{18}$, —CONR$^{19}$R$^{20}$, —NR$^{19}$R$^{20}$, -G-(R$^{35}$)$_r$, —CH$_2$—PO (OR$^{36}$)$_2$ or —CH(PO(OR$^{36}$)$_2$)$_2$, R$^{18}$ is hydrogen atom, C1–4 alkyl, phenyl or C1–4 alkyl substituted with phenyl, R$^{19}$ and R$^{20}$ independently represent hydrogen atom, C1–4 alkyl, phenyl or C1–4 alkyl substituted with phenyl, R$^{19}$ and R$^{20}$ are taken together with nitrogen atom to which they are attached, to represent 5–7 membered mono-cyclic heteroring containing 1–2 of nitrogen, 1 of nitrogen and oxygen atom, or 1 of nitrogen or sulfur atom, G is C3–10 mono- or bi-cyclic carboring or 5–18 membered mono- or bi- or tricyclic heteroring containing 1 to 3 of nitrogen atom(s), 1 of oxygen atom and/or 1 of sulfur atom and r is an integer of 1 to 5, R$^{35}$ is (i) hydrogen atom, (ii) C1–8 alkyl, (iii) halogen atom, (iv) nitoro, (v) CF$_3$, (vi) cyano, (vii) —OR$^{37}$, (viii) —NR$^{37}$R$^{38}$, (ix) —SR$^{37}$, (x) —COOR$^{37}$, (xi) —COR$^{37}$, (xii) —CO—NR$^{19}$R$^{20}$, (xiii) a C3–10 mono- or bi-cyclic carboring, (xiv) a 5–18 membered mono-, bi- or tricyclic heteroring containing 1 to 3 of nitrogen atom(s), 1 of oxygen atom, and/or 1 of sulfur atom, (xv) C1–8 alkyl substituted with a 3–10 membered mono- or bi-cyclic carboring or a 5–18 membered mono-, bi- or tricyclic heteroring containing 1 to 3 of nitrogen atom(s), 1 of oxygen atom and/or 1 of sulfur atom, which ring may be substituted with 1 to 5 group(s) selected from the following groups: C1–8 alkyl, phenyl, C1–4 alkyl substituted with phenyl, halogen atom, nitro, CF$_3$, cyano, tetrazole, —OR$^{39}$, —NR$^{39}$R$^{40}$, —SR$^{39}$, —COOR$^{39}$ or —COR$^{39}$, R$^{36}$ is hydrogen atom, C1–8 alkyl, cyano, phenyl, C1–8 alkyl substituted with phenyl or cyano, C1–4 alkyl sub-sutituted with 1 to 3 halogen atom(s), R$^{37}$ is hydrogen atom, C1–4 alkyl, phenyl, C1–4 alkyl substituted with phenyl, R$^{38}$ is hydrogen atom, C1–4 alkyl, phenyl, C1–4 alkyl substituted with phenyl, C2–5 acyl or COCF$_3$, R$^{39}$ and R$^{40}$ independently represent hydrogen atom, C1–4 alkyl, phenyl, C1–4 alkyl substituted with phenyl, with the proviso that when (i) Z represents —SO—, E does not represent hydrogen atom and when (ii)

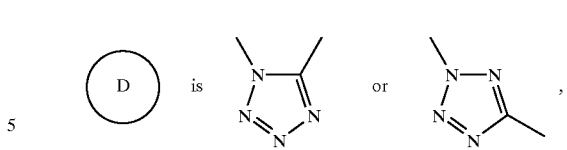

R$^7$ and R$^8$ do not represent C1 alkyl substituted with —COR$^{65}$, (iii) CycA included in R, R$^1$, R$^2$, R$^4$, R$^5$, R$^7$, R$^8$ and R$^{16}$ may be the same or different and CycA, CycB, CycC, CycD, CycE and CycF, independently, may be substituted with 1 to 5 of R$^{27}$;

R$^{27}$ is
(1) C1–8 alkyl,
(2) halogen atom,
(3) —NR$^{11}$R$^{12}$,
(4) —OR$^{13}$,
(5) a C5–10 mono-or bi-cyclic carboring,
(6) nitro,
(7) CF$_3$,
(8) cyano,
(9) a 5–10 membered mono- or bi-cyclic heteroring
(10) —SR$^{14}$,
(11) —COR$^{15}$,
(12) oxo,
(13) —SO$_2$R$^{15}$,
(14) —OCF$_3$ or
(15) C1–8 alkyl substituted with 1 to 5 of group(s) selected from the following (a) to (m):
(a) halogen, (b) —NR$^{11}$R$^{12}$, (c) —OR$^{13}$, (d) C5–10 mono- or bi-cyclic carboring, (e) nitro, (f) CF$_3$, (g) cyano, (h) 5–10 membered mono- or bi-cyclic heteroring, (j) —SR$^{14}$, (k) —COR$^{15}$, (l) —SO$_2$R$^{15}$, or (m) —OCF$_3$, wherein R$^{11}$ and R$^{12}$ are the same or different to represent hydrogen, C1–4 alkyl, —COO—(C1–4 alkyl), phenyl or C1–4 alkyl substituted with phenyl, R$^{13}$ and R$^{14}$ are the same or different to represent hydrogen, C1–4 alkyl, phenyl or C1–4 alkyl substituted with phenyl, R$^{15}$ is C1–4 alkyl, phenyl, —NR$^{11}$R$^{12}$, wherein all symbols have the same meanings as above, —OR$^{13}$, wherein R$^{13}$ has the same meaning as above, or C1–4 alkyl substituted with phenyl, 2) a method for the preparation thereof and 3) a pharmaceutical agent comprising the N-containing five-membered ring compound and non-toxic salt thereof as active ingredient.

DETAILED DESCRIPTION OF THE PRESENT INVENTION

In the compound of formula (I), in

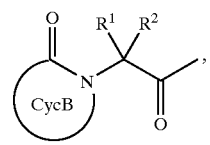

which AA¹ and R together form,

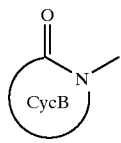

is a 5–12 membered heteroring containing 1–3 of nitrogen, 1 of oxygen, and/or 1 of sulfur (this heteroring may be substituted with 1–5 of $R^{27}$).

And to describe

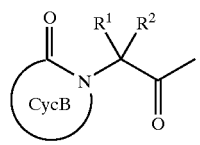

concretely, it is

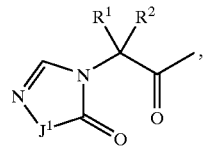
(i)

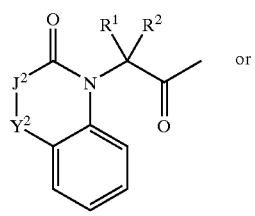
(ii) or

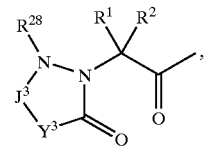
(iii)

wherein $J^1$ is oxygen, sulfur, —$NR^{29}$—, wherein $R^{29}$ is hydrogen, C1–4 alkyl, CycA or C1–4 alkyl substituted with CycA, C1–3 alkylene or C2–3 alkenylene,
$J^2$ is a single bond or C1–2 alkylene,
$Y^2$ is —N=CH—, —CH=N— or C1–2 alkylene,
$J^3$ is carbonyl or C1–3 alkylene,
$Y^3$ is C1–3 alkylene, oxygen or —$NR^{29}$—, wherein $R^{29}$ is the same meaning as above,
$R^{28}$ is hydrogen, C1–4 alkyl, CycA or C1–4 alkyl substituted with CycA, or
$R^{28}$ is taken together with $R^1$ to form C2–4 alkylene, and the other symbols have the same meaning as above and each ring may be substituted with 1–5 of $R^{27}$.

In the compound of formula (I), in

(iii)

which $AA^2$ represents, CycC is a 3–17 membered heteroring which contains 1–2 of nitrogen, 1 of oxygen and/or 1 of sulfur (this ring may be substituted with 1–5 of $R^{27}$).

And to describe

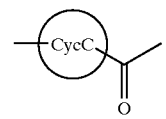

concretely,

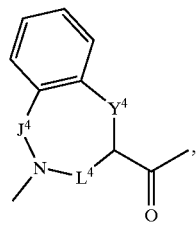
(iii-1)

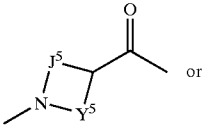
(iii-2) or

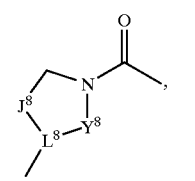
(iii-3)

wherein $J^4$, $Y^4$ and $L^4$ are the same or different to represent a single bond or C1–3 alkylene, wherein $J^4$, $Y^4$ and $L^4$ do not represent a single bond at the same time,
$J^5$ is C1–6 alkylene,
$Y^5$ is a single bond, C1–3 alkylene or —$NR^{67}$—, wherein $R^{67}$ is hydrogen,
C1–4 alkyl, phenyl or C1–4 alkyl substituted with phenyl,
$J^8$ is C1–5 alkylene, wherein one carbon atom may be replaced by oxygen,
$Y^8$ is a single bond or C1–4 alkylene,
$L^8$ is —N— or —CH—, and the other symbols have the same meaning as above and each ring may be substituted with 1–5 of $R^{27}$.

And in

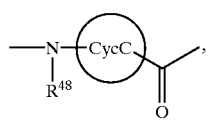
(iv)

which AA² represents, CycD is a C3–14 mono- or bi-cyclic carboring or 3–14 membered heteroring which contains 1–2 of nitrogen, 1 of oxygen and/or 1 of sulfur (this carboring and heteroring may be substituted with 1–5 of $R^{27}$).

And to describe

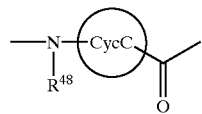

concretely, it is

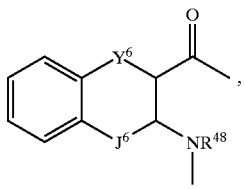
(iv-1)

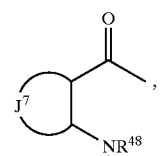
(iv-2)

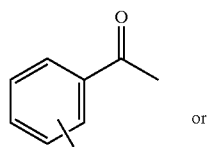
(iv-3)

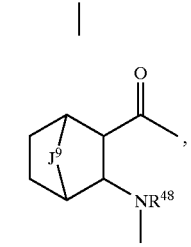
(iv-4)

wherein $J^6$ and $Y^6$ are the same or different to represent a single bond or C1–3 alkylene, wherein $J^6$ and $Y^6$ do not represent a single bond at the same time, $J^7$ is C1–6 alkylene, wherein one carbon atom may be replaced by oxygen, sulfur or —$NR^{67}$—, wherein $R^{67}$ has the same meaning as above, $J^9$ is C1–3 alkylene, oxygen, sulfur or —$NR^{67}$—, wherein $R^{67}$ is the same meaning as above, and the other symbols have the same meanings as above and each ring may be replaced by 1–5 of $R^{27}$.

In the compounds of the formula (I), in

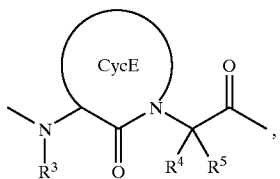
(i)

which AA¹ and AA² together form,

CycE is a 4–18 membered heteroring which contains 1–2 of nitrogen, 1 of oxygen and/or 1 of —$S(O)_p$— (this heteroring may be substituted with 1–5 of $R^{27}$).

And to describe

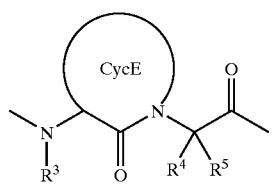

concretely, it is

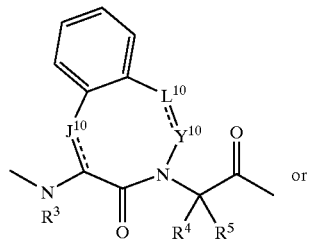
(i-1)

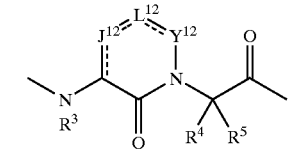
(i-2)

wherein === is a single bond or a double-bond, $J^{10}$ and $Y^{10}$ are the same or different to represent a single bond or C1–3 alkylene, $L^{10}$ is a single bond, C1–3 alkylene, —$NR^{57}$—, wherein $R^{57}$ is hydrogen, C1–4 alkyl, phenyl or C1–4 alkyl substituted with phenyl, —N═, oxygen or —$S(O)_p$—, wherein p is 0 or an integer of 1 to 2, $J^{12}$ and $Y^{12}$ are the same or different to represent a single bond or C1–3 alkylene, $L^{12}$ is C1–3 alkylene, —$NR^{57}$—, wherein $R^{57}$ is the same meaning as above), —N═, ═N—, oxygen or —$S(O)_p$—, wherein p has the same meaning as above, and the other symbols have the same meanings as above and each ring may be substituted with 1–5 of $R^{27}$.

And in

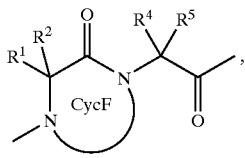

(ii)

which AA$^1$ and AA$^2$ together form,
CycF is a 5–8 membered heteroring containing 2 of nitrogen.

And to describe

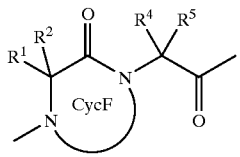

concretely, it is

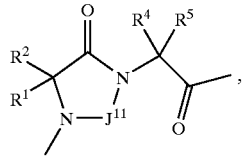

wherein J$^{11}$ is carbonyl or C2–4 alkylene and the other symbols have the same meaning as above and the ring therein may be substituted with 1–5 of R$^{27}$.

In the present specification, C1–4 alkyl is methyl, ethyl, propyl, butyl and isomers thereof.

In the present specification, C1–8 alkyl is methyl, ethyl, propyl, butyl, pentyl, hexyl, heptyl, octyl and isomers thereof.

In the present specification, C2–8 alkenyl is, ethyl, propyl, butyl, pentyl, hexyl, heptyl, octyl containing 1–3 of double bond and isomers thereof. For example, vinyl, propenyl, butenyl, hexenyl, hexadienyl, octadienyl, etc. are included.

In the present specification, C2–8 alkynyl is ethyl, propyl, butyl, pentyl, hexyl, heptyl, octyl containing 1–3 of triple bond and isomers thereof. For example, ethynyl, propynyl, butynyl, pentynyl, hexynyl, heptynyl, octynyl, etc. are included.

In the present specification, C1–4 alkyl substituted with phenyl is phenylmethyl, phenylethyl, phenylpropyl, phenylbutyl and isomers thereof.

In the present specification, diphenyl(C1–4)alkyl is methyl, ethyl, propyl, butyl substituted with 2 of phenyl and isomers thereof.

In the present specification, C2–5 acyl is acetyl, propionyl, butyryl, valeryl and isomers thereof.

In the present specification, C1–2 alkylene is, methylene, ethylene and isomers thereof.

In the present specification, C1–3 alkylene is, methylene, ethylene, trimethylene and isomers thereof.

In the present specification, C1–4 alkylene is methylene, ethylene, trimethylene, tetramethylene and isomers thereof.

In the present specification, C1–5 alkylene is methylene, ethylene, trimethylene, tetramethylene, pentamethylene and isomers thereof.

In the present specification, C1–6 alkylene is methylene, ethylene, trimethylene, tetramethylene, pentamethylene, hexamethylene and isomers thereof.

In the present specification, C2–4 alkylene is ethylene, trimethylene, tetramethylene and isomers thereof.

In the present specification, C2–6 alkylene is ethylene, trimethylene, tetramethylene, pentamethylene, hexamethylene and isomers thereof.

In the present specification, C2–8 alkylene is ethylene, trimethylene, tetramethylene, pentamethylene, hexamethylene, heptamethylene, octamethylene and isomers thereof.

In the present specification, C2–3 alkenylene is vinylene, propenylene and isomers thereof.

In the present specification, C2–6 alkenylene is vinylene, propenylene, butenylene, pentenylene, hexenylene and isomers thereof.

In the present specification, C2–6 alkynylene is ethynylene, propynylene, butynylene, pentynylene, hexynylene and isomers thereof.

In the present specification, C2–8 alkylene is ethylene, trimethylene, tetramethylene, pentamethylene, hexamethylene, heptamethylene, octamethylene and isomers thereof.

In the present specification, C2–6 alkylene whose one carbon atom may be replaced by oxygen, sulfur, —NR$^{20}$—, —NR$^{40}$— or —NR$^{60}$— is ethylene, trimethylene, tetramethylene, pentamethylene, hexamethylene and isomers thereof, wherein one carbon atom thereof may be replaced by oxygen, sulfur, —NR$^{20}$—, —NR$^{40}$—, or —NR$^{60}$—, for example, such groups are —CH$_2$—O—CH$_2$—, —CH$_2$—CH$_2$—O—CH$_2$—, —CH$_2$—CH$_2$—S—CH$_2$—, —CH$_2$—CH$_2$—NH—CH$_2$—, —CH$_2$—CH$_2$—O—CH$_2$—CH$_2$—, —CH$_2$—CH$_2$—S—CH$_2$—CH$_2$—, —CH$_2$—CH$_2$—NH—CH$_2$—CH$_2$—, —CH$_2$—CH$_2$—N(CH$_3$)—CH$_2$—CH$_2$—, etc.

In the present specification, C2–8 alkylene whose one carbon atom may be replaced by oxygen, sulfur, —NR$^{20}$—, —NR$^{40}$— or —NR$^{60}$— is ethylene, trimethylene, tetramethylene, pentamethylene, hexamethylene, heptamethylene, octamethylene and isomers thereof, wherein one carbon atom may be replaced by oxygen, sulfur, —NR$^{20}$—, —NR$^{40}$— or —NR$^{60}$—, for example, such groups are —CH$_2$—O—CH$_2$—, —CH$_2$—CH$_2$—O—CH$_2$—, —CH$_2$—CH$_2$—S—CH$_2$—, —CH$_2$—CH$_2$—NH—CH$_2$, —CH$_2$—CH$_2$—O—CH$_2$—CH$_2$—, —CH$_2$—CH$_2$—S—CH$_2$—CH$_2$—, —CH$_2$—CH$_2$—NH—CH$_2$—CH$_2$—, —CH$_2$—CH$_2$—N(CH$_3$)—CH$_2$—CH$_2$—, etc.

In the present specification, C1–4 alkoxy is methoxy, ethoxy, propoxy, butoxy and isomers thereof.

In the present specification, halogen atom means chlorine, fluorine, bromine and iodine atom.

In the present specification, C1–4 alkyl substituted with 1 to 3 of halogen atom(s) means methyl, ethyl, propyl, butyl which is substituted with 1 to 3 of atom(s) selected from chlorine, fluorine, bromine or iodine.

In the present specification, mono- or bi-cyclic C5–10 carboring is mono- or bi-cyclic C5–10 carboaryl or partially or completely saturated one thereof. For example, cyclopentane, cyclohexane, cycloheptane, cyclopentene, cyclohexene, cyclopentadiene, cyclohexadiene, benzene, pentalene, indene, naphthalene, azulene, perhydropentalene, perhydroindene, perhydronaphthalene, perhydroazulene, adamantyl ring, etc. are included.

In the present specification, mono-, bi- or tri-cyclic C3–15 carboring is mono-, bi- or tri-cyclic carboaryl or partially or completely saturated one thereof. For example, cyclopropane, cyclobutane, cyclopentane, cyclohexane, cycloheptane, cyclopentene, cyclohexene, cyclopentadiene, cyclohexadiene, benzene, pentalene, indene, naphthalene, azulene, fluorene, phenanthrene, anthracene, acenaphthylene, biphenylene, perhydropentalene, perhydroindene, perhydronaphthalene, perhydroazulene, perhydrofluorene, perhydrophenanthrene, perhydroanthracene, perhydroacenaphthylene, perhydrobiphenylene, adamantyl ring etc. are included.

In the present specification, mono- or bi-cyclic 5–10 membered heteroring containing 1–4 of nitrogen, 1 of oxygen and/or sulfur is mono- or bi-cyclic 5–10 membered heteroaryl containing 1–4 of nitrogen, 1 of oxygen and/or sulfur or partially or completely saturated one thereof.

Above 5–10 membered mono- or bi-cyclic heteroaryl containing 1–4 of nitrogen, 1 of oxygen and/or 1 of sulfur is, for example, pyrrole, imidazole, triazole, tetrazole, pyrazole, pyridine, pyrazine, pyrimidine, pyridazine, azepine, diazepine, furan, pyrane, oxepine, thiophene, thiaine (thiopyrane), thiepine, oxazole, isooxazole, thiazole, isothiazole, oxadiazole, oxazine, oxadiazine, oxazepine, oxadiazepine, thiadiazole, thiazine, thiadiazine, thiazepine, thiadiazepine, indole, isoindole, benzofuran, isobenzofuran, benzothiophene, isobenzothiophene, indazole, quinoline, isoquinoline, phthalazine, naphthyridine, quinoxaline, quinazoline, cinnoline, benzoxazole, benzothiazole, benzoimidazole, etc.

Above partially or completely saturated mono- or bi-cyclic 5–10 membered heteroaryl containing 1–4 of nitrogen, 1 of oxygen and/or 1 of sulfur is, for example, pyrroline, pyrrolidine, imidazoline, imidazolidine, triazoline, triazolidine, tetrazoline, tetrazolidine, pyrazoline, pyrazolidine, piperidine, piperazine, tetrahydropyridine, tetrahydropyrimidine, tetrahydropyridazine, dihydrofuran, tetrahydrofuran, dihydropyrane, tetrahydropyrane, dihydrothiophene, tetrahydrothiophene, dihydrothiaine (dihydrothiopyrane), tetrahydrothiaine (tetrahydrothiopyrane), oxazoline (dihydrooxazole), oxazolidine (tetrahydroxazole), dihydroisoxazole, tetrahydroisoxazole, oxadiazoline (dihydroxadiazole), oxadiazolidine (tetrahydroxadiazole), thiazoline (dihydrothiazole), thiazolidine (tetrahydrothiazole), dihydroisothiazole, tetrahydroisothiazole, morpholine, thiomorpholine, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzoxazole, perhydrobenzoxazole, dihydrobenzothiazole, perhydrobenzothiazole, dihydrobenzoimidazole, perhydrobenzoimidazole, etc.

In the present specification, a 3–15 membered mono-, bi- or tri-cyclic heteroring containing 1–4 of nitrogen, 1–2 of oxygen and/or 1 of sulfur is 3–15 membered mono-, bi- or tri-cyclic heteroaryl containing 1–4 of nitrogen, 1–2 of oxygen and/or 1 of sulfur or partially or completely saturated one thereof.

Above 3–15 membered mono-, bi- or tri-cyclic heteroring containing 1–4 of nitrogen, 1–2 of oxygen and/or 1 of sulfur is, for example, pyrrole, imidazole, triazole, tetrazole, pyrazole, pyridine, pyrazine, pyrimidine, pyridazine, azepine, diazepine, furan, pyrane, oxepine, oxazepine, thiophene, thiaine (thiopyrane), thiepine, oxazole, isoxazole, thiazole, isothiazole, oxadiazole, oxazine, oxadiazine, oxazepine, oxadiazepine, thiadiazole, thiazine, thiadiazine, thiazepine, thiadiazepine, indole, isoindole, benzofuran, isobenzofuran, benzothiophene, isobenzothiophene, indazole, quinoline, isoquinoline, phthalazine, naphthyridine, quinoxaline, quinazoline, cinnoline, benzoxazole, benzoxadiazole, benzothiazole, benzoimidazole, carbazole, acridine ring, etc.

Above partially or completely saturated mono-, bi- or tri-cyclic 3–15 membered heteroring containing 1–4 of nitrogen, 1–2 of oxygen and/or 1 of sulfur is, aziridine, oxirane, azetidine, oxetane, thiirane, thietane, pyrroline, pyrrolidine, imidazoline, imidazolidine, triazoline, triazolidine, tetrazoline, tetrazolidine, pyrazoline, pyrazolidine, piperidine, piperazine, tetrahydropyridine, tetrahydropyrimidine, tetrahydropyridazine, dihydrofuran, tetrahydrofuran, dihydropyrane, tetrahydropyrane, dihydrothiophene, tetrahydrothiophene, dihydrothiaine (dihydrothiopyrane), tetrahydrothiaine (tetrahydrothiopyrane), oxazoline (dihydroxazole), oxazolidine (tetrahydroxazole), dihydroisoxazole, tetrahydroisoxazole, oxadiazoline (dihydroxadiazole), oxadiazolidine (tetrahydroxadiazole), thiazoline (dihydrothiazole), thiazolidine (tetrahydrothiazole), dihydroisothiazole, tetrahydroisothiazole, morpholine, thiomorpholine, indoline, isoindoline, dihydrobenzofuran, perhydrobenzofuran, dihydroisobenzofuran, perhydroisobenzoturan, dihydrobenzothiophene, perhydrobenzothiophene, dihydroisobenzothiophene, perhydroisobenzothiophene, dihydroindazole, perhydroindazole, dihydroguinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocirinoline, tetrahydrocinnoline, perhydrocinnoline, dihydrobenzoxazole, perhydrobenzoxazole, dihydrobenzothiazole, perhydrobenzothiazole, dihydrobenzoimidazole, perhydrobenzoimidazole, benzoxazepine, benzoxadiazepine, benzothiazepine, benzothiadiazepine, benzazepine, benzodiazepine, indoloxazepine, indolotetrahydroxazepine, indoloxadiazepine, indolotetrahydroxadiazepine, indolothiazepine, indolotetrahydrothiazepine, indolothiadiazepine, indolotetrahydrothiadiazepine, indolazepine, indolotetrahydroazepine, indolodiazepine, indolotetrahydrodiazepine, benzofurazane, benzothiadiazole, benzotriazole, camphor, imidazothiazole, dihydrocarbazole, tetrahydrocarbazole, perhydrocarbazole, dihydroacridine, tetrahydroacridirie, perhydroacridine, dioxolane, dioxane, dioxazine ring etc.

In the present specification, a 5–12 membered heteroring containing 1–3 of nitrogen, 1 of oxygen and/or 1 of sulfur atom, i.e.

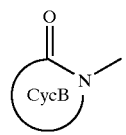

is, for example, a ring represented by

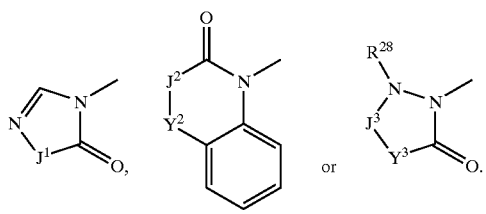

Specifically, 2-oxo-1,3,4-triazoline, 5-oxo-1,2,4-oxadiazoline, 5-oxo-1,2,4-thiadiazoline, 4-oxoimidazoline, 3,4-dihydro-4-oxopyrimidine, 3,4,5,6-tetrahydro-4-oxopyrimidine, 2-oxoindoline, 2-oxo-tetrahydroquinoline, 1,2-dihydro-2-oxoquinazoline, 1,2-dihydro-2-oxoquinoxaline, 3-oxopyrazolidine, perhydro-3-oxopyridazine, 2-oxo-1,3,4-oxadiazolidine, perhydro-2-oxo-1,3,4-oxadiazine, etc. are included.

In the specification, 3–17 membered heterering containing 1–2 of nitrogen, 1 of oxygen and/or 1 of sulfur represented by CycC is, for example, a ring represented by

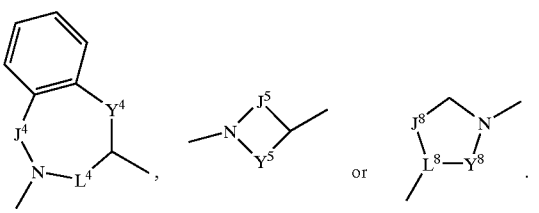

Specifically, pyrrolidine, imidazolidine, pyrazolidine, piperidine, piperazine, perhydropyrimidine, perhydropyridazine, thiazolidine, indoline, isoindoline, tetrahydroquinoline, tetrahydroisoquinoline, etc. are included.

In the specification, a C3–14 mono- or bi-cyclic carboring or 3–14 membered heterering containing 1–2 of nitrogen, 1 of oxygen, and/or 1 of sulfur represented by CycD is, for example, a ring represented by

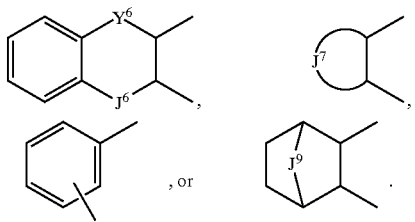

Specifically, cyclopentane, cyclohexane, cycloheptane, benzene, indan, tetrahydronaphthalene, oxorane, oxane, thiorane, thian, pyrrolidine, piperidine, bicyclo[2.2.1]heptane, bicyclo[2.2.2]octane, 7-azabicyclo[2.2.1]heptane, 7-oxobicyclo[2.2.1]heptane, 7-thiabicyclo[2.2.1]heptane, etc. are included.

In the specification, 4–18 membered heterering containing 1–2 of nitrogen, 1 of oxygen and/or 1 of —S(O)$_p$—, i.e. CycE is, for example, a ring represented by

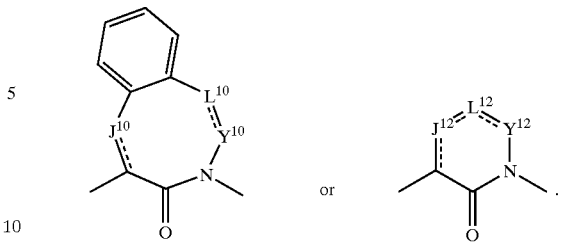

Specifically, 2-oxopyrrolidine, 2-oxopiperidine, 2-oxoperhydroazepine, 2-oxopiperazine, 3-oxomorpholine, 1,1,-dioxo-3-isothiazolidine, 1,1-dioxo-3-isothiazine, 4-oxodiazepine, 2-oxoindoline, 2-oxo-tetrahydroquinoline, 1,1-dioxo-3-benzisothiazolidine, 1,1-dioxo-3-benzisothiazine, etc. are included.

In the present invention, 5–8 membered heterering which contains 2 of nitrogen. i.e. CycF is, for example, a ring represented by

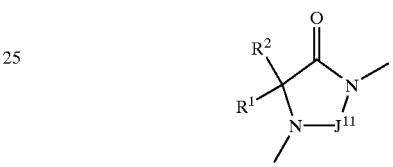

Specifically, 2,4-dioxoimidazolidine, 2-oxopiperazine, 2-oxoperhydrodiazepine substituted by $R^1$ and $R^2$ are included.

In the present invention, as may be easily understood by those skilled in the art, the symbol:⬛
indicates that the substituent attached thereto is in front of the sheet (β-position) unless specified,⬛
indicates that the substituent attached thereto is behind the sheet (α-position) unless specified, and⬛
indicates that the substituent attached thereto is in β-position or α-position or a mixture thereof.

In the formula (I), all groups represented by R are preferable, but preferably, R is (i) hydrogen,
(ii) C1–8 alkyl,
(iii) CycA,
(iv) C1–8 alkyl substituted with a group selected from CycA and nitro, (v)

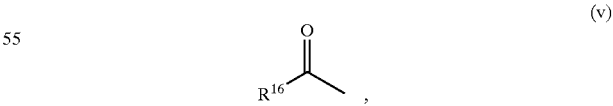

(vi)

(vii)

-continued

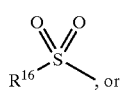
(viii)

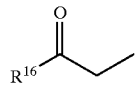
(ix)

more preferably, C1–8 alkyl or C1–8 alkyl substituted with CycA or nitro, or

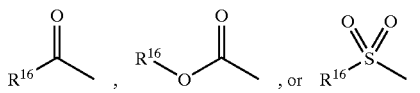

Any group represented by $R^{16}$ is preferable, but more preferably, $R^{16}$ is

[I] (1) C1–8 alkyl,
(2) C2–8 alkenyl,
(3) C2–8 alkynyl,
(4) CycA, or
(5) C1–8 alkyl substituted with a group selected from CycA or —NHC(O)-CycA,
(6) C2–8 alkenyl substituted with CycA or
(7) C2–8 alkynyl substituted with CycA,
wherein CycA may be substituted with 1–5 of $R^{27a}$, and $R^{27a}$ is (1) C1–8 alkyl,
(2) halogen,
(3) —$NR^{11}R^{12}$,
(4) —$OR^{13}$,
(5) phenyl,
(6) nitro,
(7) $CF_3$,
(8) cyano,
(9) tetrazole,
(10) —$SR^{14}$,
(11) —$COR^{15}$,
(12) oxo or
(13) C1–8 alkyl substituted with 1–5 of group selected from the following (a) to (k):
(a) halogen, (b) —$NR^{11}R^{12}$, (c) —$OR^3$, (d) phenyl, (e) nitro, (f) $CF_3$, (g) cyano, (h) tetrazole, (j) —$SR^{14}$, (k) —$COR^{15}$, or
[II] (a) C1–8 alkyl, C2–8 alkenyl or C2–8 alkynyl substituted with a group selected from halogen, $CF_3$, nitro, cyano or $NR^{18}R^{19}$ or
(b) (1) CycA containing 1–5 of substituent $R^{27}$ or
(2) C1–8 alkyl, C2–8 alkenyl or C2–8 alkynyl substituted with CycA, which contains 1–5 of substituent $R^{27}$, wherein at least one of R27 described in (1) and (2) is selected from (i) a C5–10 mono- or bi-cyclic carboring,
(ii) a 5–10 membered mono- or bi-cyclic heteroring,
(iii) —$SO_2R^{15}$, (iv) —$OCF_3$ or
(v) C1–8 alkyl substituted with 1–5 of the group selected from (a) halogen, (b) —$NR^{11}R^{12}$, (c) —$OR^{13}$, (d) a C5–10 mono- or bi-cyclic carboring, (e) nitro, (f) $CF_3$, (g) cyano, (h) a 5–10 membered mono- or bi-cyclic heteroring, (j) —$SR^{14}$, (k) —$COR^{15}$, (l) —$SO_2R^{15}$ and (m) —$OCF_3$ (at least one is a C5–10 mono- or bi-cyclic carboring, a 5–10 mono- or bi-cyclic heteroring, —$SO_2R^{15}$ or —$OCF_3$))

Particularly preferably,

[I] (1) C1–8 alkyl,
(2) C2–8 alkenyl,
(3) C2–8 alkynyl,
(4) CycA or
(5) C1–8 alkyl substituted with a group selected from CycA or —NHC(O)-CycA,
(6) C2–8 alkenyl substituted with CycA or
(7) C2–8 alkynyl substituted with CycA,
wherein CycA is a mono- or bi-cyclic C5–10 carboaryl which may be substituted with 1–5 of $R^{27}$ or partially or completely saturated one thereof, or mono- or bi-cyclic 5–10 membered heteroaryl containing 1–2 of nitrogen, 1–2 of oxygen and/or 1 of sulfur atom, or partially or completely saturated one thereof or
[II] (a) C1–8 alkyl, C2–8 alkenyl or C2–8 alkynyl substituted with a group selected from halogen atom, $CF_3$, nitro, cyano and $NR^{18}R^{19}$ or
(b) CycA containing 1–5 of substituent $R^{27}$ or
(2) C1–8 alkyl, C2–8 alkenyl or C2–8 alkynyl substituted with CycA, which contains 1–5 of substituent $R^{27}$,
wherein at least one of $R^{27}$ described in (1) and (2) is selected from (i) a C5–10 mono- or bi-cyclic carboring,
(ii) a 5–10 membered mono- or bi-cyclic heteroring,
(iii) —$SO_2R^{15}$, (iv) —$OCF_3$ or
(v) C1–8 alkyl substituted with 1–5 of group selected from
(a) halogen, (b) —$NR^{11}R^{12}$, (c) —$OR^{13}$, (d) a C5–10 mono- or bi-cyclic carboring, (e) nitro, (f) $CF_3$, (g) cyano, (h) a 5–10 membered mono- or bi-cyclic heteroring, (j) —$SR^{14}$, (k) —$COR^{15}$, (l) —$SO_2R^{15}$ and (m) $OCF_3$,
wherein at least one group is selected from a C5–10 mono- or bi-cyclic carboring or a 5–10 membered mono- or bi-cyclic heteroring, —$SO_2R^{15}$ or $OCF_3$,
above CycA is C5–10 mono- or bi-cyclic carboaryl or partially or completely saturated one, or 5–10 membered mono- or bi-cyclic heteroaryl containing 1–2 of nitrogen, 1–2 of oxygen and/or 1 of sulfur, or partially or completely saturated one thereof.

Particularly preferably, [I] (1) C1–4 alkyl, (2) C2–4 alkenyl, (3) C2–4 alkynyl, (4) CycA or (5) C1–4 alkyl, C2–4 alkenyl or C2–4 alkynyl substituted with CycA which is preferably cyclopentane, cyclohexane, benzene, naphthalene, pyrrolidine, piperidine, piperazine, morpholine, pyrrole, furan, thiophene, pyridine, pyrimidine, pyrazine, pyridazine, indole, isoindole, quinoline, isoquinoline, quinazoline, quinoxaline, phthalazine, benzothiophene, benzofuran, benzoxazole, tetrahydroquinoline, tetrahydroquinazoline, tetrahydroquinoxaline, optionally substituted with 1–5 of $R^{27a}$ or
[II] (a) C1–8 alkyl, C2–8 alkenyl or C2–8 alkynyl substituted with a group selected from halogen, $CF_3$, nitro, cyano or $NR^{18}R^{19}$ or
(b) (1) CycA which contains 1–5 of substituent $R^{27}$, or
(2) C1–8 alkyl, C2–8 alkenyl or C2–8 alkynyl substituted with CycA which contains 1–5 of substituent $R^{27}$, wherein at least one of $R^{27}$ described in (1) and (2) is selected from (i) a C5–10 mono- or bi-cyclic carboring,
(ii) a 5–10 membered mono- or bi-cyclic heteroring,
(iii) —SO$_2$R$^{15}$, (iv) —OCF$_3$, or
(v) C1–8 alkyl substituted with 1–5 of group selected from
(a) halogen atom, (b) —NR$^{11}$R$^{12}$, (c) —OR$^{13}$, (d) a C5–10 mono- or bi-cyclic carboring, (e) nitro, (f) CF$_3$, (g) cyano, (h) a 5–10 membered mono- or bi-cyclic heteroring, (j) —SR$^{14}$, (k) —COR$^{15}$, (l) —SO$_2$R$^{15}$ or (m) —OCF$_3$, wherein at least one group is selected from a C5–10 mono- or bi-cyclic carboring, a 5–10 membered mono- or bi-cyclic heteroring, —SO$_2$R$^{15}$ or —OCF$_3$, and CycA is preferably cyclopentane, cyclohexane, benzene, naphthalene, pyrrolidine, piperidine, piperazine, morpholine, pyrrole, furan, thiophene, pyridine, pyrimidine, pyrazine, pyridazine, indole, isoindole, quinoline, isoquinoline, quinazoline, quinoxaline, phthalazine, benzothiophene, benzofuran, benzoxadiazole, tetrahydroquinoline, tetrahydroquinazoline, or tetrahydroquinoxaline.

In the formula (I), AA$^1$ is preferably a single bond,

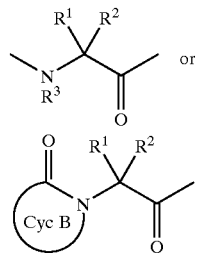

which is formed with R, but more preferably, AA$^1$ is a single bond or

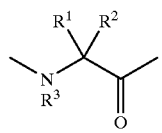

Any group represented by R$^1$ is preferable, but more preferably, R$^1$ is hydrogen, C1–8 alkyl, phenyl or C1–8 alkyl substituted with NH$_2$, C1–4 alkoxy, SH, SCH$_3$, phenyl, hydroxyphenyl, COOH, CONH$_2$, guanidino, imidazole or indole. Particularly preferably, R$^1$ is hydrogen, C1–8 alkyl, phenyl or C1–8 alkyl substituted with C1–4 alkoxy or phenyl. Then, any group represented by R$^2$ is preferable, but hydrogen is particularly preferable.

And C3–6 alkylene which R$^1$ and R$^2$ together form is also preferable.

Any group represented by R$^3$ is preferable, but more preferably R$^3$ is hydrogen or C1–4 alkyl.

And C2–4 alkylene which R$^3$ and R$^1$ together form is also preferable.

In the formula (I), Any group represented AA$^2$ is preferable, but more preferably, AA$^2$ is a single bond,

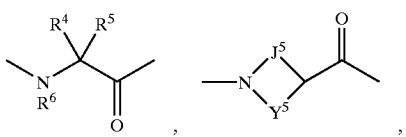

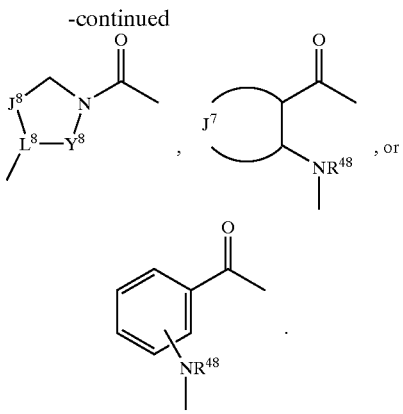

Particularly preferably, AA$^2$ is a single bond,

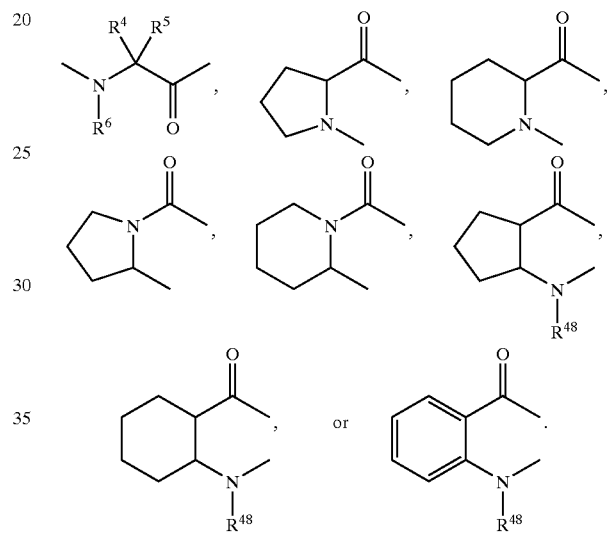

Any group represented by R$^4$ is preferable, but more preferably, R$^4$ is hydrogen, C1–8 alkyl, phenyl or C1–8 alkyl substituted with NH$_2$, C1–4 alkoxy, SH, SCH$_3$, phenyl, hydroxyphenyl, COOH, CONH$_2$, guanidino, imidazole or indole. Particularly preferably, R$^4$ is hydrogen, C1–8 alkyl, phenyl or C1–8 alkyl substituted with C1–4 alkoxy or phenyl. Then, any group represented by R$^5$ is preferable, and hydrogen is particularly preferable.

And C3–6 alkylene which R$^4$ and R$^5$ together form is also preferable.

Any group represented by R$^6$ is preferable, but more preferably R$^6$ is hydrogen or C1–4 alkyl.

And C2–4 alkylene which R$^6$ and R$^4$ together form is also preferable.

Any group represented by R$^{48}$ is all preferable, but more preferably, R$^{48}$ is
[I] hydrogen, C1–4 alkyl, phenyl or C1–4 alkyl substituted with phenyl, or
[II] C2–6 alkylene, wherein one carbon atom may be replaced by oxygen, sulfur or —NR$^{47}$—, wherein R$^{47}$ is hydrogen or C1–4 alkyl to be formed together with R$^4$, when AA$^1$ is a single bond. Particularly preferably, R$^{48}$ is
[I] hydrogen atom or C1–4 alkyl, or
[II] when AA$^1$ is a single bond, taken together with R to form tetramethylene, pentamethylene, —CH$_2$—CH$_2$—O—CH$_2$—CH$_2$—, —CH$_2$—CH$_2$—NH—CH$_2$—CH$_2$— or —CH$_2$—CH$_2$—N(CH$_3$)—CH$_2$—CH$_2$—.

In the formula (I), any group which AA$^1$ and AA$^2$ together form is preferable, but preferably, it is

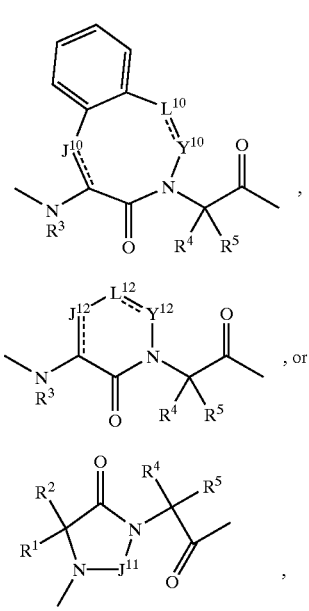

(i), (ii), (iii)

particularly preferably, it is

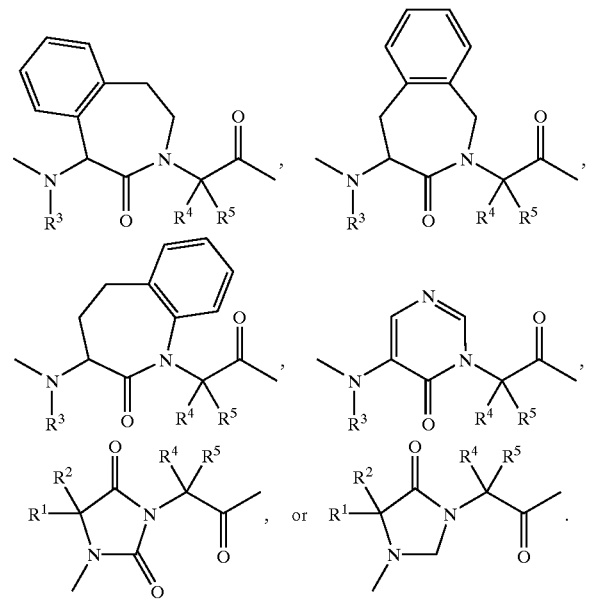

Any group represented by R$^7$ is preferable. More preferably, R$^7$ is hydrogen atom, C1–8 alkyl, phenyl, or C1–8 alkyl substituted with NH$_2$, C1–4 alkoxy, SH, SCH$_3$, phenyl, hydroxyphenyl, COOH, CONH$_2$, guanidino, imidazole or indole.

Particularly preferably, R$^7$ is hydrogen, C1–8 alkyl, phenyl, or C1–8 alkyl substituted with C1–4 alkoxy or phenyl. Then, any group represented by R$^8$ is preferable, but hydrogen is most preferable.

And C3–6 alkylene which R$^7$ and R$^8$ together form is also preferable.

Any group represented by R$^9$ is preferable, but more preferably R$^9$ is hydrogen or C1–4 alkyl.

And C2–4 alkylene which R$^9$ and R$^7$ together form is also preferable.

And when D ring is

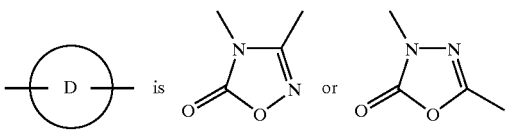

R$^7$ and R$^8$ are preferably C1–8 alkyl substituted with —COR$^{65}$, in addition to the groups described above. More preferably, carboxymethyl, 2-carboxyethyl, carbamoylmethyl, 2-carbamoylethyl, etc. are included in addition to the above groups.

Any of q, which represents an integer of 1 to 4, is preferable, but particularly preferably q is 1.

Any group represented by Z is preferable, but more preferably, Z is a single bond, C1-6alkylene, oxygen atom, sulfur atom, or C1–6 alkylene whose one carbon atom is replaced by —O—, —S— or —NR$^{10}$—.

Any group represented by E described above is preferable, but more preferably E is hydrogen atom, C1–4 alkyl, —COOR$^{18}$, —G—(R$^{35}$)$_r$, wherein G is preferably C5–10 mono- or bi-cyclic carboring or 5–10 membered mono- or bi-cyclic heteroring containing 1 to 3 of nitrogen atom(s), 1 of oxygen and/or 1 of sulfur atom.

Preferable compounds in the present invention are the compounds of formula (I-1A)

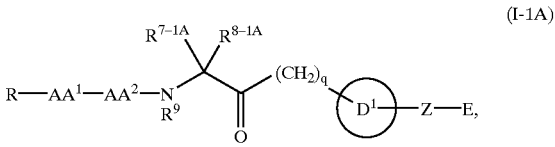

(I-1A)

wherein R$^{7-1A}$ and R$^{8-1A}$ are each independently, (1) hydrogen atom,
(2) C1–8 alkyl,
(3) Cyc, or
(4) C1–8 alkyl substituted with 1 to 5 of group(s) selected from the following (a) to (h):
(a) —NR$^{61}$R$^{62}$ (b) —OR$^{63}$, (c) —SR$^{64}$, (d) —NR$^{66}$CONR$^{61}$R$^{62}$, (e) guanidino, (f) Cyc, (g) —NR$^{66}$SO$_2$R$^{64}$ or (h) —CONR$^{61}$SO$_2$R$^{64}$, or R$^{7-1A}$ and R$^{8-1A}$ are taken together to form C2–8 alkylene, wherein one carbon atom may be replaced by oxygen atom, sulfur atom or —NR$^{60}$— and the alkylene may be substituted with —NR$^{61}$R$^{62}$ or —OR$^{63}$,

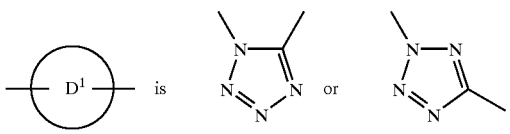

and the other symbols have the same meanings as above, and the compound of formula (I-1B)

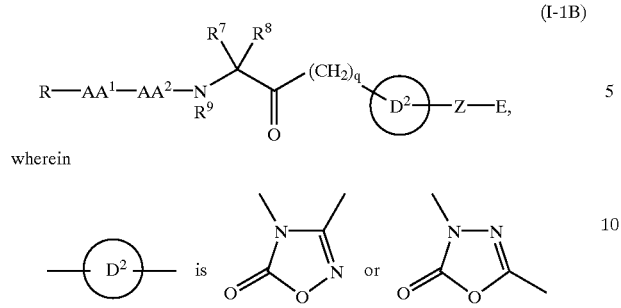

wherein and the other symbols have the same meanings as above, a non-toxic salt thereof and a hydrate thereof.

In the compounds of the present invention, the following compounds, non-toxic salts thereof and hydrates thereof are preferred;

the compound of formula (I-2A)

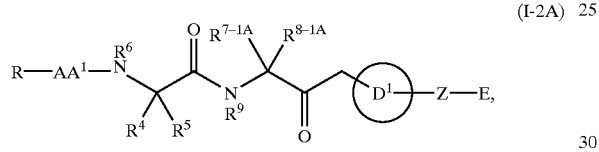

wherein all symbols have the same meanings as above, the compound of formula (I-2B)

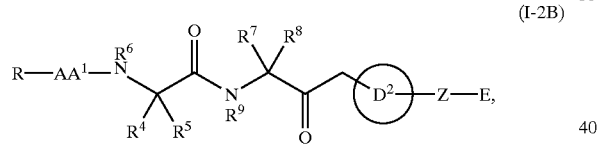

wherein all symbols have the same meanings as above, the compound of formula (I-3A)

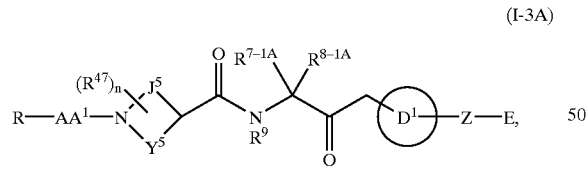

wherein all symbols have the same meanings as above, the compound of formula (I-3B)

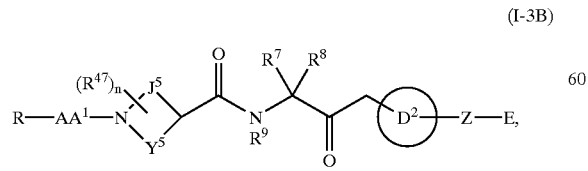

wherein all symbols have the same meanings as above, the compound of formula (I-4A)

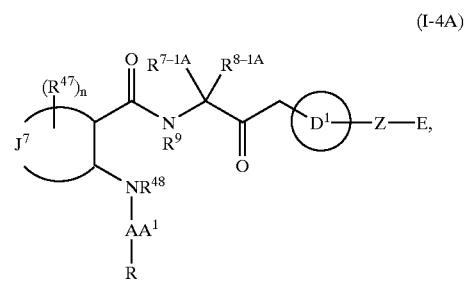

wherein all symbols have the same meanings as above, the compound of formula (I-4B)

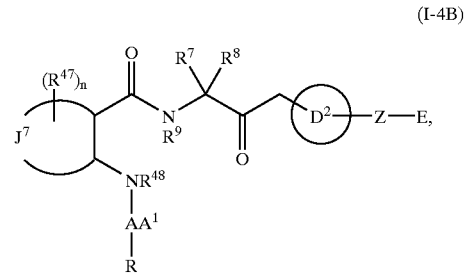

wherein all symbols have the same meanings as above.

Concretely, the compounds described in the following tables 1 to 30, non-toxic salts thereof, hydrates thereof and the compounds described in the examples are preferable.

TABLE 1

TABLE 1-continued
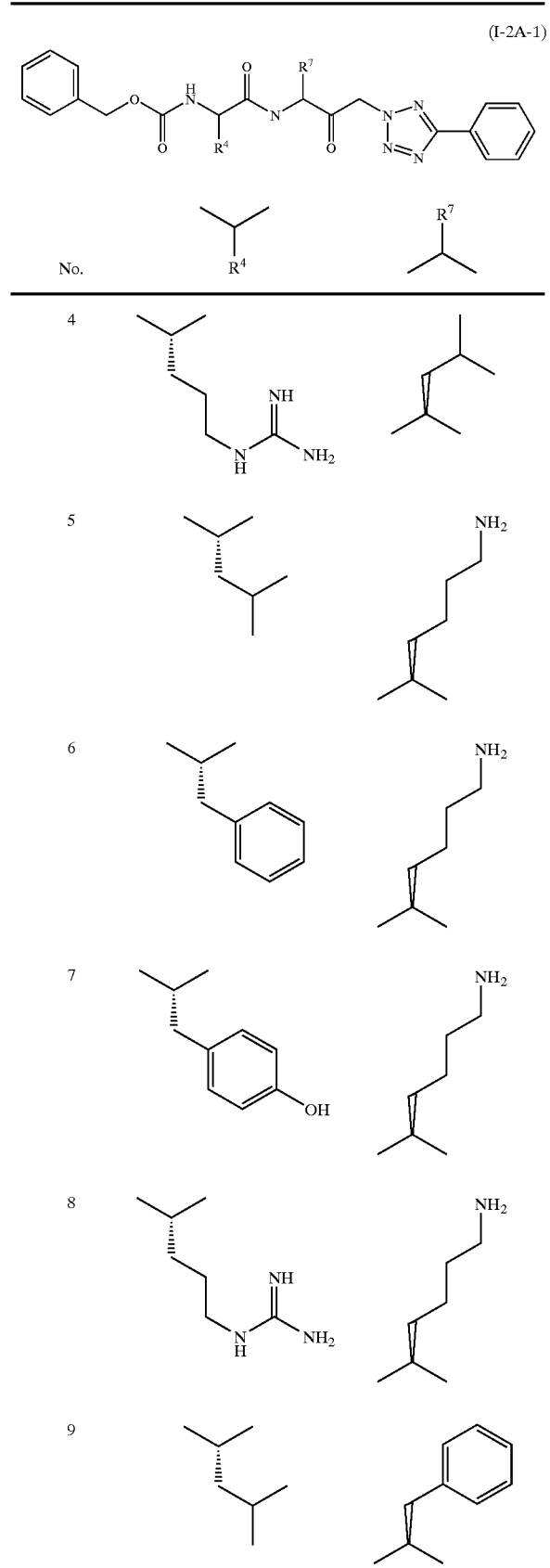
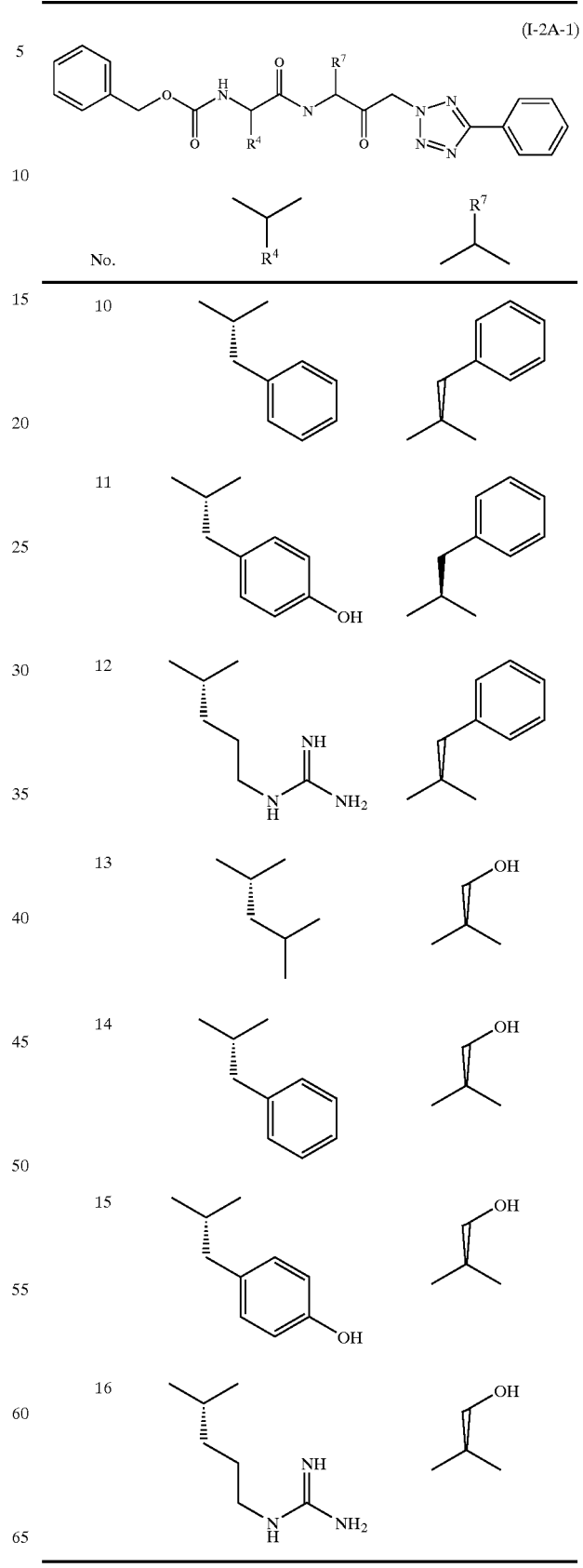

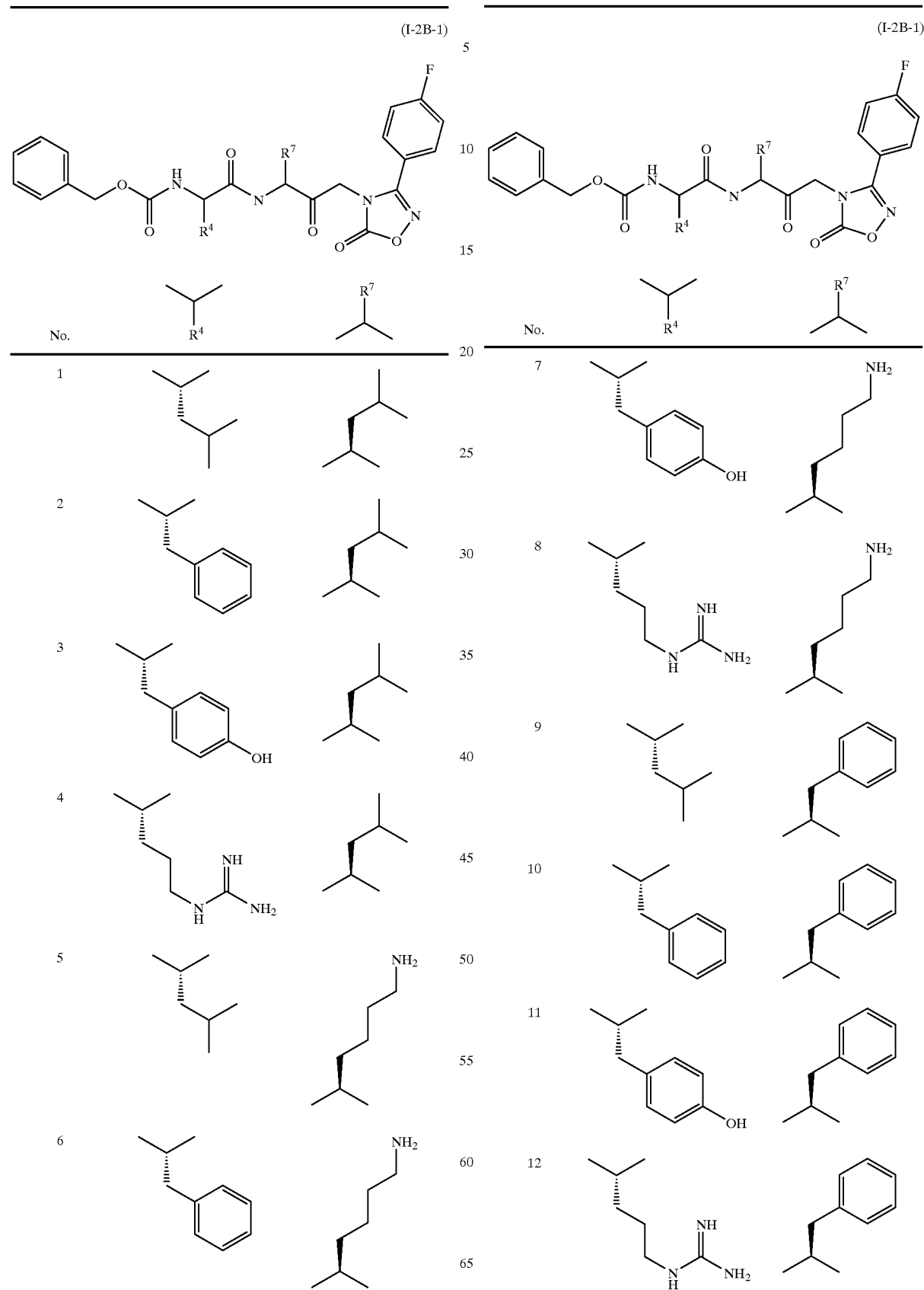

TABLE 2-continued (I-2B-1)

| No. | R⁴ | R⁷ |
|-----|----|----|
| 13 | (isobutyl-methyl) | (2-hydroxy-1-methylethyl)-OH |
| 14 | (benzyl) | (2-hydroxy-1-methylethyl)-OH |
| 15 | (4-hydroxybenzyl) | (2-hydroxy-1-methylethyl)-OH |
| 16 | (4-guanidinobutyl) | (2-hydroxy-1-methylethyl)-OH |

TABLE 3

(I-2B0-2)

| No. | R⁴ | R⁷ |
|-----|----|----|
| 1 | (isobutyl-methyl) | (4-methyl-2-pentenyl) |
| 2 | (benzyl) | (4-methyl-2-pentenyl) |
| 3 | (4-hydroxybenzyl) | (isohexyl) |
| 4 | (4-guanidinobutyl) | (4-methyl-2-pentenyl) |
| 5 | (isobutyl-methyl) | (5-amino-pentenyl)-NH₂ |
| 6 | (benzyl) | (5-amino-pentenyl)-NH₂ |
| 7 | (4-hydroxybenzyl) | (5-amino-pentenyl)-NH₂ |

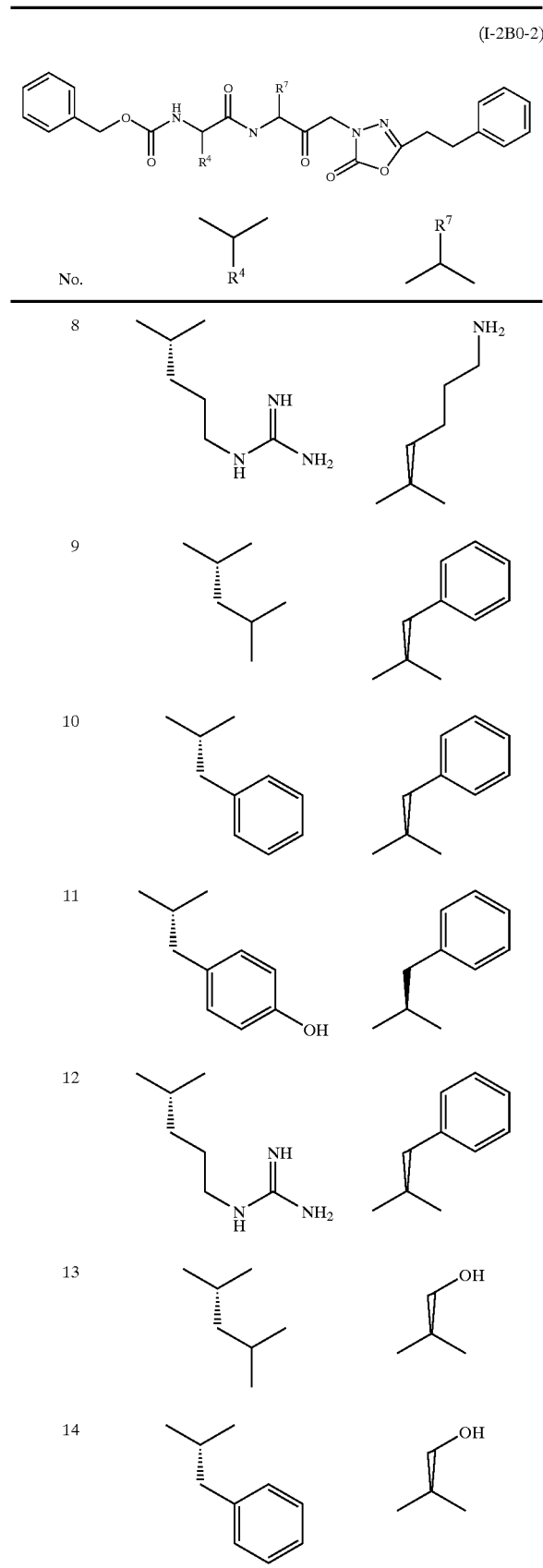
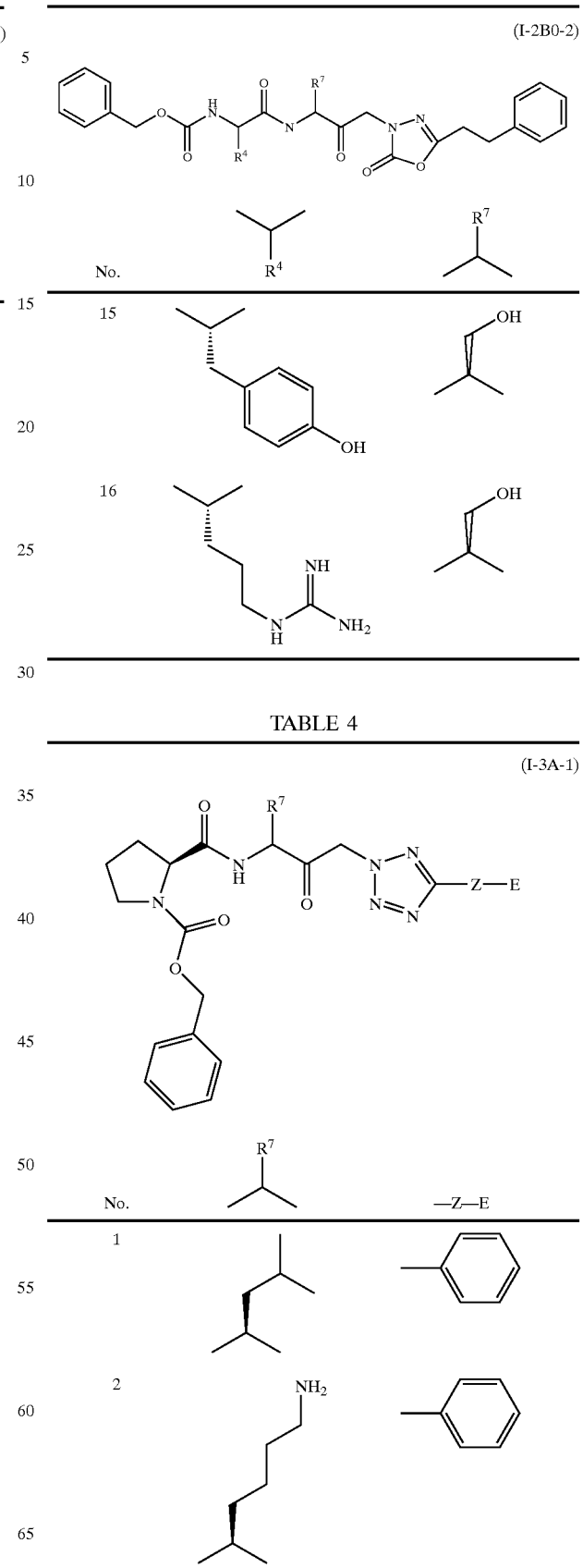

TABLE 4-continued (I-3A-1)

| No. | R⁷ | —Z—E |
|---|---|---|
| 3 | isobutyl-benzyl | phenyl |
| 4 | isobutyl-CH₂OH | phenyl |
| 5 | diisobutyl | 4-F-phenyl |
| 6 | 5-amino-4-methylpentyl | 4-F-phenyl |
| 7 | isobutyl-benzyl | 4-F-phenyl |
| 8 | isobutyl-CH₂OH | 4-F-phenyl |
| 9 | diisobutyl | 4-pyridyl |
| 10 | 5-amino-4-methylpentyl | 4-pyridyl |
| 11 | isobutyl-benzyl | 4-pyridyl |
| 12 | isobutyl-CH₂OH | 4-pyridyl |
| 13 | diisobutyl | phenylpropyl |
| 14 | 5-amino-4-methylpentyl | phenylpropyl |
| 15 | isobutyl-benzyl | phenylpropyl |

TABLE 4-continued (I-3A-1)

| No. | R⁷ | —Z—E |
|---|---|---|
| 16 | isobutyl-CH₂OH | 3-phenylpropyl |

TABLE 5

(I-3A-2)

| No. | R⁷ | —Z—E |
|---|---|---|
| 1 | 2,4-dimethylpentyl | phenyl |
| 2 | 5-aminopentyl | phenyl |
| 3 | isobutylbenzyl | phenyl |
| 4 | isobutyl-CH₂OH | phenyl |
| 5 | 2,4-dimethylpentyl | 4-fluorophenyl |
| 6 | 5-aminopentyl | 4-fluorophenyl |
| 7 | isobutylbenzyl | 4-fluorophenyl |
| 8 | isobutyl-CH₂OH | 4-fluorophenyl |
| 9 | 2,4-dimethylpentyl | 4-pyridyl |

TABLE 5-continued
(I-3A-2)
| No. | R⁷ | —Z—E |
|---|---|---|
| 10 |  | 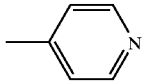 |
| 11 |  | 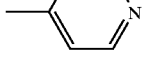 |
| 12 |  | 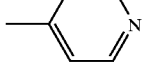 |
| 13 |  | 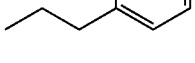 |
| 14 |  | 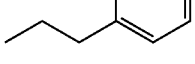 |
| 15 |  | 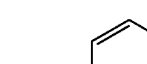 |
| 16 |  | 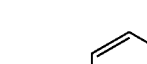 |
TABLE 6
(I-3B-1)
| No. | R⁷ | —Z—E |
|---|---|---|
| 1 |  | 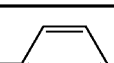 |
| 2 |  | 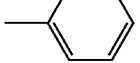 |
| 3 |  | 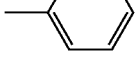 |
| 4 |  | 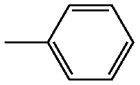 |
| 5 |  | 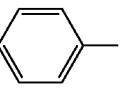 |
| 6 |  | 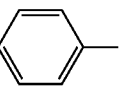 |

TABLE 6-continued
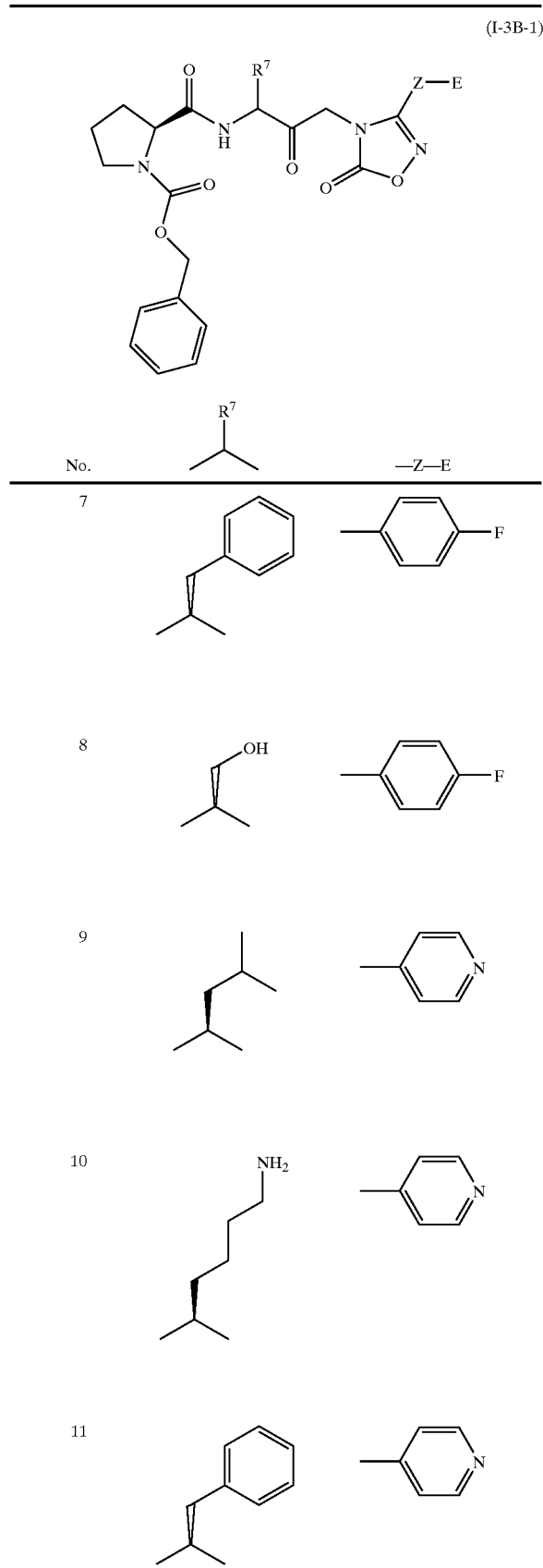
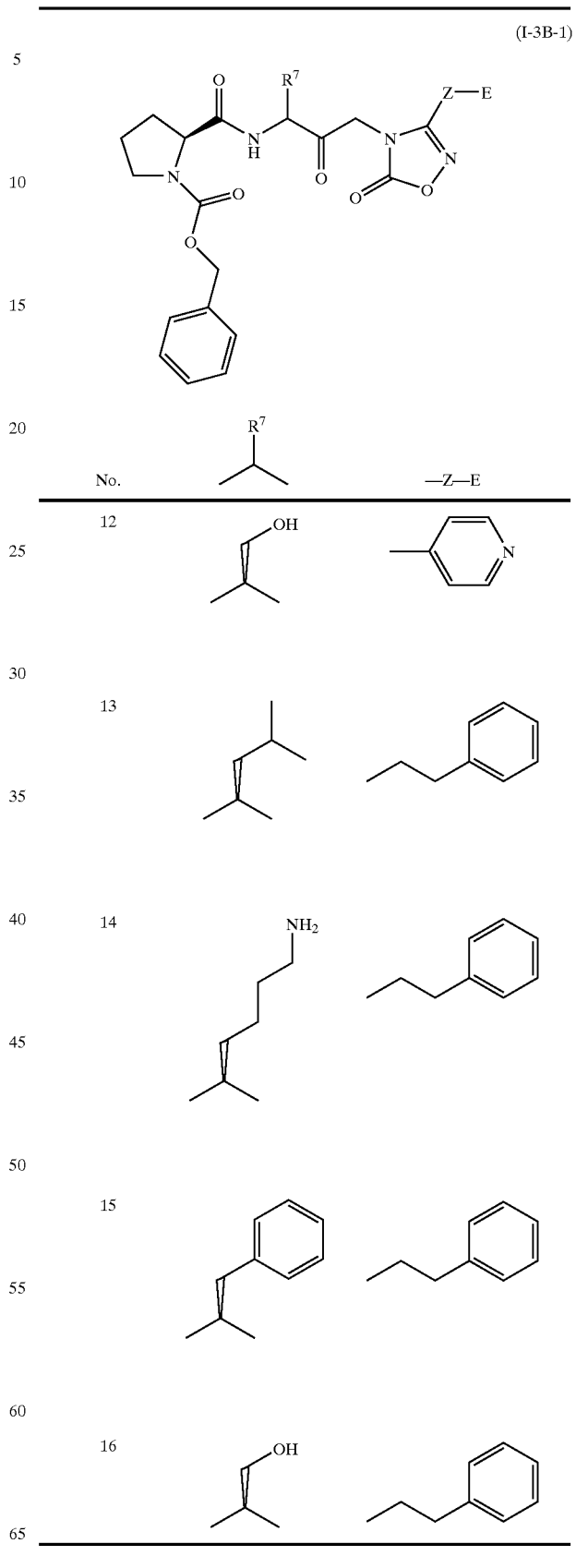

TABLE 7
(I-3B-2)
| No. | R⁷ | —Z—E |
|---|---|---|
| 1 | | |
| 2 | | |
| 3 | | |
| 4 | | |
| 5 | | |
| 6 | | |
| 7 | | |
| 8 | | |
| 9 | | |
| 10 | | |
| 11 | | |
| 12 | | |
| 13 | | |
| 14 | | |

TABLE 7-continued
(I-3B-2)
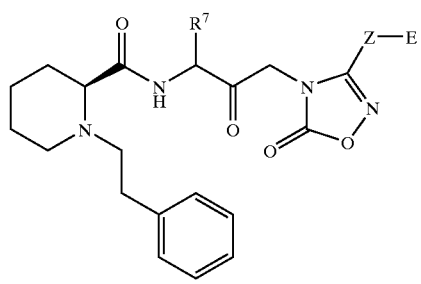
| No. |  R⁷ | —Z—E |
|---|---|---|
| 15 | 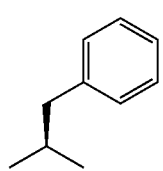 | 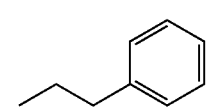 |
| 16 | 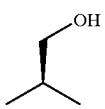 | 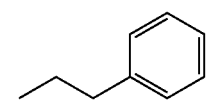 |
TABLE 8
(I-3B-3)
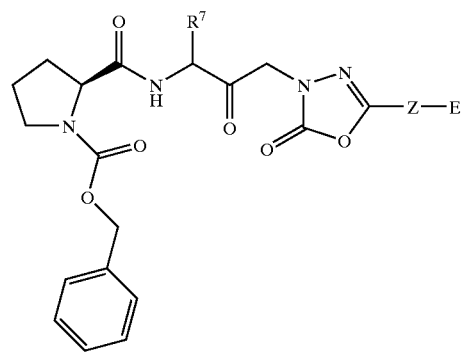
| No. |  R⁷ | —Z—E |
|---|---|---|
| 1 | 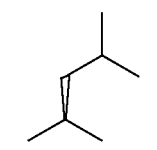 | 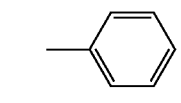 |
TABLE 8-continued
(I-3B-3)
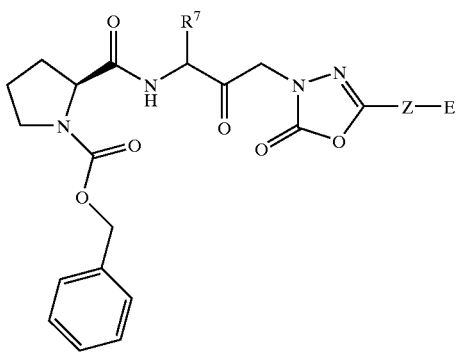
| No. |  R⁷ | —Z—E |
|---|---|---|
| 2 | 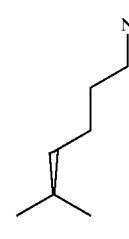 | 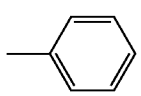 |
| 3 | 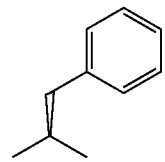 | 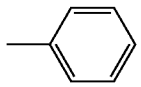 |
| 4 | 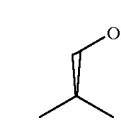 | 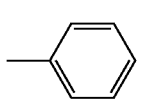 |
| 5 | 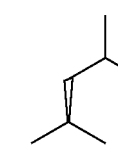 | 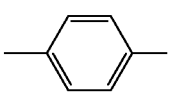 |
| 6 | 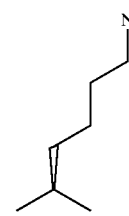 |  |
| 7 | 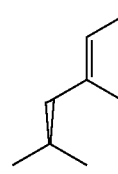 | 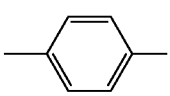 |

TABLE 8-continued
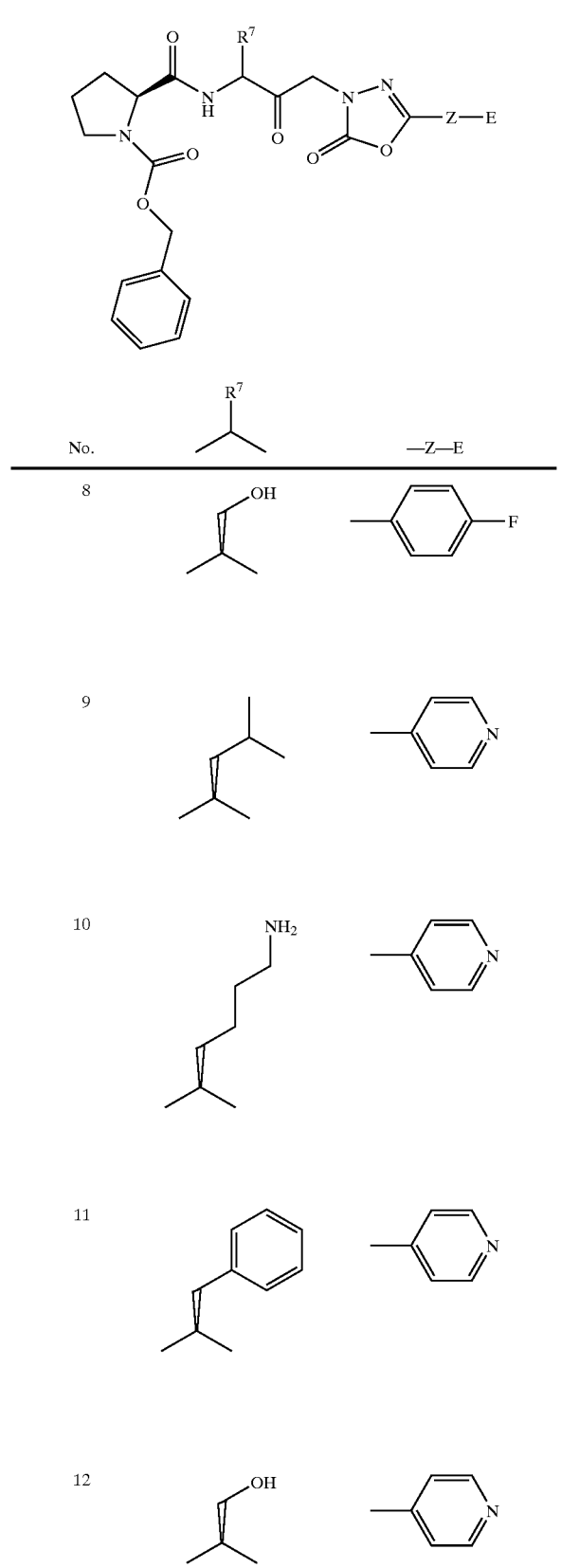
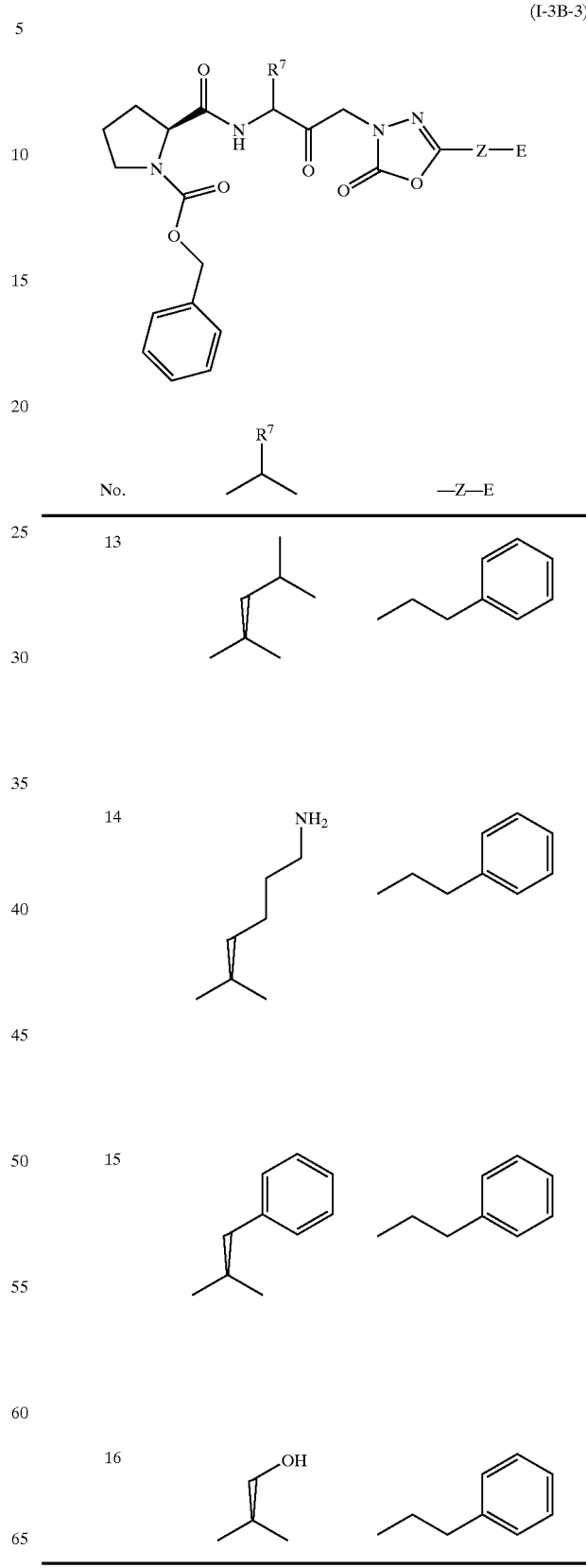

TABLE 9
(I-3B-4)
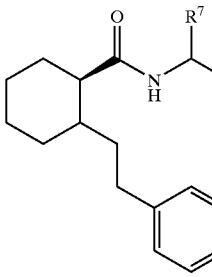
| No. | R⁷ | —Z—E |
|---|---|---|
| 1 | 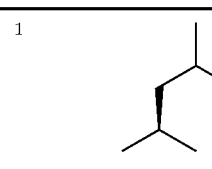 | 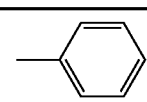 |
| 2 | 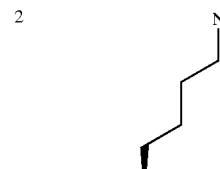 | 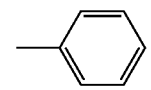 |
| 3 | 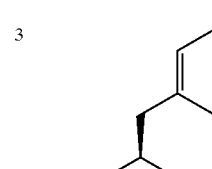 | 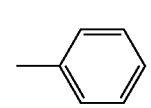 |
| 4 | 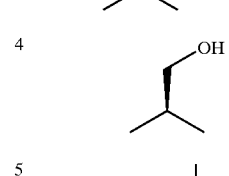 | 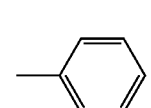 |
| 5 | 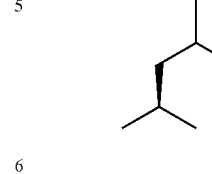 | 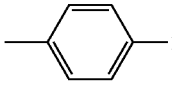 |
| 6 | 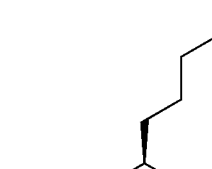 | 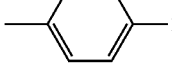 |
| 7 | 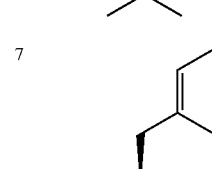 |  |
TABLE 9-continued
(I-3B-4)
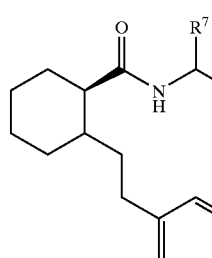
| No. | R⁷ | —Z—E |
|---|---|---|
| 8 | 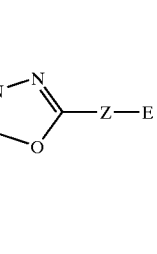 | 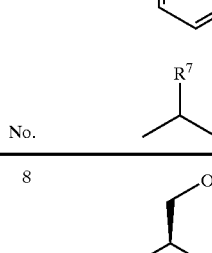 |
| 9 | 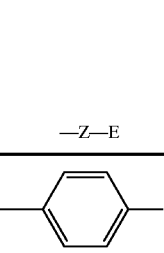 | 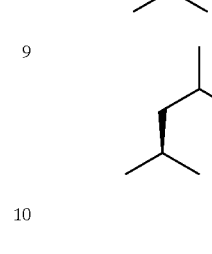 |
| 10 | 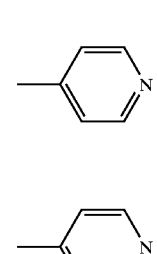 | 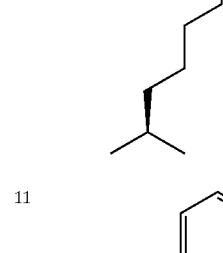 |
| 11 | 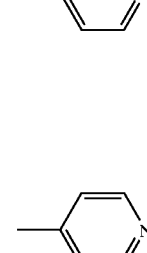 | 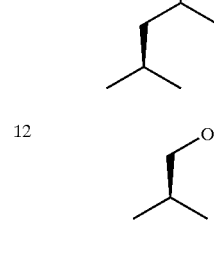 |
| 12 | 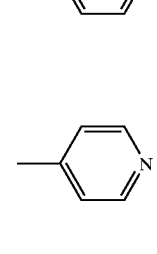 | 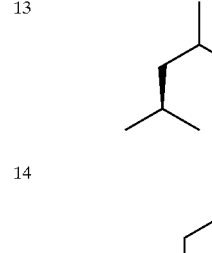 |
| 13 | 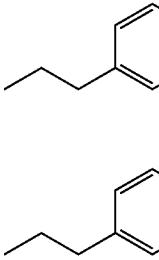 | 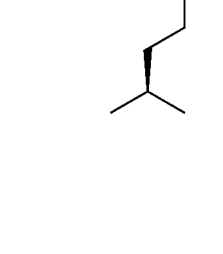 |
| 14 |  | |

TABLE 9-continued
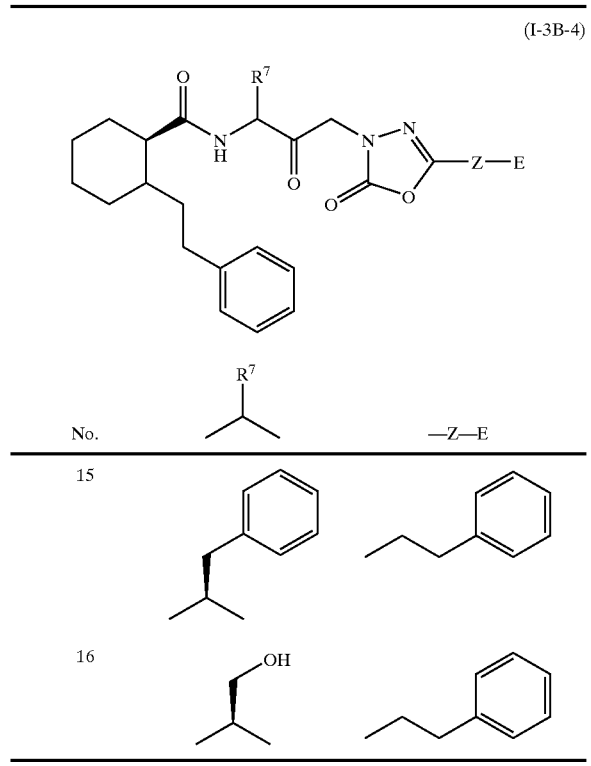
TABLE 10
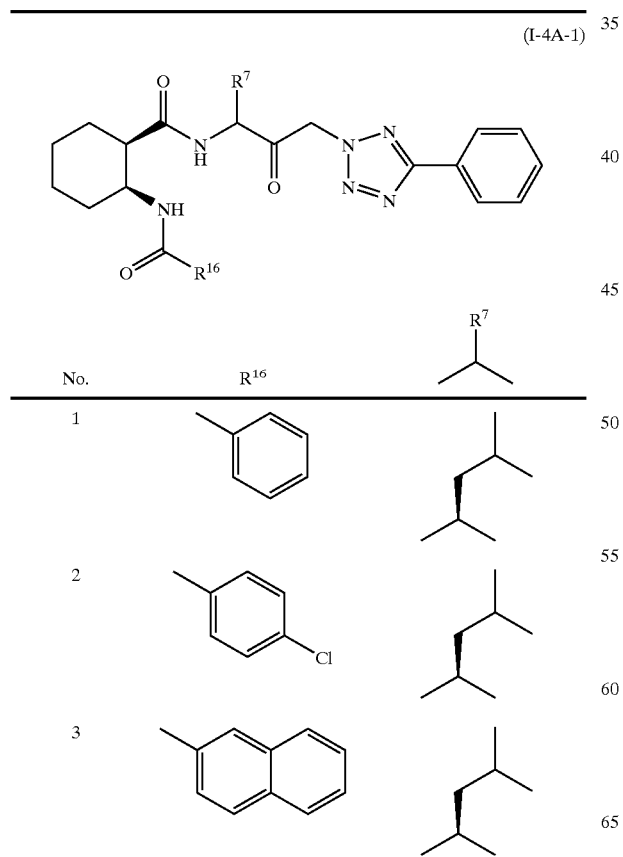
TABLE 10-continued
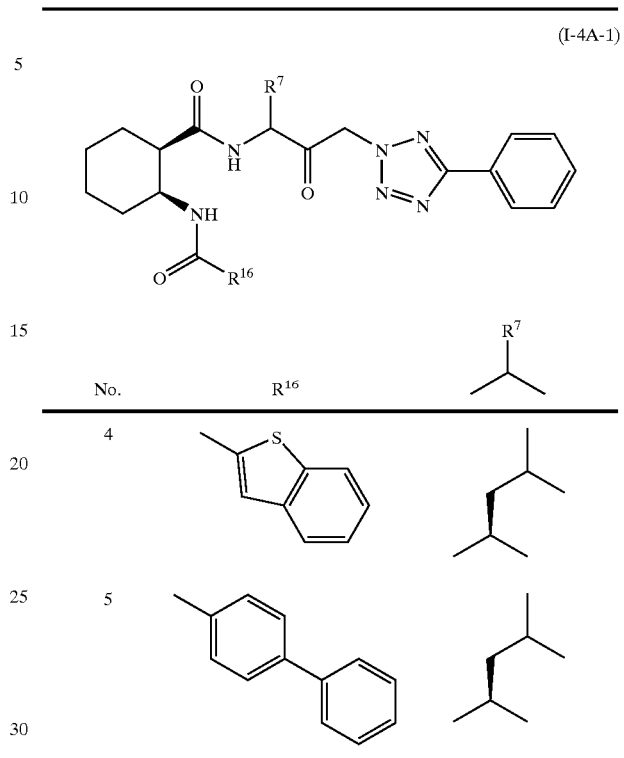
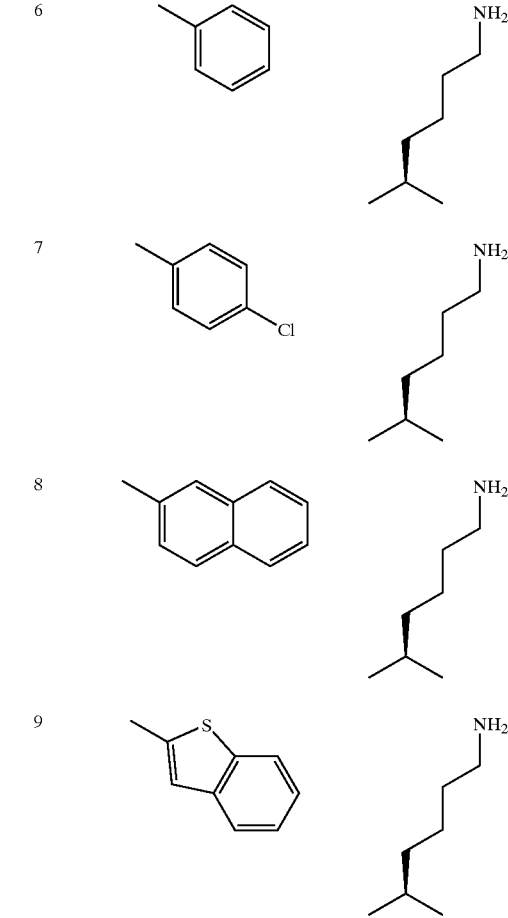

TABLE 10-continued
(I-4A-1)
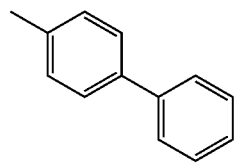
| No. | R¹⁶ | R⁷ |
|---|---|---|
| 10 | 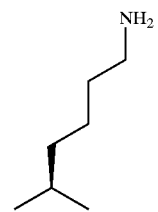 | 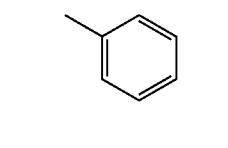 |
| 11 | 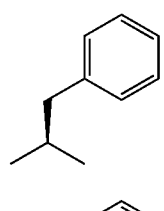 | 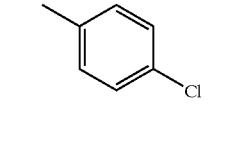 |
| 12 | 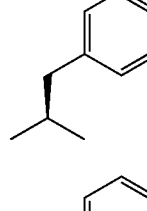 | 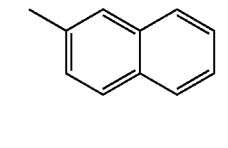 |
| 13 | 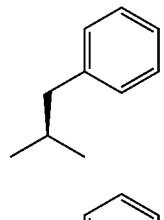 | 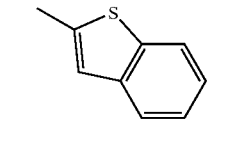 |
| 14 | 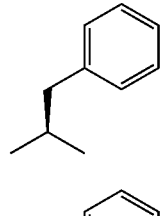 | 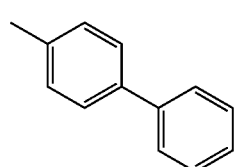 |
| 15 | 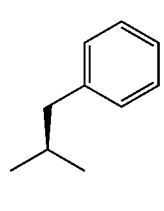 | 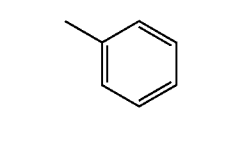 |
| 16 | 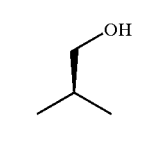 | 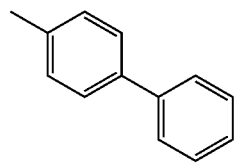 |
TABLE 10-continued
(I-4A-1)
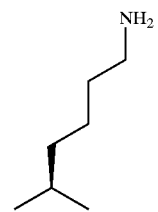
| No. | R¹⁶ | R⁷ |
|---|---|---|
| 17 | 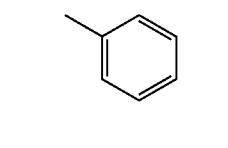 | 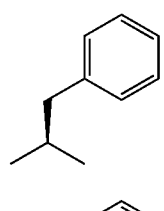 |
| 18 | 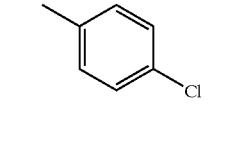 | 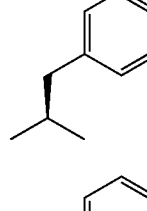 |
| 19 | 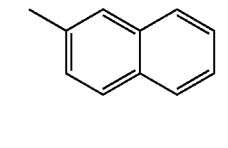 | 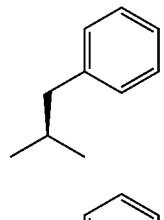 |
| 20 | 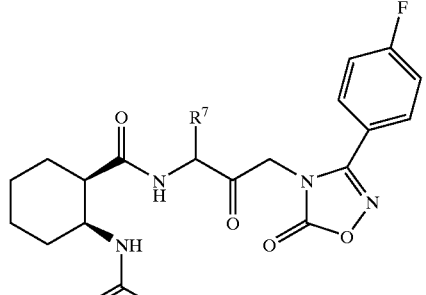 | 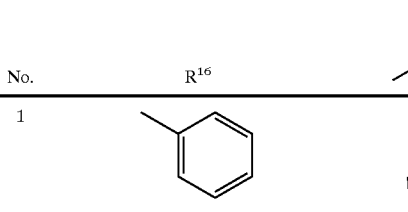 |
TABLE 11
(I-4B-1)

TABLE 11-continued
(I-4B-1)
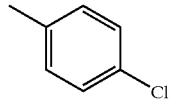
| No. | R16 | R7 |
|---|---|---|
| 2 | 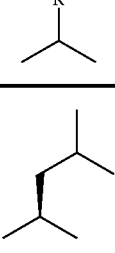 | 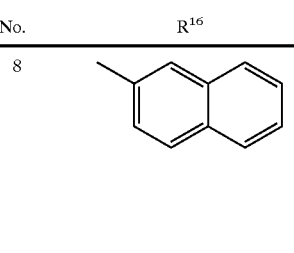 |
| 3 | 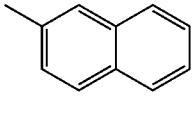 | 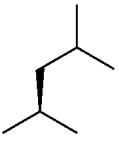 |
| 4 | 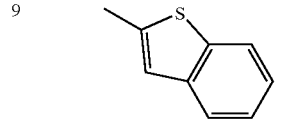 | 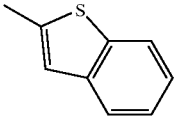 |
| 5 | 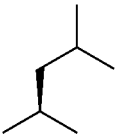 | 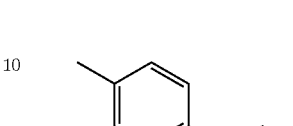 |
| 6 | 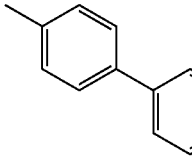 | 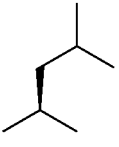 |
| 7 | 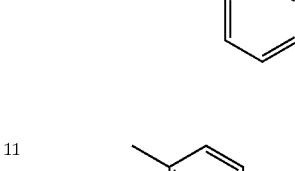 | 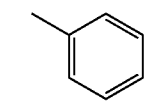 |
TABLE 11-continued
(I-4B-1)
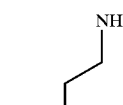
| No. | R16 | R7 |
|---|---|---|
| 8 |  | 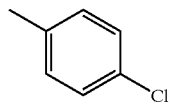 |
| 9 | 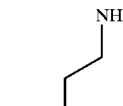 | 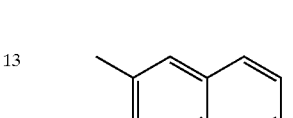 |
| 10 | 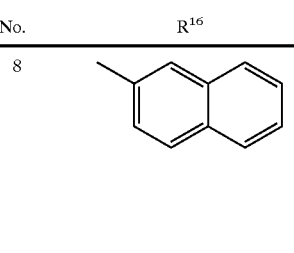 | 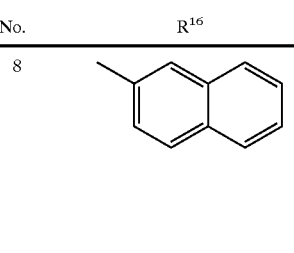 |
| 11 | 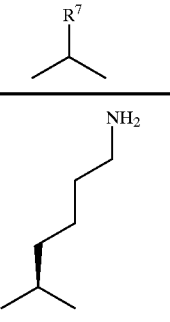 | 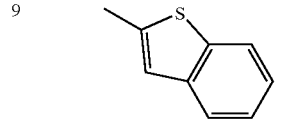 |
| 12 | 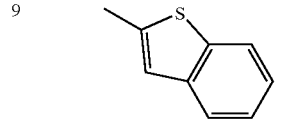 | 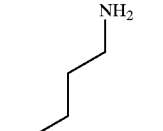 |
| 13 | 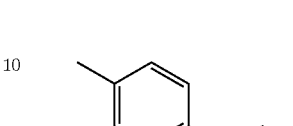 | 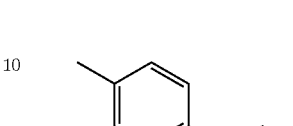 |

TABLE 11-continued (I-4B-1)

TABLE 12

(I-4B-2)

TABLE 12-continued
(I-4B-2)
| No. | R¹⁶ | R⁷ |
|---|---|---|
| 8 | 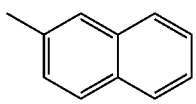 | 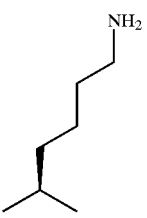 |
| 9 | 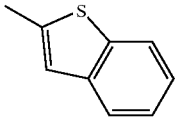 | 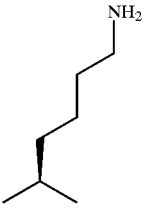 |
| 10 | 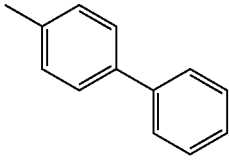 | 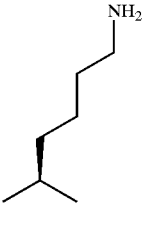 |
| 11 | 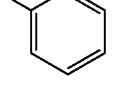 | 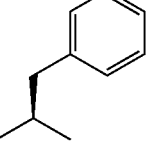 |
| 12 | 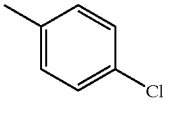 | 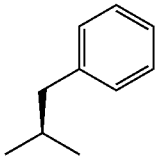 |
| 13 | 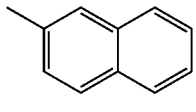 | 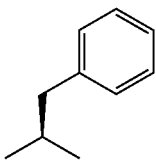 |
| 14 | 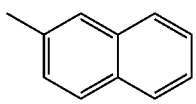 | 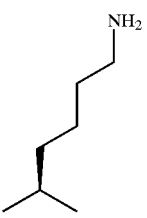 |
| 15 | 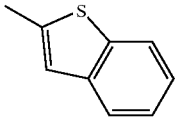 | 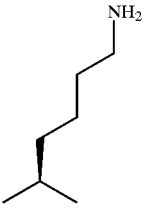 |
| 16 | 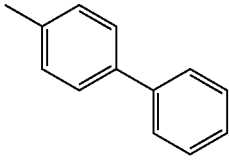 | 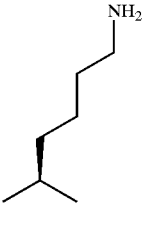 |
| 17 | 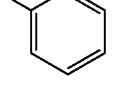 | 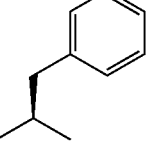 |
| 18 | 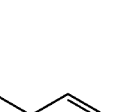 | 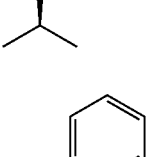 |
| 19 | 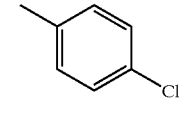 | 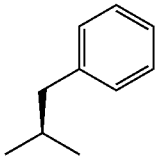 |
| 20 | 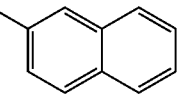 | 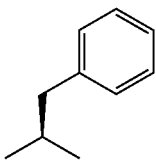 |

TABLE 13
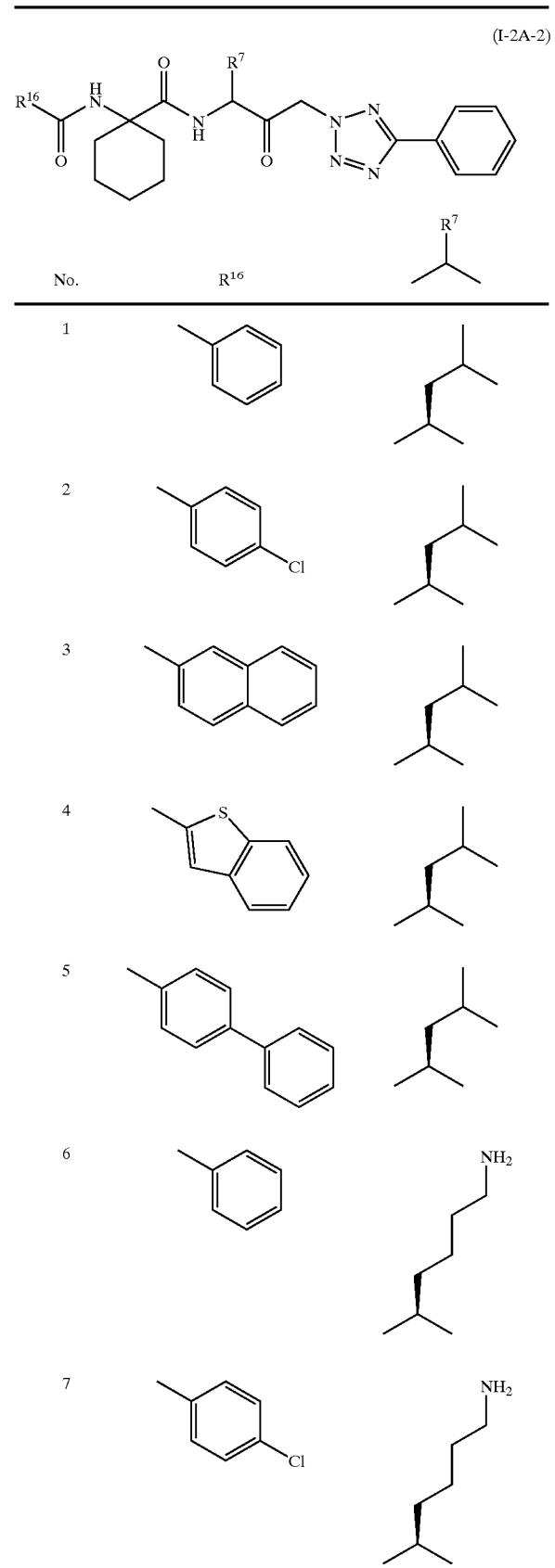
TABLE 13-continued
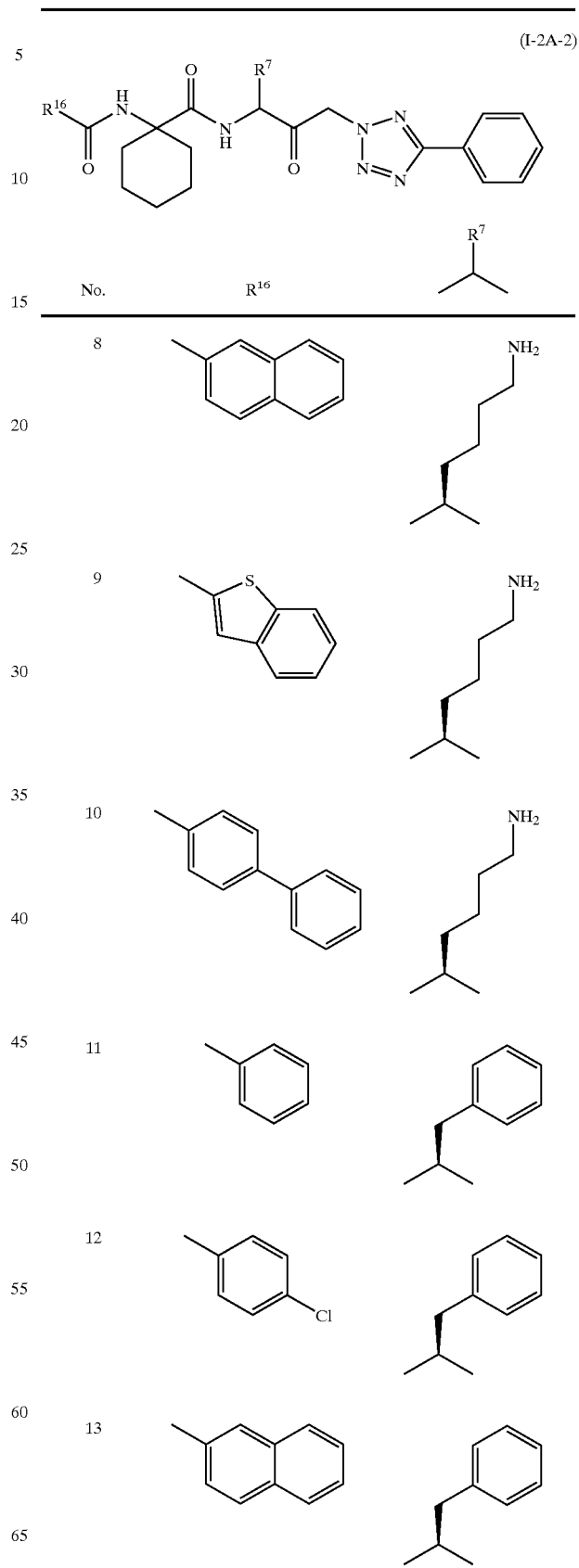

TABLE 13-continued
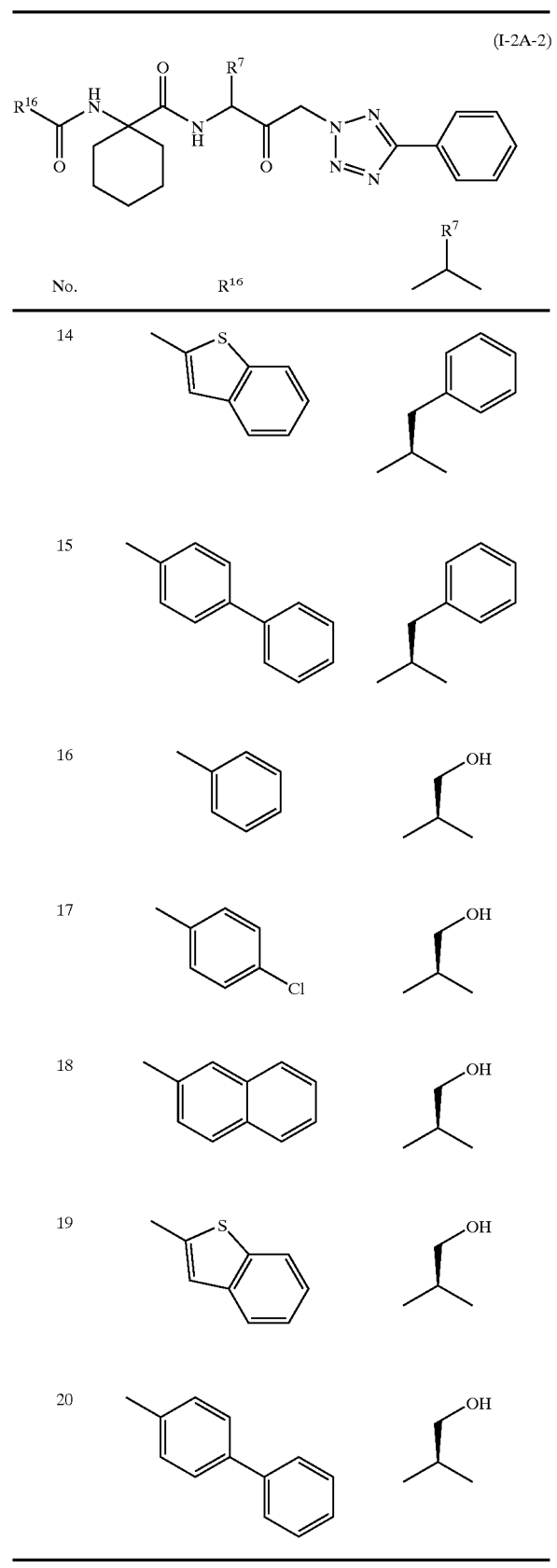
TABLE 14
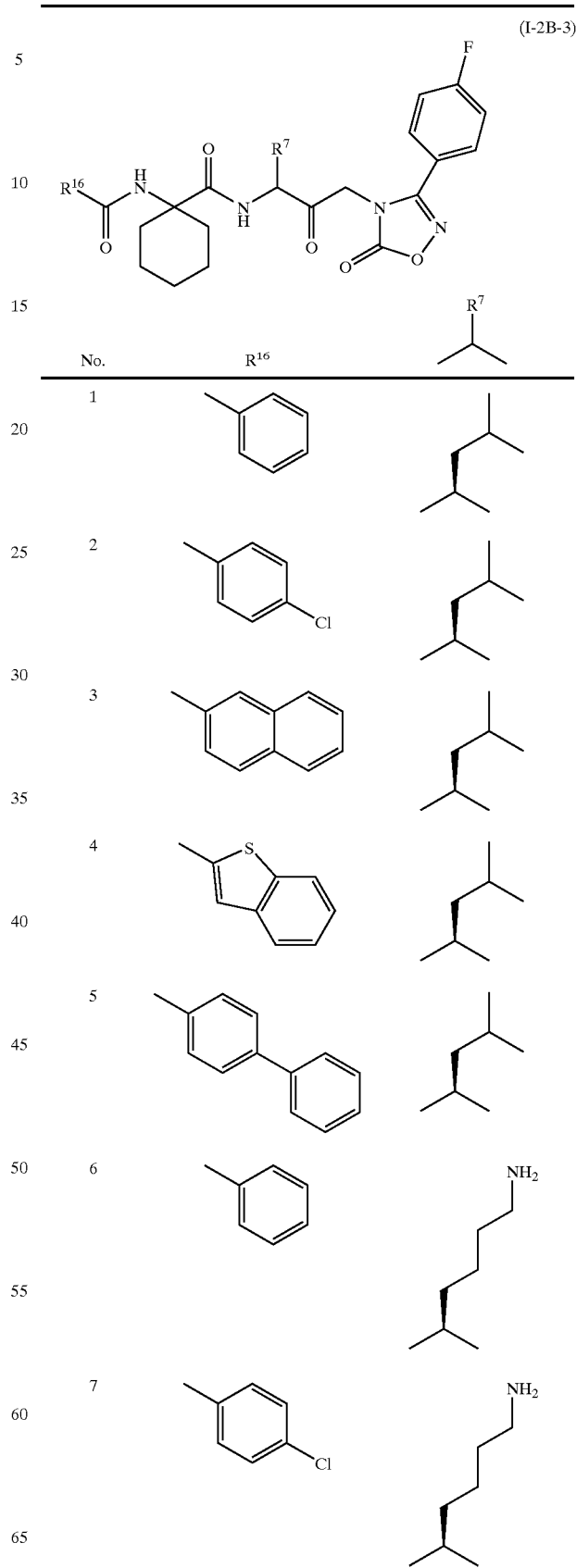

TABLE 14-continued
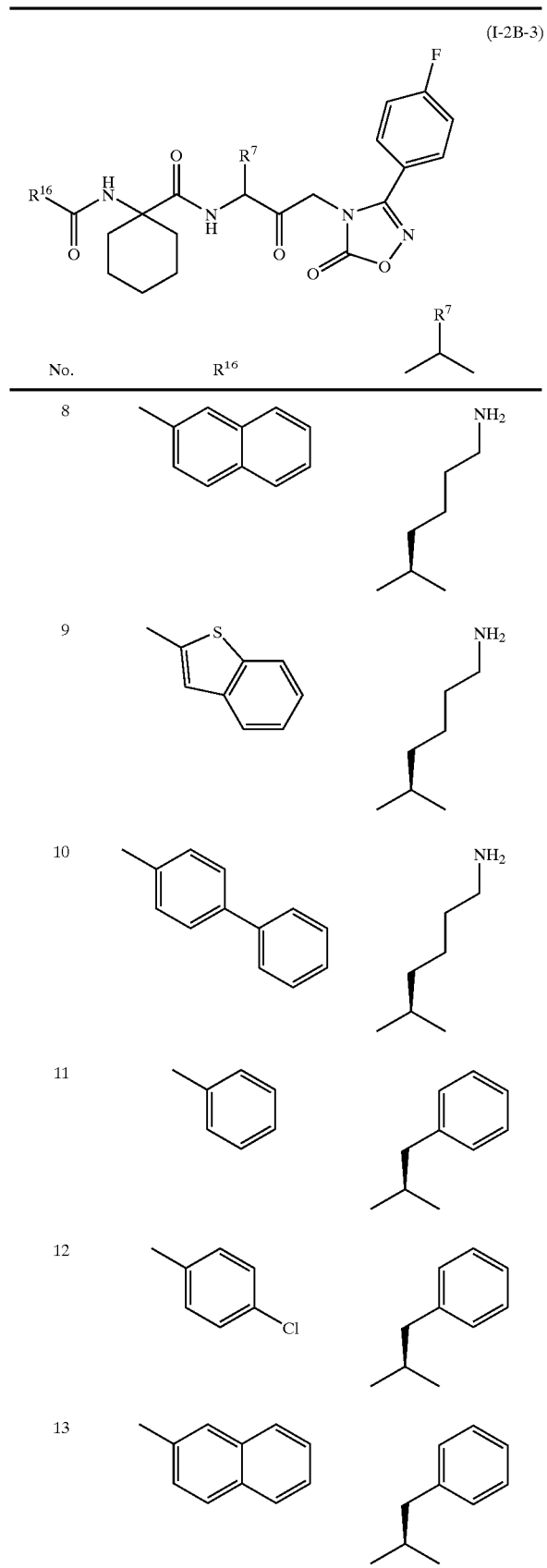
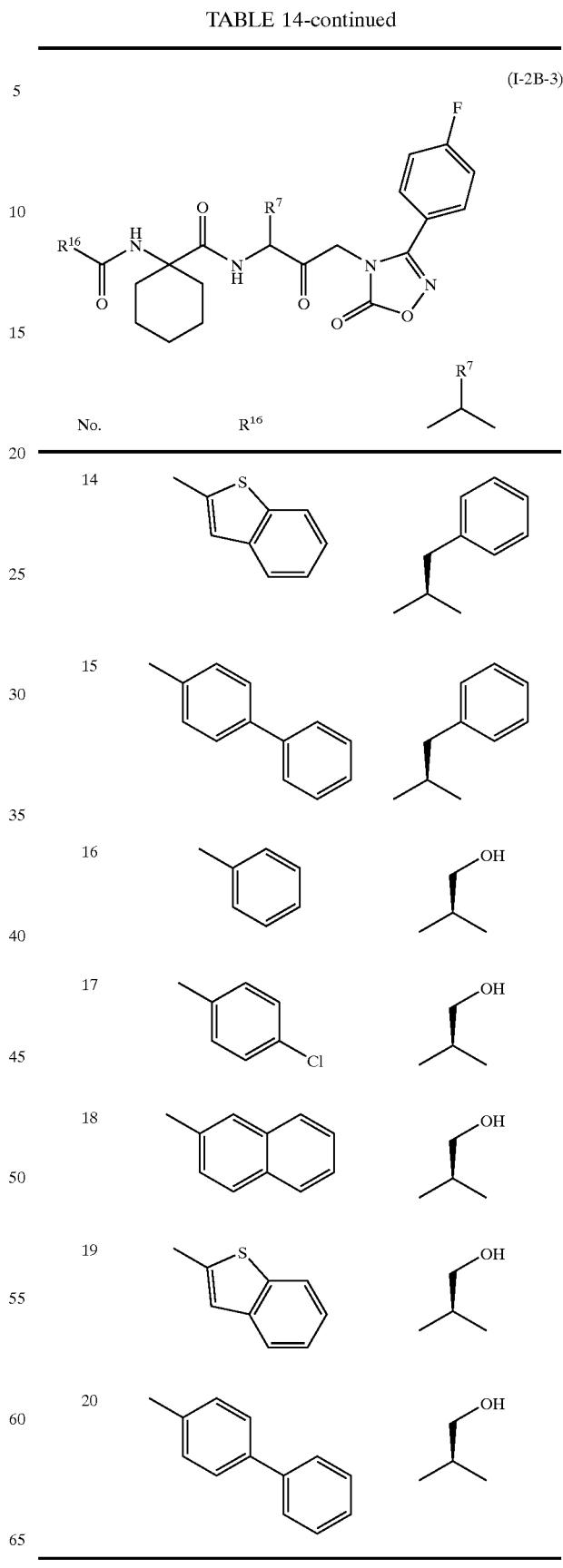

TABLE 15
(I-2B-4)
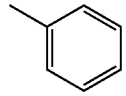
| No. | R16 | R7 (isobutyl shown) |
|---|---|---|
| 1 | 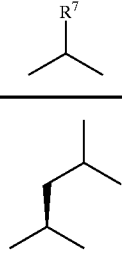 | 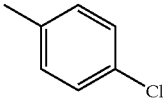 |
| 2 | 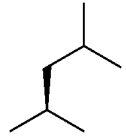 | 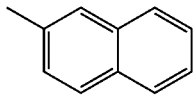 |
| 3 | 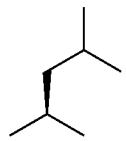 | 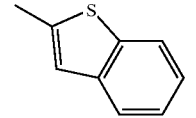 |
| 4 | 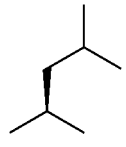 | 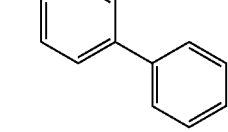 |
| 5 | 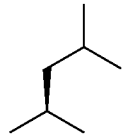 | 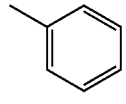 |
| 6 | 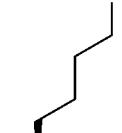 | 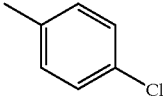 |
| 7 | 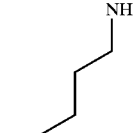 | 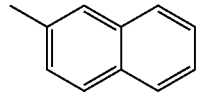 |
TABLE 15-continued
(I-2B-4)
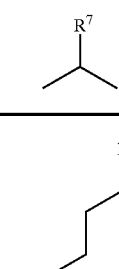
| No. | R16 | R7 |
|---|---|---|
| 8 | 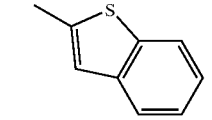 | 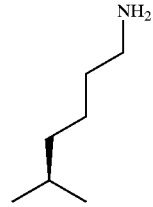 |
| 9 | 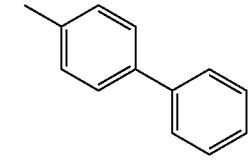 | 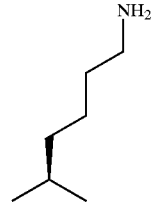 |
| 10 | 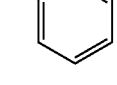 | 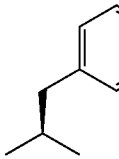 |
| 11 | 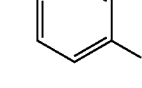 | 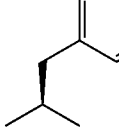 |
| 12 | 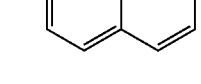 | |
| 13 | 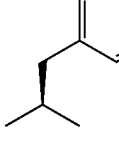 | |

TABLE 15-continued (I-2B-4)

| No. | R¹⁶ | R⁷ |
|---|---|---|
| 14 | 2-methylbenzothiophene | phenylisobutyl |
| 15 | 4-methylbiphenyl | phenylisobutyl |
| 16 | toluene | isobutanol |
| 17 | 4-chlorotoluene | isobutanol |
| 18 | 2-methylnaphthalene | isobutanol |
| 19 | 2-methylbenzothiophene | isobutanol |
| 20 | 4-methylbiphenyl | isobutanol |

TABLE 16

(I-2A-3)

| No. | R²⁷ |
|---|---|
| 1 | 2-CH₂N(CH₃)₂ |
| 2 | 3-CH₂N(CH₃)₂ |
| 3 | 4-CH₂N(CH₃)₂ |
| 4 | 2-CH₂-pyrrolidinyl |
| 5 | 3-CH₂-pyrrolidinyl |
| 6 | 4-CH₂-pyrrolidinyl |
| 7 | 2-CH₂-morpholinyl |
| 8 | 3-CH₂-morpholinyl |
| 9 | 4-CH₂-morpholinyl |

TABLE 17

(I-2B-4)

| No. | R²⁷ |
|---|---|
| 1 | 2-CH₂N(CH₃)₂ |
| 2 | 3-CH₂N(CH₃)₂ |
| 3 | 4-CH₂N(CH₃)₂ |
| 4 | 2-CH₂-pyrrolidinyl |

TABLE 17-continued
(I-2B-4)
| No. | R²⁷ |
|---|---|
| 5 | 3- 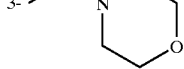 |
| 6 | 4-  |
| 7 | 2- 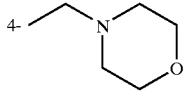 |
TABLE 17-continued
(I-2B-4)
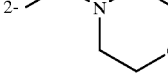
| No. | R²⁷ |
|---|---|
| 8 | 3-  |
| 9 | 4- 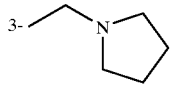 |
TABLE 18
(I-2B-4)
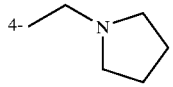
| No. | R²⁷ |
|---|---|
| 1 | 2-$CH_2N(CH_3)_2$ |
| 2 | 3-$CH_2N(CH_3)_2$ |
| 3 | 4-$CH_2N(CH_3)_2$ |
| 4 | 2- (pyrrolidinylmethyl) |
| 5 | 3- (pyrrolidinylmethyl) |
| 6 | 4- (pyrrolidinylmethyl) |

TABLE 18-continued
(I-2B-4)
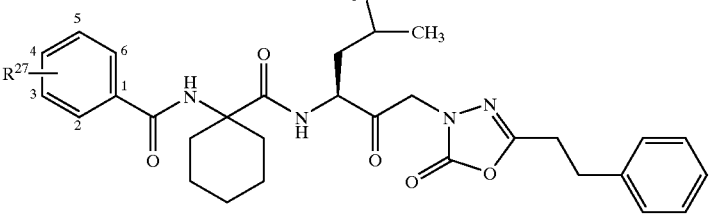
| No. | R²⁷ |
|---|---|
| 7 | 2- 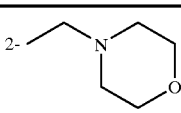 |
| 8 | 3- 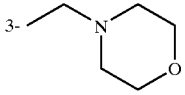 |
| 9 | 4- 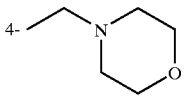 |
TABLE 19
(I-4A-2)
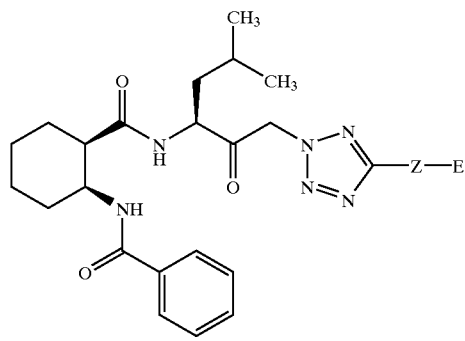
| No. | -Z-E |
|---|---|
| 1 | 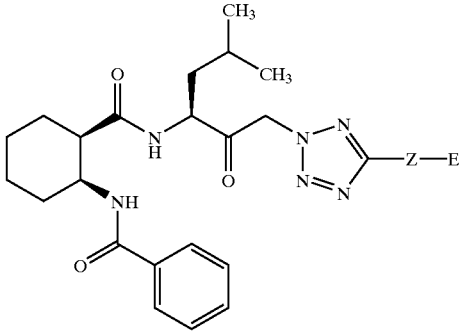 |
| 2 | 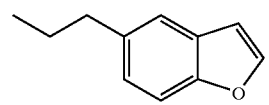 |
| 3 | 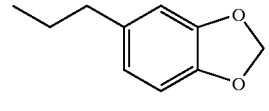 |
TABLE 19-continued
(I-4A-2)
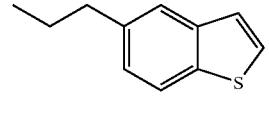
| No. | -Z-E |
|---|---|
| 4 | 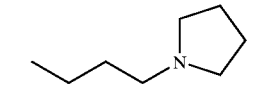 |
| 5 | |
| 6 | |
| 7 | |

TABLE 19-continued (I-4A-2)

| No. | -Z-E |
|---|---|
| 8 | morpholine-N-butyl |
| 9 | (E)-CH=CH-COOH (crotonic acid) |
| 10 | (E)-CH=CH-COOC₂H₅ (ethyl crotonate) |
| 11 | -(CH₂)₄-N(CH₃)₂ |
| 12 | -(CH₂)₃-N(CH₃)₂ |
| 13 | morpholine-N-pentyl |
| 14 | propyl-naphthyl |
| 15 | propyl-indanyl |
| 16 | propyl-2,3-dihydrobenzofuranyl |

TABLE 20

(I-3A-3)

| No. | -Z-E |
|---|---|
| 1 | propyl-benzofuran-2-yl |
| 2 | propyl-1,3-benzodioxol-2-yl |
| 3 | propyl-benzothiophen-2-yl |
| 4 | propyl-benzofuran-5-yl |
| 5 | propyl-1,3-benzodioxol-5-yl |
| 6 | propyl-benzothiophen-5-yl |
| 7 | pyrrolidine-N-butyl |
| 8 | morpholine-N-butyl |
| 9 | (E)-CH=CH-COOH |
| 10 | (E)-CH=CH-COOC₂H₅ |

TABLE 20-continued
(I-3A-3)
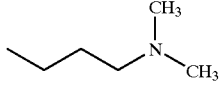
| No. | -Z-E |
|---|---|
| 11 | 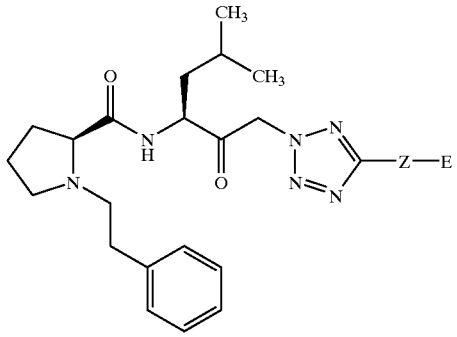 |
| 12 | 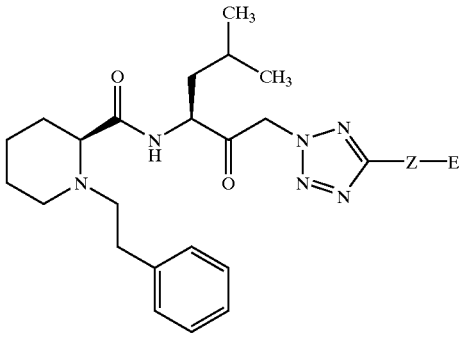 |
| 13 |  |
| 14 | 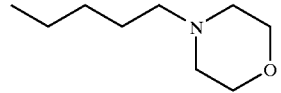 |
| 15 | 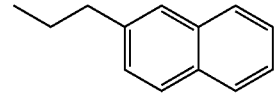 |
| 16 | 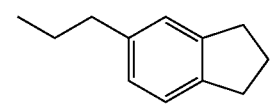 |
TABLE 21
(I-3A-4)
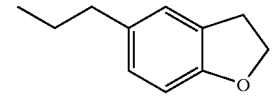
| No. | —Z—E |
|---|---|
| 1 |  |
| 2 | 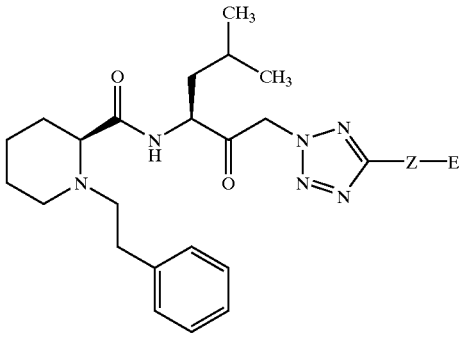 |
| 3 |  |
| 4 |  |
| 5 |  |
| 6 |  |
| 7 |  |
| 8 |  |
| 9 |  |
| 10 |  |

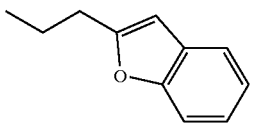

TABLE 22-continued
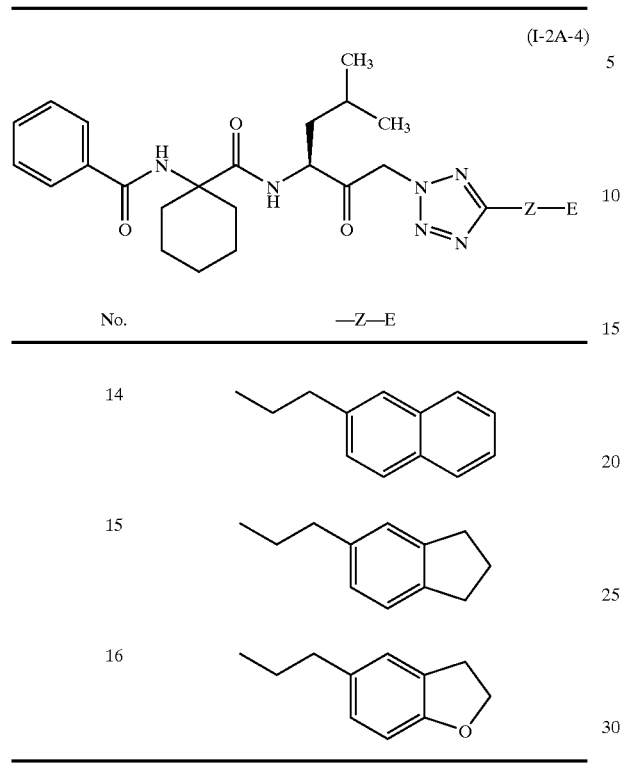
TABLE 23
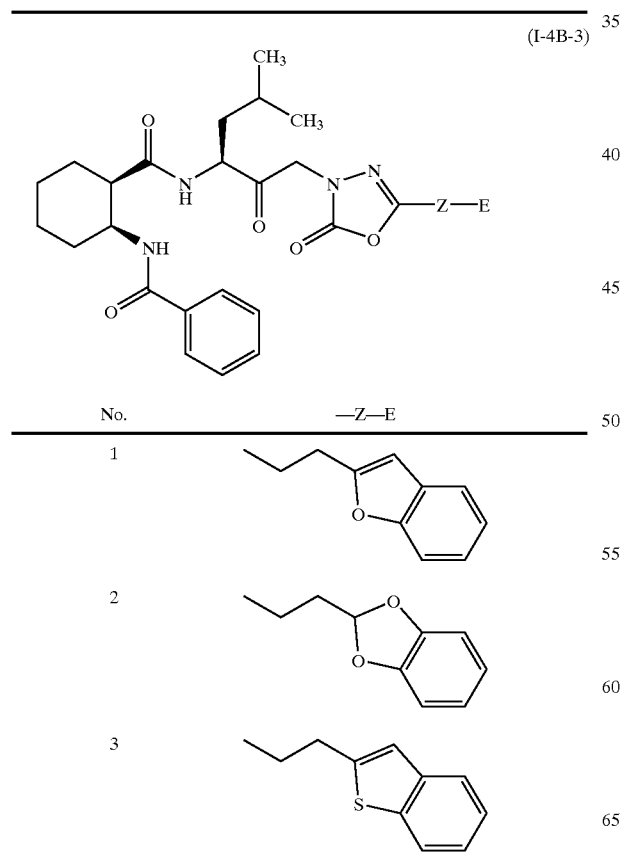
TABLE 23-continued
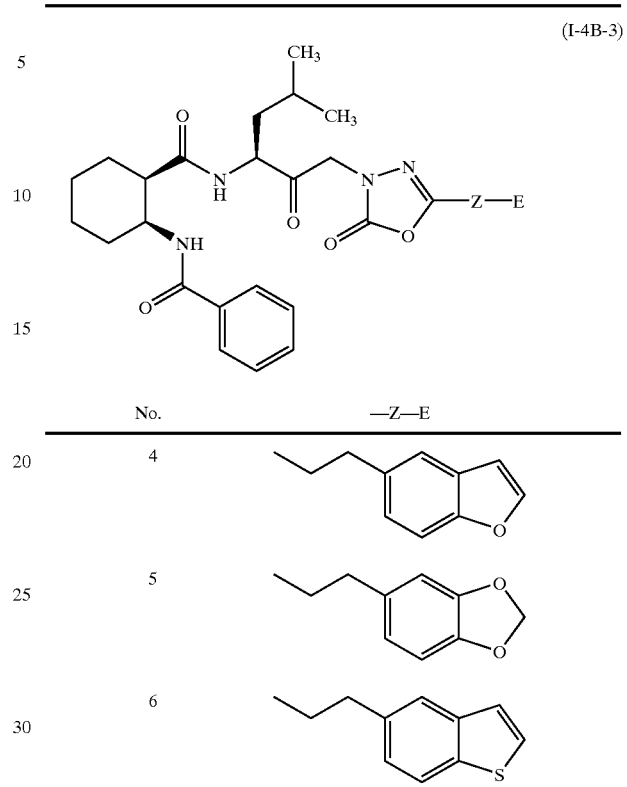
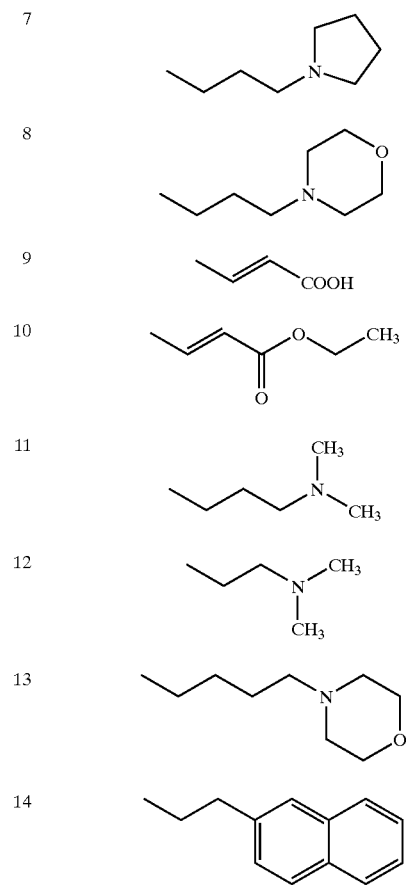

TABLE 23-continued (I-4B-3)

[Structure: cyclohexane with cis-substituents: one carboxamide linked to NH-CH(CH2CH(CH3)2)-C(=O)-CH2-N(N=C(Z-E)-O-C(=O)) (1,3,4-oxadiazol-2(3H)-one), and adjacent NH-C(=O)-phenyl]

| No. | —Z—E |
|---|---|
| 15 | [5-propyl-2,3-dihydro-1H-indene] |
| 16 | [5-propyl-2,3-dihydrobenzofuran] |

TABLE 24

(I-3B-5)

[Structure: 1-(2-phenylethyl)pyrrolidine-2-carboxamide linked to NH-CH(CH2CH(CH3)2)-C(=O)-CH2-N(N=C(Z-E)-O-C(=O)) 1,3,4-oxadiazol-2(3H)-one]

| No. | —Z—E |
|---|---|
| 1 | [2-propylbenzofuran] |
| 2 | [2-propyl-1,3-benzodioxole] |
| 3 | [2-propylbenzothiophene] |

TABLE 24-continued (I-3B-5)

[Structure: 1-(2-phenylethyl)pyrrolidine-2-carboxamide linked to NH-CH(CH2CH(CH3)2)-C(=O)-CH2-N(N=C(Z-E)-O-C(=O)) 1,3,4-oxadiazol-2(3H)-one]

| No. | —Z—E |
|---|---|
| 4 | [5-propylbenzofuran] |
| 5 | [5-propyl-1,3-benzodioxole] |
| 6 | [5-propylbenzothiophene] |
| 7 | [1-butylpyrrolidine] |
| 8 | [4-butylmorpholine] |
| 9 | [(E)-but-2-enoic acid] |
| 10 | [ethyl (E)-but-2-enoate] |
| 11 | [N,N-dimethylbutan-1-amine] |
| 12 | [N,N-dimethylpropan-1-amine] |
| 13 | [4-pentylmorpholine] |
| 14 | [6-propylnaphthalene] |

TABLE 24-continued
(I-3B-5)
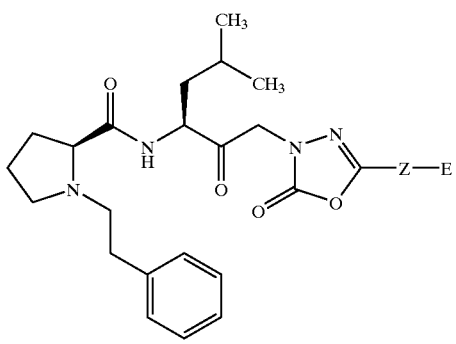
| No. | —Z—E |
|---|---|
| 15 | 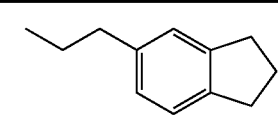 |
| 16 | 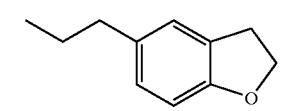 |
TABLE 25
(I-3B-6)
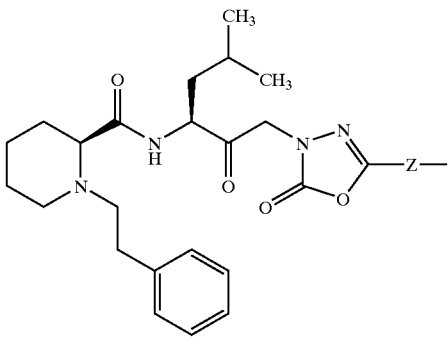
| No. | —Z—E |
|---|---|
| 1 | 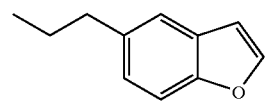 |
| 2 | 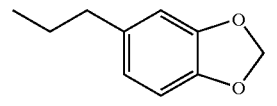 |
| 3 | 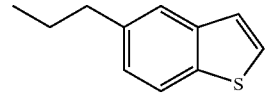 |
TABLE 25-continued
(I-3B-6)
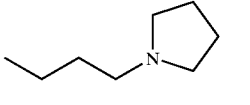
| No. | —Z—E |
|---|---|
| 4 | 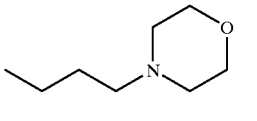 |
| 5 | 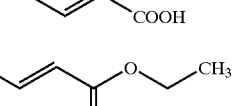 |
| 6 | 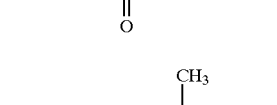 |
| 7 | 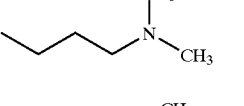 |
| 8 | 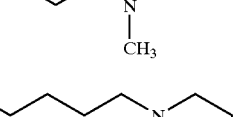 |
| 9 | 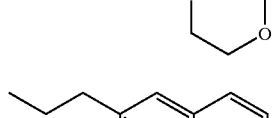 |
| 10 | 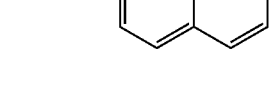 |
| 11 | 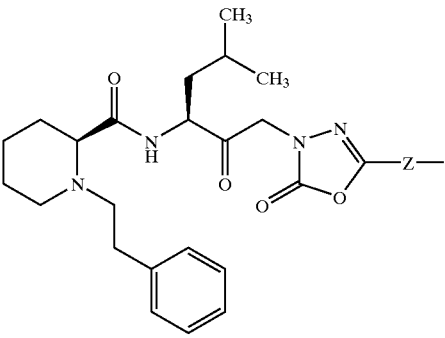 |
| 12 | 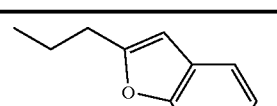 |
| 13 | 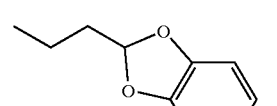 |
| 14 | 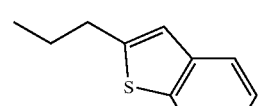 |

TABLE 25-continued
(I-3B-6)
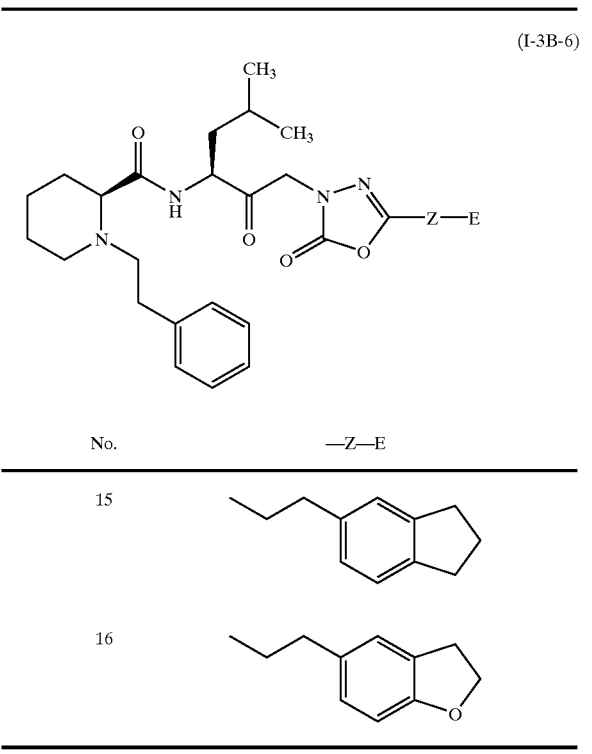
| No. | —Z—E |
|---|---|
| 15 | |
| 16 | |
TABLE 26
(I-2B-7)
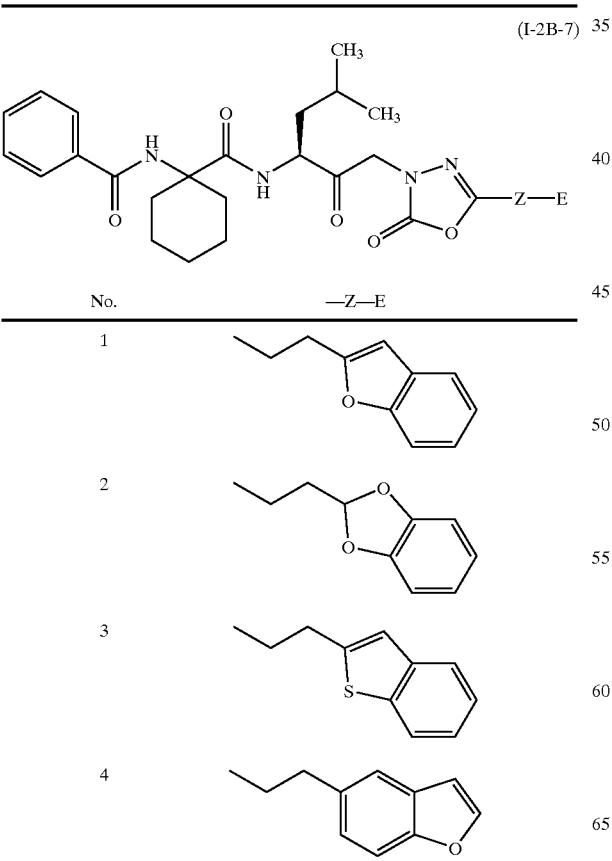
| No. | —Z—E |
|---|---|
| 1 | |
| 2 | |
| 3 | |
| 4 | |
TABLE 26-continued
(I-2B-7)
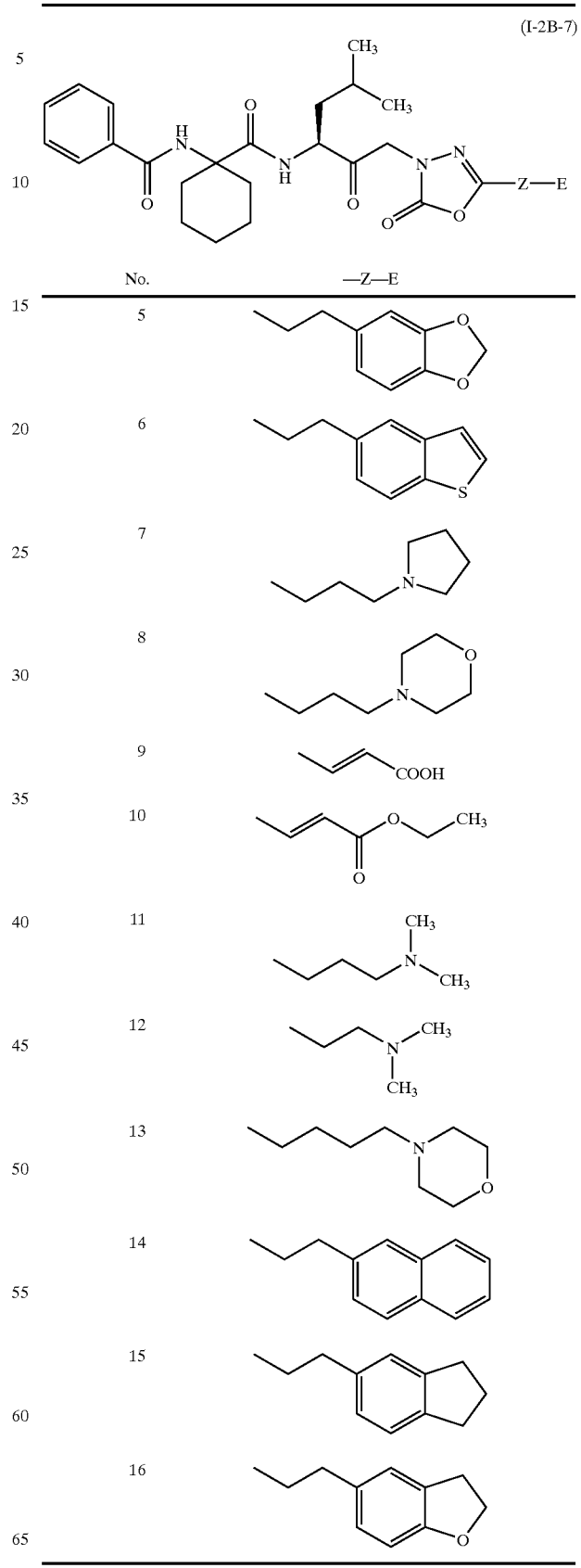
| No. | —Z—E |
|---|---|
| 5 | |
| 6 | |
| 7 | |
| 8 | |
| 9 | |
| 10 | |
| 11 | |
| 12 | |
| 13 | |
| 14 | |
| 15 | |
| 16 | |

TABLE 27
(I-4B-4)
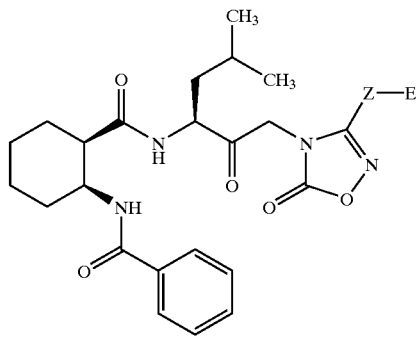
| No. | —Z—E |
|---|---|
| 1 | 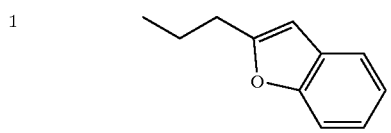 |
| 2 | 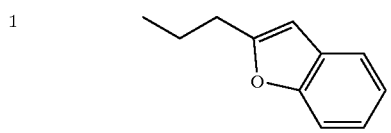 |
| 3 | 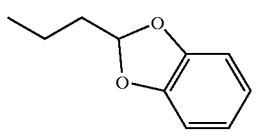 |
| 4 | 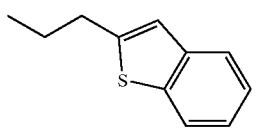 |
| 5 | 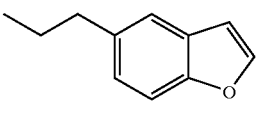 |
| 6 | 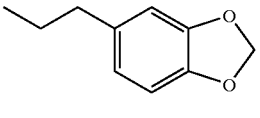 |
| 7 | 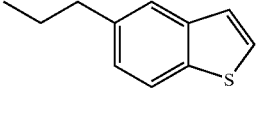 |
| 8 | 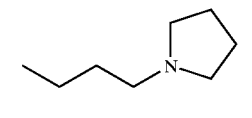 |
| 9 | 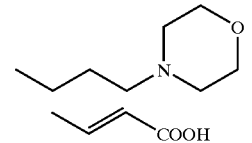 |
TABLE 27-continued
(I-4B-4)
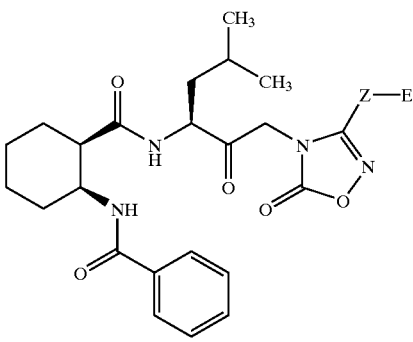
| No. | —Z—E |
|---|---|
| 10 | 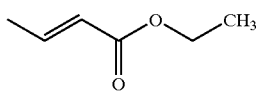 |
| 11 | 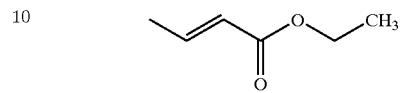 |
| 12 | 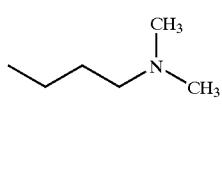 |
| 13 | 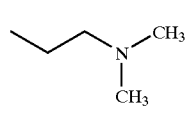 |
| 14 | 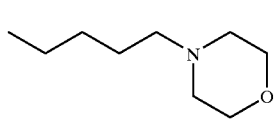 |
| 15 | 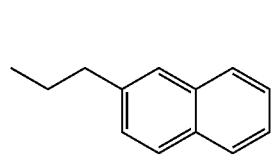 |
| 16 | 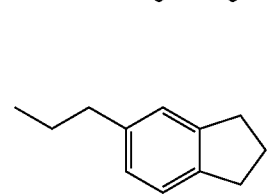 |

TABLE 28
(I-3B-7)
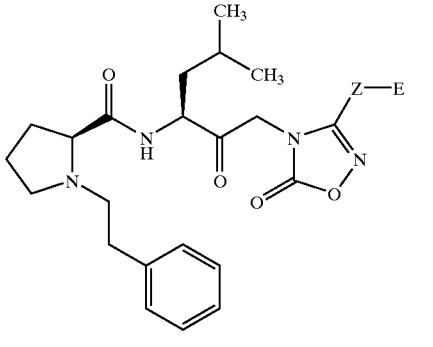
| No. | —Z—E |
|---|---|
| 1 | 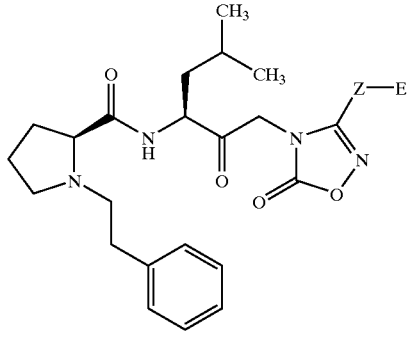 |
| 2 | 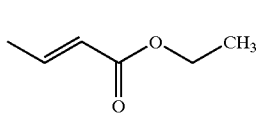 |
| 3 | 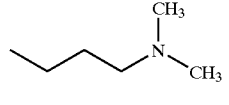 |
| 4 | 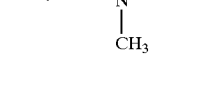 |
| 5 | 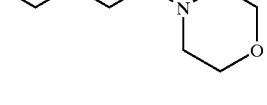 |
| 6 | 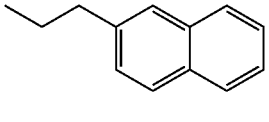 |
| 7 | 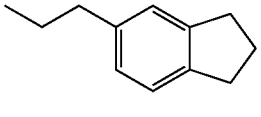 |
| 8 | 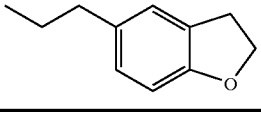 |
TABLE 28-continued
(I-3B-7)
| No. | —Z—E |
|---|---|
| 9 | 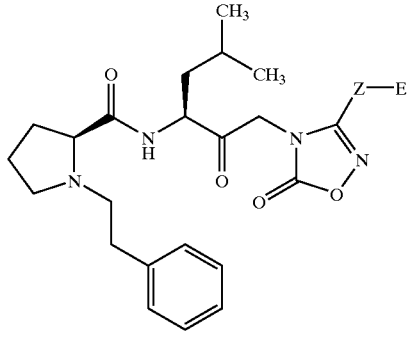 |
| 10 | 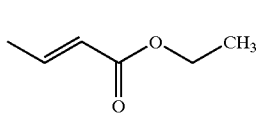 |
| 11 | 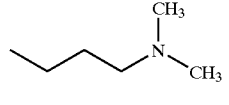 |
| 12 | 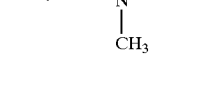 |
| 13 | 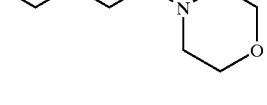 |
| 14 | 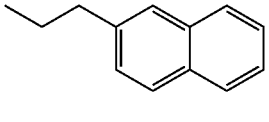 |
| 15 | 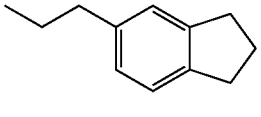 |
| 16 | 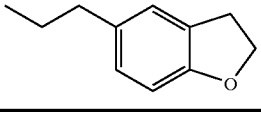 |

TABLE 29
(I-3B-8)
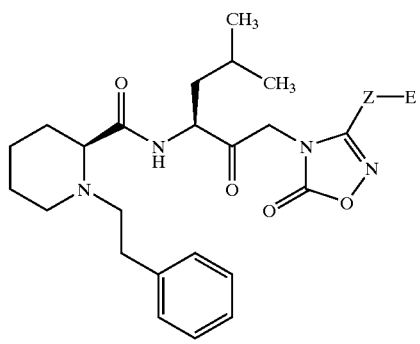
| No. | —Z—E |
|---|---|
| 1 | 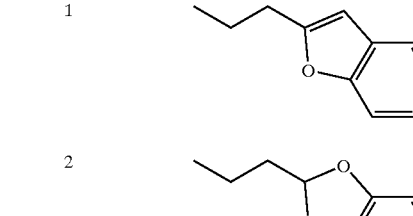 |
| 2 | 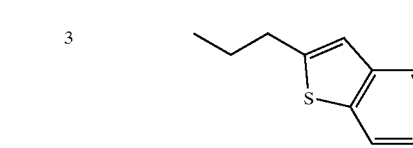 |
| 3 | 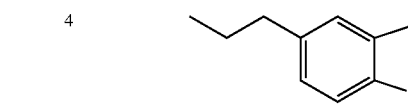 |
| 4 | 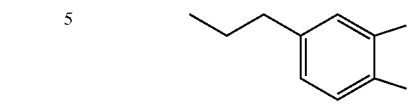 |
| 5 | 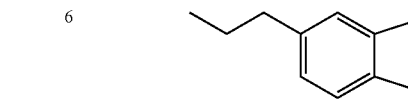 |
| 6 | 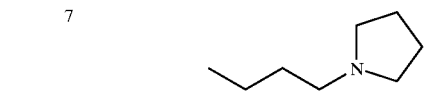 |
| 7 | 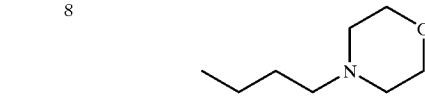 |
| 8 | 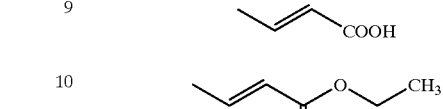 |
| 9 |  |
| 10 | 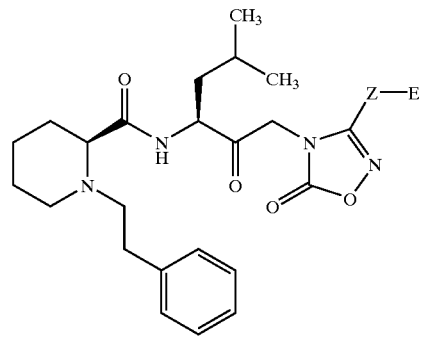 |
TABLE 29-continued
(I-3B-8)
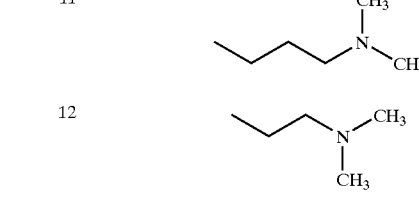
| No. | —Z—E |
|---|---|
| 11 | 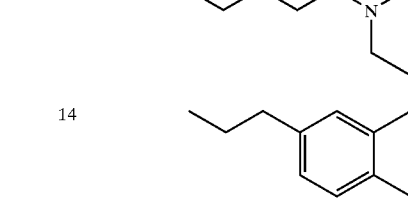 |
| 12 |  |
| 13 |  |
| 14 | 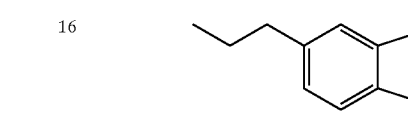 |
| 15 | 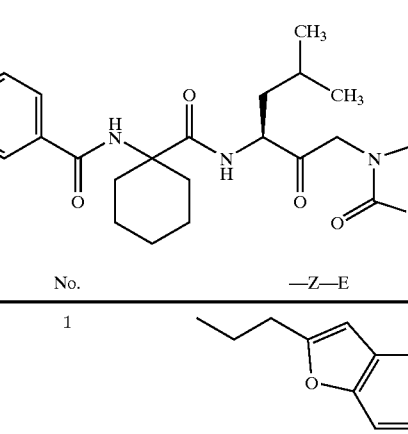 |
| 16 | |
TABLE 30
(I-2B-8)
| No. | —Z—E |
|---|---|
| 1 | |

TABLE 30-continued (I-2B-8)

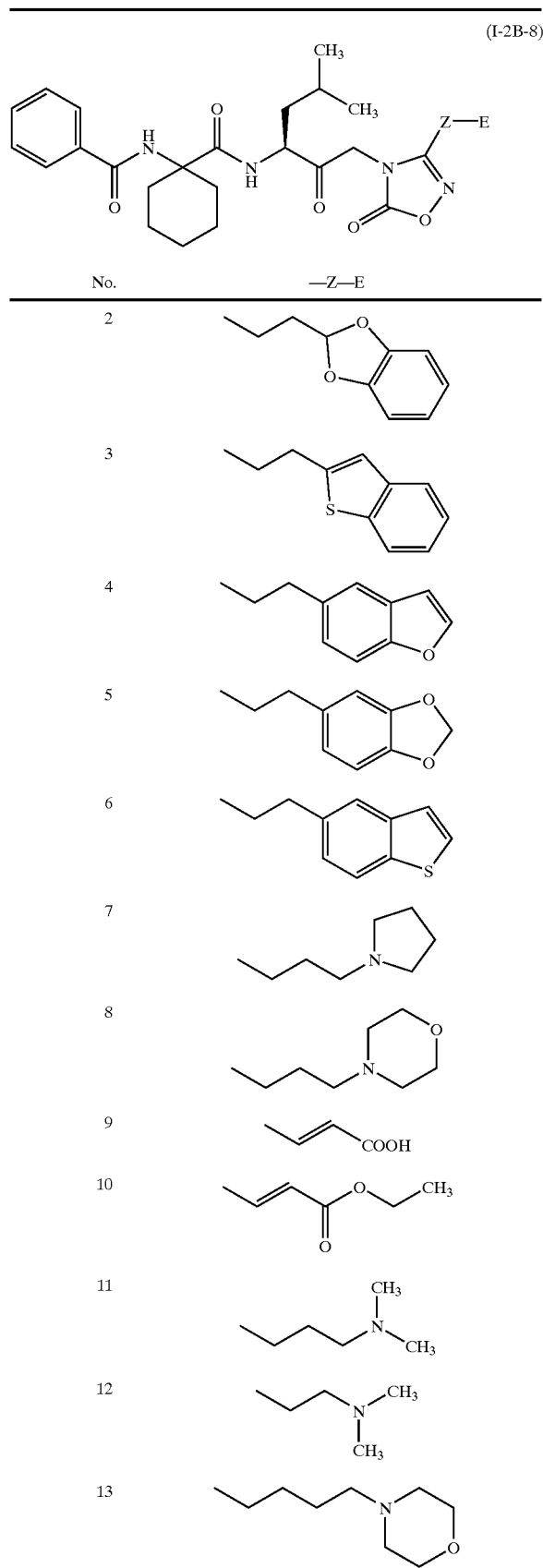

The Methods for the Preparation of the Compound of the Present Invention

The compound of formula (I) of the present invention may be prepared by the following methods.

(1) The compound wherein R is not hydrogen atom and the structure contains no carboxy, hydroxy, amino, thiol, guanidino, amidino or phosphono, i.e. the compound of formula (I-A)

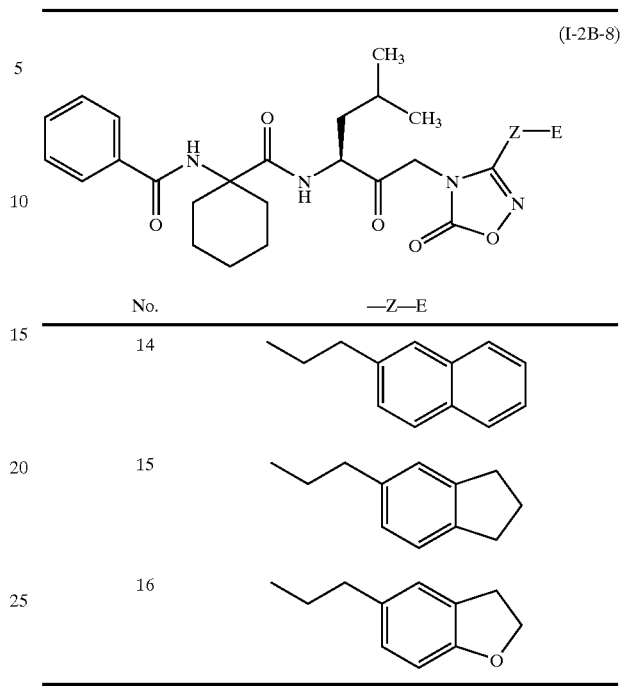

wherein $R^a$ has the same meaning as R, but it is not hydrogen atom, and $AA^{1\,a}$, $AA^{2\,a}$, $R^{7\,a}$, $R^{8\,a}$, $E^a$ have the same meanings as $AA^1$, $AA^2$, $R^7$, $R^8$ and E respectively, but none of them contains carboxy, hydroxy, amino, thiol, guanidino, amidino or phosphono, and the other symbols have the same meanings as above, may be prepared by subjecting to a reaction the compound of formula (II)

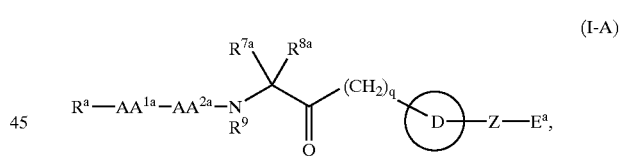

wherein X is an eliminating group, e.g. chlorine atom, bromine atom, iodine atom, mesyl, tosyl, and the other symbols have the same meanings as above, and the compound of formula (III)

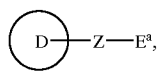
(III)

wherein all symbols have the same meanings as above.

This reaction is known and carried out, for example, in an organic solvent (dimethylformamide, methylene chloride, tetrahydrofuran, etc.), in the presence of a base, e.g. potassium fluoride, potassium carbonate, etc., at a temperature of 0 to 50° C.

The compound of formula (I-A) may also be prepared by subjecting to an amidation reaction the compound of formula (I-BB).

The compound of formula (I-A) maybe prepared by subjecting to amidation reaction the compound of formula (I-BB)

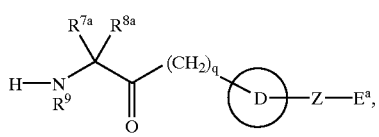
(I-BB)

wherein all symbols have the same meanings as above, and the compound of formula (IV)

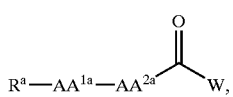
(IV)

wherein W is hydroxy, halogen atom, or —O—COO(C1-4 alkyl), and the other symbols are the same meanings as above.

Methods for amidation reaction are known, for example, (1) a method using acid halide,
(2) a method using mixed anhydride,
(3) a method using a condensing agent, etc.

To explain these methods concretely, (1) The method using acid halide is, for example, carried out by subjecting to a reaction carboxylic acid in an organic solvent (chloroform, methylene chloride, diethyl ether, tetrahydrofuran, dimethylformamide, etc.) or without a solvent, and acid-halogenating agent (oxalyl chloride, thionyl chloride, etc.) at a temperature between −20° C. and refluxing temperature, and then subjecting to a reaction thus obtained acid halide in the presence of tertiary amine (pyridine, triethylamine, dimethylaniline, dimethylaminopyridine, N-methylmorpholine, etc.) at a temperature of 0 to 40° C.

(2) The method using mixed anhydride is, for example, carried out by subjecting to a reaction in an organic solvent (chloroform, methylene chloride, diethyl ether, tetrahydrofuran, etc.) or without a solvent, in the presence of tertiary amine (pyridine, triethylamine, dimethylaniline, dimethylaminopyridine, N-methylmorpholine, etc.) carboxylic acid with acid halide (pivaloyl chloride, tosyl chloride, mesylchloride, chloroethyl formate, chloroisobutyl formate, etc.) at a temperature of −20 to 40° C., and then subjecting to a reaction thus obtained mixed anhydride with amine at a temperature of 0 to 40° C.

(3) The method using a condensing agent (1,3-dichlorohexylcarbodiimide (DCC), 1-ethyl-3-[3-(dimethylamino)propyl]carbodiimide (EDC), 2-chloro-1-methylpyridinium iodide, etc.) is carried out, for example, in an inert organic solvent (chloroform, methylene chloride, dimethylformamide, diethyl ether, etc.) or without a solvent, in the presence or absence of a tertiary amine (pyridine, triethylamine, dimethylaniline, dimethylaminopyridine, N-methylmorpholine, etc.), using a condensing reagent in the presence or absence of an activating agent such as 1-hydroxybenzotriazole, by subjecting to a reaction carboxylic acid and amine at a temperature of 0 to 40° C.

These reactions (1), (2) and (3) are desirably carried out under atmosphere of an inert gas (argon, nitrogen, etc.) under anhydrous conditions.

(2) The compound wherein R is hydrogen and/or at least one carboxy, hydroxy, amino, thiol, guanidino or phosphono is included, i.e. the compound of formula (I-B)

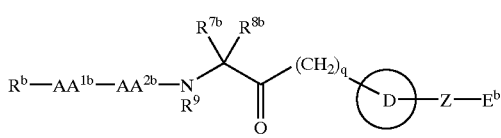
(I-B)

wherein $R^b$, $AA^{1b}$, $AA^{2b}$, $R^{7b}$, $R^{8b}$, $E^b$ have the same meanings as R, $AA^1$, $AA^2$, $R^7$, $R^8$, E, with proviso that $R^b$ is hydrogen and/or at least one of $AA^{1b}$, $AA^{2b}$, $R^{7b}$, $R^{8b}$ or $E^b$ represents a group which contains carboxy, hydroxy, amino, thiol, guanidino, amidino, or phosphono, and the other symbols are the same meanings as above, may be prepared by subjecting to one deprotection reaction or more the compound of formula (I-C)

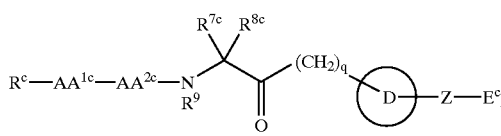
(I-C)

wherein $R^c$, $AA^{1c}$, $AA^{2c}$, $R^{7c}$, $R^{8c}$, $E^c$ have the same meanings as R, $AA^1$, $AA^2$, $R^7$, $R^8$, E, respectively, but when $R^c$ is a protective group for amino (i.e., benzyloxycarbonyl, t-butoxycarbonyl) and/or at least one of $AA^{1c}$, $AA^{2c}$, $R^{7c}$, $R^{8c}$, $E^c$ contains a protective form of carboxy, hydroxy, amino, thiol, guanidino, amidino or phosphono and the other symbols have the same meanings as above.

Protective groups for carboxy include, for example, methyl, ethyl, t-butyl, benzyl, etc.

Protective groups for hydroxy include, for example, methoxymethyl, 2-tetrahydropyranyl, t-butyldimethylsilyl, t-butyldiphenylsilyl, acetyl, benzyl, etc.

Protective groups for amino include, for example, benzyloxycarbonyl, t-butoxycarbonyl, trifluoroacetyl, 9-fluorenylmethoxycarbonyl, etc.

Protective groups for thiol include, for example, benzyl, methoxybenzyl, methoxymethyl, 2-tetrahydropyranyl, diphenylmethyl, acetyl, etc.

Protective groups for guanidino and amidino include, for example, benzyloxycarbonyl, t-butoxycarbonyl, 9-fluorenylmethoxycarbonyl, etc.

Protective groups for phosphono include, for example, methyl, ethyl, phenyl, benzyl, 2,2,2-trichloroethyl, cyanoethyl, etc.

As protective groups for carboxy, hydroxy, amino, thiol, guanidino, amidino and phosphono group, other groups than above listed, if easily and selectively eliminated, may also be used instead. For example, the groups described in T. W. Greene, Protective Groups in Organic Synthesis, Wiley, New York, 1991 may be used.

Deprotection reactions for protective groups of amino group are known, for example, (1) an alkaline hydrolysis,
(2) a deprotection reaction under acidic conditions,
(3) a deprotection reaction by hydration,
(4) A deprotection reaction of silyl-containing group, etc. may be included.

To describe these methods concretely, (1) a deprotection reaction under alkaline conditions is, for example, carried out in an organic solvent (methanol, tetrahydrofuran, dioxane, etc.) using a hydroxide of alkali metals (sodium hydroxide, potassium hydroxide, etc.), hydroxide of alkaline earth metals such as calcium hydroxide, or a solution thereof or a mixture thereof at a temperature of 0 to 40° C.
(2) a deprotection reaction under acidic conditions is carried out, for example, in an organic solvent (methylene chloride, chloroform, dioxane, ethyl acetate, water, a mixed solvent thereof, etc.), using organic acid such as trifluoroacetic acid or an inorganic acid (hydrogen chloride, hydrogen bromide, etc.) or a mixture thereof at a temperature of 0 to 120° C.
(3) a deprotection reaction by hydration is, for example, carried out in a solvent (tetrahydrofuran, dioxane, dimethoxyethane, diethyl ether, methanol, ethanol, benzene, toluene, dimethylformamide, water, ethyl acetate, acetic acid or a mixture of two or more from above, etc.) in the presence of a catalyst (palladium-carbon, palladium black, palladium hydroxide, platinum dioxide, Raneynickel, etc.) in the presence or absence of inorganic acid (chloric acid, sulfuric acid, hypochlorous acid, boric acid, tetrafluoro boroic acid, etc.) or organic acid (acetic acid, p-toluenesulfone acid, oxalic acid, trifluoroacetic acid, formic acid, etc.) under the atmosphere of hydrogen of normal or suppressed pressure, or in the presence of ammonium formate at a temperature of 0 to 200° C.
(4) A deprotection reaction of silyl-containing group is carried out, for example, in a water-miscible organic solvent (tetrahydrofuran, acetonitrile, etc.) using tetrabutylammonium fluoride at a temperature of 0 to 40° C.

Deprotection of phosphono may also be carried out by the following methods.

(1) Deprotection reaction of methyl and ethyl is carried out, for example, in an organic solvent such as chloroform using halogenated trimethylsilyl (trimethylsilyl chloride, trimethylsilyl bromide, trimethylsilyl iodide, etc.) in the presence or absence of alkali metal iodide (sodium iodide, potassium iodide, etc.) at a temperature of 0 to 40° C.
(2) Deprotection reaction of phenyl is carried out, for example, in an organic solvent (methanol, ethanol, tetrahydrofuran, etc.) or without a solvent, in the presence or absence of a catalyst (platinum oxide etc.) and an organic acid (acetic acid, etc.) or an inorganic acid (hydrochloric acid etc.) under atmosphere of hydrogen, at a temperature of 0 to 50° C. for 24 hours to 3 days.
(3) Deprotection reaction of benzyl is for example carried out according to the above described hydrogenation reaction.
(4) Deprotection reaction of 2,2,2-trichloroethyl is carried out, for example, in an organic solvent (methanol, ethanol, tetrahydrofuran, etc.) or without a solvent, using micropowder of zinc etc. and an organic acid such as acetic acid or an inorganic acid such as hydrochloric acid at a temperature of 0 to 50° C.
(5) Deprotection reaction of cyanoethyl is carried out, for example, in a solvent (water, methanol, ethanol, tetrahydrofuran, pyridine, etc.) or without a solvent, in the presence of a base (trimethylamine, dimethylamine, t-butylamine, etc.) at a temperature of 0 to 100° C.

As easily understood by those skilled in the art, the compounds of the present invention may be easily prepared by selecting these reactions.

The compounds of formula (II), (III), (IV), (I-BB), (I-C) are known per se or may be prepared by known methods.

Other starting materials and agents in the present invention are known per se or may be prepared by conventional methods.

In each reaction of the present specification, reaction products may be purified by conventional techniques. For example, purification may be carried out by distillation under atmospheric or reduced pressure, by high performance liquid chromatography, thin layer chromatography or column chromatography using silica gel or magnesium silicate, by washing or by recrystallization, etc. Purification may be carried out after each reaction, or after a series of reactions.

Pharmacological Activity of the Compounds of the Present Invention

It was confirmed by the following experiments that the compounds of the present invention of formula (I) have an inhibitory activity against cysteine protease.

(i) Measurement of Cathepsin K Inhibitory Activity

65 $\mu$L of Cathepsin K enzyme reaction buffer (50 mmol/L of 2-(N-morpholino)ethanesulfonate, 2 mmol/L of ethylenediamine tetraacetate (EDTA) and 4 mmol/L of dithiothreitol (DTT) were mixed to adjust to pH 5.5), 5 $\mu$L of cysteine protease inhibitor solution of several concentrations, 20 $\mu$L of synthesized substrate (t-butyloxycarbonyl-L-alanyl-glycyl-L-prolyl-L-arginine-4-methyl-chromanyl-7-amide) solution of several concentrations and 10 $\mu$L of cathepsin K enzyme solution were mixed and the increase of fluorescence intensity when reacted at 37° C. was measured ($\lambda$ ex (excitation wavelength)=355 nm, $\lambda$ em (fluorescence wavelength)=460 nm). As to the substrate and the compound of the present invention, enzyme reactions were carried out in combination of several appropriate concentrations and Dixon plotting was prepared, to define the absolute value of X-coordinate of the intersection point of the graph as Ki value.

As a result, for example, the Ki values of inhibitory activity of the compounds of example 1(40) and example 3(7) were 0.021 $\mu$M and 0.036 $\mu$M respectively.

(ii) Measurement of Cathepsin B Inhibitory Activity

10 $\mu$L of Synthesized substrate (carbobenzoxy-L-arginyl-L-arginine-4-methyl-chromanyl-7-amide or carbobenzoxy-L-phenylalanyl-L-arginine-4-methyl-chromanyl-7-amide) solution of several concentrations, 10 $\mu$L of cysteine protease inhibitor solution of several concentrations, 70 $\mu$L of cathepsin B enzyme reaction buffer (mixture of 400 mmol/L in acetic acid, 4 mmol/L EDTA, 8 mmol/L DDT to adjust to pH 5.5) and 10 $\mu$L of cathepsin B enzyme solution were mixed and the increase of fluorescence intensity was measured (λ ex (excitation wavelength)=355 nm, λ em (fluorescence wavelength)=460 nm) when reacted at 37° C.

(iii) Measurement of Cathepsin S Inhibitory Activity

10 μL of synthesized substrate (carbobenzoxy-L-leucyl-L-leucyl-L-arguinine-4-methyl-chromanyl-7-amide) solution and 5 μL of cysteine protease inhibitor solution of several concentrations, 75 μL of cathepsin S enzyme reaction buffer (100 mmol/L of sodium phosphate, 2 mmol/L of EDTA, 2 mmol/L of DTT were mixed to adjust to pH 6.5) and 10 μL of cathepsin S enzyme solution were mixed and the increase of fluorescence intensity was measured (λ ex(excitation wavelength)=355 nm, λ em (fluorescence wavelength)=460 nm) when reacted at 37° C.

As a result, for example, the inhibitory activity of the compound of example 3(17) was 90% at 1 μM.

(iv) Measurement of Cathepsin L Inhibitory Activity

5 μL of Synthesized substrate (carbobenzoxy-L-phenylalanyl-L-arguine-4-methyl-chromanyl-7-amide or L-prolyl-L-phenylalanyl-L-arguinine-4-methyl-chromanyl-7-amide) solution and 5 μL of cysteine protease inhibitor solution of several concentrations, 80 μL of cathepsin L enzyme reaction buffer (400 mmol/L acetic acid, 4 mmol/L EDTA, 8 mmol/L DTT were mixed to adjust to pH 5.5) and 10 μL of cathepsin L enzyme solution were mixed and the increase of fluorescence intensity was measured (λ ex (excitation wavelength)=355 nm, λ em (fluorescence wavelength)=460 nm) when reacted at 37° C.

(v) Measurement of Calpain Inhibitory Activity

The activity was measured according to the method described in Calcium-depending protease, Seibutsukagaku-Jikkenhou (Biochemistry Experimental Method) Tanpakubunkaikouso (Protease) I, 57 (1993).

(vi) Measurement of Caspase-1 Inhibitory Activity

50 μL of caspase-1 enzyme reaction solution (20 mmol/L of 4-(2-hydroxyethyl)-1-piperazinethanesulfonate-sodium hydroxide buffer pH 7.4, 10 mmol/L of potassium chloride, 1.5 mmol/L of magnesium chloride, 0.1 mmol/L EDTA, 10% glycerol) and 50 μL of cysteine protease inhibitor solution of several concentrations, 50 μL of caspase-1 enzyme solution and 100 μL of synthesized substrate (acetyl-L-tyrosinyl-L-valinyl-L-alanyl-L-aspartic acid-4-methyl-chromanyl-7-amide) solution of several concentrations were reacted at 37° C. and the fluorescence intensity was measured (λ ex (excitation wavelength)=355 nm, λ em (fluorescence wavelength)=460 nm).

(vii) Investigation in Bone Resorption Inhibitory Activity Using Mouse Calvaria Cultivation System Mouse neonatal calvaria was cultured in D-minimal essential medium containing cysteine protease inhibitor (mixture of Penicillin G potassium (final concentration 100 U/ml), streptomycin sulfate (final concentration 0.1 mg/ml), bovine serum albumin (final concentration 0.1%), glutamine (final concentration 0.3 mg/ml) in D-minimal essential medium) at 37° C. and the calcium concentration in the culture medium was measured.

(viii) Bone Resorption Pit Formation Test Using Rabbit Osteoclast Cells

Osteoclast cells collected from rabbit bones were sowed over slices of bovine cortical bone, ivory or teeth of toothed whale and were cultured at 37° C. in α-minimal essential medium containing final concentration 5% of fetal bovine serum and various concentrations of cysteine protease inhibitor. The pits formed on the slices by the osteoclast cells were observed and at the same time type-I collagen C-terminal telopeptide (CTx) concentration in culture medium was measured.

(ix) Investigation of Immune Reaction Inhibitory Effect Using Antigen-Sensitized Mouse Spleen Cells Spleen cells were collected from mice sensitized by ovalbumin (OVA) several times. Inhibitory effect of cysteine protease inhibitors against immune response induced by OVA stimulus was investigated, using cytokine concentration and immunoglobulin concentration in culture solution as indicators.

(x) Investigation in Inhibitory Effect Against Bone Resorption Using the Rat PTH Hypercalcemia Model The effect of cysteine protease inhibitor (compulsory oral administration, intraperitoneal administration) on bone resorption which was promoted by intravenous administration of parathyroid hormone (PTH) solution (30 μg/ml) was investigated in rats, using calcium concentration in blood as an indicator.

(xi) Studies on Bone Resorption Inhibitory Effect Using TPTx Rat PTHrP-Induced Hypercalcemia Model The effect of cysteine protease inhibitor (compulsory oral administration, intraperitoneal administration) on bone resorption, promoted by subcutaneous administration of parathyroid hormone related peptide (PTHrP) to a fasting rat (thyroparathyroidectomized; TPTX) was investigated, using calcium concentration in blood as an indicator.

Toxicity

The toxicity of the compounds of the present invention is very low and therefore it was confirmed that the compounds are safe for pharmaceutical use.

INDUSTRIAL APPLICABILITY

Application to Pharmaceuticals

The compound of formula (I) of the present invention has an inhibitory activity against cysteine proteases, and therefore it is useful for animals including human beings, particularly for human beings, as an agent for the prophylaxis and/or treatment of inflammatory diseases (periodontitis, arthritis, inflammatory bowel diseases, infectious diseases, pancreatitis, hepatitis, glomerulonephritis, endocarditis, myocarditis, etc.), diseases induced by apoptosis (graft versus host diseases, rejection of an organ transplantation, acquired immune deficiency syndrome (AIDS), AIDS-related complex (ARC), adult T cell leukemia, hairy cells leukemia, spondylopathy, disorders of respiratory apparatus, arthritis, HIV or HTLV-1 related diseases such as uveitis, virus-related diseases such as hepatitis C, cancer, collagenosis (systemic lupus erythematosus, rheumatoid arthritis, etc.), ulcerative colitis, Sjoegren's syndrome, primary biliary cirrhosis, spontaneous thrombocytopenic purpura, autoimmune hemolytic anemia, myasthenia gravis, autoimmune diseases such as insulin dependent (type I) diabetes, diseases accompanying thrombocytopenia (osteomyelodysplasia syndrome, periodic thrombocytopenia, aplastic anemia, spontaneous thrombocytopenia, disseminated intravascular coagulation (DIC), etc.), hepatic diseases such as viral hepatitis (type A, B, C, F, etc.) or hepatitis medicamentosa and cirrhosis, dementia such as Alzheimer's diseases and Alzheimer's senile dementia, cerebrovascular injury, nerve degeneration diseases, adult acute respiratory distress syndrome, infectious diseases, prostatomegaly, hysteromyoma, bronchial asthma, arteriosclerosis, all kinds of lusus naturae, nephropathy, senile cataract, chronic fatigue syndrome, myodystrophy, peripheral neuropathy, etc.), diseases induced by disorders of immune response (graft versus host diseases, rejection of an organ transplantation, allergic diseases (bronchial asthma, atopic dermatitis, allergic rhinitis, pollinosis, diseases induced by house dusts, irritable pneumonia, food allergy, etc.), psoriasis, rheumatoid arthritis, etc.), autoimmune diseases (insulin-dependent (type I) diabetes, systemic lupus erythematosus, Hashimoto's diseases, multiple sclerosis, etc.), desease by decomposing various proteins which compose the organism (myodystrophy, cataract, periodontitis, hepatocyte desease by bile acid such as cholestatic cirrhosis, etc.), decomposition of alveolus elastica such as pulmonary emphysema, ischemic diseases (brain ischemia, brain disorders by ischemic reperfusion, myocardial infarction, ischemic hepatopathy, etc.), shock (septic shock, systemic inflammation response syndrome, endotoxin shock, acidosis, etc.), circulatory system disorders (arteriosclerosis, restenosis after percutaneous transluminal coronary angioplasty (PTCA), etc.)), blood coagulation disorders (thrombocytopenic purpura, hemolytic uremic syndrome, etc.), malignant tumor, acquired immune deficiency syndrome (AIDS) and AIDS-related complex (ARC), parasitic diseases such as malaria, nerve degenerative diseases (Alzheimer-type dementia, Huntington's chorea, Parkinson's diseases, multiple sclerosis, traumatic encephalopathy, traumatic spondylopathy, etc.), pulmopathy such as fibroid lungs, bone resorption diseases (osteoporosis, rheumatoid arthritis, arthritis, osteoarthritis, hypercalcemia, osteometastasis of cancer etc.), endocrinesthenia such as hyperthyroidism.

For the purpose described above, the compounds of formula (I), of the present invention, non-toxic salts thereof, acid addition salts thereof or hydrates thereof may normally be administered systemically or locally, usually by oral or parenteral administration.

The doses to be administered are determined depending upon, for example, age, body weight, symptom, the desired therapeutic effect, the route of administration, and the duration of the treatment. In the human adult, the doses per person at a time are generally from 1 mg to 1000 mg, by oral administration, up to several times per day, and from 1 mg to 100 mg, by parenteral administration (preferably intravenous administration), up to several times per day, or continuous administration for from 1 to 24 hours per day from vein.

As mentioned above, the doses to be used depend upon various conditions. Therefore, there are cases wherein doses lower than or greater than the ranges specified above may be used.

The compounds of the present invention may be administered in the form of, for example, solid compositions, liquid compositions or other compositions for oral administration, injections, liniments or suppositories for parenteral administration.

Solid compositions for oral administration include compressed tablets, pills, capsules, dispersible powders and granules.

Capsules include hard capsules and soft capsules.

In such solid compositions, one or more of the active compound(s) may be used as a dosage form, as is normal practice, to admix with excipient (e.g. lactose, mannitol, glucose, microcrystalline cellulose, starch), combining agents (hydroxypropyl cellulose, polyvinyl pyrrolidone or magnesium metasilicate aluminate), disintegrating agents (e.g. cellulose calcium glycolate), lubricating agents (e.g. magnesium stearate), stabilizing agents, agents to assist dissolution (e.g. glutamic acid or asparatic acid) and the like. The agents may, if desired, be coated with coating agents (e.g. sugar, gelatin, hydroxypropyl cellulose or hydroxypropylmethyl cellulose phthalate), or be coated with two or more films. Further, coating may include containment within capsules of absorbable materials such as gelatin.

Liquid compositions for oral administration include pharmaceutically acceptable solutions, suspensions, emulsions, syrups and elixirs. In such compositions, one or more of the active compound(s) are dissolved, suspended or emulsified in diluent commonly used (e.g. purified water, ethanol or mixture thereof). Furthermore, such liquid compositions may also comprise wetting agents or suspending agents, emulsifying agents, sweetening agents, flavouring agents, perfuming agents, preserving agents buffer agent etc.

Injections for parenteral administration include solutions, suspensions, emulsions and solids which are dissolved or suspended to use at a time to use. One or more of the active compound(s) in injections are dissolved, suspended and emulsified in a solvent. The solvents are, for example, distilled water for injection, physiological salt solution, vegetable oil, propylene glycol, polyethylene glycol, alcohol such as ethanol or mixture thereof. Moreover the injections may also include stabilizing agents, agents to assist dissolution (e.g. glutamic acid, aspartic acid or POLYSORBATE80 (registered trade mark)), suspending agents, emulsifying agents, soothing agents, buffer agents, preserving agents, etc. They are sterilized in the last process or manufactured and prepared by sterile procedure. They may also be manufactured in the form of sterile solid compositions such as freeze-dried one and they may be sterilized or dissolved to use in sterile distilled water for injection or some other solvents immediately before use.

Other compositions for parenteral administration include liquids for external use, and ointment, endermic liniments, inhale, spray, suppositories for rectal administration and pessaries for vaginal administration which comprise one or more of the active compound(s) and are prescribed by methods known per se.

Spray compositions may comprise additional substances other than diluents: e.g. stabilizing agents (e.g. sodium sulfitehydride), isotonic buffers (e.g. sodium chloride, sodium citrate or citric acid). For preparation of such spray compositions, for example, the method described in the U.S. Pat. No. 2,868,691 or U.S. Pat. No. 3,095,355 may be used.

BEST MODE FOR CARRYING OUT THE INVENTION

The following Reference Examples and Examples illustrate the present invention, but do not limit the present invention.

The solvents in the parentheses show the eluting or developing solvents and the ratios of the solvents used are by volume in chromatographic separations or TLC.

The solvents in the parentheses in NMR show the solvents used in measurement.

REFERENCE EXAMPLE 1

N-benzyloxycarbonyl-L-leucyl-L-leucine t-butyl ester

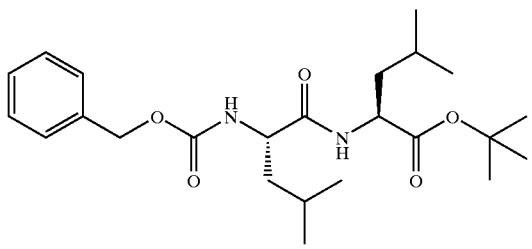

Under atmosphere of argon, to a solution of N-benzyloxycarbonylleucine (26.5 g) and leucine t-butyl ester hydrochloride (22.4 g) in methylene chloride (20.0 ml) were added 1-hydroxybenzotriazole (HOBt) (14.2 g) and 1-ethyl-3-[3-(dimethylamino)propyl]carbodiimide (EDC) hydrochloride (20.1 g) at 0° C. Thereto was added N-methylmorpholine (11.5 ml) over a period of 5 minutes and the mixture was stirred for 20 hours at room temperature. The reaction solution was concentrated and to the residue were added ice-water and ethyl acetate. In order to dissolve HOBt that appeared, was added sodium bicarbonate. The aqueous layer was extracted with ethyl acetate and combined organic layer was washed with 10% aqueous solution of citric acid, a saturated aqueous solution of sodium bicarbonate and saturated aqueous solution of sodium chloride, dried over anhydrous magnesium sulfate, and was concentrated to give the title compound (43.2 g) having the following physical data.

TLC: Rf 0.48 (n-hexane:ethyl acetate=3:1); NMR (CDCl$_3$): δ 7.34 (s, 5H, Ph), 6.28 (d, J=8.2 Hz, 1H, NH of Leu-Leu), 5.19 (d, J=7.8 Hz, 1H, NH of cbz-Leu), 5.11 (s, 2H, CH$_2$ of cbz), 4.54–4.38 (m, 1H, CH of Leu), 4.28–4.06 (m, 1H, CH of Leu), 1.80–1.40 (m, 6H, CH$_2$ and CH of Leu), 1.46 (s, 9H, tBu) 1.05–0.80 (m, 12H, CH$_3$ of Leu).

REFERENCE EXAMPLE 2

N-benzyloxycarbonyl-L-leucyl-L-leucine

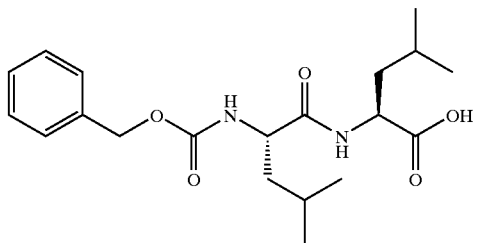

To the compound prepared in reference example 1 (42.9 g) was added 90% trifluoroacetic acid (200 ml) at 0° C. and the mixture was added for 3 hours at room temperature. The reaction solution was concentrated and was a zeotroped with toluene and the residue was dried under reduced pressure. The residue was dissolved in ether/petroleum ether (100 ml/400 ml) and the mixture was stirred for 2 hours. White crystals that appeared was collected, and was dried to give the title compound (36.7 g) having the following physical data.

TLC: Rf 0.28 (chloroform methanol=9:1); NMR (DMSO-d$_6$): δ 8.04 (d, J=7.8 Hz, 1H, NH of Leu-Leu), 7.40–7.20 (br, 6H, Ph and NH of cbz-Leu), 5.02 (s, 2H, CH$_2$ of cbz), 4.30–4.00 (m, 2H, CH of Leu), 1.75–1.30 (m, 6H, CH$_2$ and CH of Leu), 1.00–0.70 (m, 12H, CH$_3$ of Leu).

REFERENCE EXAMPLE 3

2(S)-N-(3(S)-1-bromo-5-methyl-2-oxo-3-hexyl)-2-benzyloxycarbonylamino-4-methylpentanamide

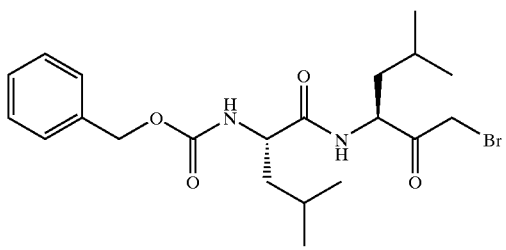

Under atmosphere of argon, to a solution of the compound prepared in reference example 2 (18.9 g) in tetrahydrofuran (10.0 ml) was added N-methylmorpholine (7.15 ml) at −8° C. and the mixture was stirred for 10 minutes. Thereto was added chloroethyl formate (5.74 ml) over a period of 15 minutes and the mixture was stirred for 1 hour at −8° C. To the reaction solution was added a solution of diazomethane in ether and the mixture was stirred for 2 hours. After confirming generation of diazoketone by TLC, to the reaction solution was added 47% hydrobromic acid/acetic acid (1/1) at 0° C. and the mixture was stirred for 15 minutes. To the reaction solution was added water, ethyl acetate and hexane. The aqueous layer was extracted with ethyl acetate. The combined organic layer was washed with water (5 times) and a saturated aqueous solution of sodium bicarbonate and saturated aqueous solution of sodium chloride, dried over anhydrous sodium sulfate and was concentrated. The residue was purified by column chromatography on silica gel (n-hexane:ethyl acetate=9:1→4:1) to give the title compound (10.0 g) having the following physical data.

TLC: 0.50 (n-hexane:ethyl acetate=7:3); NMR (CDCl$_3$): δ 7.35 (s, 5H, Ph), 6.53 (br, 1H, NH of Leu-Leu), 5.16 (d, J=7.8 Hz, 1H, NH of cbz-Leu), 4.86–4.70 (m, 1H, CH of Leu), 4.28–3.90 (m, 3H, CH of Leu, and CH$_2$ of LeuCH$_2$Br), 1.80–1.40 (m, 6H, CH$_2$ and CH of Leu), 1.05–0.80 (m, 12H, CH$_3$ of Leu).

EXAMPLE 1

2(S)-N-[3(S)-1-(5-phenyltetrazol-2-yl)-2-oxo-5-methyl-3-hexyl]-2-benzyloxycarbonylamino-4-methylpentanamide

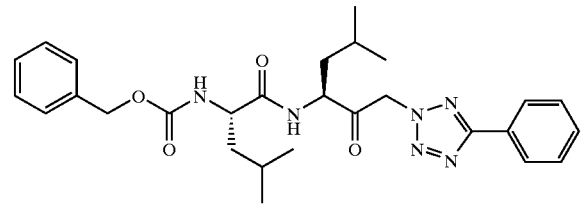

Under atmosphere of argon, a solution of 5-phenyltetrazole (193 mg) and potassium fluoride (153 mg) in dimethylformamide (DMF) (5 ml) was stirred for 30 minutes. Thereto was added the compound prepared in reference example 3 (300 mg) at room temperature and the mixture was stirred for 2 hours. To the reaction mixture was added ice-water and ethyl acetate and was extracted with ethyl acetate. The combined organic layer was washed with a saturated aqueous solution of sodium bicarbonate, water and saturated aqueous solution of sodium chloride successively, dried over sodium sulfate and was concentrated. The residue was purified by column chromatography on silica gel (chloroform:methanol=200:1) to give the title compound (290 mg) having the following physical data.

TLC: Rf 0.38 (n-hexane:ethyl acetate=7:3); NMR (200 MHz, DMSO-$d_6$): δ 8.55 (d, J=7.8 Hz, 1H, NH of Leu-Leu), 8.14–8.00 (m, 2H, 2- and 6-CH of Ph-tet), 7.70–7.50 (m, 4H, other CH of Ph-tet, and NH of cbz-Leu), 7.40–7.20 (m, 5H, Ph of cbz), 5.99 (d, J=17.7 Hz, 1H, CH of COCH$_2$N), 5.87 (d, J=17.7 Hz, 1H, CH of COCH$_2$N), 5.04 (s, 2H, CH$_2$ of PhCH$_2$), 4.60–4.42 (m, 1H, CH of Leu), 4.20–4.00 (m, 1H, CH of Leu), 1.80–1.35 (m, 6H, CH$_2$ and CH of Leu), 1.00–0.70 (m, 12H, CH$_3$ of Leu).

EXAMPLE 1(1)–1(54)

By the same procedure as described in example 1 using the compound prepared in reference example 3 or a substitute compound therewith and a corresponding tetrazole compound, the following compounds were given. In the examples, there exist couple of compounds having different substitution position (concretely, 1-position and 2-position), but they were given by chromatography separation in the final process of example 1.

EXAMPLE 1(1)

2(S)-N-[3(S)-1-(5-morpholinotetrazol-2-yl)-2-oxo-5-methyl-3-hexyl]-2-benzyloxycarbonylamino-4-methylpentanamide

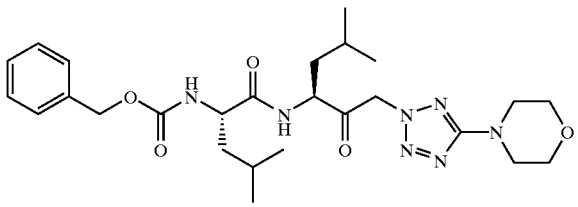

TLC: Rf 0.57 (chloroform:methanol=19:1); NMR (200 MHz, CDCl$_3$): δ 7.33 (brs, 5H, Ph), 6.64 (d, J=6.8 Hz, 1H, NH of Leu-Leu), 5.48 (d, J=18.2 Hz, 1H, CH of COCH$_2$N), 5.32 (d, J=18.2 Hz, 1H, CH of COCH$_2$N), 5.19 (d, J=8.2 Hz, 1H, NH of cbz-Leu), 5.10 (s, 2H, CH$_2$ of PhCH$_2$), 4.65 (brs, 1H, CH of Leu), 4.19 (brs, 1H, CH of Leu), 3.80 (t, J=4.6 Hz, 4H, OCH$_2$ of Mor.), 3.47 (t, J=4.6 Hz, 4H, NCH$_2$ of Mor.), 2.00–1.40 (m, 6H, CH$_2$ and CH of iBu), 1.05–0.70 (m, 12H, CH$_3$ of iBu).

EXAMPLE 1(2)

2(S)-N-[3(S)-1-(tetrazol-2-yl)-2-oxo-5-methyl-3-hexyl]-2-benzyloxycarbonylamino-4-methylpentanamide

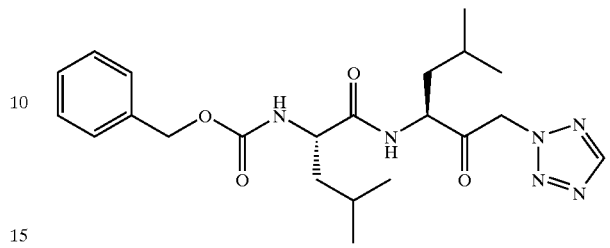

TLC: Rf 0.44 (chloroform:methanol=19:1); NMR (200 MHz, DMSO-$d_6$): δ 9.02 (s, 1H, 5-CH of tet.), 8.52 (d, J=7.2 Hz, 1H, NH of Leu-Leu), 7.54 (d, J=6.8 Hz, 1H, NH of cbz-Leu), 7.34 (s, 5H, Ph), 6.05–5.80 (m, 2H, CH$_2$ of COCH$_2$N), 5.03 (s, 2H, CH$_2$ of PhCH$_2$), 4.55–4.38 (m, 1H, CH of Leu), 4.15–4.00 (m, 1H, CH of Leu), 1.80–1.30 (m, 6H, CH$_2$ and CH of iBu), 1.00–0.70 (m, 12H, CH$_3$ of iBu).

EXAMPLE 1(3)

2(S)-N-[3(S)-1-(tetrazol-1-yl)-2-oxo-5-methyl-3-hexyl]-2-benzyloxycarbonylamino-4-methylpentanamide

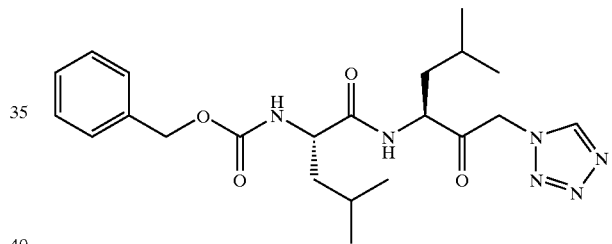

TLC: Rf 0.35 (chloroform:methanol=19:1); NMR (200 MHz, DMSO-$d_6$): δ 9.23 (s, 1H, 5-CH of tet.), 8.52 (d, J=6.6 Hz, 1H, NH of Leu-Leu), 7.56 (d, J=7.2 Hz, 1H, NH of cbz-Leu), 7.40–7.20 (m, 5H, Ph), 5.90–5.50 (m, 2H, CH$_2$of COCH$_2$N), 5.03 (s, 2H, CH$_2$ of PhCH$_2$), 4.60–4.40 (m, 1H, CH of Leu), 4.15–4.00 (m, 1H, CH of Leu), 1.80–1.35 (m, 6H, CH$_2$and CH of iBu), 1.00–0.70 (m, 12H, CH$_3$ of iBu).

EXAMPLE 1(4)

2(S)-N-[3(S)1-(5-(pyrrolidin-1-yl)tetrazol-2-yl)-2-oxo-5-methyl-3-hexyl]-2-benzyloxycarbonylamino-4-methyl pentanamide

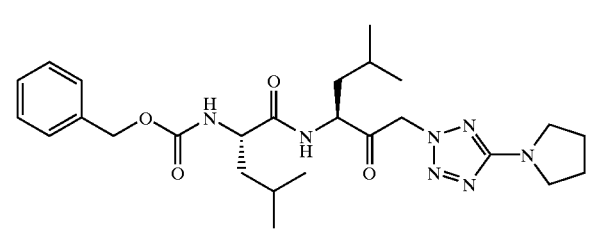

TLC: Rf 0.60 (n-hexane:ethyl acetate=1:1); NMR (200 MHz, DMSO-$d_6$): δ 8.44 (d, J=6.6 Hz, 1H, NH of Leu-Leu), 7.52 (d, J=6.4 Hz, 1H, NH of cbz-Leu), 7.34 (s, 5H, Ph), 5.63 (d, J=17.6 Hz, 1H, CH of COCH$_2$N), 5.51 (d, J=17.6 Hz, 1H, CH of COCH$_2$N), 5.03 (s, 2H, CH$_2$ of PhCH$_2$), 4.55–4.35 (m, 1H, CH of Leu), 4.20–3.95 (m, 1H, CH of Leu), 3.50–3.20 (m, 4H, NCH$_2$ of pyrrolidine), 1.93 (brs, 4H, other of pyrrolidine), 1.80–1.30 (m, 6H, CH$_2$ and CH of Leu), 1.00–0.70 (m, 12H, CH$_3$ of Leu).

EXAMPLE 1(5)

2(S)-N-[3(S)-1-(5-benzyltetrazol-2-yl)-2-oxo-5-methyl-3-hexyl]-2-benzyloxycarbonylamino-4-methylpentanamide

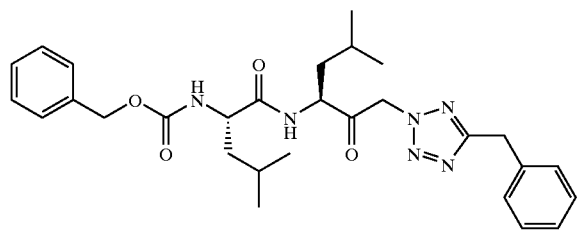

TLC: Rf 0.30 (n-hexane:ethyl acetate=7:3); NMR (200 MHz, DMSO-d$_6$): δ 8.52 (d, J=7.2 Hz, 1H, NH of Leu-Leu), 7.55 (d, J=7.6 Hz, 1H, NH of cbz-Leu), 7.45–7.00 (m, 10H, two Ph), 5.88 (d, J=19.1 Hz, 1H, CH of COCH$_2$N), 5.75 (d, J=19.1 Hz, 1H, CH of COCH$_2$N), 5.03 (s, 2H, CH$_2$ of PhCH$_2$), 4.55–4.30 (m, 1H, CH of Leu), 4.26 (s, 2H, CH$_2$ of PhCH$_2$tet), 4.20–4.00 (m, 1H, CH of Leu), 1.80–1.30 (m, 6H, CH$_2$ and CH of Leu), 0.89 (brs, 12H, CH$_3$ of Leu).

EXAMPLE 1(6)

2(S)-N-[3(S)-1-(5-benzyltetrazol-1-yl)-2-oxo-5-methyl-3-hexyl]-2-benzyloxycarbonylamino-4-methylpentanamide

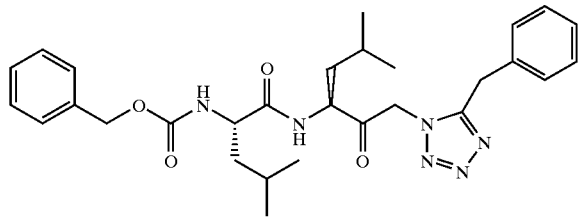

TLC: Rf 0.14 (n-hexane:ethyl acetate=7:3); NMR (200 MHz, DMSO-d$_6$): δ 8.62 (d, J=6.6 Hz, 1H, NH of Leu-Leu), 7.57 (d, J=6.8 Hz, 1H, NH of cbz-Leu), 7.40–7.10 (m, 10H, two Ph), 5.68 (d, J=18.8 Hz, 1H, CH of COCH$_2$N), 5.56 (d, J=18.8 Hz, 1H, CH of COCH$_2$N), 5.00 (s, 2H, CH$_2$ of PhCH$_2$), 4.50–4.30 (m, 1H, CH of Leu), 4.20–4.00 (m, 3H, CH of Leu, and CH$_2$ of PhCH$_2$tet), 1.80–1.30 (m, 6H, CH$_2$ and CH of Leu), 1.00–0.70 (m, 12H, CH$_3$ of Leu).

EXAMPLE 1(7)

2(S)-N-[3(S)-1-(5-ethylthiotetrazol-2-yl)-2-oxo-5-methyl-3-hexyl]-2-benzyloxycarbonylamino-4-methylpentanamide

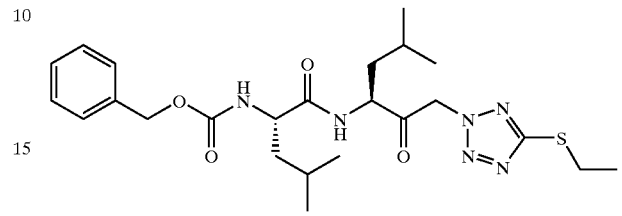

TLC: Rf 0.67 (n-hexane:ethyl acetate=6:4); NMR (200 MHz, DMSO-d$_6$): δ 8.53 (d, J=6.8 Hz, 1H, NH of Leu-Leu), 7.55 (d, J=8.2 Hz, 1H, NH of cbz-Leu), 7.33 (s, 5H, Ph), 5.89 (d, J=17.4 Hz, 1H, CH of COCH$_2$N), 5.76 (d, J=17.4 Hz, 1H, CH of COCH$_2$N), 5.02 (s, 2H, CH$_2$ of PhCH$_2$), 4.60–4.35 (m, 1H, CH of Leu), 4.20–4.00 (m, 1H, CH of Leu), 3.18 (q, J=7.2 Hz, 2H, CH$_2$ of SEt), 1.80–1.40 (m, 6H, CH$_2$ and CH of Leu), 1.33 (t, J=7.2 Hz, 3H, CH$_3$ of SEt), 1.00–0.70 (m, 12H, CH$_3$ of Leu).

EXAMPLE 1(8)

2(S)-N-[3(S)-1-(5-ethylthiotetrazol-1-yl)-2-oxo-5-methyl-3-hexyl]-2-benzyloxycarbonylamino-4-methylpentanamide

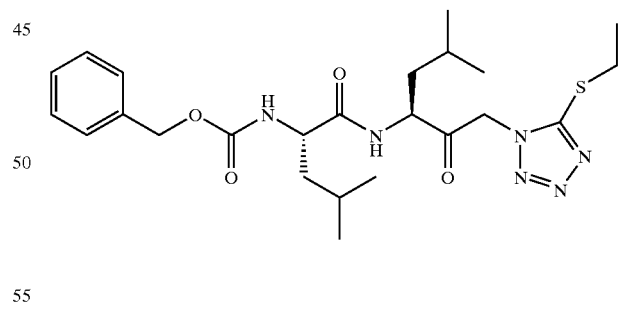

TLC: Rf 0.43 (n-hexane:ethyl acetate=6:4); NMR (200 MHz, DMSO-d$_6$): δ 8.55 (d, J=6.4 Hz, 1H, NH of Leu-Leu), 7.56 (d, J=7.6 Hz, 1H, NH of cbz-Leu), 7.34 (s, 5H, Ph), 5.54 (d, J=18.6 Hz, 1H, CH of COCH$_2$N), 5.40 (d, J=18.6 Hz, 1H, CH of COCH$_2$N), 5.03 (s, 2H, CH$_2$ of PhCH$_2$), 4.50–4.35 (m, 1H, CH of Leu), 4.20–3.95 (m, 1H, CH of Leu), 3.22 (q, J=7.2 Hz, 2H, CH$_2$ of SEt), 1.80–1.40 (m, 6H, CH$_2$ and CH of Leu), 1.31 (t, J=7.2 Hz, 3H, CH$_3$ of SEt), 1.00–0.70 (m, 12H, CH$_3$ of Leu).

EXAMPLE 1(9)

2(S)-N-[1-(5-methyltetrazol-2-yl)-2-oxo-5-methyl-3-hexyl]-2-benzyloxycarbonylamino-4-methylpentanamide

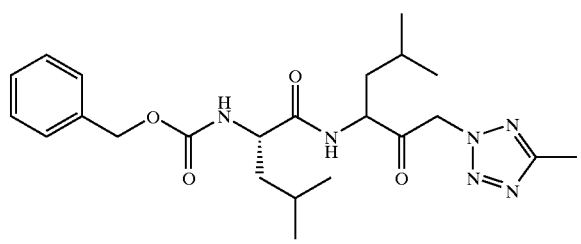

TLC: Rf 0.57 and 0.50 (n-hexane:ethyl acetate=6 4, HPTLC) NMR (200 MHz, DMSO-$d_6$): δ 8.65 and 8.52 (each d, each J=7.0 Hz, 1H, NH of Leu-Leu), 7.62–7.48 (m, 1H, NH of cbz-Leu), 7.34 (brs, 5H, Ph), 5.95–5.60 (m, 2H, COCH$_2$N), 5.03 (s, 2H, CH$_2$of PhCH$_2$), 4.53–4.35 (m, 1H, CH of Leu), 4.15–4.00 (m, 1H, CH of Leu), 2.47 (s, 3H, CH$_3$tet), 1.80–1.30 (m, 6H, CH$_2$ and CH of Leu), 1.00–0.70 (m, 12H, CH$_3$ of Leu).

EXAMPLE 1(10)

2(S)-N-[1-(5-methyltetrazol-1-yl)-2-oxo-5-methyl-3-hexyl]-2-benzyloxycarbonylamino-4-methylpentanamide

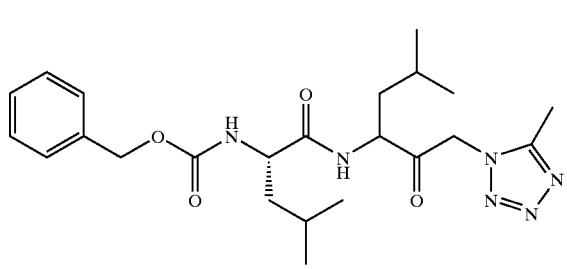

TLC: Rf 0.14 and 0.10 (n-hexane:ethyl acetate=6:4, HPTLC); NMR (200 MHz, DMSO-d6): δ 8.80–8.60 (m, 1H, NH of Leu-Leu), 7.65–7.55 (m, 1H, NH of cbz-Leu), 7.40–7.20 (m, 5H, Ph),5.75–5.40 (m, 2H, COCH$_2$N), 5.02 (s, 2H, CH$_2$ of PhCH$_2$), 4.50–4.30 (m, 1H, CH of Leu), 4.20–3.95 (m, 1H, CH of Leu), 2.31 (s, 3H, CH$_3$tet), 1.80–1.30 (m, 6H, CH$_2$ and CH of Leu), 1.05–0.70 (m, 12H, CH$_3$ of Leu).

EXAMPLE 1(11)

2(S)-N-[3(S)-1-(5-piperidinotetrazol-2-yl)-2-oxo-5-methyl-3-hexyl]-2-benzyloxycarbonylamino-4-methylpentanamide

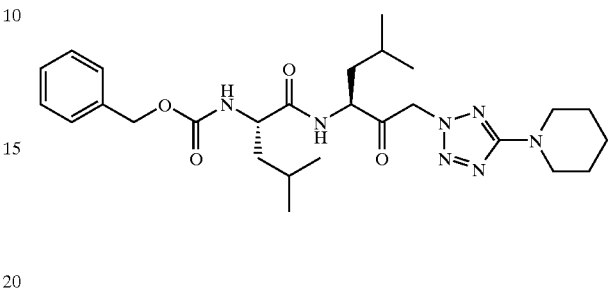

TLC: Rf 0.57 (n-hexane:ethyl acetate=6:4); NMR (200 MHz, DMSO-$d_6$): δ 8.47 (d, J=7.8 Hz, 1H, NH of Leu-Leu), 7.53 (d, J=7.4 Hz, 1H, NH of cbz-Leu), 7.32 (s, 5H, Ph of cbz), 5.65 (d, J=18.0 Hz, 1H, CH of COCH$_2$N), 5.51 (d, J=18.0 Hz, 1H, CH of COCH$_2$N), 5.03 (s, 2H, CH$_2$ of cbz), 4.50–4.35 (m, 1H, CH of Leu), 4.20–4.00 (m, 1H, CH of Leu), 3.50–3.20 (m, 4H, NCH$_2$ of piperidine), 1.80–1.30 (m, 12H, CH$_2$ and CH of Leu, and the other CH$_2$ of piperidine), 1.00–0.70 (m, 12H, CH$_3$ of Leu).

EXAMPLE 1(12)

2(S)-N-[3(S)-1-(5-(3-pyridyl)tetrazol-2-yl)-2-oxo-5-methyl-3-hexyl]-2-benzyloxycarbonylamino-4-methylpentanamide

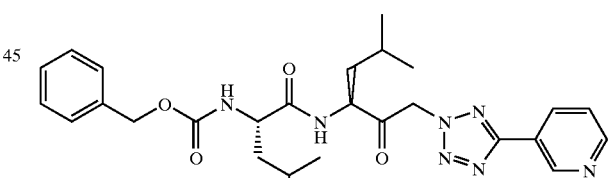

TLC: Rf 0.37 (chloroform:methanol 9:1); NMR (200 MHz, DMSO-$d_6$): δ 9.23 (d, J=2.0 Hz, 1H, 2-CH of pyridine), 8.75 (dd, J=4.8, 2.0 Hz, 1H, 6-CH of pyridine), 8.58 (d, J=7.0 Hz, 1H, NH of Leu-Leu), 8.41 (ddd, J=8.0, 2.0, 2.0 Hz, 1H, 4-CH of pyridine), 7.62 (dd, J=8.0, 4.8 Hz, 1H, 5-CH of pyridine), 7.57 (d, J=6.6 Hz, 1H, NH of cbz-Leu), 7.33 (s, 5H, Ph), 6.03 (d, J=17.9 Hz, 1H, CH of COCH$_2$N), 5.91 (d, J=17.9 Hz, 1H, CH of COCH$_2$N), 5.04 (s, 2H, CH$_2$ of cbz), 4.60–4.40 (m, 1H, CH of Leu), 4.20–4.00 (m, 1H, CH of Leu), 1.80–1.40 (m, 6H, CH$_2$ and CH of Leu), 0.90 (d, J=6.0 Hz, 6H, CH$_3$ of Leu), 0.88 (d, J=6.0 Hz, 6H, CH$_3$ of Leu).

EXAMPLE 1(13)

2(S)-N-[3(S)-1-(5-(2-pyridyl)tetrazol-2-yl)-2-oxo-5-methyl-3-hexyl]-2-benzyloxycarbonylamino-4-methylpentanamide

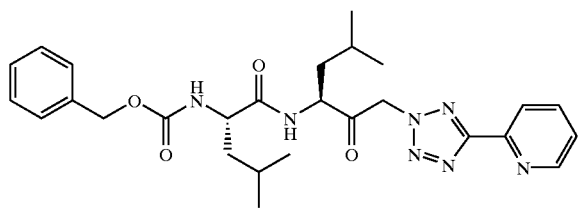

TLC: Rf 0.24 (n-hexane:ethyl acetate=1:1); NMR (200 MHz, DMSO-$d_6$): δ 8.75 (d, J=4.8 Hz, 1H, 6-CH of pyridine), 8.58 (d, J=7.2 Hz, 1H, NH of Leu-Leu), 8.15 (d, J=7.8 Hz, 1H, 3-CH of pyridine), 8.02 (ddd, J=7.8, 7.8, 2.0 Hz, 1H, 4-CH of pyridine), 7.64–7.52 (m, 2H, 5-CH of pyridine, and NH of cbz-Leu), 7.34 (s, 5H, Ph), 6.03 (d, J=18.2 Hz, 1H, CH of COCH$_2$N), 5.91 (d, J=18.2 Hz, 1H, CH of COCH$_2$N), 5.04 (s, 2H, CH$_2$ of cbz), 4.60–4.40 (m, 1H, CH of Leu), 4.20–4.00 (m, 1H, CH of Leu), 1.80–1.35 (m, 6H, CH$_2$ and CH of Leu), 1.00–0.70 (m, 12H, CH$_3$ of Leu).

EXAMPLE 1(14)

2(S)-N-[3(S)-1-(5-(2-pyridyl)tetrazol-1-yl)-2-oxo-5-methyl-3-hexyl]-2-benzyloxycarbonylamino-4-methylpentanamide

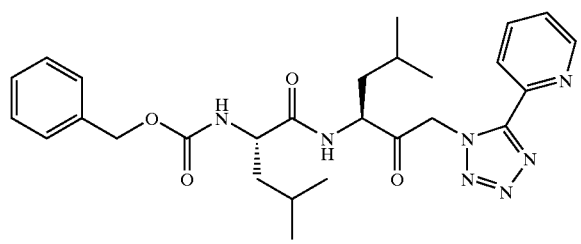

TLC: Rf 0.50 (n-hexane:ethyl acetate=1:1); NMR (200 MHz, DMSO-$d_6$): δ 8.67 (d, J=4.0 Hz, 1H, 6-CH of pyridine), 8.50 (d, J=7.6 Hz, 1H, NH of Leu-Leu), 8.31 (d, J=7.8 Hz, 1H, 3-CH of pyridine), 8.08 (ddd, J=7.8, 7.8, 1.6 Hz, 1H, 4-CH of pyridine), 7.68–7.50 (m, 2H, 5-CH of pyridine, and NH of cbz-Leu), 7.33 (s, 5H, Ph), 5.94 (s, 2H, COCH$_2$N), 5.03 (s, 2H, CH$_2$ of cbz), 4.70–4.50 (m, 1H, CH of Leu), 4.20–4.00 (m, 1H, CH of Leu), 1.80–1.30 (m, 6H, CH$_2$ and CH of Leu), 1.00–0.70 (m, 12H, CH$_3$ of Leu).

EXAMPLE 1(15)

2(S)-N-[3(S)-1-(5-(4-pyridyl)tetrazol-2-yl)-2-oxo-5-methyl-3-hexyl]-2-benzyloxycarbonylamino-4-methylpentanamide

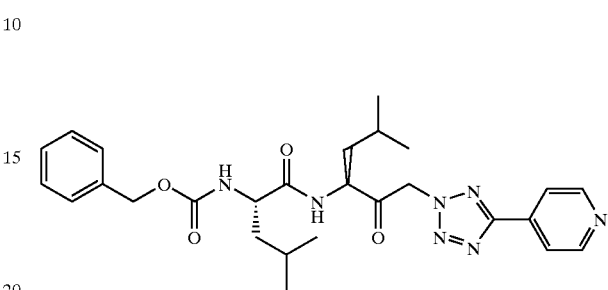

TLC: Rf 0.58 (chloroform:methanol=9:1); NMR (200 MHz, DMSO-$d_6$): δ 8.80 (d, J=6.0 Hz, 2H, 2- and 6-CH of pyridine), 8.59 (d, J=7.2 Hz, 1H, NH of Leu-Leu), 7.99 (d, J=6.0 Hz, 2H, 3- and 5-CH of pyridine), 7.58 (d, J=7.2 Hz, 1H, NH of cbz-Leu), 7.34 (s, 5H, Ph), 6.06 (d, J=18.1 Hz, 1H, CH of COCH$_2$N), 5.93 (d, J=18.1 Hz, 1H, CH of COCH$_2$N), 5.04 (s, 2H, CH$_2$ of cbz), 4.60–4.40 (m, 1H, CH of Leu), 4.20–4.00 (m, 1H, CH of Leu), 1.80–1.30 (m, 6H, CH$_2$ and CH of Leu), 1.00–0.70 (m, 12H, CH$_3$ of Leu).

EXAMPLE 1(16)

2(S)-N-[3(S)-1-(5-(1,1'-biphenyl-4-yl)tetrazol-2-yl)-2-oxo-5-methyl-3-hexyl]-2-benzyloxycarbonylamino-4-methylpentan amide

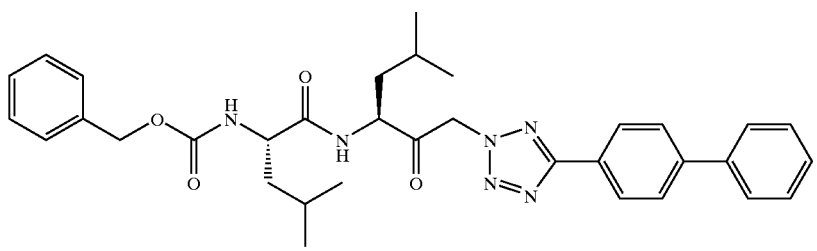

TLC: Rf 0.37 (n-hexane:ethyl acetate=1:1); NMR (200 MHz, CDCl$_3$): δ 7.89–7.84 (m, 1H, aromatic), 7.59–7.42 (m, 3H, aromatic), 7.32 (s, 5H, C6H5CH$_2$), 7.30–7.16 (m, 5H, aromatic), 6.58 (d, J=7.0 Hz, 1H, NHCH), 5.57 (d, J=17.2 Hz, 1H, COCHH), 5.38 (d, J=17.2 Hz, 1H, COCHH), 5.11 (d, J=8.2 Hz, 1H, NHCH), 5.09 (s, 2H, PhCH$_2$O), 4.64–4.54 (m, 1H, NCH), 4.23–4.13 (m, 1H, NCH), 1.66–1.45 (m, 6H, CHCH$_2$CH), 0.96–0.84 (m, 12H, CH$_3$).

EXAMPLE 1(17)

2(S)-N-[3(S)-1-(5-(1,1'-biphenyl-4-yl)tetrazol-1-yl)-2-oxo-5-methyl-3-hexyl]-2-benzyloxycarbonylamino-4-methylpentan amide

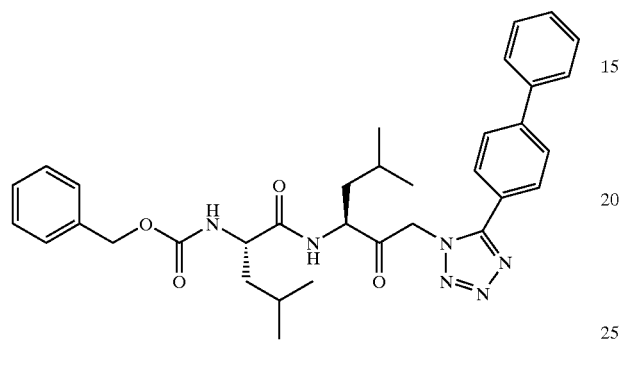

TLC: Rf 0.30 (n-hexane:ethyl acetate=2:1); NMR (200 MHz, CDCl$_3$): δ 7.67–7.44 (m, 4H, aromatic), 7.33–7.13 (m, 10H, Cbz-aromatic and aromatic), 6.38 (d, J=6.6 Hz, 1H, CONH of P1 Leu), 5.06–5.01 (m, 3H, PhCH$_2$O and CONH of P2 Leu), 4.75 (d, J=18.4 Hz, 1H, COCH$_2$), 4.52 (d, J=18.4 Hz, 1H, COCH$_2$), 4.34–4.24 (m, 1H, NCH of P1 Leu), 4.12–4.01 (m, 1H, NCH of P2 Leu), 1.65–1.11 (m, 6H, CH$_2$CHMe$_2$ of each Leu), 0.92–0.89 (m, 6H, CH$_3$ of Leu), 0.81 (d, J=6.2 Hz, 3H, CH$_3$ of Leu), 0.78 (d, J=5.8 Hz, 3H, CH$_3$ of Leu).

EXAMPLE 1(18)

2(S)-N-[3(S)-1-(5-(2-phenylethyl)tetrazol-2-yl)-2-oxo-5-methyl-3-hexyl]-2-benzyloxycarbonylamino-4-methylpentanamide

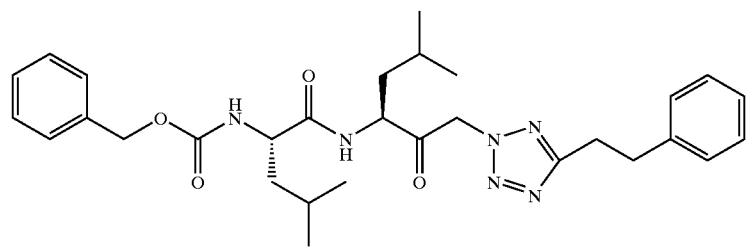

TLC: Rf 0.37 (n-hexane:ethyl acetate=2:1); NMR (200 MHz, CDCl$_3$): δ 7.35 (s, 5H, Cbz-aromatic), 7.29–7.19 (m, 5H, aromatic), 6.62 (d, J=7.2 Hz, 1H, CONH), 5.64 (d, J=18.0 Hz, 1H, COCHH), 5.47 (d, J=18.0 Hz, 1H, COCHH), 5.17 (d, J=7.4 Hz, 1H, CONH), 5.11 (s, 2H, PhCH$_2$O), 4.73–4.58 (m, 1H, NCH), 4.26–4.15 (m, 1H, NCH), 3.27–3.06 (m, 4H, PhCH$_2$CH$_2$), 1.68–1.43 (m, 6H, CHCH$_2$CH), 0.96–0.87 (m, 12H, CH$_3$).

EXAMPLE 1(19)

2(S)-N-[3(S)-1-(5-(2-phenylethyl)tetrazol-1-yl)-2-oxo-5-methyl-3-hexyl]-2-benzyloxycarbonylamino-4-methylpentanamide

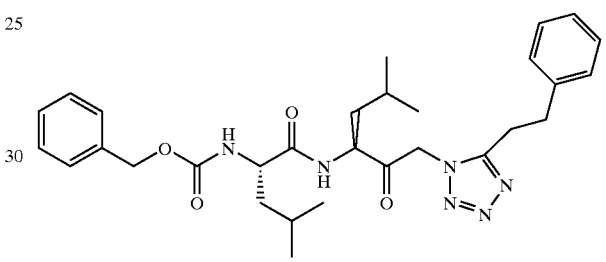

TLC: Rf 0.61 (n-hexane:ethyl acetate=1:1); NMR (200 MHz, CDCl$_3$): δ 7.32 (s, 5H, Cbz-aromatic), 7.29–7.15 (m, 5H, aromatic), 6.75 (d, J=5.6 Hz, 1H, CONH), 5.21–4.93 (m, 5H, CONH, COCH$_2$ and PhCH$_2$O), 4.44–4.34 (m, 1H, NCH), 4.22–4.12 (m, 1H, NCH), 3.16–2.95 (m, 4H, PhCH$_2$CH$_2$), 1.67–1.44 (m, 6H, CHCH$_2$CH), 0.96–0.87 (m, 12H, CH$_3$).

EXAMPLE 1(20)

2(S)-N-[3(S)-1-(5-(3-phenylpropyl)tetrazol-2-yl)-2-oxo-5-methyl-3-hexyl]-2-benzyloxycarbonylamino-4-methylpentanamide

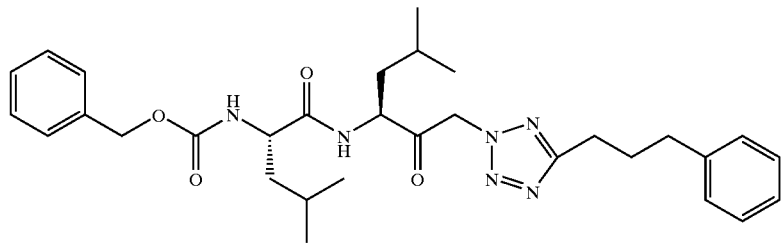

TLC: Rf 0.69 (n-hexane:ethyl acetate=1:1); NMR (200 MHz, CDCl$_3$): δ 7.33 (s, 5H, Cbz-aromatic), 7.30–7.17 (m, 5H, aromatic), 6.59 (d, J=7.0 Hz, 1H, CONH), 5.63 (d, J=18.0 Hz, 1H, COCHH), 5.47 (d, J=18.0 Hz, 1H, COCHH), 5.13 (d, J=8.8 Hz, 1H, CONH), 5.10 (s, 2H, PhCH$_2$O), 4.73–4.59 (m, 1H, NCH), 4.25–4.14 (m, 1H, NCH), 2.93 (t, J=7.6Hz, 2H, CCH$_2$CH$_2$), 2.70 (t, J=8.0 Hz, 2H, PhCH$_2$), 1.78–1.43 (m, 6H, CHCH$_2$CH), 0.96–0.86 (m, 12H, CH$_3$).

EXAMPLE 1(21)

2(S)-N-[3(S)-1-(5-(3-phenylpropyl)tetrazol-1-yl)-2-oxo-5-methyl-3-hexyl]-2-benzyloxycarbonylamino-4-methylpentanamide

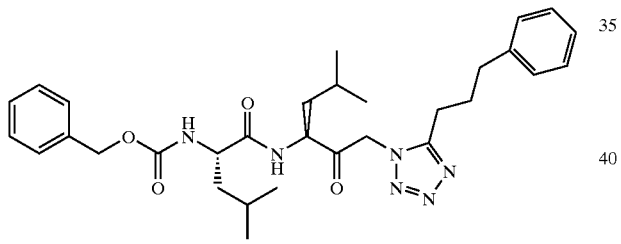

TLC: Rf 0.46 (n-hexane:ethyl acetate=1:1); NMR (200 MHz, CDCl$_3$): δ 7.32 (s, 5H, Cbz-aromatic), 7.28–7.16 (m, 5H, aromatic), 6.85 (d, J=9.0 Hz, 1H, CONH), 5.38 (d, J=18.4 Hz, 1H, COCHH), 5.13 (d, J=18.0 Hz, 1H, CONH), 5.13 (d, J=8.8 Hz, 1H, COCHH), 5.09 (s, 2H, PhCH$_2$O), 4.49–4.39 (m, 1H, NCH), 4.23–4.13 (m, 1H, NCH), 2.76–2.63 (m, 4H, CCH$_2$ and PhCH$_2$), 2.20–2.05 (m, 2H, CH$_2$CH$_2$CH$_2$), 1.77–1.41 (m, 6H, CHCH$_2$CH), 0.97–0.88 (m, 12H, CH$_3$).

EXAMPLE 1(22)

2(S)-N-[3(S)-1-(5-(4-phenylbutyl) tetrazol-2-yl)-2-oxo-5-methyl-3-hexyl]-2-benzyloxycarbonylamino-4-methylpentanamide

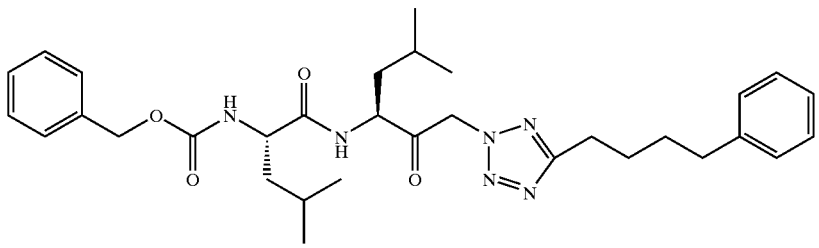

TLC: Rf 0.58 (n-hexane:ethyl acetate=3:2); NMR (200 MHz, CDCl$_3$): δ 7.42–7.10 (m, 10H, two Phs), 6.58 (d, J=6.2 Hz, 1H, NH of Leu-Leu), 5.63 (d, J=17.7 Hz, 1H, CH of COCH$_2$N), 5.47 (d, J=17.7 Hz, 1H, CH of COCH$_2$N), 5.23–5.05 (m, 3H, NH of cbz-Leu, and CH$_2$ of cbz), 4.73–4.55 (m, 1H, CH of Leu), 4.30–4.10 (m, 1H, CH of Leu), 2.93 (d, J=7.4 Hz, 2H, CH$_2$tet), 2.65 (d, J=7.4 Hz, 2H, CH$_2$Ph), 1.90–1.40 (m, 10H, CH$_2$ and CH of Leu, and CH$_2$Ctet and CH$_2$CPh), 1.05–0.80 (m, 12H, CH3 of Leu).

EXAMPLE 1(23)

2(S)-N-[3(S)-1-(5-(4-phenylbutyl)tetrazol-1-yl)-2-oxo-5-methyl-3-hexyl]-2-benzyloxycarbonylamino-4-methylpentanamide

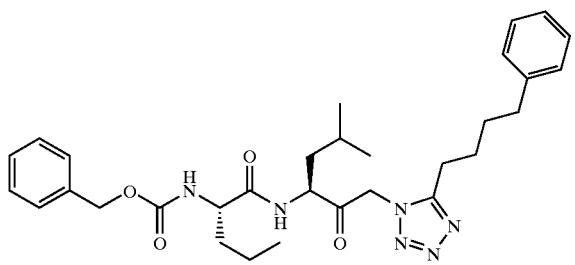

TLC: Rf 0.29 (n-hexane:ethyl acetate=3:2); NMR (200 MHz, CDCl$_3$): δ 7.40–7.10 (m, 10H, two Phs), 6.85 (brs, 1H, NH of Leu-Leu), 5.42 (d, J=18.4 Hz, 1H, CH of COCH$_2$N), 5.25–5.00 (m, 4H, NH of cbz-Leu, CH$_2$ of cbz, and CH of COCH$_2$N), 4.50–4.35 (m, 1H, CH of Leu), 4.25–4.10 (m, 1H, CH of Leu), 2.75–2.50 (m, 4H, CH$_2$tet and CH$_2$Ph), 1.90–1.40 (m, 10H, CH$_2$ and CH of Leu, and CH$_2$Ctet and CH$_2$CPh), 1.05–0.80 (m, 12H, CH$_3$ of Leu).

EXAMPLE 1(24)

2(S)-N-[3(S)-1-(5-(1,1'-biphenyl-3-yl)tetrazol-2-yl)-2-oxo-5-methyl-3-hexyl]-2-benzyloxycarbonylamino-4-methylpentan amide

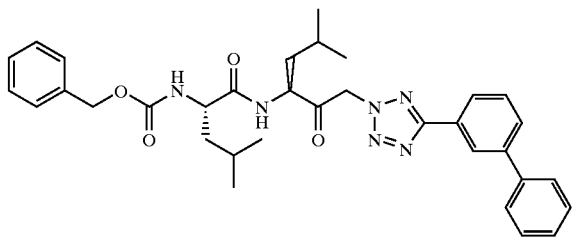

TLC: Rf 0.49 (n-hexane:ethyl acetate 2:1); NMR (200 MHz, CDCl$_3$): δ 8.40 (t, J=1.8 Hz, 1H, aromatic), 8.13 (dt, J=7.2, 1.8 Hz, 1H, aromatic), 7.73–7.37 (m, 7H, aromatic), 7.32 (s, 5H, Cbz-aromatic), 6.66 (d, J=7.8 Hz, 1H, CONH of P1 Leu), 5.75 (d, J=17.6 Hz, 1H, COCH$_2$), 5.59 (d, J=17.6 Hz, 1H, COCH$_2$), 5.18 (d, J=7.8 Hz, 1H, CONH of P2 Leu), 5.11 (s, 2H, PhCH$_2$O), 4.75–4.65 (m, 1H, NCH of P1 Leu), 4.28–4.17 (m, 1H, NCH of P2 Leu), 1.79–1.48 (m, 6H, CH$_2$CHMe$_2$ of each Leu), 0.97–0.88 (m, 12H, CH$_3$ of each Leu).

EXAMPLE 1(25)

2(S)-N-[3(S)-1-(5-(1,1-biphenyl-3-yl)tetrazol-1-yl)-2-oxo-5-methyl-3-hexyl]-2-benzyloxycarbonylamino-4-methylpentan amide

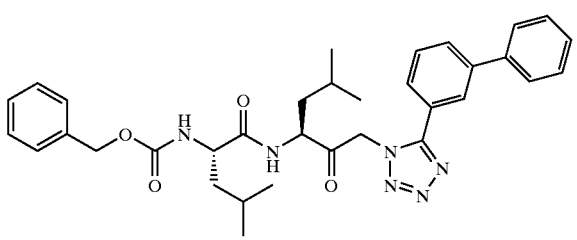

TLC: Rf 0.47 (toluene:ethyl acetate=2:1); NMR (200 MHz, CDCl$_3$): δ 7.84–7.76 (m, 2H, aromatic), 7.64–7.41 (m, 7H, aromatic), 7.41 (s, 5H, Cbz-aromatic), 6.72 (d, J=7 Hz, 1H, CONH of P1 Leu), 5.58 (d, J=18.2 Hz, 1H, COCH$_2$), 5.35 (d, J=18.2 Hz, 1H, COCH$_2$), 5.06–5.03 (m, 3H, PhCH$_2$O and CONH of P2 Leu), 4.57–4.47 (m, 1H, NCH of P1 Leu), 4.19–4.08 (m, 1H, NCH of P2 Leu), 1.64–1.40 (m, 6H, CH$_2$CHMe$_2$ of each Leu), 0.93–0.84 (m, 12H, CH$_3$ of each Leu).

EXAMPLE 1(26)

2(S)-N-[3(S)-1-(5-phenoxymethyltetrazol-2-yl)-2-oxo-5-methyl-3-hexyl]-2-benzyloxycarbonylamino-4-methylpentanamide

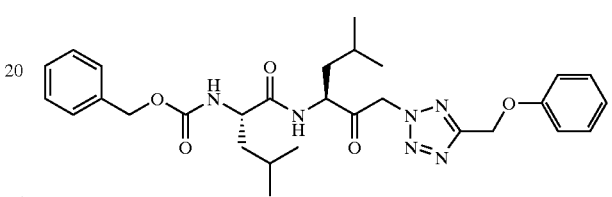

TLC: Rf 0.32 (n-hexane:ethyl acetate=2:1); NMR (200 MHz, CDCl$_3$): δ 7.45–7.20 (m, 7H, Ph of cbz, and 3- and 5-CH of OPh), 7.10–6.95 (m, 3H, 2-, 4- and 6-CH of OPh), 6.63 (br, 1H, NH of Leu-Leu), 5.72 (d, J=17.8 Hz, 1H, CH of COCH$_2$N), 5.54 (d, J=17.8 Hz, 1H, CH of COCH$_2$N), 5.34 (s, 2H, CH$_2$OPh), 5.15 (d, J=7.4 Hz, 1H, NH of cbz-Leu), 5.10 (s, 2H, CH$_2$ of cbz), 4.70–4.55 (m, 1H, CH of Leu), 4.30–4.15 (m, 1H, CH of Leu), 1.80–1.40 (m, 6H, CH$_2$ and CH of Leu), 1.05–0.80 (m, 12H, CH$_3$ of Leu).

EXAMPLE 1(27)

2(S)-N-[3(S)-1-(5-phenoxymethyltetrazol-1-yl)-2-oxo-5-methyl-3-hexyl]-2-benzyloxycarbonylamino-4-methylpentanamide

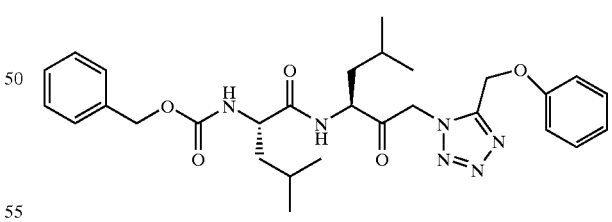

TLC: Rf 0.20 (n-hexane:ethyl acetate=2:1); NMR (200 MHz, CDCl$_3$): δ 7.40–7.20 (m, 7H, Ph of cbz, and 3- and 5-CH of OPh), 7.10–6.90 (m, 3H, 2-, 4- and 6-CH of OPh), 6.73 (br, 1H, NH of Leu-Leu), 5.63 (d, J=17.8 Hz, 1H, CH of COCH$_2$N), 5.43 (d, J=17.8 Hz, 1H, CH of COCH$_2$N), 5.34 (s, 2H, CH$_2$OPh), 5.20–5.05 (m, 3H, NH of cbz-Leu, and CH$_2$ of cbz), 4.60–4.45 (m, 1H, CH of Leu), 4.25–4.10 (m, 1H, CH of Leu), 1.75–1.35 (m, 6H, CH$_2$ and CH of Leu), 1.00–0.75 (m, 12H, CH$_3$ of Leu).

EXAMPLE 1(28)

2 (S)-N-[3(S)-1-(5-benzyloxymethyltetrazol-2-yl)-2-oxo-5-methyl-3-hexyl]-2-benzyloxycarbonylamino-4-methylpentanamide

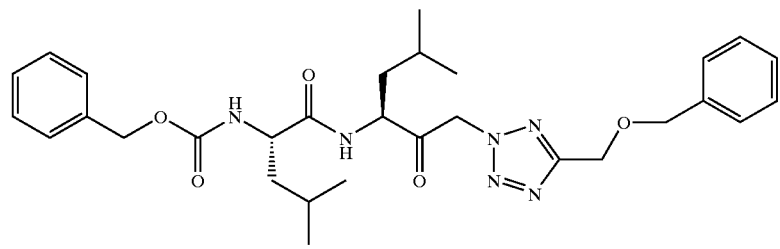

TLC: Rf 0.38 (n-hexane:ethyl acetate=2:1); NMR (200 MHz, CDCl$_3$): δ 7.45–7.20 (m, 10H, Ph), 6.63 (d, J=6.4 Hz, 1H, NH of Leu-Leu), 5.70 (d, J=17.0 Hz, 1H, CH of COCH$_2$N), 5.53 (d, J=17.0 Hz, 1H, CH of COCH$_2$N), 5.17 (d, J=7.6 Hz, 1H, NH of cbz-Leu), 5.10 (s, 2H, CH$_2$of cbz), 4.81 (s, 2H, tetCH$_2$O), 4.70–4.55 (m, 1H, CH of Leu), 4.66 (s, 2H, OCH$_2$Ph), 4.30–4.15 (m, 1H, CH of Leu), 1.80–1.40 (m, 6H, CH$_2$and CH of Leu), 1.05–0.85 (m, 12H, CH$_3$ of Leu).

EXAMPLE 1(29)

2(S)-N-[3(S)-1-(5-benzyloxymethyltetrazol-1-yl)-2-oxo-5-methyl-3-hexyl]-2-benzyloxycarbonylamino-4-methylpentanamide

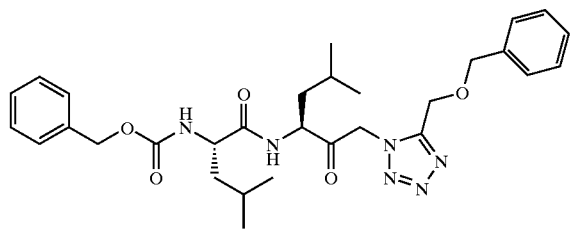

TLC: Rf 0.25 (n-hexane:ethyl acetate=2:1); NMR (200 MHz, CDCl$_3$): δ 7.45–7.20 (m, 10H, Ph), 6.51 (d, J=7.0 Hz, 1H, NH of Leu-Leu), 5.57 (d, J=17.8 Hz, 1H, CH of COCH$_2$N), 5.36 (d, J=17.8 Hz, 1H, CH of COCH$_2$N), 5.20–5.05 (m, 3H, NH of cbz-Leu, and CH$_2$of cbz), 4.80 (s, 2H, tetCH$_2$O), 4.60–4.40 (m, 1H, CH of Leu), 4.48 (s, 2H, OCH$_2$Ph), 4.30–4.10 (m, 1H, CH of Leu), 2.00–1.20 (m, 6H, CH$_2$ and CH of Leu), 1.05–0.75 (m, 12H, CH$_3$ of Leu).

EXAMPLE 1(30)

2 (S)-N-[3(S)-1-(5(4-pyridylmethyl) tetrazol-2-yl)-2-oxo-5-methyl-3-hexyl]-2-benzyloxycarbonylamino-4-methylpentanamide

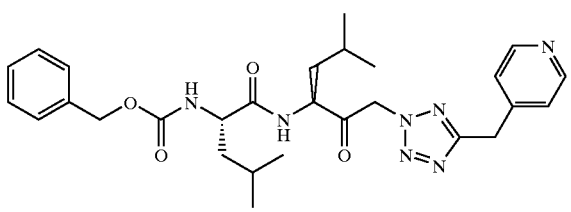

TLC: Rf 0.52 (chloroform:methanol=9:1); NMR (200 MHz, CDCl$_3$):67 8.54 (d, J=6.0 Hz, 2H, 2- and 6-CH of pyr.), 7.33 (s, 5H, Ph), 7.23 (d, J=6.0 Hz, 2H, 3- and 5-CH of pyr.), 6.80–6.55 (m, 1H, NH of Leu-Leu), 5.68 and 5.65 (each d, J=17.8 Hz, total 1H, CH of COCH$_2$N), 5.50 and 5.48 (each d, J=17.8 Hz, total 1H, CH of COCH$_2$N), 5.24–5.05 (m, 3H, NH of cbz-Leu, and CH$_2$of cbz), 4.70–4.55 (m, 1H, CH of Leu), 4.30–4.10 (m, 3H, CH of Leu, and CH$_2$ of tetCH$_2$pyr.), 1.90–1.40 (m, 6H, CH$_2$ and CH of Leu), 1.05–0.80 (m, 12H, CH$_3$ of Leu).

EXAMPLE 1(31)

2(S)-N-[3(S)-1-(5-(4-pyridylmethyl)tetrazol-1-yl)-2-oxo-5-methyl-3-hexyl]-2-benzyloxycarbonylamino-4-methylpentanamide

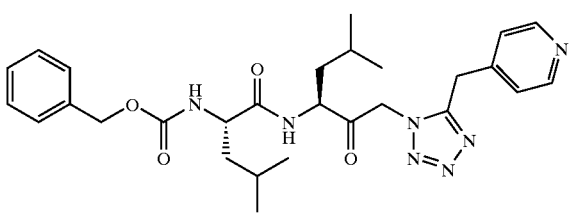

TLC: Rf 0.48 (chloroform:methanol=9:1); NMR (200 MHz, CDCl$_3$): δ 8.55 (d, J=6.2 Hz, 2H, 2- and 6-CH of pyr.), 7.33 (s, 5H, Ph), 7.23 (d, J=6.2 Hz, 2H, 3- and 5-CH of pyr.), 6.75 (br, 1H, NH of Leu-Leu), 5.40–5.00 (m, 5H, CH$_2$ of COCH$_2$N and cbz, and NH of cbz-Leu), 4.40–4.00 (m, 4H, CH of Leu, and CH$_2$ of tetCH$_2$pyr.), 1.90–1.40 (m, 6H, CH$_2$ and CH of Leu), 1.05–0.80 (m, 12H, CH$_3$ of Leu).

EXAMPLE 1(32)

2(S)-N-[3(S)-1-(5-(2-(3-pyridyl)ethyl)tetrazol-2-yl)-
2-oxo-5-methyl-3-hexyl]-2-
benzyloxycarbonylamino-4-methylpentan amide

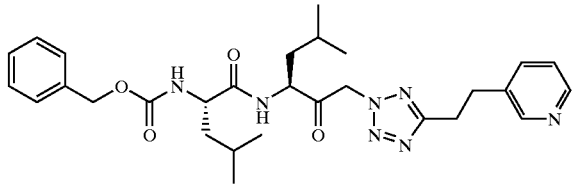

TLC: Rf 0.64 (chloroform:methanol=9:1); NMR (200 MHz, CDCl$_3$): δ 8.50–8.40 (m, 2H, 2- and 6-CH of pyr.), 7.52 (dt, J=7.8, 2.2 Hz, 1H, 4-CH of pyr.), 7.33 (s, 5H, Ph), 7.21 (dd, J=7.8, 4.9 Hz, 1H, 5-CH of pyr.), 6.78 (d, J=6.8 Hz, 1H, NH of Leu-Leu), 5.65 (d, J=17.2 Hz, 1H, CH of COCH$_2$N), 5.48 (d, J=17.2 Hz, 1H, CH of COCH$_2$N), 5.32 (d, J=7.4 Hz, 1H, NH of cbz-Leu), 5.10 (s, 2H, CH$_2$ of cbz), 4.70–4.55 (m, 1H, CH of Leu), 4.30–4.10 (m, 1H, CH of Leu), 3.30–3.05 (m, 4H, CH$_2$ of tetCH$_2$CH$_2$pyr.), 1.80–1.40 (m, 6H, CH$_2$ and CH of Leu), 1.05–0.80 (m, 12H, CH$_3$ of Leu).

EXAMPLE 1(33)

2(S)-N-[3(S)-1-(5-(2-(3-pyridyl)ethyl)tetrazol-1-yl)-
2-oxo-5-methyl-3-hexyl]-2-
benzyloxycarbonylamino-4-methylpentan amide

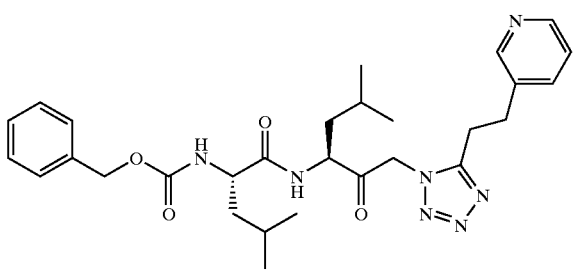

TLC: Rf 0.57 (chloroform:methanol=9:1); NMR (200 MHz, CDCl$_3$): δ 8.54 (d, J=2.0 Hz, 1H, 2-CH of pyr.), 8.44 (dd, J=5.0, 2.0 Hz, 1H, 6-CH of pyr.), 7.53 (dt, J=7.8, 2.0 Hz, 1H, 4-CH of pyr.), 7.31 (s, 5H, Ph), 7.17 (dd, J=7.8, 5.0 Hz, 1H, 5-CH of pyr.), 6.96 (br, 1H, NH of Leu-Leu), 5.66 (d, J=6.2 Hz, 1H, NH of cbz-Leu), 5.30–5.10 (m, 2H, CH$_2$ of COCH$_2$N), 5.08 (s, 2H, CH$_2$ of cbz), 4.35–4.10 (m, 2H, CH of Leu), 3.20–2.90 (m, 4H, CH$_2$ of tetCH$_2$CH$_2$pyr.), 1.75–1.40 (m, 6H, CH$_2$ and CH of Leu), 1.05–0.80 (m, 12H, CH$_3$ of Leu).

EXAMPLE 1(34)

2(S)-N-[3(S)-1-(5-(2,6-difluorophenyl)tetrazol-2-yl)-
2-oxo-5-methyl-3-hexyl]-2-
benzyloxycarbonylamino-4-methylpentan amide

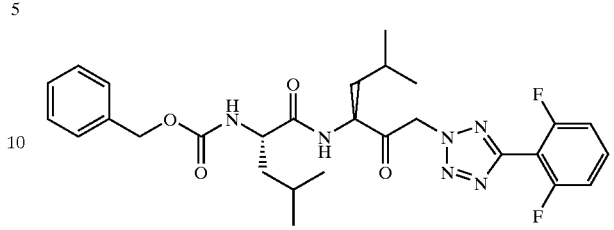

TLC: Rf 0.71 (n-hexane:ethyl acetate=1:1); NMR (200 MHz, CDCl$_3$): δ 7.46 (m, 1H, para H against Tetrazole), 7.32 (brs, 5H, Phenyl Hs), 7.07 (t, J=8.2 Hz, 2H, meta Hs against Tetrazole), 6.67 (brd, J=7.2 Hz, 1H, NH), 5.80 and 5.64 (each d, J=17.5 Hz, each 1H, COCH$_2$), 5.15 (d, J=7.8 Hz, 1H, NH), 5.10 (s, 2H, PhCH$_2$O), 4.69 (m, 1H, alfa CH of Leu), 4.21 (m, 1H, alfa CH of Leu), 1.81–1.38 (m, 6H, CHs and CH$_2$s of isoBu), 1.07–0.78 (m, 12H, CH$_3$s of isoBu).

EXAMPLE 1(35)

2(S)-N-[3(S)-1-(5-(2,6-difluorophenyl)tetrazol-1-yl)-
2-oxo-5-methyl-3-hexyl]-2-
benzyloxycarbonylamino-4-methylpentan amide

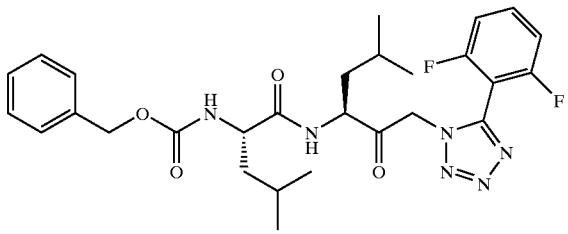

TLC: Rf 0.54 (n-hexane:ethyl acetate=1:1); NMR (200 MHz, CDCl$_3$): δ 7.55 (m, 1H, para H against Tetrazole) 7.34 (brs, 5H, Phenyl Hs), 7.09 (t, J=8.2 Hz, 2H, meta Hs against Tetrazole), 6.52 (brd, J=7.2 Hz, 1H, NH), 5.48 and 5.31 (each d, J=18.3 Hz, each 1H, COCH$_2$), 5.09 (s, 2H, PhCH$_2$O), 5.04 (d, J=7.4 Hz, 1H, NH), 4.44 (m, 1H, alfa CH of Leu), 4.11 (m, 1H, alfa CH of Leu), 1.85–1.20 (m, 6H, CHs and CH$_2$s of isoBu), 1.02—0.78 (m, 12H, CH$_3$S of isoBu).

EXAMPLE 1(36)

2(S)-N-[3(S)-1-(5-(4-trifluoromethylphenyl)
tetrazol-2-yl)-2-oxo-5-methyl-3-hexyl]-2-
benzyloxycarbonylamino-4-methyl pentanamide

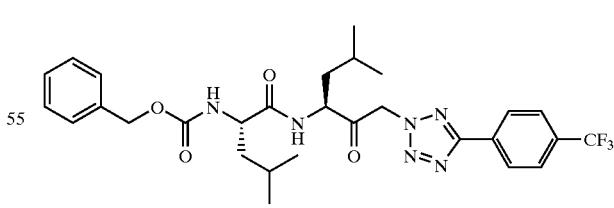

TLC: Rf 0.38 (ethyl acetate:n-hexane=1:2); NMR (200 MHz, CDCl$_3$): δ 8.27 (d, J=8.0 Hz, 2H, m-position against CF$_3$), 7.75 (d, J=8.0 Hz, 2H, o-position against CF$_3$), 7.33 (m, 5H, aromatic Hs), 6.61 (brd, J=9.4 Hz, 1H, NH of amide), 5.76 and 5.60 (each d, J=17.4 Hz, each 1H, COCH$_2$Het), 5.13 (m, 3H, NH of Z-Leu, and CH$_2$ of Z), 4.70 (m, 1H, CHCO of P1-Leu), 4.21 (m, 1H, CHCO of P2-Leu), 1.85–1.45 (m, 6H, CHCH$_2$ of i-Bu), 1.05–0.85 (m, 12H, CH$_3$ of i-Bu).

EXAMPLE 1(37)

2(S)-N-[3(S)-1-(5-(3,5-difluoro-4-dimethylaminophenyl) tetrazol-2-yl)-2-oxo-5-methyl-3-hexyl]-2-benzyloxycarbonyl amino-4-methylpentanamide

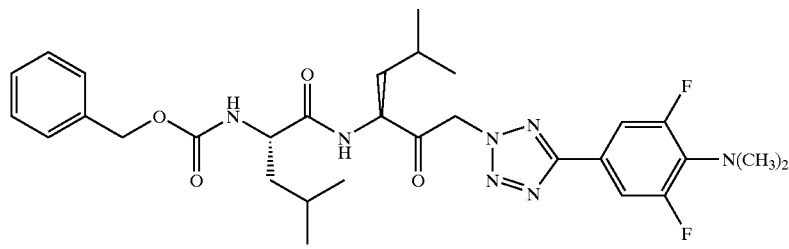

TLC: Rf 0.29 (n-hexane:ethyl acetate=7:3); NMR (200 MHz, CDCl$_3$): δ 7.61 (d, J=9.3 Hz, 2H, ortho Hs against Tetrazole), 7.33 (brs, 5H, Phenyl Hs), 6.65 (brd, J=7.2 Hz, 1H, NH), 5.70 and 5.55 (each d, J=17.6 Hz, each 1H, COCH$_2$), 5.18 (d, J=7.4 Hz, 1H, NH), 5.11 (s, 2H, PhCH$_2$O), 4.68 (m, 1H, alfa CH of Leu), 4.22 (m, 1H, alfa CH of Leu), 2.96 (t, J=2.0 Hz, 6H, N(CH$_3$)$_2$), 1.80–1.40 (m, 6H, CHs and CH$_2$s of isoBu), 1.04–0.83 (m, 12H, CH$_3$s of isoBu).

EXAMPLE 1(38)

2(S)-N-[3(S)-1-(5-(4-fluorophenyl)tetrazol-2-yl)-2-oxo-5-methyl-3-hexyl]-2-benzyloxycarbonylamino-4-methylpentanamide

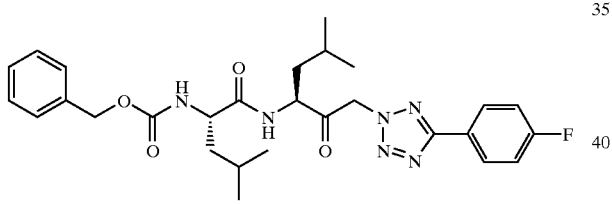

TLC: Rf 0.59 (n-hexane:ethyl acetate=6:4); NMR (200 MHz, CDCl$_3$): δ 8.13 (dd, J=9.0, 5.5 Hz, 2H, meta CH against F), 7.32 (s, 5H, Ph of cbz), 7.16 (t, J=9.0 Hz, 1H, ortho CH against F), 6.73 (d, J=6.4 Hz, 1H, NH of Leu-Leu), 5.73 (d, J=17.6 Hz, 1H, CH of LeuCH$_2$N), 5.57 (d, J=17.6 Hz, 1H, CH of LeuCH$_2$N), 5.23 (d, J=7.4 Hz, 1H, NH of cbz-Leu), 5.10 (s, 2H, CH$_2$ of cbz), 4.75–4.60 (m, 1H, CH of Leu), 4.30–4.15 (m, 1H, CH of Leu), 1.85–1.40 (m, 6H, CH$_2$ and CH of Leu), 1.05–0.75 (m, 12H, CH$_3$ of Leu).

EXAMPLE 1(39)

2(S)-N-[3(S)-1-(5-(4-benzyloxyphenyl)tetrazol-2-yl)-2-oxo-5-methyl-3-hexyl]-2-benzyloxycarbonylamino-4-methylpentanamide

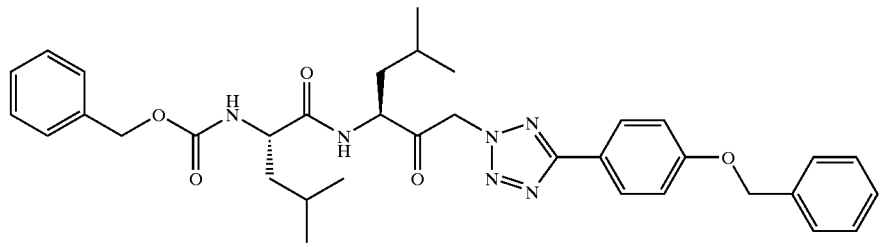

TLC: Rf 0.51 (n-hexane:ethyl acetate=6:4); NMR (200 MHz, CDCl$_3$): δ 8.07 (d, J=9.0 Hz, 2H, ortho CH against tet.), 7.50–7.20 (m, 10H, two Phs), 7.06 (t, J=9.0 Hz, 1H, meta CH against tet.), 6.63 (d, J=7.4 Hz, 1H, NH of Leu-Leu), 5.69 (d, J=17.5 Hz, 1H, CH of LeuCH$_2$N), 5.55 (d, J=17.5 Hz, 1H, CH of LeuCH$_2$N), 5.17 (d, J=7.8 Hz, 1H, NH of cbz-Leu), 5.12 (s, 2H, CH$_2$ of PhCH$_2$O), 5.11 (s, 2H, CH$_2$ of PhCH$_2$O), 4.75–4.60 (m, 1H, CH of Leu), 4.30–4.10 (m, 1H, CH of Leu), 1.80–1.40 (m, 6H, CH$_2$ and CH of Leu), 1.05–0.80 (m, 12H, CH$_3$ of Leu).

EXAMPLE 1(40)

2(S)-N-[3(S)-1-(5-(perfluorophenyl)tetrazol-2-yl)-2-oxo-5-methyl-3-hexyl]-2-benzyloxycarbonylamino-4-methylpentanamide

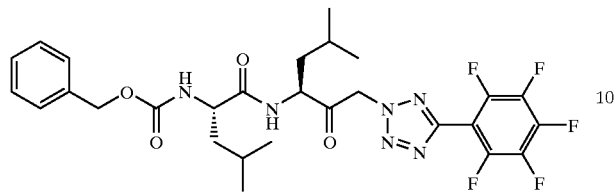

TLC: Rf 0.40 (n-hexane:ethyl acetate=7:3); NMR (200 MHz, CDCl$_3$): δ 7.33 (brs, 5H, Phenyl Hs), 6.61 (brd, J=7.6 Hz, 1H, NH), 5.81 and 5.65 (each d, J=17.4 Hz, each 1H, COCH$_2$), 5.18–5.07 (m, 1H, NH), 5.11 (s, 2H, PhCH$_2$O), 4.67 (m, 1H, alfa CH of Leu), 4.21 (m, 1H, alfa CH of Leu), 1.81–1.40 (m, 6H, CHs and CH$_2$S of isoBu), 1.03–0.84 (m, 12H, CH$_3$s of isoBu).

EXAMPLE 1(41)

2(S)-N-[3(S)-1-(5-(perfluorophenyl)tetrazol-1-yl)-2-oxo-5-methyl-3-hexyl]-2-benzyloxycarbonylamino-4-methylpentanamide

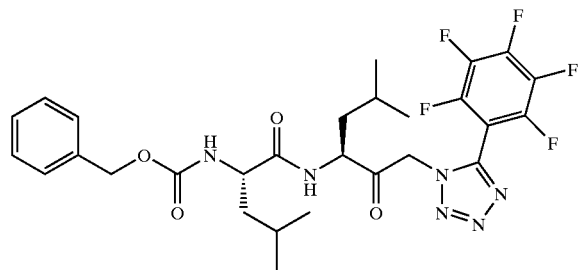

TLC: Rf 0.27 (n-hexane:ethyl acetate=7:3); NMR (200 MHz, CDCl$_3$): δ 7.34 (brs, 5H, Phenyl Hs), 6.52 (brs, 1H, NH), 5.43 (s, 2H, COCH$_2$), 5.10 (s, 2H, PhCH$_2$O), 4.94 (d, J=6.9 Hz, 1H, NH), 4.22 (m, 1H, alfa CH of Leu), 4.04 (m, 1H, alfa CH of Leu), 1.72–1.30 (m, 6H, CHs and CH$_2$s of isoBu), 1.02–0.78 (m, 12H, CH$_3$s of isoBu).

EXAMPLE 1(42)

2(S)-N-[3(S)-1-(5-(2,6-bis(trifluoromethyl)phenyl)tetrazol-2-yl)-2-oxo-5-methyl-3-hexyl]-2-benzyloxycarbonylamino-4-methylpentanamide

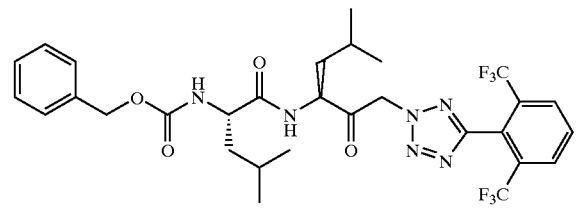

TLC: Rf 0.31 (n-hexane:ethyl acetate=7:3); NMR (200 MHz, CDCl$_3$): δ 8.04 (d, J=8.2 Hz, 2H, meta Hs against Tetrazole), 7.81 (brt, J=8.2 Hz, 1H, para H against Tetrazole), 7.34 (brs, 5H, Phenyl Hs), 6.57 (brd, J=6.8 Hz, 1H, NH), 5.79 and 5.65 (each d, J=18.2 Hz, each 1H, COCH$_2$), 5.17–5.07 (m, 1H, NH), 5.11 (s, 2H, PhCH$_2$O), 4.69 (m, 1H, alfa CH of Leu), 4.21 (m, 1H, alfa CH of Leu), 1.82–1.44 (m, 6H, CHs and CH$_2$s of isoBu), 1.01–0.80 (m, 12H, CH$_3$s of isoBu).

EXAMPLE 1(43)

2(S)-N-[3(S)-1-(5-(2,6-bis(trifluoromethyl)phenyl)tetrazol-1-yl)-2-oxo-5-methyl-3-hexyl]-2-benzyloxycarbonyl amino-4-methylpentanamide

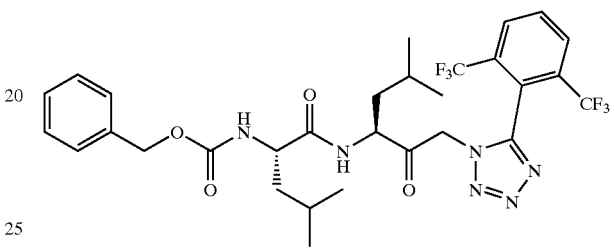

TLC: Rf 0.44 (n-hexane:ethyl acetate=1:1); NMR (200 MHz, CDCl$_3$): δ 8.14–8.02 (m, 2H, meta Hs against Tetrazole), 7.92 (brt, J=8.2 Hz, 1H, para H against Tetrazole), 7.34 (brs, 5H, Phenyl Hs), 6.55 (brd, J=6.8 Hz, 1H, NH), 5.15 and 4.99 (each d, J=17.8 Hz, each 1H, COCH$_2$), 5.12–4.97 (m, 1H, NH), 5.05 (s, 2H, PhCH$_2$O), 4.45 (m, 1H, alfa CH of Leu), 4.07 (m, 1H, alfa CH of Leu), 1.72–1.30 (m, 6H, CHs and CH$_2$s of isoBu), 1.00–0.78 (m, 12H, CH$_3$s of isoBu).

EXAMPLE 1(44)

2(S)-N-[3(S)-1-(5-(4-nitrophenyl)tetrazol-2-yl)-2-oxo-5-methyl-3-hexyl]-2-benzyloxycarbonylamino-4-methylpentanamide

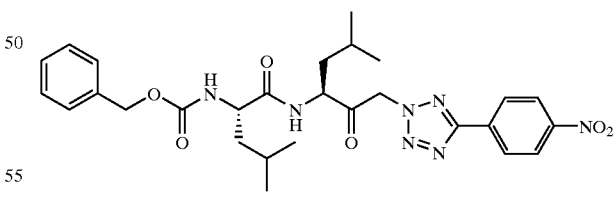

TLC: Rf 0.17 (n-hexane:ethyl acetate=7:3); NMR (200 MHz, CDCl$_3$): δ 8.34 (s, 4H, CHs of Nitrophenyl), 7.33 (brs, 5H, Phenyl Hs), 6.66 (brd, J=6.8 Hz, 1H, NH), 5.78 and 5.63 (each d, J=17.5 Hz, each 1H, COCH$_2$), 5.17 (d, J=7.2 Hz, 1H, NH), 5.13 and 5.10 (each d, J=12.0 Hz, each 1H, PhCH$_2$O), 4.69 (m, 1H, alfa CH of Leu), 4.23 (m, 1H, alfa CH of Leu), 1.83–1.64 (m, 6H, CHs and CH$_2$s of isoBu), 1.07–0.84 (m, 12H, CH$_3$s of isoBu).

EXAMPLE 1(45)

2(S)-N-[3(S)-1-(5-(3-benzyloxyphenyl)tetrazol-2-yl)-2-oxo-5-methyl-3-hexyl]-2-benzyloxycarbonylamino-4-methylpentanamide

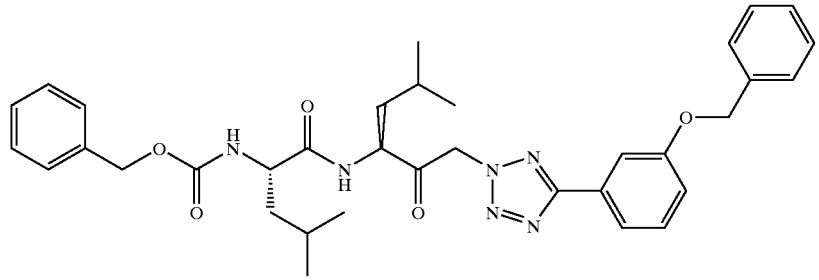

TLC: Rf 0.65 (n-hexane:ethyl acetate=6:4); NMR (200 MHz, CDCl$_3$): δ 7.85–7.70 (m, 2H, ortho CH against tet.), 7.50–7.20 (m, 11H, Ph of cbz and BnO, and meta CH against tet.), 7.08 (ddd, J=8.4, 2.6, 1.0 Hz, 1H, para CH against tet.), 6.64 (d, J=8.0 Hz, 1H, NH of Leu-Leu), 5.72 (d, J=17.2 Hz, 1H, CH of LeuCH$_2$N), 5.58 (d, J=17.2 Hz, 1H, CH of LeuCH$_2$N), 5.25–5.00 (m, 5H, NH of cbz-Leu, and CH$_2$ of cbz and BnO), 4.75–4.60 (m, 1H, CH of Leu), 4.30–4.15 (m, 1H, CH of Leu), 1.80–1.40 (m, 6H, CH$_2$ and CH of Leu), 1.05–0.80 (m, 12H, CH$_3$ of Leu).

EXAMPLE 1(46)

2(S)-N-[3(S)-1-(5-(2-benzyloxyphenyl)tetrazol-2-yl)-2-oxo-5-methyl-3-hexyl]-2-benzyloxycarbonylamino-4-methylpentanamide

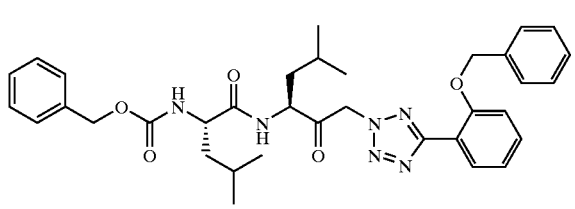

TLC: Rf 0.49 (n-hexane:ethyl acetate=6:4); NMR (300 MHz, CDCl$_3$): δ 8.02 (dd, J=7.8, 1.8 HZ, 1H, ortho CH against tet.), 7.50–7.25 (m, 11H, CH of Phs), 7.15–7.05 (m, 2H, meta CH against tet.), 6.57 (d, J=7.2 Hz, 1H, NH of Leu-Leu), 5.71 (d, J=17.6 Hz, 1H, CH of LeuCH$_2$N), 5.60 (d, J=17.6 Hz, 1H, CH of LeuCH$_2$N), 5.23 (s, 2H, CH$_2$ of BnOPh), 5.20–5.00 (m, 3H, NH of cbz-Leu, and CH$_2$ of cbz), 4.75–4.60 (m, 1H, CH of Leu), 4.25–4.15 (m, 1H, CH of Leu), 1.75–1.40 (m, 6H, CH$_2$ and CH of Leu), 1.05–0.80 (m, 12H, CH$_3$ of Leu).

EXAMPLE 1(47)

2(S)-N-[4-methyl-2-oxo-1-(tetrazol-2-yl)-3-pentyl]-1-benzyl oxycarbonyl-2-pyrrolidinecarboxamide

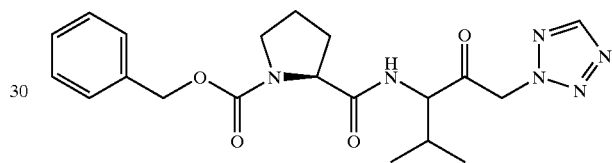

TLC: Rf 0.74 (ethyl acetate); NMR (DMSO-d$_6$): δ 8.98–8.96 (1H, m), 8.57–8.40 (1H, m), 7.37–7.16 (5H, m), 6.00–5.65 (2H, m), 5.13–4.87 (2H, m), 4.48–4.24 (2H, m), 3.60–3.34 (2H, m), 2.37–2.03 (2H, m), 2.03–1.75 (3H, m), 0.95–0.77 (6H, m).

EXAMPLE 1(48)

2(S)-N-[4-methyl-2-oxo-1-(tetrazol-1-yl)-3-pentyl]-1-benzyl oxycarbonyl-2-pyrrolidinecarboxamide

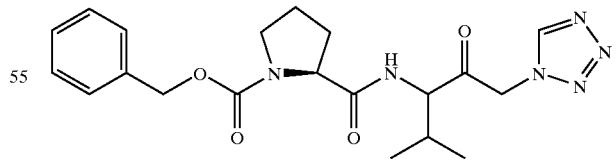

TLC: Rf 0.49 (ethyl acetate); NMR (200 MHz, DMSO-d$_6$): δ 9.27–9.19 (1H, m), 8.56–8.39 (1H, m), 7.35–7.15 (5H, m), 5.76–5.28 (2H, m), 5.11–4.86 (2H, m), 4.49–4.25 (2H, m), 3.58–3.20 (2H, m), 2.38–2.03 (2H, m), 2.03–1.72 (3H, m), 0.93–0.74 (6H, m).

EXAMPLE 1(49)

N-[2-oxo-4-phenyl-1-(tetrazol-2-yl)-3-butyl]-2-benzyloxy carbonylaminoacetamide

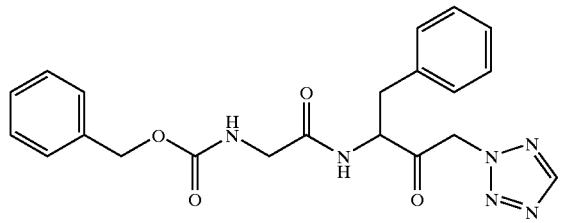

TLC: Rf 0.51 (chloroform:methanol:water=9:1:0.1); NMR (200 MHz, DMSO-$d_6$): δ 8.99 (1H, s), 8.56 (1H, d, J=7.6 Hz), 7.51 (1H, t, J=6.0 Hz), 7.37–7.18 (10H, m), 6.00 (1H, d, J=18 Hz), 5.84 (1H, d, J=18 Hz), 5.03 (2H, s), 4.75–4.63 (1H, m), 3.62 (2H, d, J=6.0 Hz), 3.18 (1H, dd, J=5.0, 14 Hz), 2.89 (1H, dd, J=9.6, 14 Hz).

EXAMPLE 1(50)

N-[2-oxo-4-phenyl-1-(tetrazol-1-yl)-3-butyl]-2-benzyloxy carbonylaminoacetamide

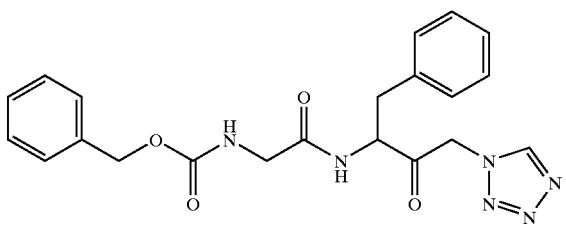

TLC: Rf 0.42 (chloroform:methanol:water=9:1:0.1); NMR (200 MHz, DMSO-$d_6$): δ 9.20 (1H, s), 8.58 (1H, d, J=8.0 Hz), 7.51 (1H, t, J=5.8 Hz), 7.34–7.17 (10H, m), 5.74 (1H, d, J=18.6 Hz), 5.57 (1H, d, J=18.6 Hz), 5.03 (2H, s), 4.71–4.60 (1H, m), 3.62 (2H, dd, J=2.2, 5.8 Hz), 3.17 (1H, dd, J=4.4, 14.0 Hz), 2.89 (1H, dd, J=10.0, 14.0 Hz).

EXAMPLE 1(51)

2(S)-N-[3(S)-4-methyl-2-oxo-1-(5-phenyltetrazol-2-yl)-3-pentyl]-1-(2(S)-2-methoxycarbonylamino-3-methylbutyryl)-2-pyrrolidinecarboxamide

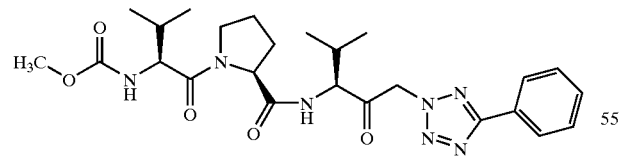

TLC: Rf 0.52 (chloroform:methanol=9:1); NMR (300 MHz, CDCl$_3$): δ 8.19–8.11 and 7.55–7.46 (m, total 6H, aromatic Hs and NH), 5.71 and 5.58 (each d, J=17.4 Hz, each 1H, COCH$_2$tet), 5.39 (brd, J=9.3 Hz, 1H, NH), 4.66–4.58, 4.53–4.46 and 4.35–4.26 (each m, each 1H, NCHCO), 3.84–3.57 (m, 2H, NCH$_2$ of Pro), 3.67 (s, 3H, Me of MeOCON), 2.43–1.87 (m, total 6H, CHs of isopropyl group, and other CH$_2$s of Pro), 1.07–0.94 (m, 12H, Mes of Val).

EXAMPLE 1(52)

2(S)-N-[3(S)-4-methyl-2-oxo-1-(5-phenyltetrazol-1-yl)-3-pentyl]-1-(2(S)-2-methoxycarbonylamino-3-methylbutyryl)-2-pyrrolidinecarboxamide

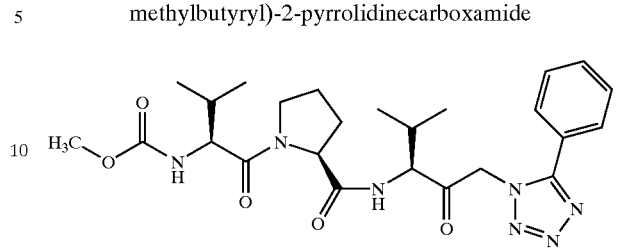

TLC: Rf 0.50 (chloroform:methanol=9:1); NMR (300 MHz, CDCl$_3$): δ 7.67–7.45 (m, total 6H, aromatic Hs and NH), 5.50 and 5.36 (each d, J=18.4 Hz, each 1H, COCH$_2$tet), 5.31 (d, J=9.0 Hz, 1H, NH), 4.60 (dd, J=8.1 Hz, 3.0 Hz, 1H, NCHCO of Pro), 4.35–4.24 (m, total 2H, NCHCO of Val), 3.83–3.55 (m, 2H, NCH$_2$ of Pro), 3.67 (s, 3H, Me of MeOCON), 2.40–1.85 (m, total 6H, CHs of isopropyl group, and other CH$_2$s of Pro), 1.08–0.83 (m, 12H, Mes of Val).

EXAMPLE 1(53)

2(S)-N-[3(S)-4-methyl-2-oxo-1-(tetrazol-2-yl)-3-pentyl]-1-(2(S)-2-methoxycarbonylamino-3-methylbutyryl)-2-pyrrolidine carboxamide

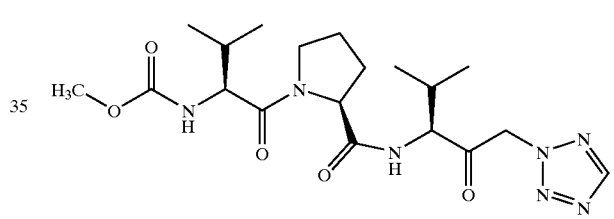

TLC: Rf 0.59 (chloroform:methanol=9:1); NMR (200 MHz, CDCl$_3$): δ 8.57 (s, 1H, H5 of tet), 7.61–7.46 (m, 1H, NH), 5.75 and 5.58 (each d, J=17.6 Hz, each 1H, COCH$_2$tet), 5.42 (brd, J=9.2 Hz, 1H, NH), 4.66–4.53, 4.51–4.48 and 4.48–4.41 (each m, each 1H, NCHCO), 3.90–3.54 (m, 2H, NCH$_2$ of Pro), 3.67 (s, 3H, Me of MeOCON), 2.48–1.82 (m, total 6H, CHs of isopropyl group, and other CH$_2$s of Pro), 1.10–0.83 (m, 12H, Mes of Val).

EXAMPLE 1(54)

2(S)-N-[3(S)-4-methyl-2-oxo-1-(tetrazol-1-yl)-3-pentyl]-1-(2(S)-2-methoxycarbonylamino-3-methylbutyryl)-2-pyrrolidine carboxamide

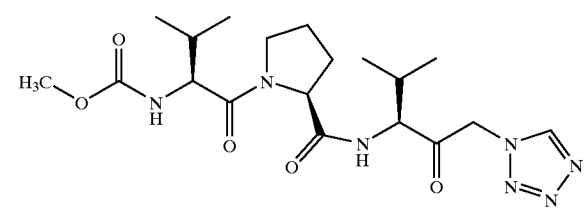

TLC: Rf 0.55 (chloroform:methanol=9:1); NMR (200 MHz, CDCl$_3$): δ 8.79 (s, 1H, H5 of tet), 7.75–7.61 (m, 1H, NH), 5.54 and 5.39 (each d, J=18.4 Hz, each 1H, COCH₂tet), 5.42–5.33 (m, 1H, NH), 4.65–4.57 (m, 1H, NCHCO), 4.35–4.15 (m, 2H, NCHCO), 3.90–3.50 (m, 2H, NCH₂ of Pro), 3.68 (s, 3H, Me of MeOCON), 2.43–1.82 (m, total 6H, CHs of isopropyl group, and other CH₂s of Pro), 1.10–0.83 (m, 12H, Mes of Val).

EXAMPLE 2(1)–2(10)

By the same procedure described in Reference Example3→Example 1 (optionally followed by conversion to salt) using the compound corresponding to reference example 2, the following compounds were given.

EXAMPLE 2(1)

3-benzyloxycarbonylamino-1-[5-(2,6-dichlorophenylthio) tetrazol-2-yl]butan-2-one

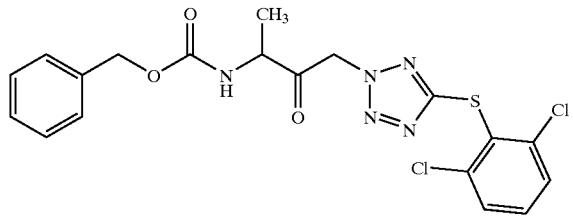

TLC: Rf 0.57 (n-hexane:ethyl acetate=1:1).

EXAMPLE 2(2)

3-benzyloxycarbonylamino-1-[5-(2,6-dichlorophenylthio) tetrazol-1-yl]butan-2-one

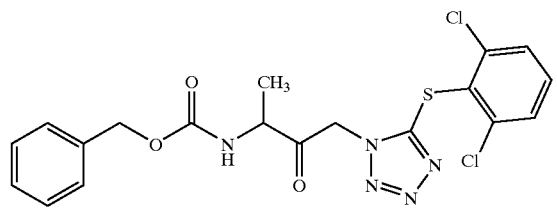

TLC: Rf 0.45 (n-hexane:ethyl acetate=1:1); NMR (200 MHz, CDCl₃): δ 7.47–7.27 (8H, m), 5.49 (2H, m), 5.35 (1H, m), 5.16 (2H, s), 4.51 (1H, m), 1.46 (3H, d, J=7.2 Hz).

EXAMPLE 2(3)

7-amino-3-benzyloxycarbonylamino-1-[5-(2,6-dichlorophenyl thio)tetrazol-2-yl]heptan-2-one trifluoroacetate

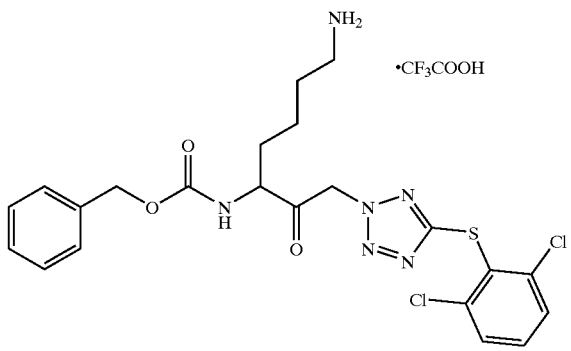

TLC: Rf 0.32 (chloroform:methanol:acetic acid=8:1:1); NMR (200 MHz, DMSO-d₆): δ 7.83 (1H, d, J=7.5 Hz, NH), 7.79–7.46 (6H, m, NH3 and aromatic Hs), 7.47–7.26 (5H, m, aromatic Hs), 5.98 (2H, brs, COCH₂tet), 5.07 (2H, s, PhCH₂O), 4.36–4.19 (1H, m, CH of Lys), 2.87–2.65 (2H, m, CH₂N). 1.92–1.17 (6H, m, CH₂s of Lys).

EXAMPLE 2(4)

7-amino-3-benzyloxycarbonylamino-1-[5-(2,6-dichlorophenyl thio)tetrazol-1-yl]heptan-2-one trifluoroacetate

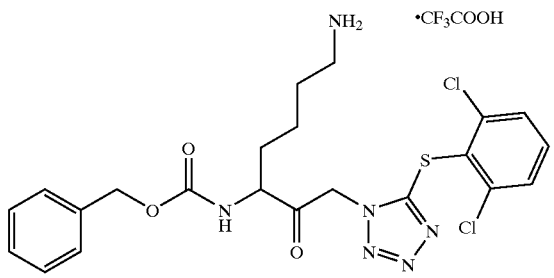

TLC: Rf 0.26 (chloroform:methanol:acetic acid=8:1:1); NMR (200 MHz, DMSO-d₆): δ 7.97 (1H, d, J=7.0 Hz, NH), 7.85–7.49 (6H, m, NH3 and aromatic Hs), 7.45–7.19 (5H, m, aromatic Hs), 5.79 (2H, brs, COCH₂tet), 5.10 (2H, s, PhCH₂O), 4.44–4.26 (1H, m, CH of Lys), 2.90–2.67 (2H, m, CH₂N). 1.96–1.15 (6H, m, CH₂s of Lys).

EXAMPLE 2(5)

3-benzyloxycarbonylamino-4-methyl-1-(tetrazol-2-yl)pentan-2-one

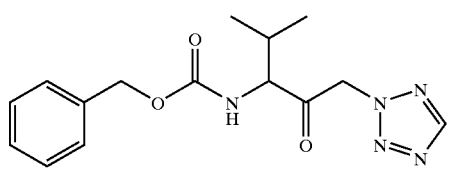

TLC: Rf 0.58 (n-hexane:ethyl acetate=1:1); NMR (200 MHz, CDCl₃): δ 8.57 (1H, s), 7.36 (5H, s), 5.72 (1H, d, J=25.6 Hz), 5.58 (1H, d, J=25.6 Hz), 5.28 (1H, brs), 5.13 (2H, s), 4.41 (1H, m), 2.34–2.17 (1H, m), 1.07 (3H, d, J=6.8 Hz), 0.94 (3H, d, J=6.8 Hz).

EXAMPLE 2(6)

3-benzyloxycarbonylamino-4-methyl-1-(tetrazol-1-yl)pentan-2-one

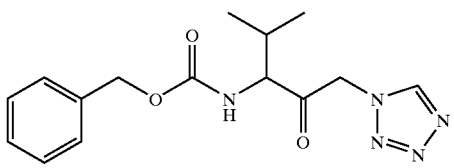

TLC: Rf 0.20 (n-hexane:ethyl acetate=1:1); NMR (200 MHz, CDCl$_3$): δ 8.71 (1H, s), 7.36 (5H, s), 5.45 (2H, s), 5.30 (1H, brs), 5.12 (2H, s), 4.29 (1H, m), 2.31–2.14 (1H, m), 1.07 (3H, d, J=6.8 Hz), 0.96 (3H, d, J=6.8 Hz).

EXAMPLE 2(7)

3-benzyloxycarbonylamino-4-phenyl-1-(tetrazol-2-yl)butan-2-one

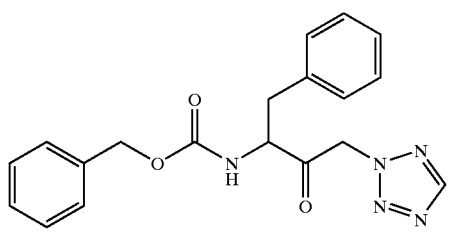

TLC: Rf 0.68 (n-hexane:ethyl acetate=1:1); NMR (200 MHz, DMSO-d$_6$): δ 8.98 (1H, s), 7.90 (1H, d, J=8.2 Hz), 7.40–7.13 (10H, m), 6.01 (2H, s), 5.01 (2H, s), 4.68–4.50 (1H, m), 3.25–3.15 (1H, m), 2.88–2.76 (1H, m).

EXAMPLE 2 (8)

3-benzyloxycarbonylamino-4-phenyl-1-(tetrazol-1-yl)butan-2-one

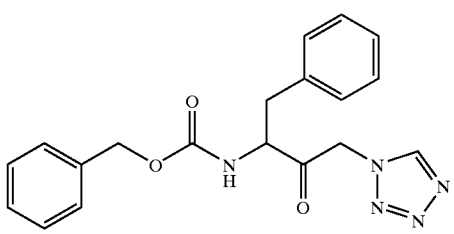

TLC: Rf 0.22 (n-hexane:ethyl acetate=1:1); NMR (200 MHz, DMSO-d$_6$): δ 9.27 (1H, s), 7.92 (1H, d, J=8.0 Hz), 7.40–7.10 (10H, m), 5.76 (2H, s), 5.01 (2H, s), 4.62–4.51 (1H, m), 3.24–3.15 (1H, m), 2.86–2.74 (1H, m).

EXAMPLE 2(9)

3-benzyloxycarbonylamino-4-(4-hydroxyphenyl)-1-(5-(2,6-dichlorophenylthio)tetrazol-2-yl)butan-2-one

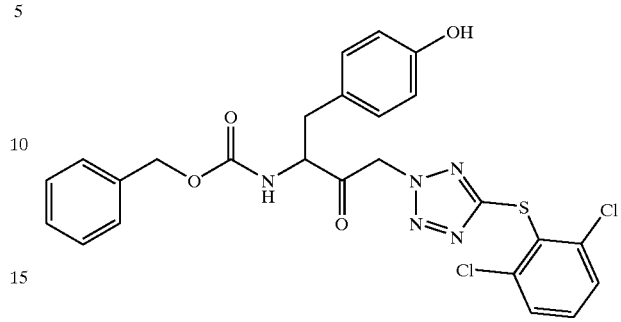

TLC: Rf 0.51 (n-hexane:ethyl acetate=1:1); NMR (200 MHz, CDCl$_3$): δ 7.58–7.14 (m, 8H, aromatic Hs), 6.98 (d, J=8.4 Hz, 2H, aromatic Hs), 6.74 (d, J=8.4 Hz, 2H, aromatic Hs), 5.59–4.97 (m, 4H, NH, OH and COCH$_2$), 5.09 (s, 2H, PhCH$_2$O), 4.67–4.42 (m, 1H, CH of Tyr), 2.99 (d, J=7.0 Hz, 2H, CH$_2$ of Tyr).

EXAMPLE 2(10)

3-benzyloxycarbonylamino-4-(4-hydroxyphenyl)-1-(5-(2,6-dichlorophenylthio)tetrazol-1-yl)butan-2-one

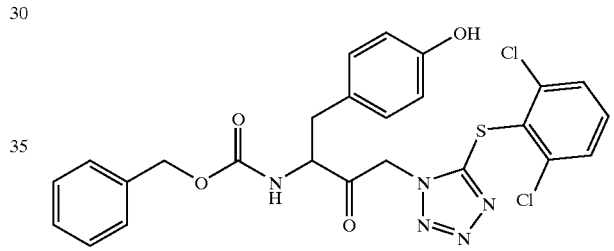

TLC: Rf 0.38 (n-hexane:ethyl acetate=1:1); NMR (200 MHz, CDCl$_3$): δ 7.49–7.14 (m, 8H, aromatic Hs), 7.04 (d, J=8.8 Hz, 2H, aromatic Hs), 6.83 (d, J=8.8 Hz, 2H, aromatic Hs), 5.53–5.00 (m, 4H, NH, OH and COCH$_2$), 5.15 (s, 2H, PhCH$_2$O), 4.70–4.52 (m, 1H, CH of Tyr), 3.13–2.95 (m, 2H, CH$_2$ of Tyr).

EXAMPLE 3

2(S)-N-[3(S)-1-(5-oxo-3-phenyl-1,2,4-oxadiazolin-4-yl)-2-oxo-5-methyl-3-hexyl]-2-benzyloxycarbonylamino-4-methyl pentanamide

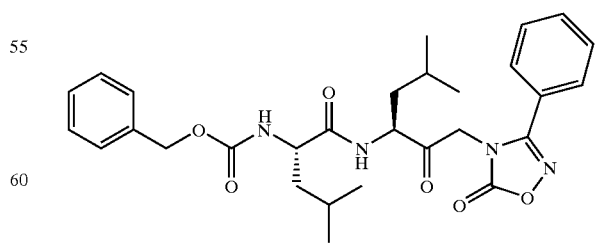

Under atmosphere of argon, a solution of 5-oxo-3-phenyl-1,2,4-oxadiazoline (214 mg) and potassium carbonate (364 mg) in DMF (5 ml) was stirred for 30 minutes at room temperature. Thereto was added the compound prepared in reference example 3 (300 mg) and the mixture was stirred for 2 hours at room temperature. To the reaction solution was added water and was extracted with ethyl acetate. The aqueous layer was extracted with ethyl acetate and the combined organic layer was washed with water, a saturated aqueous solution of sodium bicarbonate and saturated aqueous solution of sodium chloride, dried and was concentrated. The residue was purified by column chromatography on silica gel (n-hexane:ethyl acetate=3:1) to give the title compound (234 mg) having the following physical data.

TLC: Rf 0.36 (ethyl acetate:n-hexane=1:2, HPTLC); NMR (300 MHz, DMSO-d$_6$): δ 8.56 and 8.42 (each d, J=7.2 Hz, totally 1H, NH of amide), 7.70–7.04 (m, 11H, aromatic Hs and NH of amide), 5.10–4.90 (m, 2H, CH$_2$ of Z), 4.90–4.50 (m, 2H, COCH$_2$Het), 4.23 (m, 1H, CHCO of P1-Leu), 3.99 (m, 1H, CHCO of P2-Leu), 1.70–1.20 (m, 6H, CHCH$_2$ of Leu), 0.95–0.64 (m, 12H, CH$_3$ of Leu).

EXAMPLE 3(1)–3(17)

By the same procedure as described in example 1 or example 3 using the compounds prepared in reference example 3 or a corresponding compound, the following compound were given.

EXAMPLE 3(1)

2(S)-N-[3(S)-1-(5-oxo-3-benzyl-1,2,4-oxadiazolin-4-yl)-2-oxo-5-methyl-3-hexyl]-2-benzyloxycarbonylamino-4-methyl pentanamide

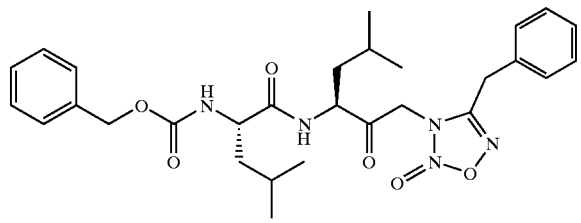

TLC: Rf 0.20 (ethyl acetate:n-hexane=1:2); NMR (200 MHz, DMSO-d$_6$): δ 8.50 (d, J=7.0 Hz, 1H, NH of Z-Leu), 7.53 (d, J=7.6 Hz, 1H, NH of Leu-Leu), 7.39–7.20 (m, 10H, aromatic Hs), 5.00 (s, 2H, CH$_2$ of CBZ), 4.70 (d, J=18.8 Hz, 1H, COCH$_2$), 4.51 (d, J=18.8 Hz, 1H, COCH$_2$) 4.29 (m, 1H, alfa CH of P1-Leu), 4.05 (m, 1H, alfa CH of P2-Leu), 3.84 (s, 2H, CH$_2$Het), 1.78–1.30 (m, 6H, CHCH$_2$ of i-Bu), 0.90–0.80 (m, 12H, CH$_3$ of i-Bu).

EXAMPLE 3(2)

2(S)-N-[3(S)-1-(5-oxo-3-(2-pyridyl)-1,2,4-oxadiazolin-4-yl)-2-oxo-5-methyl-3-hexyl]-2-benzyloxycarbonylamino-4-methylpentanamide

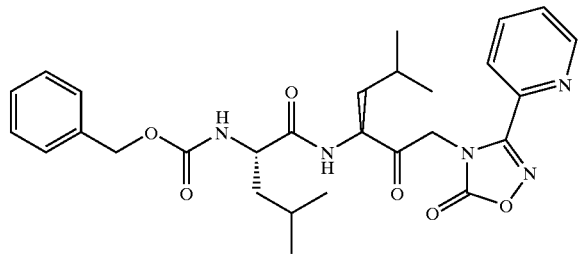

TLC: Rf 0.65 (n-hexane:ethyl acetate=1:1); NMR (200 MHz, CDCl$_3$): δ 8.59 (brd, J=5.4 Hz, 1H, 6-position of Py), 8.05 (d, J=7.8 Hz, 1H, 3-position of Py), 7.80 (dt, J=1.6, 7.8 Hz, 1H, 4-position of Py), 7.41 (dd, J=7.8, 5.4 Hz, 1H, 5-position of Py), 7.33 (s, 5H, aromatic Hs), 6.59 (brd, J=7.8 Hz, 1H, NH of amide), 5.24–5.05 (m, 5H, NH of Z-Leu, CH$_2$ of Z, and COCH$_2$N), 4.87 (m, 1H, CHCO of P1-Leu), 4.20 (m, 1H, CHCO of P2-Leu), 1.80–1.40 (m, 6H, CHCH$_2$ of i-Bu), 1.00–0.82 (m, 12H, CH$_3$ of i-Bu).

EXAMPLE 3(3)

2(S)-N-[3(S)-1-(5-oxo-3-(3-pyridyl)-1,2,4-oxadiazolin-4-yl)-2-oxo-5-methyl-3-hexyl]-2-benzyloxycarbonylamino-4-methylpentanamide

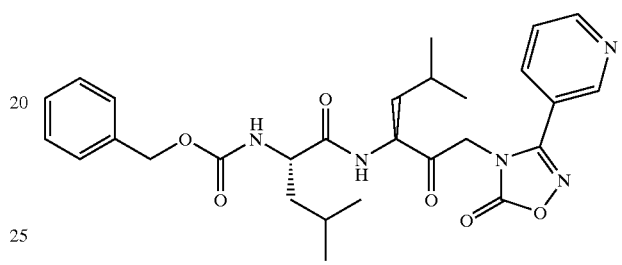

TLC: Rf 0.58 (chloroform:methanol=9:1); NMR (300 MHz, CDCl$_3$): δ 8.80 (brd, J=5.4 Hz, 1H, 6-position of Py), 8.76 (brs, 1H, 2-position of Py), 7.82 (brd, J=6.9 Hz, 1H, 4-position of Py), 7.46 (brdd, J=6.9, 5.4 Hz, 1H, 5-position of Py), 7.34 (s, 5H, aromatic Hs), 6.60 (br, 1H, NH of amide), 5.10 (m, 3H, NH of Z-Leu, and CH$_2$ of Z), 4.64 and 4.50 (each d, J=18.6 Hz, each 1H, COCH$_2$N), 4.34 (m, 1H, CHCO of P1-Leu), 4.10 (m, 1H, CHCO of P2-Leu), 1.72–1.41 (m, 6H, CHCH$_2$ of i-Bu), 1.00–0.82 (m, 12H, CH$_3$ of i-Bu).

EXAMPLE 3(4)

2(S)-N-[3(S)-1-(5-oxo-3-(4-pyridyl)-1,2,4-oxadiazolin-4-yl)-2-oxo-5-methyl-3-hexyl]-2-benzyloxycarbonylamino-4-methylpentanamide

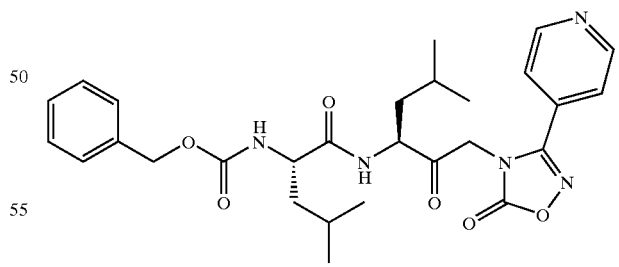

TLC: Rf 0.54 (chloroform:methanol=9:1); NMR (300 MHz, CDCl$_3$): δ 8.81 (d, J=4.4 Hz, 2H, 2 and 6-position of Py), 7.45 (brd, J=4.4 Hz, 2H, 3 and 5-position of Py), 7.34 (s, 5H, aromatic Hs), 6.61 (m, 1H, NH of amide), 5.12–5.02 (m, 3H, NH of Z-Leu, CH$_2$ of Z), 4.70 and 4.56 (each d, J=18.3 Hz, each 1H, COCH$_2$N), 4.34 (m, 1H, CHCO of P1-Leu), 4.11 (m, 1H, CHCO of P2-Leu), 1.70–1.41 (m, 6H, CHCH$_2$ of i-Bu), 1.00–0.82 (m, 12H, CH$_3$ of i-Bu).

EXAMPLE 3(5)

2(S)-N-[3(S)-1-(5-oxo-3-(4-benzyloxyphenyl)-1,2,4-oxadiazolin-4-yl)-2-oxo-5-methyl-3-hexyl]-2-benzyloxy carbonylamino-4-methylpentanamide

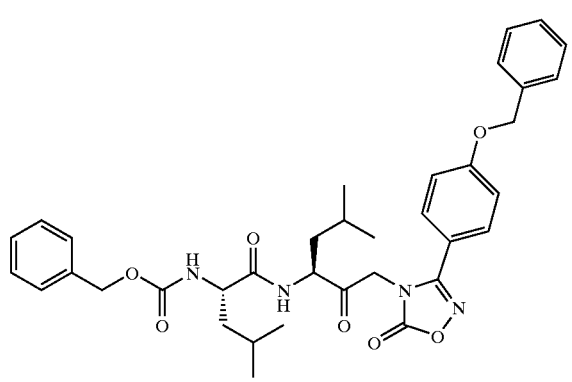

TLC: Rf 0.38 (n-hexane:ethyl acetate=6:4); NMR (200 MHz, CDCl$_3$): δ 7.50–7.20 (m, 12H, two Phs and meta CH against BnO), 7.07 (d, J=8.8 Hz, 1H, ortho CH against BnO), 6.53 (br, 1H, NH of Leu-Leu), 5.10 (s, 2H, CH$_2$ of PhCH$_2$O), 5.09 (s, 2H, CH$_2$ of PhCH$_2$O), 5.03 (d, J=7.4 Hz, 1H, NH of cbz-Leu), 4.75–4.35 (m, 3H, CH of Leu and CH$_2$ of LeuCH$_2$N), 4.20–4.05 (m, 1H, CH of Leu), 1.80–1.40 (m, 6H, CH$_2$ and CH of Leu), 1.05–0.80 (m, 12H, CH$_3$ of Leu).

EXAMPLE 3(6)

2(S)-N-[3(S)-1-(5-oxo-3-(1(S)-3-methyl-1-t-butoxycarbonyl aminobutyl)-1,2,4-oxadiazolin-4-yl)-2-oxo-5-methyl-3-hexyl]-2-benzyloxycarbonylamino-4-methylpentanamide

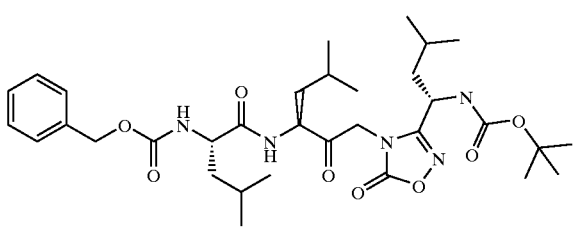

TLC: Rf 0.54 (ethyl acetate:n-hexane=1:2); NMR (300 MHz, CDCl$_3$): δ 7.35 (s, 5H, aromatic Hs), 6.60 (br, 1H, NH of amide), 5.40–4.95 (m, 4H, NH of carbamate, and CH$_2$ of Z), 4.80 and 4.57 (each brd, J=18.0 Hz, each 1H, COCH$_2$N), 4.43 (m, 2H, CHCO of P1-Leu and HetCHN), 4.20 (m, 1H, CHCO of P2-Leu), 1.84–1.40 (m, 18H, Boc, and CHCH$_2$ of i-Bu), 1.05–0.91 (m, 18H, CH$_3$ of i-Bu).

EXAMPLE 3(7)

2(S)-N-[3(S)1-(5-oxo-3-(4-fluorophenyl)-1,2,4-oxadiazolin-4-yl)-2-oxo-5-methyl-3-hexyl]-2-benzyloxycarbonylamino-4-methylpentanamide

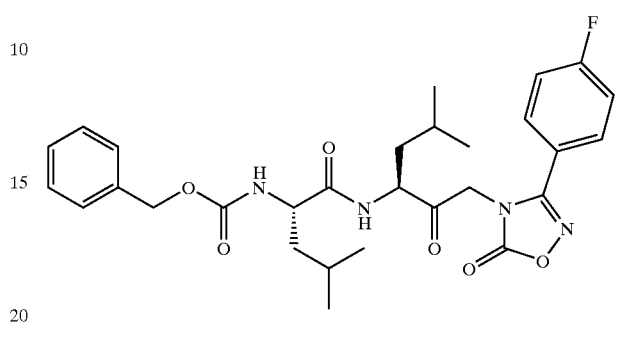

TLC: Rf 0.57 (n-hexane:ethyl acetate=2:1); NMR (200 MHz, CDCl$_3$): δ 7.49 (m, 2H, m-position against F), 7.34 (s, 5H, aromatic Hs), 7.20 (t, J=8.4 Hz, 2H, o-position against F), 6.60 (brd, J=5.8 Hz, 1H, NH of amide), 5.10–5.00 (m, 3H, NH of carbamate, and CH$_2$ of Z), 4.80–4.32 (m, 3H, CHCOCH$_2$N), 4.13 (m, 1H, CHCO of P2-Leu), 1.84–1.40 (m, 6H, CHCH$_2$ of i-Bu), 1.05–0.91 (m, 12H, CH$_3$ of i-Bu).

EXAMPLE 3(8)

2(S)-N-[3(S)-1-(5-oxo-3-(3-benzyloxyphenyl)-1,2,4-oxadiazolin-4-yl)-2-oxo-5-methyl-3-hexyl]-2-benzyloxy carbonylamino-4-methylpentanamide

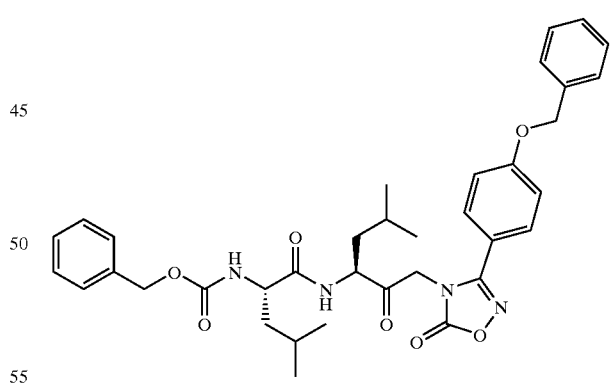

TLC: Rf 0.48 (n-hexane:ethyl acetate=6:4); NMR (200 MHz, CDCl$_3$): δ 7.50–7.25 (m, 11H, Ph of cbz and BnO, and meta CH against BnO), 7.20–6.95 (m, 3H, ortho and para CH against BnO), 6.69 (d, J=7.0 Hz, 1H, NH of Leu-Leu), 5.20–5.00 (m, 5H, CH$_2$ of cbz and BnO, and NH of cbz-Leu), 4.75–4.35 (m, 3H, CH of Leu, and CH$_2$ of LeuCH$_2$N), 4.25–4.05 (m, 1H, CH of Leu), 1.70–1.30 (m, 6H, CH$_2$ and CH of Leu), 1.00–0.80 (m, 12H, CH$_3$ of Leu).

EXAMPLE 3(9)

2(S)-N-[3(S)-1-(5-oxo-3-(4-fluorobenzyl)-1,2,4-oxadiazolin-4-yl)-2-oxo-5-methyl-3-hexyl]-2-benzyloxycarbonylamino-4-methylpentanamide

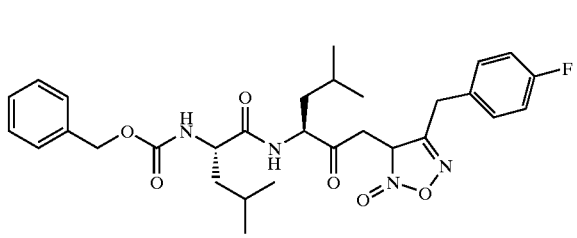

TLC: Rf 0.40 (n-hexane:ethyl acetate=6:4); NMR (200 MHz, CDCl₃): δ 7.45–7.20 (m, 7H, Ph of cbz, and meta CH against F), 7.08 (t, J=8.6 Hz, 2H, ortho CH against F), 6.59 (br, 1H, NH of Leu-Leu), 5.10 (s, 2H, CH₂ of cbz), 5.05 (d, J=7.4 Hz, 1H, NH of cbz-Leu), 4.45–4.10 (m, 4H, CH of Leu, and CH₂ of LeuCH₂N), 3.84 (d, J=16.6 Hz, 1H, CH of FPhCH₂), 3.73 (d, J=16.6 Hz, 1H, CH of FPhCH₂), 1.80–1.40 (m, 6H, CH₂ and CH of Leu), 1.05–0.80 (m, 12H, CH₃ of Leu).

EXAMPLE 3(10)

2(S)-N-[3(S)-1-(5-oxo-3-(2-pyridyl)methyl-1,2,4-oxadiazolin-4-yl)-2-oxo-5-methyl-3-hexyl]-2-benzyloxycarbonylamino-4-methylpentanamide

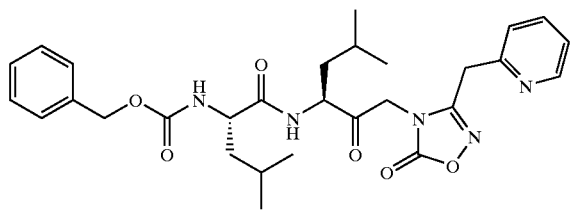

TLC: Rf 0.35 (chloroform:methanol=19:1); NMR (300 MHz, CDCl₃): δ 8.50 (d, J=4.8 Hz, 1H, 6-CH of pyr.), 7.68 (dt, J=1.8, 7.8 Hz, 1H, 4-CH of pyr.), 7.45–7.15 (m, 7H, Ph of cbz, and 3- and 5-CH of pyr.), 6.61 (br, 1H, NH of Leu-Leu), 5.20–5.00 (m, 3H, NH of cbz-Leu, and CH₂ of cbz), 4.81 (d, J=18.1 Hz, 1H, CH of LeuCH₂N), 4.66 (d, J=18.1 Hz, 1H, CH of LeuCH₂N), 4.55–4.45 (m, 1H, CH of Leu), 4.25–4.10 (m, 1H, CH of Leu), 3.99 (s, 2H, CH₂ of CH₂pyr.), 1.80–1.40 (m, 6H, CH₂ and CH of Leu), 1.00–0.80 (m, 12H, CH₃ of Leu).

EXAMPLE 3(11)

2(S)-N-[3(S)-1-(5-oxo-2-phenyl-1,3,4-oxadiazolin-4-yl)-2-oxo-5-methyl-3-hexyl]-2-benzyloxycarbonylamino-4-methyl pentanamide

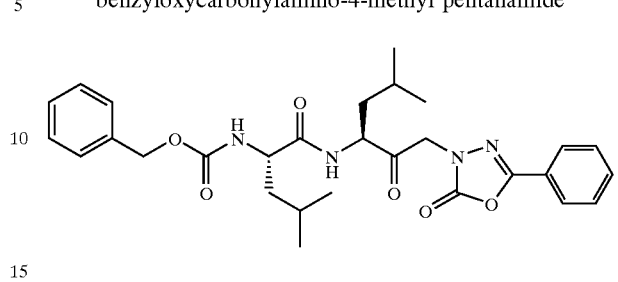

TLC: Rf 0.67 (n-hexane:ethyl acetate=1:1); NMR (300 MHz, CDCl₃): δ 7.83 (d, J=6.6 Hz, 2H, aromatic Hs of Ph-Het), 7.48 (m, 3H, aromatic Hs of Ph-Het), 7.33 (s, 5H, aromatic Hs of Z), 6.50 (d, J=7.5 Hz, 1H, NH of amide), 5.12 (m, 3H, NH of carbamate, and CH₂ of Z), 4.70 (m, 3H, COCH₂N, and CHCO of P1-Leu), 4.20 (m, 1H, CHCO of P2-Leu), 1.78–1.43 (m, 6H, CHCH₂ of i-Bu), 1.00–0.83 (m, 12H, CH₃ of i-Bu).

EXAMPLE 3(12)

2(s)-N-[1-(5-oxo-2-(1(S)-3-methyl-1-benzyloxycarbonylamino butyl)-1,3,4-oxadiazolin-4-yl)-2-oxo-5-methyl-3-hexyl]-2-benzyloxycarbonylamino-4-methylpentanamide

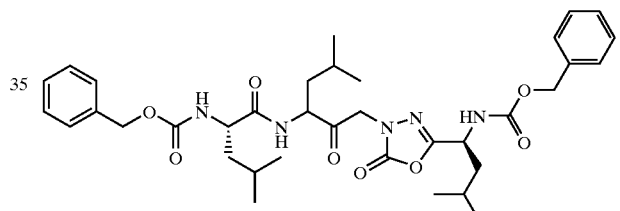

TLC: Rf 0.62 (n-hexane:ethyl acetate=1:1); NMR (300 MHz, CDCl₃): δ 7.34 (s, 10H, aromatic Hs), 6.64 and 6.50 (each d, J=8.1 Hz, totally 1H, NH of amide), 5.25–5.02 (m, 6H, NH of carbamate, and CH₂ of Z), 4.79 (m, 1H, CHHet), 4.58 (m, 3H, CHCO of P1-Leu, and COCH₂N), 4.20 (m, 1H, CHCO of P2-Leu), 1.80–1.40 (m, 9H, CHCH₂of i-Bu), 1.00–0.84 (m, 18H, CH₃ of i-Bu).

EXAMPLE 3(13)

2(S)-N-[3(S)-1-(5-oxo-2-benzyl-1,3,4-oxadiazolin-4-yl)-2-oxo-5-methyl-3-hexyl]-2-benzyloxycarbonylamino-4-methyl pentanamide

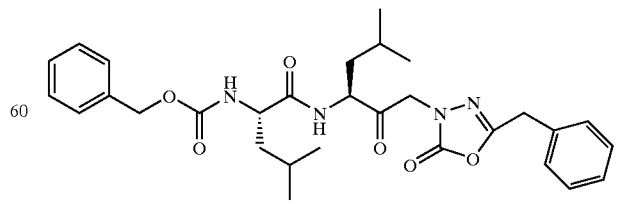

TLC: Rf 0.64 (n-hexane:ethyl acetate=1:1); NMR (300 MHz, CDCl₃): δ 7.40–7.24 (m, 10H, aromatic Hs), 6.42

(brd, J=9.0 Hz, 1H, NH of amide), 5.10 (m, 3H, NH of carbamate, and CH$_2$ of Z), 4.63 (m, 3H, COCH$_2$N, and CHCO of P1-Leu), 4.18 (m, 1H, CHCO of P2-Leu), 3.87 (s, 2H, CH$_2$Het), 1.74–1.40 (m, 6H, CHCH$_2$ of i-Bu), 1.00–0.84 (m, 12H, CH$_3$ of i-Bu).

EXAMPLE 3(14)

2(S)-N-[3(S)-1-(5-oxo-3-(2-phenylethyl)-1,2,4-oxadiazolin-4-yl)-2-oxo-5-methyl-3-hexyl]-2-benzyloxycarbonylamino-4-methylpentanamide

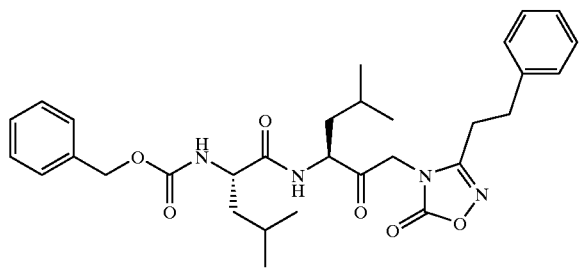

TLC: Rf 0.65 (chloroform:methanol=19:1); NMR (300 MHz, CDCl$_3$): δ 7.43–7.18 (m, 10H, Phenyl Hs), 6.57(brd, J=5.1 Hz, 1H, NH), 5.09 (s, 2H, PhCH$_2$O), 4.99 (brd, J=7.2 Hz, 1H, NH), 4.50–4.25 (m, 3H, COCH$_2$ and alfa CH of Leu), 4.12 (m, 1H, alfa CH of Leu), 2.99 and 2.69 (each brt, J=7.5 Hz, each 2H, PhCH$_2$CH$_2$), 1.76–1.39 (m, 6H, CHs and CH$_2$s of isoBu), 1.08–0.82 (m, 12H, CH$_3$s of isoBu).

EXAMPLE 3(15)

2(S)-N-[3(S)-1-(5-oxo-3-(2-fluorophenyl)-1,2,4-oxadiazolin-4-yl)-2-oxo-5-methyl-3-hexyl]-2-benzyloxycarbonylamino-4-methylpentanamide

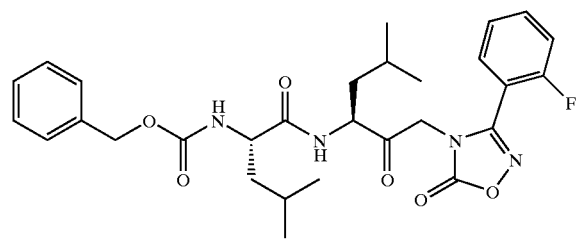

TLC: Rf 0.60 (n-hexane:ethyl acetate=1:1); NMR (300 MHz, CDCl$_3$): δ 7.65–7.48 (m, 2H, aromatic Hs), 7.40–7.18 (m, 7H, aromatic Hs), 6.38 (brd, J=8.0 Hz, 1H, NH of amide), 5.10 (s, 2H, CH$_2$ of Z), 4.98 (brd, J=7.5 Hz, 1H, NH of carbamate), 4.63 and 4.48 (each d, J=18.3 Hz, each 1H, COCH$_2$N), 4.40 (m, 1H, CHCO of P1-Leu), 4.09 (m, 1H, CHCO of P2-Leu), 1.65–1.23 (m, 6H, CHCH$_2$ of i-Bu), 1.00–0.80 (m, 12H, CH$_3$ of i-Bu).

EXAMPLE 3(16)

2(S)-N-[3(S)-1-(5-oxo-3-(3-fluorophenyl)-1,2,4-oxadiazolin-4-yl)-2-oxo-5-methyl-3-hexyl]-2-benzyloxycarbonylamino-4-methylpentanamide

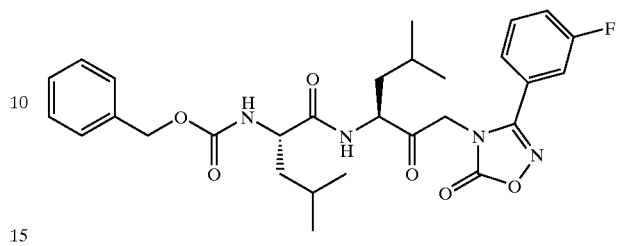

TLC: Rf 0.39 (toluene:ethyl acetate=2:1); NMR (200 MHz, CDCl$_3$): δ 7.58–7.20 (m, 9H, aromatic Hs), 6.48 (brd, J=6.6 Hz, 1H, NH of amide), 5.10 (s, 2H, CH$_2$ of Z), 5.01 (brd, J=7.4 Hz, 1H, NH of carbamate), 4.72–4.32 (m, 3H, COCH$_2$N, and CHCO of P1-Leu), 4.13 (m, 1H, CHCO of P2-Leu), 1.80–1.40 (m, 6H, CHCH$_2$ of i-Bu), 1.00–0.80 (m, 12H, CH$_3$ of i-Bu).

EXAMPLE 3(17)

2(S)-N-[3(S)-1-(5-oxo-2-(2-phenylethyl)-1,3,4-oxadiazolin-4-yl)-2-oxo-5-methyl-3-hexyl]-2-benzyloxycarbonylamino-4-methylpentanamide

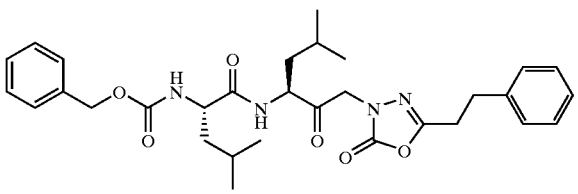

TLC: Rf 0.40 (n-hexane:ethyl acetate=7:3); NMR (300 MHz, CDCl$_3$): δ 7.40–7.26 (m, 10H, aromatic Hs), 6.54 (brd, J=7.2 Hz, 1H, NH of amide), 5.18 (m, 1H, NH of carbamate), 5.11 (s, 2H, CH$_2$of Z), 4.70–4.50 (m, 3H, CHCO of P1-Leu and COCH$_2$N), 4.19 (m, 1H, CHCO of P2-Leu), 3.00 and 2.84 (each m, each 2H, PhCH$_2$CH$_2$), 1.80–1.40 (m, 6H, CH$_2$ and CH of i-Bu), 1.00–0.83 (CH$_3$ of i-Bu).

EXAMPLE 4

2(S)-N-[4-methyl-2-oxo-1-(tetrazol-2-yl)-3-pentyl]-2-pyrrolidinecarboxamide hydrochloride

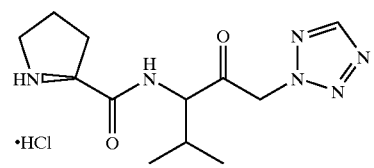

Under atmosphere of argon, the compound prepared in example 1 (47) (80 mg) in ethanol (1.9 ml) and 1N hydrochloric acid (64 μl) and thereto was added 5% palladium carbon (8 mg, 10% w/w). The mixture was stirred for 3 hours at room temperature under atmosphere of hydrogen. The reaction mixture was filtered over celite and the filtrate was concentrated to give the title compound (65 mg) having the following physical data.

TLC: Rf 0.49 (chloroform:methanol:water=7:3:0.3); NMR (200 MHz, DMSO-$d_6$): δ 9.28–9.09 (m, 1H), 8.99 (s, 1H), 8.58 (brs, 1H), 6.08–6.02 (m, 2H), 4.61–4.51 (m, 1H), 4.48–4.28 (m, 1H), 3.31–3.10 (m, 2H), 2.44–2.31 (m, 2H), 1.96–1.85 (m, 3H), 1.07–0.91 (m, 6H).

EXAMPLE 4(1)–4(7)

By the same procedure as described in example 4 using the compounds prepared in example 1 (48)–1(50) and example 2(5)–2(8), the following compounds were given.

EXAMPLE 4(1)

2(S)-N-[4-methyl-2-oxo-1-(tetrazol-1-yl)-3-pentyl]-2-pyrrolidinecarboxamide hydrochloride

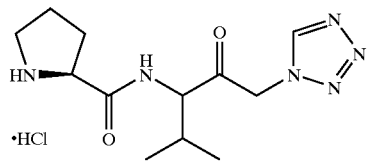

TLC: Rf 0.32 (chloroform:methanol:water=7:3:0.3); NMR (200 MHz, DMSO-$d_6$): δ 9.36–9.33 (1H, m), 9.26–9.11 (1H, m), 8.60 (1H, brs), 5.88–5.65 (2H, m), 4.60–4.53 (1H, m), 4.41–4.35 (1H, m), 3.31–3.22 (2H, m), 2.48–2.23 (2H, m), 2.00–1.80 (3H, m), 1.00–0.89 (6H, m).

EXAMPLE 4(2)

2-amino-N-[2-oxo-4-phenyl-1-(tetrazol-2-yl)-3-butyl]acetamide hydrochloride

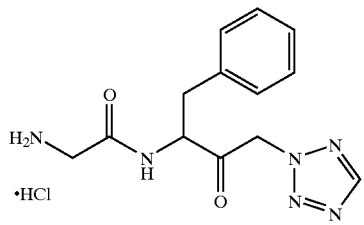

TLC: Rf 0.35 (chloroform:methanol:water=9:1:0.1); NMR (200 MHz, DMSO-$d_6$): δ 9.30 (1H, d, J=7.6 Hz), 9.00 (1H, s), 8.22 (3H, brs), 7.32–7.22 (5H, m), 6.15 (1H, d, J=18 Hz), 5.99 (1H, d, J=18 Hz), 4.83–4.72 (1H, m), 3.62–3.51 (2H, m), 3.22 (1H, dd, J=4.4, 14 Hz), 2.92 (1H, dd, J=9.8, 14 Hz).

EXAMPLE 4(3)

2-amino-N-[2-oxo-4-phenyl-1-(tetrazol-1-yl)-3-butyl]acetamide hydrochloride

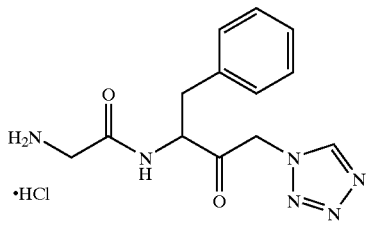

TLC: Rf 0.14 (chloroform:methanol:water=9:1:0.1); NMR (200 MHz, DMSO-$d_6$): δ 9.33 (1H, s), 9.30 (1H, d, J=8.0 Hz), 8.24 (3H, brs), 7.32–7.21 (5H, m), 5.93 (1H, d, J=18 Hz), 5.76 (1H, d, J=18 Hz), 4.75–4.70 (1H, m), 3.62–3.52 (2H, m), 3.22 (1H, dd, J=4.4, 14 Hz), 2.88 (1H, dd, J=10, 14 Hz).

EXAMPLE 4(4)

3-amino-4-methyl-1-(tetrazol-2-yl)pentan-2-one hydrochloride

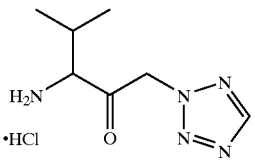

TLC: Rf 0.38 (chloroform:methanol:water=9:1:0.1); NMR (200 MHz, DMSO-$d_6$): δ 9.06 (1H, s), 8.62 (3H, brs), 6.26 (1H, d, J=18.8 Hz), 6.15 (1H, d, J=18.8 Hz), 4.40 (1H, d, J=4.2 Hz), 2.60–2.40 (1H, m), 1.11 (3H, d, J=6.8 Hz), 0.96 (3H, d, J=6.8 Hz).

EXAMPLE 4(5)

3-amino-4-methyl-1-(tetrazol-1-yl)pentan-2-one hydrochloride

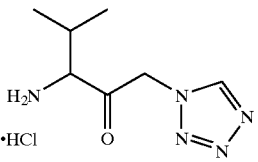

TLC: Rf 0.11 (chloroform:methanol:water=9:1:0.1); NMR (200 MHz, DMSO-$d_6$): δ 9.42 (1H, s), 8.65 (3H, brs), 5.93 (2H, s), 4.37 (1H, d, J=4.2 Hz), 2.58–2.36 (1H, m), 1.10 (3H, d, J=6.8 Hz), 0.96 (3H, d, J=6.8 Hz).

EXAMPLE 4(6)

3-amino-4-phenyl-1-(tetrazol-2-yl)butan-2-one hydrochloride

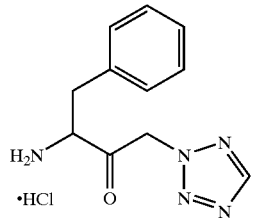

TLC: Rf 0.50 (chloroform:methanol:water=9:1:0.1); NMR (200 MHz, DMSO-$d_6$): δ 9.05 (1H, s), 8.67 (3H, brs), 7.46–7.26 (5H, m), 6.19 (1H, d, J=18.6 Hz), 6.03 (1H, d, J=18.6 Hz), 4.77–4.71 (1H, m), 3.49–3.20 (2H, m).

EXAMPLE 4(7)

3-amino-4-phenyl-1-(tetrazol-1-yl)butan-2-one hydrochloride

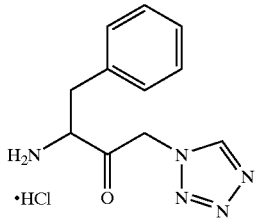

TLC: Rf 0.33 (chloroform:methanol:water=9:1:0.1); NMR (200 MHz, DMSO-$d_6$): δ 9.36 (1H, s), 8.65 (3H, brs), 7.50–7.25 (5H, m), 5.90 (1H, d, J=18.8 Hz), 5.76 (1H, d, J=18.8 Hz), 4.73–4.66 (1H, m), 3.45–3.13 (2H, m).

REFERENCE EXAMPLE 4

N-((3S)-1-bromo-2-oxo-5-methyl-3-hexyl)-t-butoxycarboxamide

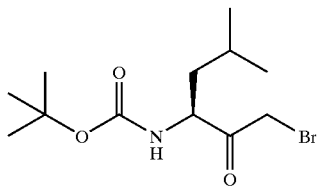

By the same procedure as described in reference example 3 using N-t-butoxycarbonylleucine monohydrate (37.4 g), the title compound (27.4 g) having the following physical data was obtained.

TLC: Rf 0.56 (n-hexane:ethyl acetate=3:1); NMR (CDCl$_3$): δ 4.89 (m, 1H, NH), 4.53 (m, 1H, CH of Leu), 4.08 (m, 2H, CH$_2$ of LeuCH$_2$Br), 1.80–1.31 (m, 12H, CH$_2$ and CH of Leu, and tBu), 0.97 (m, 6H, CH$_3$ of Leu).

EXAMPLE 5

N-[(3S)-1-(5-phenyltetrazol-2-yl)-2-oxo-5-methyl-3-hexyl]-t-butoxycarboxamide

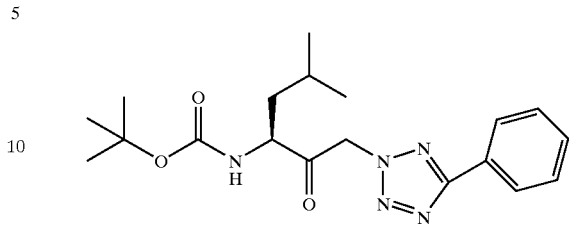

Under atmosphere of argon, a solution of 5-phenyltetrazole (3.29 g) and potassium fluoride (2.61 g) in DMF (30 ml) was stirred for 1 hour. To the reaction solution was added the compound prepared in reference example 4 (4.62 g) and the mixture was stirred for 2 hours. To the reaction solution was added ice-water and ethyl acetate. The aqueous layer was extracted with ethyl acetate. The combined organic layer was washed with a saturated aqueous solution of sodium bicarbonate, water and saturated aqueous solution of sodium chloride successively, dried over anhydrous sodium sulfate, and was concentrated. The residue was purified by column chromatography on silica gel (n-hexane:ethyl acetate=5:1→4:1→3:2) to give the title compound having the following physical data (4.76 g).

TLC: Rf 0.56 (n-hexane:ethyl acetate=7:3); NMR (CDCl$_3$): δ 8.20–8.10 (m, 2H, ortho CH against tet.), 7.55–7.45 (m, 3H, meta and para CH against tet.), 5.74 (d, J=17.6 Hz, 1H, CH of LeuCH$_2$N), 5.64 (d, J=17.6 Hz, 1H, CH of LeuCH$_2$N), 4.90 (d, J=6.6 Hz, 1H, NH), 4.43 (br, 1H, CH of Leu), 1.80–1.40 (m, 12H, CH$_2$ and CH of Leu, and tBu), 0.98 (d, J=6.6 Hz, 3H, CH$_3$ of Leu), 0.95 (d, J=6.0 Hz, 3H, CH$_3$ of Leu).

EXAMPLE 5(1)–5(4)

By the same procedure as described in example 5 using the compound prepared in reference example 4 and a corresponding compound, the following compounds were given.

EXAMPLE 5(1)

N-[3(S)-1-(3-phenyl-5-oxo-1,2,4-oxadiazolin-4-yl)-2-oxo-5-methyl-3-hexyl]-t-butoxycarboxamide

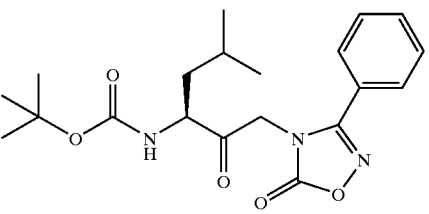

TLC: Rf 0.32 (n-hexane:ethyl acetate=7:3); NMR (200 MHz, CDCl$_3$): δ 7.63–7.44 (m, 5H, phenyl Hs), 4.84 (brd, J=6.2 Hz, 1H, NH), 4.67 and 4.56 (each d, J=18.5 Hz, each 1H, COCH$_2$), 4.19 (m, 1H, alfa CH of Leu), 1.78–1.16 (m, 3H, CH$_2$ and CH of iBu), 1.40 (s, 9H, CH$_3$s of tBu), 0.93 (d, J=6.0 Hz, 3H, CH$_3$ of iBu), 0.91 (d, J=6.0 Hz, 3H, CH$_3$ of iBu).

EXAMPLE 5(2)

N-[3(S)-1-(3-(4-fluorophenyl)-5-oxo-1,2,4-oxadiazolin-4-yl)-2-oxo-5-methyl-3-hexyl]-t-butoxycarboxamide

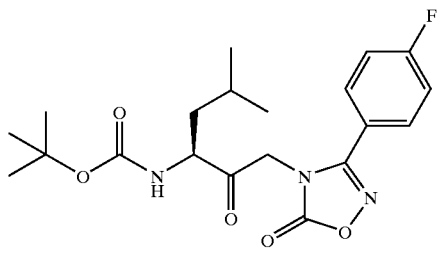

TLC: Rf 0.70 (n-hexane:ethyl acetate=7:3); NMR (300 MHz, CDCl$_3$): δ 7.55 (dd, J=8.7, 5.4 Hz, 2H, meta CH against F), 7.20 (t, J=8.7 Hz, 2H, ortho Chs against F), 4.84 (d, J=6.3 Hz, 1H, NH), 4.65 (d, J=18.3 Hz, 1H, NCH$_2$CO), 4.55 (d, J=18.3 Hz, 1H, NCH$_2$CO), 4.18 (m, 1H, NCHCO), 1.80–1.50 (m, 3H, CHCH$_2$), 1.40 (s, 9H, Boc), 0.95 and 0.93 (each d, each J=6.0 Hz, each 3H, CH$_3$).

EXAMPLE 5(3)

N-[3(S)-1-(2-(2-phenylethyl)-5-oxo-1,3,4-oxadiazolin-4-yl)-2-oxo-5-methyl-3-hexyl]-t-butoxycarboxamide

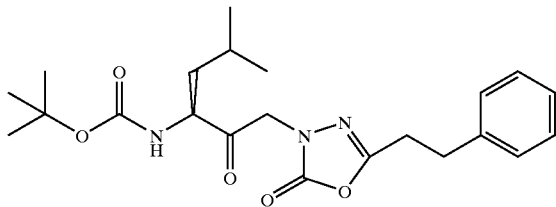

TLC: Rf 0.45 (n-hexane:ethyl acetate=7:3); NMR (300 MHz, CDCl$_3$): δ 7.37–7.17 (m, 5H, Chs of Ph), 4.90 (d, J=7.5 Hz, 1H, NH), 4.68 and 4.60 (each d, each J=18.3 Hz, each 1H, NCH$_2$CO), 4.37 (m, 1H, NCHCO), 3.05–2.95 and 2.90–2.81 (each m, each 2H, PhCH$_2$CH$_2$), 1.80–1.50 (m, 3H, CHCH$_2$), 1.46 (s, 9H, Boc), 0.95 and 0.94 (each d, each J=6.3 Hz, each 3H, CH$_3$).

EXAMPLE 5(4)

N-[3(S)-1-(3-(2-pyridyl)-5-oxo-1,2,4-oxadiazolin-4-yl)-2-oxo-5-methyl-3-hexyl]-t-butoxycarboxamide

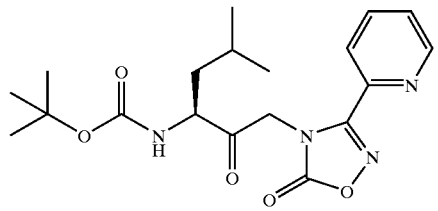

TLC: Rf 0.27 (n-hexane:ethyl acetate=3:1); NMR (CDCl$_3$): δ 8.60 (d, J=4.4 Hz, 1H, 6-CH of pyr.), 8.08 (d, J=7.9 Hz, 1H, 3-CH of pyr.), 7.84 (dt, J=1.8, 7.9 Hz, 1H, 4-CH of pyr.), 7.48–4.36 (m, 1H, 5-CH of pyr.), 5.19 (s, 2H, CH$_2$ of LeuCH$_2$N), 4.88 (d, J=8.8 Hz, 1H, NH), 4.62–4.45 (m, 1H, CH of Leu), 1.80–1.30 (m, 3H, CH$_2$ and CH of Leu), 1.45 (s, 9H, tBu), 0.97 (d, J=6.2 Hz, 6H, CH$_3$ of Leu).

EXAMPLE 6

3(S)-3-amino-5-methyl-1-(5-phenyltetrazol-2-yl)hexan-2-one hydrochloride

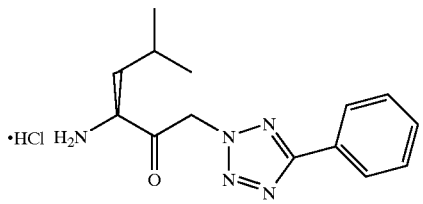

The compound prepared in example 5 (373 mg) was dissolved in 4N hydrochloric acid in 1,4-dioxane (2 ml) at 0° C. and the mixture was stirred for 1 hour. The reaction mixture was concentrated to give the title compound. It was used in the next reaction without further purification.

EXAMPLE 7

(1R,2S)-2-benzoylamino-N-[3(S)-1-(5-phenyltetrazol-2-yl)-2-oxo-5-methyl-3-hexyl]cyclohexanecarboxamide

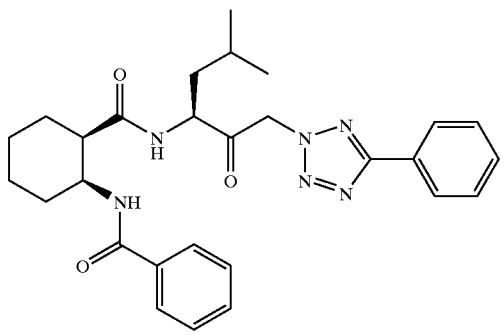

To a solution of the compound prepared in example 6 (373 mg) in DMF (2 ml) were added (−)-2-benzamidecyclohexanecarboxylic acid (272 mg), HOBt (176 mg), EDC hydrochloride (250 mg) and N-methylmorpholine(143 µl) and the mixture was stirred for 5 hours. To the reaction solution was added ice-water and ethyl acetate and the aqueous layer was extracted with ethyl acetate. The combined organic layer was washed with a saturated aqueous solution of sodium bicarbonate, water and saturated aqueous solution of sodium chloride successively, dried over anhydrous sodium sulfate and was concentrated. The residue was purified by column chromatography on silica gel (n-hexane:ethyl acetate=7:3→6:4→1:1) to give the title compound (306 mg) having the following physical data.

TLC: Rf 0.31 (n-hexane:ethyl acetate=1:1); NMR (300 MHz, CDCl$_3$): δ 8.20–8.10 (m, 2H, ortho CH against tet.), 7.80–7.73 (m, 2H, ortho CH against NCO), 7.55–7.40 (m, 6H, Ph), 7.07 (d, J=8.1 Hz, 1H, NH of NHchx), 6.35 (d, J=7.5 Hz, 1H, NH of Leu), 5.71 (d, J=17.4 Hz, 1H, CH of LeuCH$_2$N), 5.60 (d, J=17.4 Hz, 1H, CH of LeuCH$_2$N), 4.75–4.60 (m, 1H, CH of Leu), 4.40–4.30 (m, 1H, NCH of chx), 2.86 (q, J=5.1 Hz, 1H, COCH of chx), 2.20–1.40 (m, 11H, CH$_2$ of chx, and CH$_2$ and CH of Leu), 0.82 (d, J=6.0 Hz, 3H, CH$_3$ of Leu), 0.78 (d, J=6.3 Hz, 3H, CH$_3$ of Leu).

EXAMPLE 8

N-[3(S)-1-(5-phenyltetrazol-2-yl)-2-oxo-5-methyl-3-hexyl]benzamide

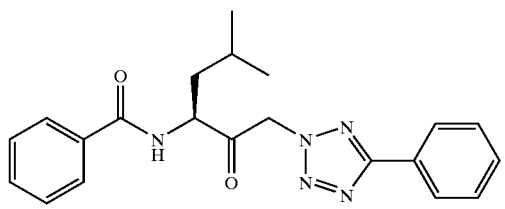

To a solution of the compound, which was prepared by the same procedure as described in example 6 using the compound prepared in example 5 (373 mg), in DMF (2 ml) were added benzoyl chloride (130 μl) and N-methylmorpholine (132 μl) and the mixture was stirred for 2 hours. To the reaction solution were added ice-water and ethyl acetate and the aqueous layer was extracted with ethyl acetate. The combined organic layer was washed with a saturated aqueous solution of sodium bicarbonate, water and saturated aqueous solution of sodium chloride successively, dried over anhydrous sodium sulfate and was concentrated. The residue was washed with ether to give the title compound (190 mg) having the following physical data.

TLC: Rf 0.56 (n-hexane:ethyl acetate=3:2); NMR (300 MHz, CDCl$_3$): δ 8.20–8.10 (m, 2H, ortho CH against tet.), 7.82 (dd, J=6.8, 1.4 Hz, 2H, ortho CH against NCO), 7.60–7.40 (m, 6H, Ph), 6.56 (br, 1H, NH of Leu), 5.81 (d, J=17.6 Hz, 1H, CH of LeuCH$_2$N), 5.72 (d, J=17.6 Hz, 1H, CH of LeuCH$_2$N), 5.05–4.90 (m, 1H, CH of Leu), 1.85–1.60 (m, 3H, CH$_2$ and CH of Leu), 1.01 (d, J=6.6 Hz, 3H, CH$_3$ of Leu), 0.99 (d, J=6.6 Hz, 3H, CH$_3$ of Leu).

EXAMPLE 9

N-[3(S)-1-(5-phenyltetrazol-2-yl)-2-oxo-5-methyl-3-hexyl]cyclohexanecarboxamide

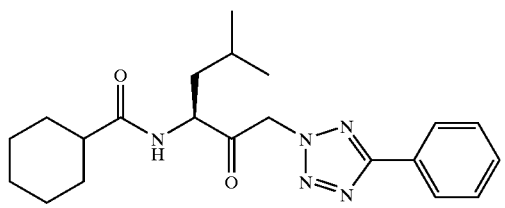

To a solution of mixed anhydride, which was prepared from cyclohexanecarboxylic acid (128 mg) and chloroethyl formate (100 μl) and N-methylmorpholine (121 μl), was added a solution of the compound, which was prepared by the same procedure as described in example 6 using the compound prepared in example 5 (485 mg), in DMF (2 ml), and thereto was added N-methylmorpholine (176 μl) and the mixture was stirred for 2.5 hours. To the reaction mixture was added ice-water and ethyl acetate. The aqueous layer was extracted with ethyl acetate. The combined organic layer was washed with 10% aqueous solution of citric acid, a saturated aqueous solution of sodium bicarbonate, water and saturated aqueous solution of sodium chloride, dried over anhydrous sodium sulfate and was concentrated. The residue was washed with diisopropyl ether to give the title compound (345 mg) having the following physical data.

TLC: Rf 0.62 (n-hexane:ethyl acetate=3:2); NMR (300 MHz, CDCl$_3$): δ 8.20–8.10 (m, 2H, ortho CH against tet.), 7.55–7.45 (m, 3H, meta and para CH against tet.), 5.83 (br, 1H, NH of Leu), 5.71 (d, J=17.7 Hz, 1H, CH of LeuCH$_2$N), 5.62 (d, J=17.7 Hz, 1H, CH of LeuCH$_2$N), 4.80–4.70 (m, 1H, CH of Leu), 2.18 (tt, J=11.6, 3.5 Hz, 1H, COCH of chx), 1.95–1.20 (m, 13H, CH$_2$ of chx, and CH$_2$ and CH of Leu), 0.98 (d, J=6.6 Hz, 3H, CH$_3$ of Leu), 0.94 (d, J=6.3 Hz, 3H, CH$_3$ of Leu).

EXAMPLE 10(1)–10(8)

By the same procedure as described in example 7, example 8 or example 9 using the compound prepared in example 6 or a corresponding compound, the following compounds were given.

EXAMPLE 10(1)

(1S,2R)-2-benzoylamino-N-[3(S)-1-(5-phenyltetrazol-2-yl)-2-oxo-5-methyl-3-hexyl]cyclohexanecarboxamide

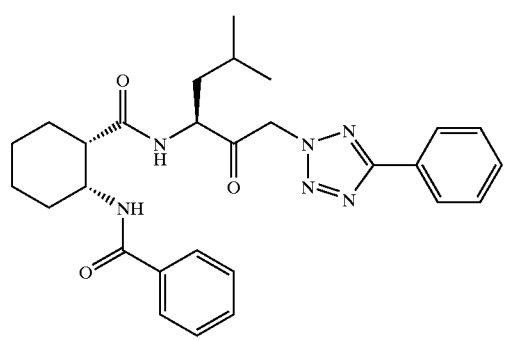

TLC: Rf 0.36 (n-hexane:ethyl acetate=1:1); NMR (300 MHz, CDCl$_3$): δ 8.15–8.08 (m, 2H, ortho CH against tet.), 7.73 (dd, J=8.1, 1.5 Hz, 2H, ortho CH against NCO), 7.53–7.43 (m, 3H, meta and para CH against tet.), 7.43–7.28 (m, 3H, meta and para CH against NCO), 7.07 (d, J=8.4 Hz, 1H, NH of NHchx), 6.49 (d, J=6.9 Hz, 1H, NH of Leu), 5.64 (d, J=17.4 Hz, 1H, CH of LeuCH$_2$N), 5.52 (d, J=17.4 Hz, 1H, CH of LeuCH$_2$N), 4.67–4.55 (m, 1H, CH of Leu), 4.45–4.30 (m, 1H, NCH of chx), 2.90 (q, J=4.8 Hz, 1H, COCH of chx), 2.13–1.40 (m, 11H, CH$_2$ of chx, and CH$_2$ and CH of Leu),0.91 (d, J=6.6 Hz, 3H, CH$_3$ of Leu), 0.89 (d, J=6.3 Hz, 3H, CH$_3$ of Leu).

EXAMPLE 10 (2)

N-[3(S)-1-(5-phenyltetrazol-2-yl)-2-oxo-5-methyl-3-hexyl]-4-benzyloxybenzamide

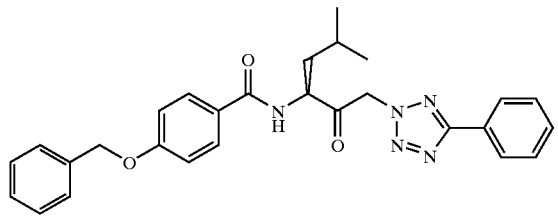

TLC: Rf 0.61 (n-hexane:ethyl acetate=3:2); NMR (300 MHz, CDCl$_3$): δ 8.20–8.10 (m, 2H, ortho CH against tet.), 7.78 (d, J=8.7 Hz, 2H, ortho CH against NCO), 7.50–7.30 (m, 8H, Ph), 7.01 (d, J=8.7 Hz, 2H, ortho CH against BnO), 6.48 (d, J=7.5 Hz, 1H, NH of Leu), 5.81 (d, J=17.4 Hz, 1H, CH of LeuCH$_2$N), 5.70 (d, J=17.4 Hz, 1H, CH of LeuCH$_2$N), 5.12 (s, 2H, CH$_2$ of BnO), 5.00–4.90 (m, 1H, CH of Leu), 1.85–1.50 (m, 3H, CH$_2$ and CH of Leu), 1.00 (d, J=6.6 Hz, 3H, CH$_3$ of Leu), 0.97 (d, J=6.0 Hz, 3H, CH$_3$ of Leu).

EXAMPLE 10 (3)

N-[3(S)-1-(5-phenyltetrazol-2-yl)-2-oxo-5-methyl-3-hexyl]-3-benzyloxybenzamide

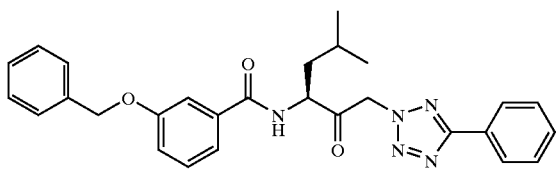

TLC: Rf 0.63 (n-hexane:ethyl acetate =3:2); NMR (300 MHz, CDCl$_3$): δ 8.20–8.10 (m, 2H, ortho CH against tet.), 7.50–7.30 (m, 11H, Ph), 7.20–7.10 (m, 1H, para CH against CO), 6.54 (d, J=7.5 Hz, 1H, NH of Leu), 5.80 (d, J=17.6 Hz, 1H, CH of LeuCH$_2$N), 5.70 (d, J=17.6 Hz, 1H, CH of LeuCH$_2$N), 5.11 (s, 2H, CH$_2$ of BnO), 5.00–4.90 (m, 1H, CH of Leu), 1.85–1.50 (m, 3H, Ch$_2$ and CH of Leu), 1.01 (d, J 6.3 Hz, 3H, CH$_3$ of Leu), 0.98 (d, J=6.3 Hz, 3H, CH$_3$ of Leu).

EXAMPLE 10 (4)

N-[3(S)-1-(5-phenyltetrazol-2-yl)-2-oxo-5-methyl-3-hexyl]-3-phenylpropenamide

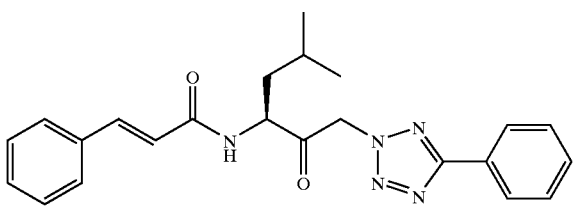

TLC: Rf 0,56 (n-hexane:ethyl acetate=3:2); NMR )300 MHz, DMSO-d$_6$): δ 8.69 (d, J=6.8 Hz, 1H, NH), 8.15–8.00 (m, 2H, ortho CH against tet.), 7.65–7.30 (m, 9H, CH of Phs and CHPh), 6.75 (d, J=16.2 Hz, 1H, CH of CHCONH), 6.06 (s, 2H, CH$_2$ of LeuCH$_2$N), 4.75–4.60 (m, 1H, CH of Leu), 1.85–1.50 (m, 3H, CH$_2$ and CH of Leu), 0.96 (d, J=6.0 Hz, 3H, CH$_3$ of Leu), 0.92 (d, J=6.0 Hz, 3H, CH$_3$ of Leu).

EXAMPLE 10 (5)

N-[3(S)-1-(5-phenyltetrazol-2-yl)-2-oxo-5-methyl-3-hexyl]-3-cyclopentylpropanamide

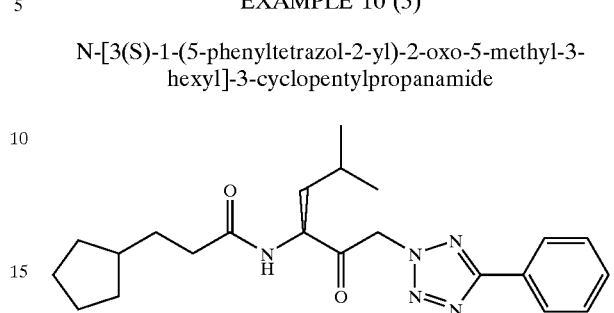

TLC: Rf 0.35 (n-hexane:ethyl acetate=7:3); NMR (300 MHz, CDCl$_3$): δ 8.20–8.10 (m, 2H, ortho CH against tet.), 7.55–7.45 (m, 3H, CH of Ph), 5.79 (d, J=7.2 Hz, 1H, NH), 5.72 (d, J=17.7 Hz, 1H, CH of LeuCH$_2$N), 5.63 (d, J=17.7 Hz, 1H, CH of LeuCH$_2$N), 4.85–4.70 (m, 1H, CH of Leu), 2.30–2.20 (m, 2H, CH$_2$ of CH$_2$CONH), 1.85–1.45 (m, 12H, aliphatic protons), 1.20–1.00 (m, 2H, aliphatic protons), 0.99 (d, J=6.3 Hz, 3H, CH$_3$ of Leu), 0.95 (d, J=6.0 Hz, 3H, CH$_3$ of Leu).

EXAMPLE 10 (6)

N-[3(S)-1-(5-phenyltetrazol-2-yl)-2-oxo-5-methyl-3-hexyl]benzenesulfonamide

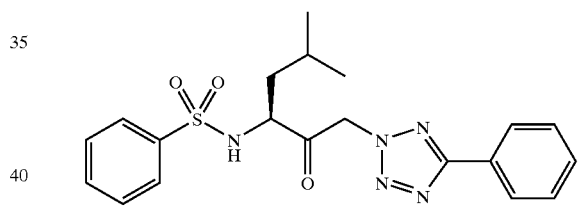

TLC: Rf 0.47 (n-hexane:ethyl acetate=3:2); NMR (300 MHz, CDCl$_3$): δ 8.20–8.10 (m, 2H, ortho CH against tet.), 7.90–7.80 (m, 2H, ortho CH against SO$_2$), 7.65–7.45 (m, 6H, Ph), 5.58 (s, 2H, CH$_2$of LeuCH$_2$N), 5.22 (d, J=7.8 Hz, 1H, NH), 4.00–3.90 (m, 1H, CH of Leu), 1.70–1.30 (m, 3H, CH$_2$ and CH of Leu), 0.84 (d, J=6.6 Hz, 3H, CH$_3$ of Leu), 0.60 (d, J=6.3 Hz, 3H, CH$_3$ of Leu).

EXAMPLE 10 (7)

N-[3(S)-1-(5-phenyltetrazol-2-yl)-2-oxo-5-methyl-3-hexyl]-3-benzoylaminopropanamide

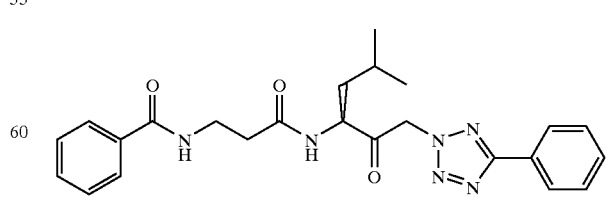

TLC: Rf 0.26 (n-hexane:ethyl acetate=2:3); NMR (300 MHz, DMSO-d$_6$): δ 8.55 (t, J=5.6 Hz, 1H, NH of beta-Ala), 8.50 (d, J=7.0 Hz, 1H, NH of Leu), 8.10–8.00 (m, 2H, ortho CH against tet.), 7.85–7.75 (m, 2H, ortho CH against NHCO), 7.65–7.55 (m, 3H, CH of Ph), 7.50–7.35 (m, 3H, CH of Ph), 5.97 (s, 2H, CH$_2$ of LeuCH$_2$N), 4.51 (q, J=7.0 Hz, 1H, CH of Leu), 3.53 (dt, J=6.9, 5.6 Hz, 2H, NCH$_2$ of beta-Ala), 2.54 (t, J=6.9 Hz, 2H, CH$_2$CO of beta-Ala), 1.70–1.50 (m, 3H, CH$_2$and CH of Leu), 0.86 (d, J=6.0 Hz, 3H, CH$_3$ of Leu), 0.83 (d, J=6.0 Hz, 3H, CH$_3$ of Leu).

EXAMPLE 10 (8)

N-[3(S)-1-(5-phenyltetrazol-2-yl)-2-oxo-5-methyl-3-hexyl]-2-benzyloxybenzamide

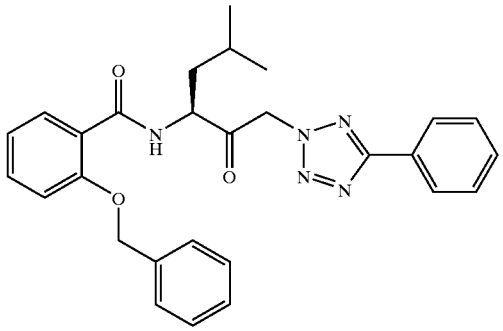

TLC: Rf 0.52 (n-hexane:ethyl acetate=3:2); NMR (300 MHz, CDCl$_3$): δ 8.30–8.20 (m, 2H, NH, and ortho CH against CO), 8.20–8.10 (m, 2H, ortho CH against tet.), 7.55–7.35 (m, 9H, CH of Ph), 7.20–7.10 (m, 2H, meta CH against CO), 5.70 (d, J=17.7 Hz, 1H, CH of LeuCH$_2$N), 5.61 (d, J=17.7 Hz, 1H, CH of LeuCH$_2$N), 5.16 (d, J=9.9 Hz, 1H, CH of BnO), 5.14 (d, J=9.9 Hz, 1H, CH of BnO), 4.75–4.65 (m, 1H, CH of Leu), 1.55–1.10 (m, 3H, CH$_2$ and CH of Leu), 0.78 (d, J=6.3 Hz, 3H, CH$_3$ of Leu), 0.73 (d, J=6.3 Hz, 3H, CH$_3$ of Leu).

EXAMPLE 11 (1)–11(37)

By the same procedure as described in example 6→(one selected from example 7, example 8 or example 9) using the compound prepared in example 5 (1), 5 (2), 5(3) or 5(4) or a corresponding compound, the following compounds were given.

EXAMPLE 11 (1)

N-[3(S)-1-(3-phenyl-5-oxo-1,2,4-oxadiazolin-4-yl)-2-oxo-5-methyl-3-hexyl]cyclohexanecarboxamide

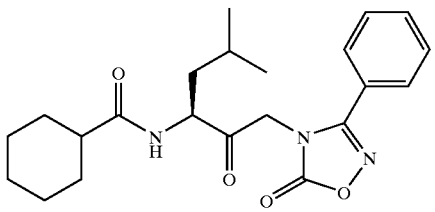

TLC: Rf 0.41 (n-hexane:ethyl acetate=3:2); NMR (200 MHz, CDCl$_3$): δ 7.70–7.45 (m, 5H, Ph), 5.73 (d, J=7.2 Hz, 1H, NH), 4.67 (d, J=18.7 Hz, 1H, CH of LeuCH$_2$N), 4.54 (d, J=18.7 Hz, 1H, CH of LeuCH$_2$N), 4.58–4.45 (m, 1H, CH of Leu), 2.20–2.00 (m, 1H, COCH of chx), 1.90–1.10 (m, 13H, CH$_2$ of chx, and CH$_2$ and CH of Leu), 0.93 (d, J=6.4 Hz, 3H, CH$_3$of Leu), 0.90 (d, J=6.4 Hz, 3H, CH$_3$ of Leu).

EXAMPLE 11(2)

N-[3(S)-1-(3-phenyl-5-oxo-1,2,4-oxadiazolin-4-yl)-2-oxo-5-methyl-3-hexyl]benzamide

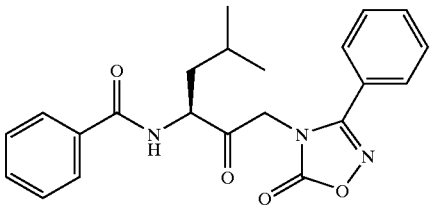

TLC: Rf 0.52 (n-hexane:ethyl acetate=1:1); NMR (300 MHz, CDCl$_3$): δ 7.74 (m, 2H, ortho Hs against CONH), 7.61–7.41 (m, 8H, Phenyl Hs), 6.54 (brd, J=6.9 Hz, 1H, NH), 4.78 and 4.63 (each d, J=18.3 Hz, each 1H, COCH$_2$), 4.73 (m, 1H, alfa CH of Leu), 1.80–1.52 (m, 3H, CH and CH$_2$ of isoBu), 0.97 and 0.95 (each d, J=6.3 Hz, each 3H, CH$_3$s of isoBu).

EXAMPLE 11 (3)

N-[3(S)-1-(3-phenyl-5-oxo-1,2,4-oxadiazolin-4-yl)-2-oxo-5-methyl-3-hexyl]-4-benzyloxybenzamide

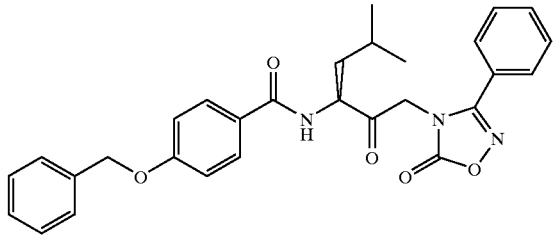

TLC: Rf 0.52 (n-hexane:ethyl acetate=1:1); NMR (300 MHz, CDCl$_3$): δ 7.70 (d, J=9.0 Hz, 2H, ortho Hs against CONH), 7.60–7.30 (m, 10H, Phenyl Hs), 7.01 (d, J=9.0 Hz, 2H, meta Hs against CONH), 6.36 (brd, J=6.6 Hz, 1H, NH), 5.13 (s, 2H, PhCH$_2$O), 4.77 and 4.62 (each d, J=18.2 Hz, each 1H, COCH$_2$), 4.69 (m, 1H, alfa CH of Leu), 1.79–1.50 (m, 3H, CH and CH$_2$ of isoBu), 0.97 and 0.95 (each d, J=6.0 Hz, each 3H, CH$_3$s of isoBu).

EXAMPLE 11(4)

(1R, 2S)-N-[3(S)-1-(3-phenyl-5-oxo-1,2,4-oxadiazolin-4-yl)-2-oxo-5-methyl-3-hexyl]-2-benzoylaminocyclohexanecarboxamide

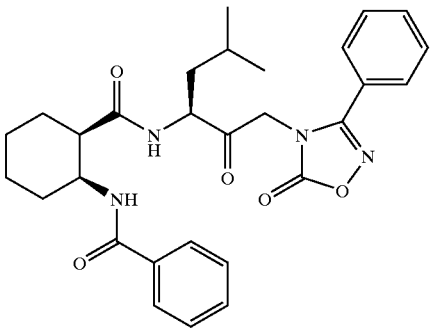

TLC: Rf 0.38 (n-hexane:ethyl acetate=2:3); NMR (300 MHz, CDCl$_3$): δ 7.75–7.70 (m, 2H, ortho CH against NHCO), 7.60–7.35 (m, 8H, Ph), 7.07 (d, J=7.8 Hz, 1H, NH of NHchx), 6.15 (d, J=6.6 Hz, 1H, NH of Leu), 4.65 (d, J=18.2 Hz, 1H, CH of LeuCH$_2$N), 4.53 (d, J=18.2 Hz, 1H, CH of LeuCH$_2$N), 4.50–4.40 (m, 1H, CH of Leu), 4.35–4.25 (m, 1H, NCH of chx), 2.80 (q, J=5.0 Hz, 1H, COCH of chx), 2.05–1.30 (m, 11H, CH$_2$ of chx, and CH$_2$ and CH of Leu), 0.82 (d, J=6.0 Hz, 3H, CH$_3$ of Leu), 0.78 (d, J=6.0 Hz, 3H, CH$_3$ of Leu).

EXAMPLE 11 (5)

(1S, 2R)-N-[3(S)-1-(3-phenyl-5-oxo-1,2,4-oxadiazolin-4-yl)-2-oxo-5-methyl-3-hexyl]-2-benzoylaminocyclohexanecarboxamide

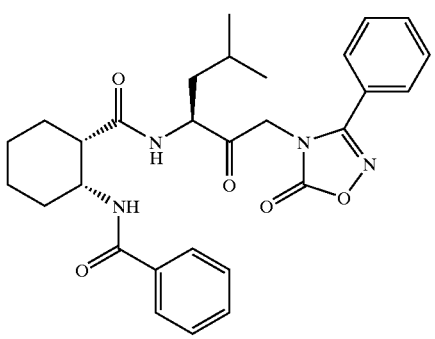

TLC: Rf 0.43 (n-hexane:ethyl acetate=2:3); NMR (300 MHz, CDCl$_3$): δ 7.75–7.70 (m, 2H, ortho CH against NHCO), 7.60–7.35 (m, 8H, Ph), 6.96 (d, J=8.1 Hz, 1H, NH of NHchx), 6.38 (br, 1H, NH of Leu), 4.63 (d, J=18.5 Hz, 1H, CH of LeuCH$_2$N), 4.48 (d, J=18.5 Hz, 1H, CH of LeuCH$_2$N), 4.45–4.30 (m, 2H, CH of Leu, and NCH of chx), 2.85 (q, J=4.5 Hz, 1H, COCH of chx), 2.00–1.25 (m, 11H, CH$_2$ of chx, and CH$_2$ and CH of Leu), 0.87 (d, J=6.0 Hz, 3H, CH$_3$ of Leu), 0.86 (d, J=6.0 Hz, 3H, CH$_3$ of Leu).

EXAMPLE 11 (6)

N-[3(S)-1-(3-phenyl-5-oxo-1,2,4-oxadiazolin-4-yl)-2-oxo-5-methyl-3-hexyl]-3-benzyloxybenzamide

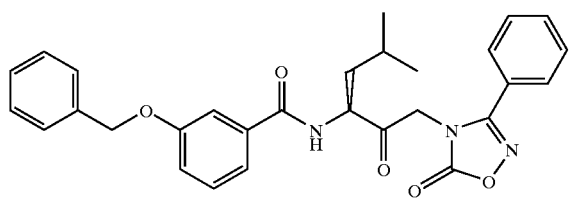

TLC: Rf 0.48 (n-hexane:ethyl acetate=3:2); NMR (300 MHz, CDCl$_3$): δ 7.60–7.20 (m, 13H, Ph), 7.15–7.10 (m, 1H, para CH against CO), 6.44 (d, J=6.9 Hz, 1H, NH of Leu), 5.11 (s, 2H, CH$_2$ of BnO), 4.75 (d, J=18.5 Hz, 1H, CH of LeuCH$_2$N), 4.75–4.65 (m, 1H, CH of Leu), 4.62 (d, J=18.5 Hz, 1H, CH of LeuCH$_2$N), 1.80–1.50 (m, 3H, CH$_2$ and CH of Leu), 1.05–0.85 (m, 6H, CH$_3$ of Leu).

EXAMPLE 11 (7)

N-[3(S)-1-(3-phenyl-5-oxo-1,2,4-oxadiazolin-4-yl)-2-oxo-5-methyl-3-hexyl]-3-phenylpropenamide

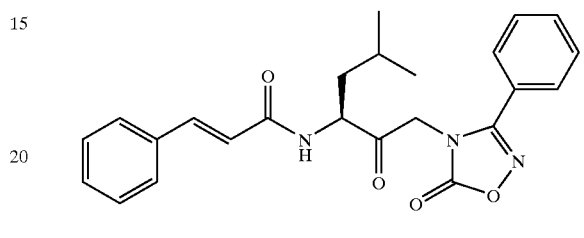

TLC: Rf 0.60 (n-hexane:ethyl acetate=1:1); NMR (300 MHz, CDCl$_3$): δ 7.65–7.38 (m, 11H, aromatic Hs and PhCHC), 6.40 (d, J=15.6 Hz, 1H, CCHCO), 5.98 (d, J=7.2 Hz, 1H, NH), 4.75 (d, J=18.3 Hz, 1H, COCH$_2$N), 4.75 (m, 1H, NCHCO of Leu), 4.60 (d, J=18.3 Hz, 1H, COCH$_2$N), 1.78–1.40 (m, 3H, CCHCH$_2$C of i-Bu), 0.94 (m, 6H, CH$_3$ of i-Bu).

EXAMPLE 11 (8)

N-[3(S)-1-(3-(4-fluorophenyl)-5-oxo-1,2,4-oxadiazolin-4-yl)-2-oxo-5-methyl-3-hexyl] cyclohexanecarboxamide

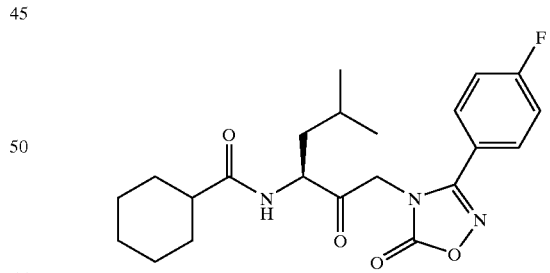

TLC: Rf 0.35 (n-hexane:ethyl acetate=7:3); NMR (300 MHz, CDCl$_3$): δ 7.60–7.45 and 7.30–7.18 (m, both totally 4H, aromatic Hs), 5.73 (d, J=6.3 Hz, 1H, NH), 4.68 (d, J=18.6 Hz, 1H, NCH$_2$CO), 4.55 (d, J=18.6 Hz, 1H, NCH$_2$CO), 4.43 (m, 1H, NCHCO), 2.10 (m, 1H, CCHCO), 1.85–1.10 (m, 13H, Cyclohexane Hs and CHCH$_2$ of i-Bu), 0.90 (m, 6H, CH$_3$ of i-Bu).

EXAMPLE 11 (9)

(1R, 2S)-N-[3(S)-1-(3-(4-fluorophenyl)-5-oxo-1,2,4-oxadiazolin-4-yl)-2-oxo-5-methyl-3-hexyl]-2-benzoylaminocyclohexanecarboxamide

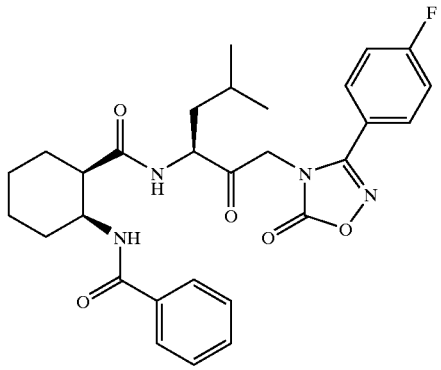

TLC: Rf 0.40 (n-hexane:ethyl acetate=1:1); NMR (300 MHz, CDCl$_3$): δ 7.72 (dd J=6.9, 1.8 Hz, 2H, ortho CH against CONH), 7.56–7.38 (m, 5H, CH of Phs, and meta CH against F), 7.19 (t, J=8.4 Hz, 2H, ortho CH against F), 6.96 (d, J=7.8 Hz, 1H, PhCONH), 6.17 (d, J=6.3 Hz, 1H, NH of P1-Leu), 4.63 and 4.51 (each d, J=18.6 Hz, each 1H, NCH$_2$CO), 4.43–4.30 (m, 2H, NCHCO and NCHC), 2.80 (m, 1H, CCHCO), 2.05–1.40 (m, 11H, C4H8 of cyclohexyl and CHCH$_2$ of i-Bu), 0.84 and 0.79 (each d, J=5.7 Hz, each 3H, CH$_3$ of i-Bu).

EXAMPLE 11 (10)

(1S, 2R)-N-[3(S)-1-(3-(4-fluorophenyl)-5-oxo-1,2,4-oxadiazolin-4-yl)-2-oxo-5-methyl-3-hexyl]-2-benzoylamino cyclohexanecarboxamide

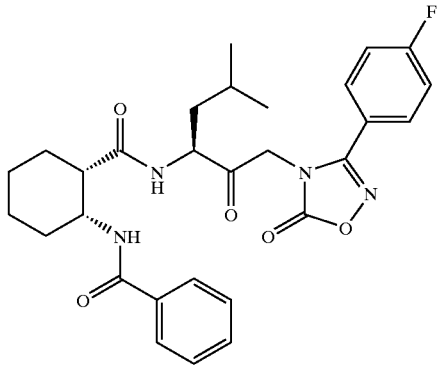

TLC: Rf 0.30 (n-hexane:ethyl acetate=1:1); NMR (300 MHz, CDCl$_3$): δ 7.72 (dd, J=6.9, 1.8 Hz, 2H, ortho CH against CONH), 7.50–7.36 (m, 5H, CH of Phs, and meta CH against F), 7.10 (t, J=8.7 Hz, 2H, ortho CH against F), 6.87 (d, J=8.7 Hz, 1H, PhCONH), 6.57 (d, J=6.0 Hz, 1H, NH of P1-Leu), 4.63 and 4.48 (each d, J=18.6 Hz, each 1H, NCH$_2$CO), 4.43–4.30 (m, 2H, NCHCO and NCHC), 2.85 (m, 1H, CCHCO), 1.95–1.30 (m, 11H, C4H 8 of cyclohexyl and CHCH$_2$ of i-Bu), 0.89 and 0.86 (each d, J=6.6 Hz, each 3H, CH$_3$ of i-Bu)

EXAMPLE 11 (11)

N-[3(S)-1-(3-(4-fluorophenyl)-5-oxo-1,2,4-oxadiazolin-4-yl)-2-oxo-5-methyl-3-hexyl]-2-benzyloxybenzamide

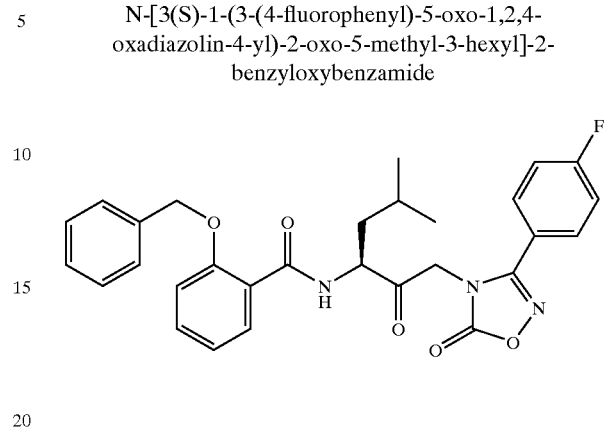

TLC: Rf 0.30 (n-hexane:ethyl acetate=7:3); NMR (300 MHz, CDCl$_3$): δ 8.20 (d, J=5.4 Hz, 1H, NH), 8.13 (dd, J=7.8, 1.8 Hz, 1H, ortho CH against CONH), 7.59–7.50 (m, 3H, para CH against CONH and CH of Phs), 7.49–7.42 (m, 5H, meta CH against F, CH of Phs), 7.20–7.10 (m, 4H, ortho CH against F, para CH against OBn, and ortho CH against OBn), 5.16 and 5.13 (each d, each J=10.2 Hz, each 1H, PhCH$_2$O), 4.74 (d, J=18.6 Hz, 1H, NCH$_2$CO), 4.54 (d, J=18.6 Hz, 1H, NCH$_2$CO), 4.44 (m, 1H, NCHCO), 1.40–1.03 (m, 3H, CHCH$_2$ of i-Bu), 0.74 and 0.68 (each d, each J=6.3 Hz, CH$_3$ of i-Bu).

EXAMPLE 11 (12)

N-[3(S)-1-(3-(4-fluorophenyl)-5-oxo-1,2,4-oxadiazolin-4-yl)-2-oxo-5-methyl-3-hexyl]-3-benzyloxybenzamide

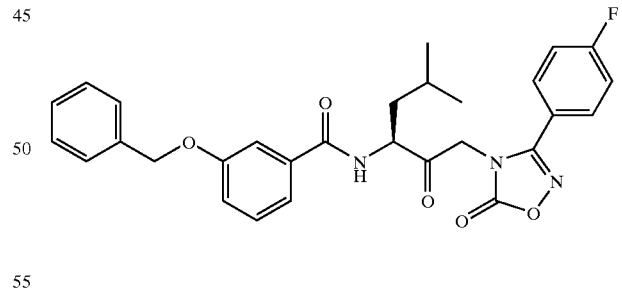

TLC: Rf 0.30 (n-hexane:ethyl acetate=7:3); NMR (300 MHz, CDCl$_3$): δ 7.55 and 7.52 (each d, each J=8.7 Hz, each 1H, ortho CH and para CH against OBn), 7.47–7.34 (m, 7H, meta CH against F and CH of Phs), 7.27 (m, 1H, ortho CH against CONH and OBn), 7.22–7.18 (m, 3H, ortho CH against F, and ortho CH against CONH), 6.39 (d, J=6.6 Hz, 1H, NH), 5.12 (s, 2H, PhCH$_2$O), 4.75 (d, J=18.3 Hz, 1H, NCH$_2$CO), 4.65 (m, 1H, NCHCO), 4.61 (d, J=18.3 Hz, 1H, NCH$_2$CO), 1.80–1.50 (m, 3H, CHCH$_2$ of i-Bu), 0.99 and 0.96 (each d, each J=6.0 Hz, CH$_3$ of i-Bu).

EXAMPLE 11 (13)

N-[3(S)-1-(3-(4-fluorophenyl)-5-oxo-1,2,4-oxadiazolin-4-yl)-2-oxo-5-methyl-3-hexyl]-4-benzyloxybenzamide

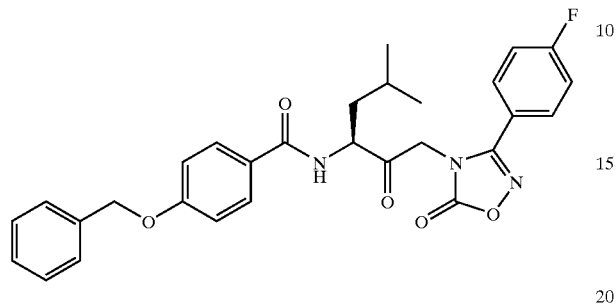

TLC: Rf 0.30 (n-hexane:ethyl acetate=7:3); NMR (300 MHz, CDCl$_3$): δ 7.70 (d, J=8.7 Hz, 2H, ortho CH of CONH), 7.54 (dd, J=8.7, 5.1 Hz, 2H, meta CH of CH$_2$O), 7.45–7.34 (m, 5H, CH of Phs, and meta CH of F), 7.18 (t, J=8.4 Hz, 2H, ortho CH of F), 7.02 (d, J=8.7 Hz, 2H, meta CH of CONH), 6.37 (d, J=6.6 Hz, 1H, NH), 5.13 (s, 2H, PhCH$_2$O), 4.78 (d, J=18.6 Hz, 1H, NCH$_2$CO), 4.62 (m, 1H, NCHCO), 4.61 (d, J=18.6Hz, 1H, NCHCO), 1.80–1.55 (m, 3H, CHCH$_2$ of i-Bu), 0.99 and 0.96 (each d, each J=6.0 Hz, CH$_3$ of i-Bu).

EXAMPLE 11 (14)

N-[3(S)-1-(3-(4-fluorophenyl)-5-oxo-1,2,4-oxadiazolin-4-yl)-2-oxo-5-methyl-3-hexyl]benzamide

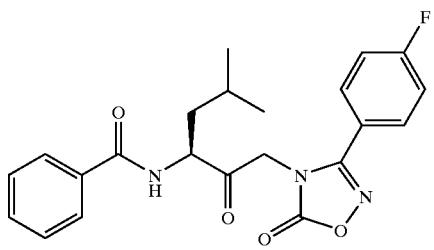

TLC: Rf 0.30 (n-hexane:ethyl acetate=7:3); NMR (300 MHz, CDCl$_3$): δ 7.73 (d, J=7.2 Hz, 2H, ortho CH against CONH), 7.58–7.42 (m, 5H, meta CH against F, and CH of Phs), 7.19 (t, J=8.4 Hz, 2H, ortho CH against F), 6.41 (d, J=6.6 Hz, 1H, NH), 4.78 (d, J=18.6 Hz, 1H, NCH$_2$CO), 4.65 (m, 1H, NCHCO), 4.63 (d, J=18.6 Hz, 1H, NCH$_2$CO), 1.80–1.50 (m, 3H, CHCH$_2$of i-Bu), 0.99 and 0.97 (each d, each J=6.0 Hz, CH$_3$ of i-Bu).

EXAMPLE 11 (15)

N-[3(S)-1(3-(4-fluorophenyl)-5-oxo-1,2,4-oxadiazolin-4-yl)-2-oxo-5-methyl-3-hexyl]-3-phenylpropenamide

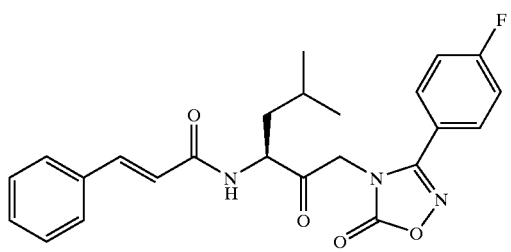

TLC: Rf 0.30 (n-hexane:ethyl acetate=7:3); NMR (300 MHz, CDCl$_3$): δ 7.60 (d, J=15.6 Hz, 1H, PhCHC), 7.56–7.48 (m, 4H, ortho and meta CH against CHCH), 7.40–7.38 (m, 3H, meta CH against F, and para CH against CHCH), 7.22 (t, J=8.7 Hz, 2H, ortho CH against F), 6.40 (d, J=15.6 Hz, 1H, CHCO), 6.02 (d, J=6.6 Hz, 1H, NH), 4.77 (d, J=18.3 Hz, 1H, NCH$_2$CO), 4.60 (m, 1H, NCHCO), 4.60 (d, J=18.3 Hz, 1H, NCH$_2$CO), 1.80–1.50 (m, 3H, CHCH$_2$ o f i-Bu), 0.98 and 0.95 (each d, each J=6.0 Hz, CH$_3$ of i-Bu).

EXAMPLE 11 (16)

N-[3(S)-1-(3-(4-fluorophenyl)-5-oxo-1,2,4-oxadiazolin-4-yl)-2-oxo-5-methyl-3-hexyl]benzenesulfonamide

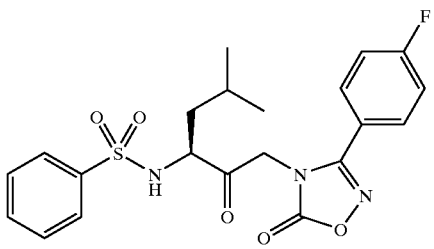

TLC: Rf 0.35 (n-hexane:ethyl acetate=7:3); NMR (300 MHz, CDCl$_3$): δ 7.83 (dd, J=7.2, 1.8 Hz, 2H, ortho CH against SO$_2$), 7.68–7.50 (m, 5H, meta and para CH against SO$_2$, and meta CH against F), 7.23 (t, J=8.7 Hz, 2H, ortho CH against F), 4.98 (d, J=6.0 Hz, 1H, NH), 4.83 (d, J=18.6 Hz, 1H, NCH$_2$CO), 4.71 (d, J=18.6 Hz, 1H, NCH$_2$CO), 3.74 (m, 1H, NCHCO), 1.50–1.37 (m, 3H, CHCH$_2$ of i-Bu), 0.78 (d, J=6.0 Hz, 3H, CH$_3$ of i-Bu), 0.50 (d, J=6.0 Hz, 3H, CH$_3$ of i-Bu).

EXAMPLE 11 (17)

N-[3(S)-1-(3-(4-fluorophenyl)-5-oxo-1,2,4-oxadiazolin-4-yl)-2-oxo-5-methyl-3-hexyl]-3-cyclopentylpropanamide

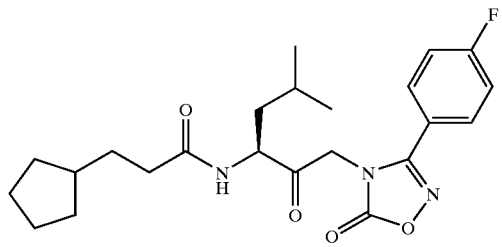

TLC: Rf 0.40 (n-hexane:ethyl acetate=7:3); NMR (300 MHz, CDCl$_3$): δ 7.53 (dd, J=9.0, 5.1 Hz, 2H, meta CH against F), 7.21 (t, J=8.1 Hz, 2H, ortho CH against F), 5.75 (d, J=6.6 Hz, 1H, NH), 4.68 (d, J=18.6 Hz, 1H, NCH$_2$CO), 4.57 (d, J=18.6 Hz, 1H, NCH$_2$CO), 4.46 (m, 1H, NCHCO), 2.20 (m, 2H, CCH$_2$CO), 1.80–1.40 and 1.18–1.00 (each m, totally 14H, CH$_2$ and CH of cyclopenthylmethyl and CHCH$_2$ of i-Bu), 0.96 (d, J=6.3 Hz, 3H, CH$_3$ of i-Bu), 0.92 (d, J=6.3 Hz, 3H, CH$_3$ of i-Bu).

EXAMPLE 11 (18)

N-[3(S)-1-(2-(2-phenylethyl)-5-oxo-1,3,4-oxadiazolin-4-yl)-2-oxo-5-methyl-3-hexyl] cyclohexanecarboxamide

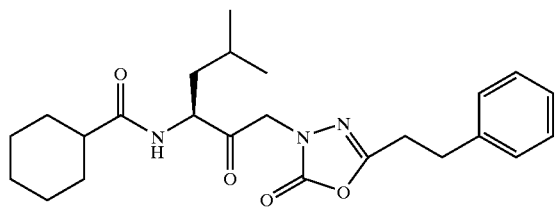

TLC: Rf 0.35 (n-hexane:ethyl acetate=7:3); NMR (300 MHz, CDCl$_3$): δ 7.38–7.18 (m, 5H, CH of Ph), 5.76 (d, J=8.1 Hz, 1H, NH), 4.71 (ddd, J=9.6, 8.1, 3.9 Hz, 1H, NCHCO), 4.65 and 4.58 (each d, each J=18.3 Hz, each 1H, NCH$_2$CO), 3.02–2.98 and 2.90–2.80 (each m, each 2H, PhCH$_2$CH$_2$), 2.14 (tt, J=11.4, 3.3 Hz, 1H, NCOCH), 1.92–1.20 (m, 13H, aliphatic Hs), 0.96 and 0.94 (each d, each J=6.3 Hz, each 3H, CH$_3$ of i-Bu).

EXAMPLE 11 (19)

N-[3(S)-1-(2-(2-phenylethyl)-5-oxo-1,3,4-oxadiazolin-4-yl)-2-oxo-5-methyl-3-hexyl]-4-benzyloxybenzamide

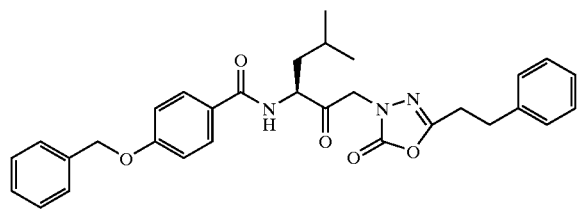

TLC: Rf 0.25 (n-hexane:ethyl acetate=7:3); NMR (300 MHz, CDCl$_3$): δ 7.76 (d, J=9.3 Hz, 2H, ortho CHs against CONH), 7.45–7.17 (m, 10H, aromatic Hs), 7.00 (d, J=9.3 Hz, 2H, meta CHs against CONH), 6.47 (d, J=8.1 Hz, 1H, NH), 5.12 (s, 2H, PhCH$_2$O), 4.92 (ddd, J=9.6, 8.1, 4.2 Hz, 1H, NCHCO), 4.74 and 4.66 (each d, each J=18.0 Hz, each 1H, NCH$_2$CO), 3.03–2.95 and 2.89–2.81 (each m, each 2H, PhCH$_2$CH$_2$), 1.80–1.52 (m, 3H, CHCH$_2$), 0.99–0.97 (m, 6H, CH$_3$).

EXAMPLE 11 (20)

N-[3(S)-1-(2-(2-phenylethyl)-5-oxo-1,3,4-oxadiazolin-4-yl)-2-oxo-5-methyl-3-hexyl]-3-phenylpropenamide

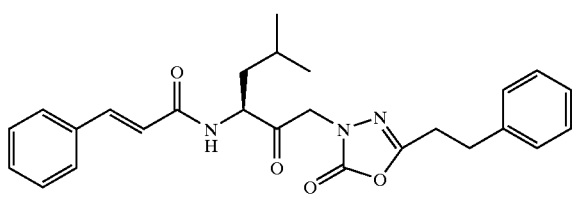

TLC: Rf 0.44 (n-hexane:ethyl acetate=3:2); NMR (200 MHz, CDCl$_3$): δ 7.67 (d, J=15.5 Hz, 1H, CH of PhCHC), 7.60–7.45 (m, 2H, ortho CH against CHCH), 7.40–7.15 (m, 8H, CH of Ph), 6.43 (d, J=15.5 Hz, 1H, CH of CHCONH), 6.00 (d, J=7.4 Hz, 1H, NH of Leu), 4.95–4.80 (m, 1H, CH of Leu), 4.73 (d, J=18.3 Hz, 1H, CH of LeuCH$_2$N), 4.66 (d, J=18.3 Hz, 1H, CH of LeuCH$_2$N), 3.10–2.80 (m, 4H, PhCH$_2$CH$_2$), 1.85–1.40 (m, 3H, CH$_2$ and CH of Leu), 0.98 (d, J=6.2 Hz, 6H, CH$_3$ of Leu).

EXAMPLE 11 (21)

(1R, 2S)-N-[3(S)-1-(2-(2-phenylethyl)-5-oxo-1,3,4-oradiazolin-4-yl)-2-oxo-5-methyl-3-hexyl]-2-benzoylaminocyclohexane carboxamide

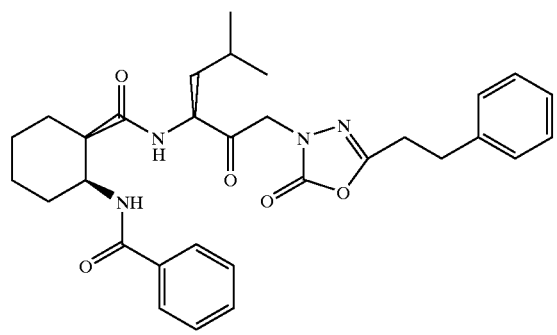

TLC: Rf 0.50 (n-hexane:ethyl acetate1:1); NMR (300 MHz, CDCl$_3$): δ 7.76 (d, J=8.1 Hz, 2H, ortho CHs against CONH), 7.50–7.17 (m, 8H, aromatic Hs), 7.11 (d, J=8.1 Hz, 1H, PhCONH), 6.14 (d, J=7.8 Hz, 1H, NH of Leu), 4.68 (m, 1H, NCHCO), 4.65 and 4.57 (each d, each J=18.3 Hz, each 1H, NCH$_2$CO), 4.35 (m, 1H, PhCONCH), 3.03–2.96 and 2.90–2.78 (each m, totally 5H, PhCH$_2$CH$_2$ and NCOCH), 2.17–1.40 (m, 11H, aliphatic Hs), 0.80 and 0.79 (each d, each J=6.3 Hz, each 3H, CH$_3$).

EXAMPLE 11 (22)

N-[3(S)-1-(2-(2-phenylethyl)-5-oxo-1,3,4-oxadiazolin-4-yl)-2-oxo-5-methyl-3-hexyl]-3-benzyloxybenzamide

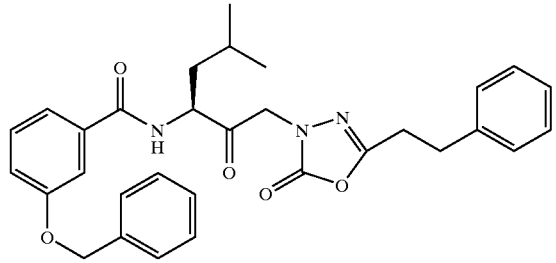

TLC: Rf 0.40 (n-hexane:ethyl acetate=7:3); NMR (200 MHz, CDCl$_3$): δ 7.50–7.10 (m, 14H, aromatic Hs), 6.50 (d, J=7.8 Hz, 1H, NH), 5.11 (s, 2H, PhCH$_2$O), 4.92 (m, 1H, NCHCO), 4.72 and 4.66 (each d, each J=18.4 Hz, each 1H, NCH$_2$CO), 3.05–2.92 and 2.91–2.80 (each m, each 2H, PhCH$_2$CH$_2$), 1.80–1.50 (m, 3H, CHCH$_2$), 1.00–0.97 (m, 6H, CH$_3$).

EXAMPLE 11 (23)

N-[3(S)-1-(2-(2-phenylethyl)-5-oxo-1,3,4-oxadiazolin-4-yl)-2-oxo-5-methyl-3-hexyl]-3-cyclopentylpropanamide

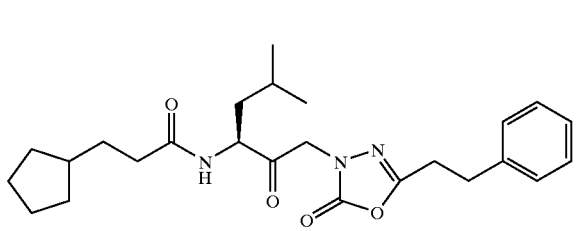

TLC: Rf 0.53 (n-hexane:ethyl acetate=3:2); NMR (200 MHz, CDCl$_3$): δ 7.40–7.15 (m, 5H, CH of Ph), 5.82 (d, J=8.0 Hz, 1H, NH of Leu), 4.80–4.65 (m, 1H, CH of Leu), 4.66 (d, J=18.4 Hz, 1H, CH of LeuCH$_2$N), 4.60 (d, J=18.4 Hz, 1H, CH of LeuCH$_2$N), 3.10–2.80 (m, 4H, PhCH$_2$CH$_2$), 2.30–2.20 (m, 2H, CH$_2$ of CH$_2$CONH), 1.90–1.40 (m, 12H, aliphatic protons), 1.20–1.00 (m, 2H, aliphatic protons), 0.96 (d, J=6.4 Hz, 3H, CH$_3$ of Leu), 0.95 (d, J=6.4 Hz, 3H, CH$_3$ of Leu).

EXAMPLE 11 (24)

(1S, 2R)-N-[3(S)-1-(2-(2-phenylethyl)-5-oxo-1,3,4-oxadiazolin-4-yl)-2-oxo-5-methyl-3-hexyl]-2-benzoylaminocyclohexane carboxamide

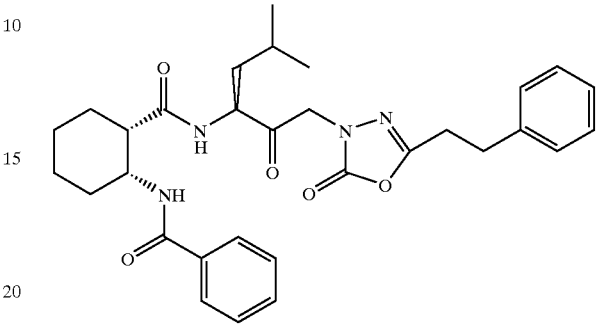

TLC: Rf 0.45 (n-hexane:ethyl acetate 1:1); NMR (200 MHz, CDCl$_3$): δ 7.78 (dd, J=8.0, 2.2 Hz, 2H, ortho CHs against CONH), 7.50–7.16 (m, 9H, aromatic Hs and PhCONH), 6.26 (d, J=7.8 Hz, 1H, NH of Leu), 4.62 (m, 1H, NCHCO), 4.60 and 4.49 (each d, each J=18.4 Hz, each 1H, NCH$_2$CO), 4.33 (m, 1H, PhCONCH), 3.03–2.77 (m, 5H, PhCH$_2$CH$_2$ and NCOCH), 2.10–1.40 (m, 11H, aliphatic Hs), 0.94–0.91 (m, 6H, CH$_3$).

EXAMPLE 11 (25)

N-[3(S)-1-(2-(2-phenylethyl)-5-oxo-1,3,4-oxadiazolin-4-yl)-2-oxo-5-methyl-3-hexyl]-2-benzyloxybenzamide

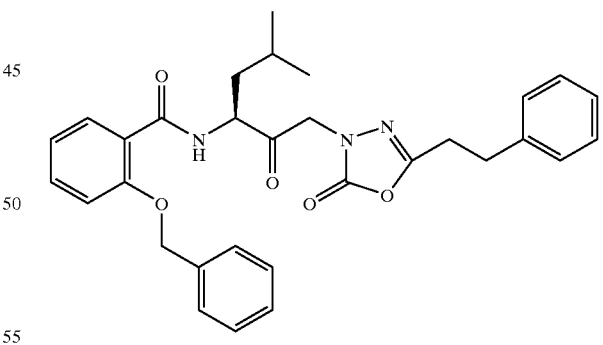

TLC: Rf 0.20 (n-hexane:ethyl acetate=7:3); NMR (200 MHz, CDCl$_3$): δ 8.23 (dd, J=8.0, 1.8 Hz, 1H, ortho CH against CONH), 8.22 (m, 1H, NH), 7.55–7.08 (m, 13H, aromatic Hs), 5.19 and 5.14 (each d, each J=10.4 Hz, each 1H, PhCH$_2$O), 4.62 (m, 1H, NCHCO), 4.68 and 4.60 (each d, each J=18.2 Hz, each 1H, NCH$_2$CO), 3.05–2.93 and 2.90–2.78 (each m, each 2H, PhCH$_2$CH$_2$), 1.50–1.05 (m, 3H, CHCH$_2$), 0.79 and 0.71 (each d, each J=6.2 Hz, each 3H, CH$_3$).

EXAMPLE 11 (26)

N-[3(S)-1-(2-(2-phenylethyl)-5-oxo-1,3,4-oxadiazolin-4-yl)-2-oxo-5-methyl-3-hexyl]benzamide

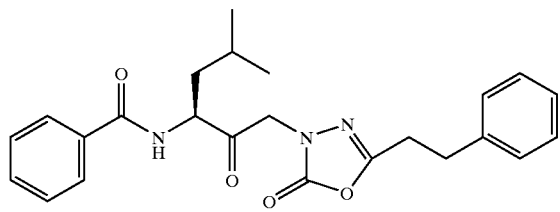

TLC: Rf 0.48 (n-hexane:ethyl acetate=3:2); NMR (200 MHz, CDCl$_3$): δ 7.80 (dd, J=8.1, 1.6 Hz, 2H, ortho CH against CONH), 7.60–7.40 (m, 3H, meta and para CH against CONH), 7.40–7.15 (m, 5H, CH of Ph), 6.58 (d, J=8.0 Hz, 1H, NH of Leu), 4.95 (ddd, J=9.2, 8.0, 4.4 Hz, 1H, CH of Leu), 4.74 (d, J=18.4 Hz, 1H, CH of LeuCH$_2$N), 4.68 (d, J=18.4 Hz, 1H, CH of LeuCH$_2$N), 3.10–2.80 (m, 4H, PhCH$_2$CH$_2$), 1.85–1.45 (m, 3H, CH$_2$ and CH of Leu), 1.00 (d, J=5.8 Hz, 3H, CH$_3$ of Leu), 0.99 (d, J=6.2 Hz, 3H, CH$_3$ of Leu).

EXAMPLE 11 (27)

N-[3(S)-1-(2-(2-phenylethyl)-5-oxo-1,3,4-oxadiazolin-4-yl)-2-oxo-5-methyl-3-hexyl]benzenesulfonamide TLC: Rf 0.48 (n-hexane:ethyl acetate=3:2); NMR (200 MHz, CDCl$_3$): δ 7.84 (dd, J=8.1, 1.6 Hz, 2H, ortho CH against SO$_2$), 7.65–7.45 (m, 3H, meta and para CH against SO$_2$), 7.40–7.15 (m, 5H, CH of Ph), 5.17 (d, J=8.4 Hz, 1H, NH of Leu), 4.53 (d, J=18.5 Hz, 1H, CH of LeuCH$_2$N), 4.45 (d, J=18.5 Hz, 1H, CH of LeuCH$_2$N), 3.97 (ddd, J=9.7, 8.4, 4.4 Hz, 1H, CH of Leu), 3.10–2.80 (m, 4H, PhCH$_2$CH$_2$), 1.80–1.20 (m, 3H, CH$_2$ and CH of Leu), 0.86 (d, J=6.6 Hz, 3H, CH$_3$ of Leu), 0.73 (d, J=6.2 Hz, 3H, CH$_3$ of Leu).

EXAMPLE 11 (28)

N-[3(S)-1-(3-(2-pyridyl)-5-oxo-1,2,4-oxadiazolin-4-yl)-2-oxo-5-methyl-3-hexyl]benzamide

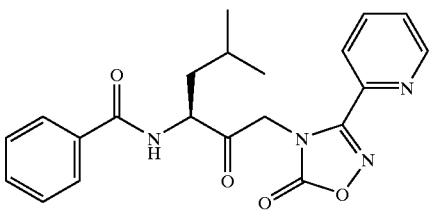

TLC: Rf 0.40 (n-hexane:ethyl acetate=3:2); NMR (200 MHz, CDCl$_3$): δ 8.57 (ddd, J=4.8, 1.8, 1.0 Hz, 1H, 6-CH of pyr.), 8.07 (dt, J=1.0, 8.0 Hz, 1H, 3-CH of pyr.), 7.90–7.70 (m, 3H, ortho CH against CON, and 4-CH of pyr.), 7.60–7.35 (m, 4H, meta and para CH against CON, and 5-CH of pyr.), 6.55 (d, J=8.4 Hz, 1H, NH), 5.28 (d, J=17.6 Hz, 1H, CH of LeuCH$_2$N), 5.25–5.10 (m, 1H, CH of Leu), 5.20 (d, J=17.6 Hz, 1H, CH of LeuCH$_2$N), 1.90–1.45 (m, 3H, CH$_2$ and CH of Leu), 1.05 (d, J=5.8 Hz, 3H, CH$_3$ of Leu), 1.00 (d, J=6.2 Hz, 3H, CH$_3$ of Leu).

EXAMPLE 11 (29)

N-[3(S)-1-(3-(2-pyridyl)-5-oxo-1,2,4-oxadiazolin-4-yl)-2-oxo-5-methyl-3-hexyl]-3-phenylpropenamide TLC: Rf 0.35 (n-hexane:ethyl acetate=3:2); NMR (200 MHz, CDCl$_3$): δ 8.61 (ddd, J=4.8, 1.6, 1.0 Hz, 1H, 6-CH of pyr.), 8.07 (d, J=8.0 Hz, 1H, 3-CH of pyr.), 7.83 (dt, J=1.6, 8.0 Hz, 1H, 4-CH of pyr.), 7.66 (d, J=15.7 Hz, 1H, CH of PhCHC), 7.55–7.30 (m, 6H, CH of Ph, and 5-CH of pyr.), 6.42 (d, J=15.7 Hz, 1H, CH of CHCONH), 6.08 (d, J=8.4 Hz, 1H, NH), 5.25 (d, J=17.8 Hz, 1H, CH of LeuCH$_2$N), 5.20–5.05 (m, 1H, CH of Leu), 5.19 (d, J=17.8 Hz, 1H, CH of LeuCH$_2$N), 1.85–1.40 (m, 3H, CH$_2$ and CH of Leu), 1.03 (d, J=5.8 Hz, 3H, CH$_3$ of Leu), 0.99 (d, J=6.2 Hz, 3H, CH$_3$ of Leu).

EXAMPLE 11 (30)

N-[3(S)-1-(3-(2-pyridyl)-5-oxo-1,2,4-oxadiazolin-4-yl)-2-oxo-5-methyl-3-hexyl]cyclohexanecarboxamide

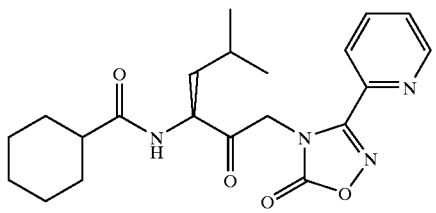

TLC: Rf 0.46 (n-hexane:ethyl acetate=3:2); NMR (200 MHz, CDCl$_3$): δ 8.60 (ddd, J=4.8, 1.8, 1.0 Hz, 1H, 6-CH of pyr.), 8.07 (dt, J=7.9, 1.0 Hz, 1H, 3-CH of pyr.), 7.84 (dt, J=1.8, 7.9 Hz, 1H, 4-CH of pyr.), 7.43 (ddd, J=7.9, 4.8, 1.0 Hz, 1H, 5-CH of pyr.), 5.82 (d, J=8.4 Hz, 1H, NH), 5.16 (s, 2H, CH$_2$ of LeuCH$_2$N), 5.05–4.90 (m, 1H, CH of Leu), 2.13 (tt, J=11.3, 3.1 Hz, 1H, CH of chx), 1.90–1.10 (m, 13H, CH$_2$ of chx, and CH$_2$ and CH of Leu), 0.98 (d, J=5.8 Hz, 3H, CH$_3$ of Leu), 0.97 (d, J=6.2 Hz, 3H, CH$_3$ of Leu).

EXAMPLE 11 (31)

(1R,2S)-N-[3(S)-1-(3-(2-pyridyl)-5-oxo-1,2,4-oxadiazolin-4-yl)-2-oxo-5-methyl-3-hexyl]-2-benzoylaminocyclohexanecarbox amide

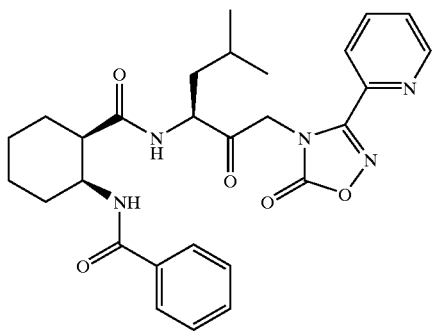

TLC: Rf 0.33 (n-hexane:ethyl acetate=1:1); NMR (200 MHz, CDCl$_3$): δ 8.57 (ddd, J=4.8, 1.8, 1.0 Hz, 1H, 6-CH of pyr.), 8.06 (dt, J=8.0, 1.0 Hz, 1H, 3-CH of pyr.), 7.83 (dt, J=1.8, 8.0 Hz, 1H, 4-CH of pyr.), 7.76 (dd, J=8.1, 1.5 Hz, 2H, ortho CH against CONH), 7.55–7.35 (m, 4H, meta and para CH against CONH, and 5-CH of pyr.), 7.13 (d, J=7.6 Hz, 1H, NH of PhCONH), 6.20 (d, J=8.4 Hz, 1H, NH), 5.16 (s, 2H, CH$_2$ of LeuCH$_2$N), 5.00–4.80 (m, 1H, CH of Leu), 4.40–4.20 (m, 1H, NCH of chx), 2.80 (q, J=4.9 Hz, 1H, COCH of chx), 2.20–1.30 (m, 11H, CH$_2$ of chx, and CH$_2$ and CH of Leu), 0.84 (d, J=6.2 Hz, 3H, CH$_3$ of Leu), 0.81 (d, J=6.2 Hz, 3H, CH$_3$ of Leu).

EXAMPLE 11 (32)

N-[3(S)-1-(3-(2-pyridyl)-5-oxo-1,2,4-oxadiazolin-4-yl)-2-oxo-5-methyl-3-hexyl]-4-benzyloxybenzamide

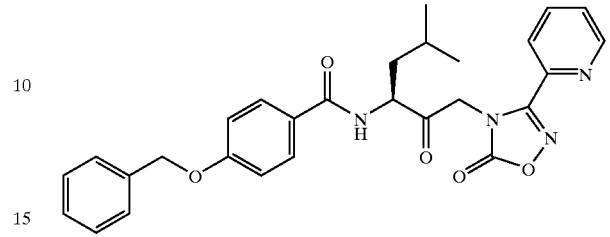

TLC: Rf 0.50 (n-hexane:ethyl acetate=3:2); NMR (200 MHz, CDCl$_3$): δ 8.56 (d, J=5.0 Hz, 1H, 6-CH of pyr.), 8.06 (d, J=8.0 Hz, 1H, 3-CH of pyr.), 7.82 (dt, J=1.4, 8.0 Hz, 1H, 4-CH of pyr.), 7.74 (d, J=8.8 Hz, 2H, ortho CH against CONH), 7.45–7.30 (m, 6H, CH of Bn, and 5-CH of pyr.), 7.00 (d, J=8.8 Hz, 2H, meta CH against CONH), 6.46 (d, J=8.4 Hz, 1H, NH), 5.26 (d, J=17.8 Hz, 1H, CH of LeuCH$_2$N), 5.20 (d, J=17.8 Hz, 1H, CH of LeuCH$_2$N), 5.20–5.10 (m, 1H, CH of Leu), 5.12 (s, 2H, CH$_2$ of Bn), 1.90–1.40 (m, 3H, CH$_2$ and CH of Leu), 1.03 (d, J=6.2 Hz, 3H, CH$_3$ of Leu), 0.99 (d, J=5.8 Hz, 3H, CH$_3$ of Leu).

EXAMPLE 11 (33)

(1S,2R)-N-[3(S)-1-(3-(2-pyridyl)-5-oxo-1,2,4-oxadiazolin-4-yl)-2-oxo-5-methyl-3-hexyl]-2-benzoylaminocyclohexanecarbox amide

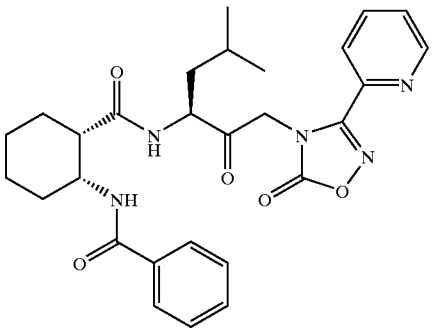

TLC: Rf 0.25 (n-hexane:ethyl acetate=1:1); NMR (200 MHz, CDCl$_3$): δ 8.46 (ddd, J=4.9, 1.8, 1.0 Hz, 1H, 6-CH of pyr.), 7.99 (dt, J=7.9, 1.0 Hz, 1H, 3-CH of pyr.), 7.80–7.65 (m, 3H, ortho CH against CONH, and 4-CH of pyr.), 7.50–7.15 (m, 5H, meta and para CH against CONH, and NH of PhCONH, and 5-CH of pyr.), 6.27 (d, J=8.2 Hz, 1H, NH of Leu), 5.12 (d, J=17.8 Hz, 1H, CH of LeuCH$_2$N), 5.05 (d, J=17.8 Hz, 1H, CH of LeuCH$_2$N), 4.90–4.70 (m, 1H, CH of Leu), 4.35–4.20 (m, 1H, NCH of chx), 2.84 (q, J=4.9 Hz, 1H, COCH of chx), 2.20–1.30 (m, 11H, CH$_2$ of chx, and CH$_2$ and CH of Leu), 0.96 (d, J=5.8 Hz, 3H, CH$_3$ of Leu), 0.94 (d, J=6.2 Hz, 3H, CH$_3$ of Leu).

EXAMPLE 11 (34)

N-[3(S)-1-(3-(2-pyridyl)-5-oxo-1,2,4-oxadiazolin-4-yl)-2-oxo-5-methyl-3-hexyl]-3-benzyloxybenzamide

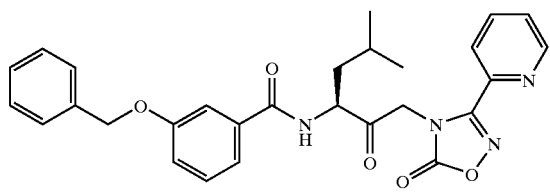

TLC: Rf 0.37 (n-hexane:ethyl acetate=3:2); NMR (200 MHz, CDCl₃): δ 8.56 (ddd, J=5.0, 1.8, 1.0 Hz, 1H, 6-CH of pyr.), 8.07 (dt, J=7.9, 1.0 Hz, 1H, 3-CH of pyr.), 7.83 (dt, J=1.8, 7.9 Hz, 1H, 4-CH of pyr.), 7.50–7.25 (m, 9H, CH of Ph, and 5-CH of pyr.), 7.13 (dt, J=6.6, 2.6 Hz, 1H, para CH against CONH), 6.52 (d, J=8.0 Hz, 1H, NH), 5.27 (d, J=17.8 Hz, 1H, CH of LeuCH₂N), 5.25–5.10 (m, 1H, CH of Leu), 5.20 (d, J=17.8 Hz, 1H, CH of LeuCH₂N), 5.11 (s, 2H, CH₂ of Bn), 1.85–1.45 (m, 3H, CH₂ and CH of Leu), 1.04 (d, J=5.8 Hz, 3H, CH₃ of Leu), 1.00 (d, J=6.2 Hz, 3H, CH₃ of Leu).

EXAMPLE 11 (35)

N-[3(S)-1-(3-(2-pyridyl)-5-oxo-1,2,4-oxadiazolin-4-yl)-2-oxo-5-methyl-3-hexyl]-2-benzyloxybenzamide

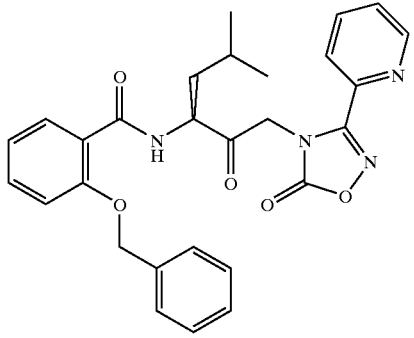

TLC: Rf 0.55 (n-hexane:ethyl acetate=3:2); NMR (200 MHz, CDCl₃): δ 8.53 (ddd, J=5.0, 1.8, 1.0 Hz, 1H, 6-CH of pyr.), 8.23 (dd, J=8.0, 2.0 Hz, 1H, ortho CH against CON), 8.21 (d, J=8.0 Hz, 1H, NH), 8.04 (dt, J=7.7, 1.0 Hz, 1H, 3-CH of pyr.), 7.81 (dt, J=1.8, 7.7 Hz, 1H, 4-CH of pyr.), 7.55–7.30 (m, 7H, CH of Ph, and 5-CH of pyr.), 7.20–7.05 (m, 2H, meta CH against CON), 5.18 (d, J=10.0 Hz, 1H, CH of LeuCH₂N), 5.17 (s, 2H, CH₂ of Bn), 5.14 (d, J=10.0 Hz, 1H, CH of LeuCH₂N), 4.95–4.80 (m, 1H, CH of Leu), 1.55–1.00 (m, 3H, CH₂ and CH of Leu), 0.83 (d, J=5.8 Hz, 3H, CH₃ of Leu), 0.74 (d, J=6.4 Hz, 3H, CH₃ of Leu).

EXAMPLE 11 (36)

N-[3(S)-1-(3-(2-pyridyl)-5-oxo-1,2,4-oxadiazolin-4-yl)-2-oxo-5-methyl-3-hexyl]-3-cyclopentylpropanamide

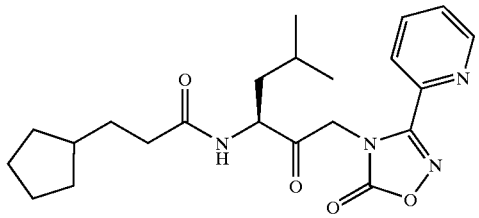

TLC: Rf 0.52 (n-hexane:ethyl acetate=3:2); NMR (200 MHz, CDCl₃): δ 8.60 (ddd, J=4.8, 1.7, 1.0 Hz, 1H, 6-CH of pyr.), 8.07 (dt, J=7.7, 1.0 Hz, 1H, 3-CH of pyr.), 7.84 (dt, J=1.7, 7.7 Hz, 1H, 4-CH of pyr.), 7.42 (ddd, J=7.7, 4.8, 1.0 Hz, 1H, 5-CH of pyr.), 5.82 (d, J=8.6 Hz, 1H, NH), 5.19 (d, J=17.6 Hz, 1H, CH of LeuCH₂N), 5.14 (d, J=17.6 Hz, 1H, CH of LeuCH₂N), 5.05–4.90 (m, 1H, CH of Leu), 2.30–2.15 (m, 2H, CH₂ of CH₂CONH), 1.85–1.35 (m, 12H, aliphatic protons), 1.20–0.90 (m, 2H, aliphatic protons), 1.00 (d, J=6.0 Hz, 3H, CH₃ of Leu), 0.97 (d, J=6.2 Hz, 3H, CH₃ of Leu).

EXAMPLE 11 (37)

N-[3(S)-1-(3-(2-pyridyl)-5-oxo-1,2,4-oxadiazolin-4-yl)-2-oxo-5-methyl-3-hexyl]benzenesulfonamide

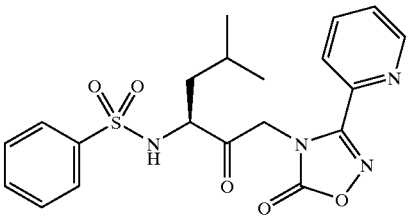

TLC: Rf 0.46 (n-hexane:ethyl acetate=3:2); NMR (200 MHz, CDCl₃): δ 8.54 (ddd, J=5.0, 1.8, 1.1 Hz, 1H, 6-CH of pyr.), 8.06 (dt, J=8.0, 1.1 Hz, 1H, 3-CH of pyr.), 7.90–7.75 (m, 3H, ortho CH against SO₂, and 4-CH of pyr.), 7.65–7.40 (m, 4H, meta and para CH against SO₂, and 5-CH of pyr.), 5.32 (d, J=18.1 Hz, 1H, CH of LeuCH₂N), 5.12 (d, J=8.4 Hz, 1H, NH), 5.05 (d, J=18.1 Hz, 1H, CH of LeuCH₂N), 4.20–4.05 (m, 1H, CH of Leu), 1.80–1.20 (m, 3H, CH₂ and CH of Leu), 0.87 (d, J=6.2 Hz, 3H, CH₃ of Leu), 0.77 (d, J=6.0 Hz, 3H, CH₃ of Leu).

EXAMPLE 12—12 (1)

By the same procedure as described in example 6→example 8 using a corresponding compound, the following compounds having the following physical data were given.

EXAMPLE 12

2(S)-N-(3(S)-1-(5-oxo-3-(2-pyridyl)-1,2,4-oxadiazolin-4-yl)-2-oxo-5-methyl-3-hexyl)-2-(4-dimethylaminomethylbenzyloxycarbonylamino)-4-methylpentanamide

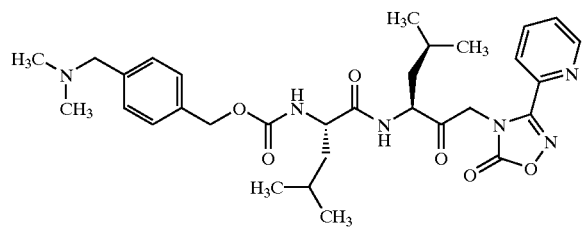

TLC: Rf 0.61 (chloroform:methanol:water=40:10:1); NMR (CDCl$_3$): δ 8.58 (d, J=4.5 Hz, 1H), 8.06 (d, J=7.8 Hz, 1H), 7.84 (dt, J=1.8, 7.8 Hz, 1H), 7.44–7.40 (m, 1H), 7.29–7.24 (m, 4H), 6.46 (d, J=8.1 Hz, 1H), 5.14–5.07 (m, 5H), 4.92–4.84 (m, 1H), 4.22–4.12 (m, 1H), 3.42 (m, 2H), 2.23 (m, 6H), 1.73–1.43 (m, 6H), 0.96–0.88 (m, 12H).

EXAMPLE 12 (1)

2(S)-N-(3(S)-1-(5-oxo-3-(3-fluorophenyl)-1,2,4-oxadiazolin-4-yl)-2-oxo-5-methyl-3-hexyl)-2-(4-dimethylaminomethylbenzyl oxycarbonylamino)-4-methylpentanamide

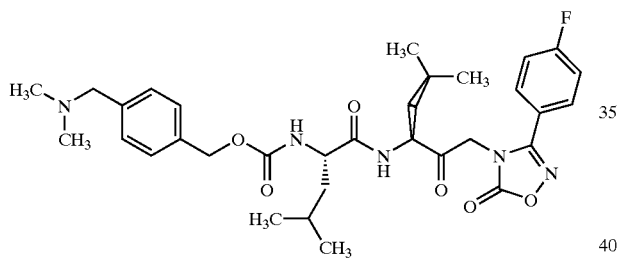

TLC: Rf 0.61 (chloroform:methanol:water=40:10:1); NMR (CDCl$_3$): δ 7.53–7.46 (m, 2H), 7.30–7.15 (m, 6H), 6.52 (d, J=6.0 Hz, 1H), 5.08–5.04 (m, 2H), 5.00 (d, J=7.5 Hz, 1H), 4.64 (d, J=15.6 Hz, 1H), 4.50 (d, J=15.6 Hz, 1H), 4.43–4.35 (m, 1H), 4.15–4.07 (m, 1H), 3.42 (m, 2H), 2.23 (m, 6H), 1.63–1.42 (m, 6H), 0.95–0.87 (m, 12H).

FORMULATION EXAMPLE

Formulation Example 1

The following components were admixed in a conventional method and punched out to give 100 tablets each containing 50 mg of active ingredient.

| | |
|---|---|
| 2(S)-N-(3(S)-1-(5-phenyltetrazol-2-yl)-2-oxo-5-methyl-3-hexyl)-2-benzyloxycarbonylamino-4-methylpentanamide | 5.0 g |
| carboxymethylcellulose calcium (disintegrating agent) | 0.2 g |
| magnesium stearate (lubricant) | 0.1 g |
| microcrystalline cellulose | 4.7 g |

Formulation Example 2

The following components were admixed in a conventional method. The solution was sterilized in conventional method, placed 5 ml portions into ampoules and freeze-dried in conventional method to give 100 ampoules each containing 20 mg of the active ingredient.

| | |
|---|---|
| 2(S)-N-(3(S)-1-(5-phenyltetrazol-2-yl)-2-oxo-5-methyl-3-hexyl)-2-benzyloxycarbonylamino-4-methylpentanamide | 2.0 g |
| mannitol | 20 g |
| distilled water | 500 ml |

What is claimed is:
1. A compound of formula (I-1A)

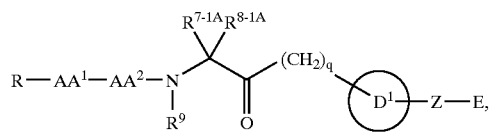

(I-1A)

wherein R is
(i) hydrogen,
(ii) C1–8 alkyl,
(iii) CycA,
(iv) C1–8 alkyl substituted with a group selected from halogen, CycA, nitro, CF$_3$ and cyano,

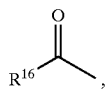
(v)

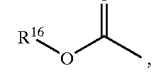
(vi)

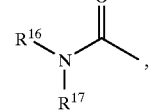
(vii)

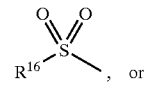
, or (viii)

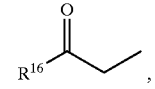
(ix)

CycA is a mono-, bi- or tri-cyclic C3–15 carboning or a mono-, bi- or tri-cyclic 3–15 membered heteroring containing 1–4 of nitrogen, 1–2 of oxygen and/or 1 of sulfur;

$R^{16}$ is
(1) C1–8 alkyl,
(2) C2–8 alkenyl,
(3) C2–8 alkynyl,
(4) CycA or
(5) C1–8 alkyl, C2–8 alkenyl or C2–8 alkynyl substituted with agroup selected from halogen, nitro, CF$_3$, cyano, CycA, NR$^{18}$R$^{19}$ or —NHC(O)CycA;

$R^{17}$, $R^{18}$ and $R^{19}$ are each independently, hydrogen or C1–4 alkyl, $AA^1$ is (i) a single bond, or

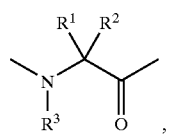

(ii)

wherein $R^1$ and $R^2$ are the same or different and represent (i) hydrogen,
(ii) C1–8 alkyl,
(iii) CycA or
(iv) C1–8 alkyl substituted with 1–5 of a group selected from the following (1)–(8):
(1) —$NR^{21}R^{22}$,
(2) —$OR^{23}$,
(3) —$SR^{24}$,
(4) —$COR^{25}$,
(5) —$NR^{26}CONR^{21}R^{22}$,
(6) guanidino,
(7) CycA, and
(8) —$NR^{26}SO_2R^{21}$; or $R^1$ and $R^2$ are taken together to form C2–8 alkylene, wherein one carbon atom may be replaced by oxygen, sulfur or —$NR^{20}$— and the alkylene may be substituted with —$NR^{21}R^{22}$ or —$OR^{23}$, $R^{20}$ is hydrogen, C1–4 alkyl, —COO-(C1–4 alkyl), phenyl or C1–4 alkyl substituted with phenyl, $R^{21}$, $R^{22}$, $R^{23}$, $R^{24}$ and $R^{26}$ are the same or different and represent hydrogen, C1–4 alkyl, phenyl or C1–4 alkyl substituted with phenyl, $R^{25}$ is C1–4 alkyl, phenyl, —$NR^{21}R^{22}$, wherein all symbols have the same meanings as above, —$OR^{23}$, wherein $R^{23}$ has the same meaning as above, or C1–4 alkyl substituted with phenyl, $R^3$ is hydrogen, C1–8 alkyl, phenyl or C1–8 alkyl substituted with phenyl or $R^3$ is taken together with $R^1$ to form C2–6 alkylene, wherein one carbon atom may be replaced by oxygen, sulfur or —$NR^{20}$— and the alkylene may be substituted with —$NR^{21}R^{22}$ or —$OR^{23}$, or when $AA^1$ is

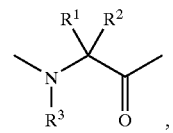

$AA^1$ and R may be taken together to form

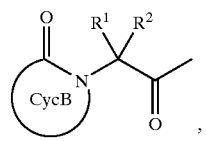

wherein

-continued

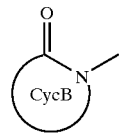

is a 5–12 membered mono- or bi-cyclic heteroring and the other symbols have the same meanings as above, $AA^2$ is (i) a single bond,

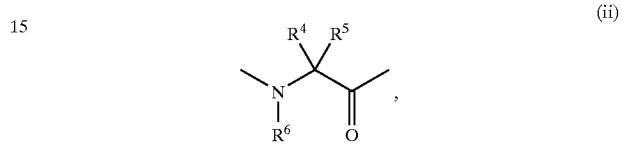

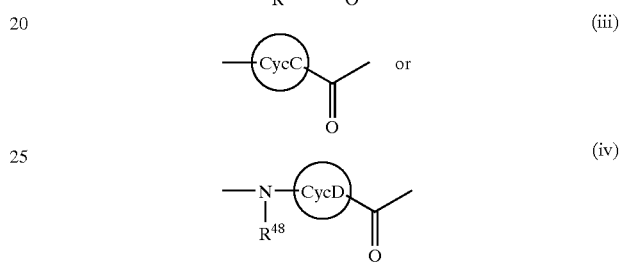

wherein $R^4$ and $R^5$ are the same or different and represent (1) hydrogen,
(2) C1–8 alkyl,
(3) CycA or
(4) C1–8 alkyl substituted with 1–5 of a group selected from the following (a)–(h):
(a) —$NR^{41}R^{42}$, (b) —$OR^{43}$, (c) —$SR^{44}$, (d) —$COR^{45}$, (e) —$NR^{46}CONR^{41}R^{42}$, (f) guanidino, (g) CycA, (h) —$NR^{46}SO_2R^{41}$; or $R^4$ and $R^5$ are taken together to form C2–8 alkylene, wherein one carbon atom may be replaced by oxygen, sulfur or —$NR^{40}$— and the alkylene may be substituted with —$NR^{41}R^{42}$ or —$OR^{43}$, $R^{40}$ is hydrogen, C1–4 alkyl, —COO—(C1–4 alkyl), phenyl or C1–4 alkyl substituted with phenyl, $R^{41}$, $R^{42}$, $R^{43}$, $R^{44}$ and $R^{46}$ are the same or different and represent hydrogen, C1–4 alkyl, phenyl or C1–4 alkyl substituted with phenyl, $R^{45}$ is C1–4 alkyl, phenyl, —$NR^{41}R^{42}$, wherein all symbols have the same meanings as above, —$OR^{43}$, wherein $R^{43}$ has the same meaning as above, or C1–4 alkyl substituted with phenyl, $R^6$ is hydrogen, C1–8 alkyl, phenyl or C1–8 alkyl substituted with phenyl or $R^6$ is taken together with $R^4$ to form C2–6 alkylene, wherein one carbon atom may be replaced by oxygen, sulfur or —$NR^{40}$— and the alkylene may be substituted with —$NR^{41}R^{42}$ or —$OR^{43}$, $R^{48}$ is hydrogen, C1–4 alkyl, phenyl or C1–4 alkyl substituted with phenyl, CycC is a 3–17 membered mono- or bi-cyclic heteroring, CycD is a C3–14 mono- or bi-cyclic carboring or a 3–14 membered mono- or bi-cyclic heteroring, or AA² and AA¹ are taken together to form

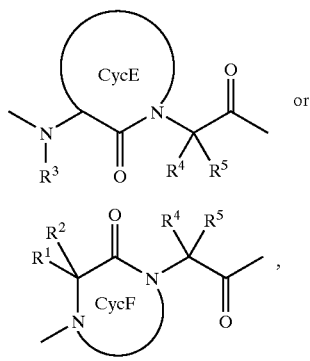

wherein CycE is a 4–18 membered mono- or bi-cyclic heteroring, CycF is a 5–8 membered monocyclic heteroring, and the other symbols have the same meanings as above, $R^{7-1A}$ and $R^{8-1A}$ are each independently.
(i) hydrogen,
(ii) C1–8 alkyl,
(iii) phenyl or,
(iv) C1–8 alkyl substituted with 1–5 of a group selected from —NH₂, C1–4 alkoxy, SH, SCH₃, phenyl, hydroxyphenyl, guanidino, imidazolyl and indolyl, or $R^{7-1A}$ and $R^{8-1A}$ are taken together to form C2–8 alkylene,
wherein one carbon atom may be replaced by oxygen, sulfur or —NR⁶⁰— and the alkylene may be substituted with —NR⁶¹R⁶² or —OR⁶³, $R^{60}$ is hydrogen, C1–4 alkyl, —COO—(C1–4 alkyl), phenyl or C1–4 alkyl substituted with phenyl, $R^{61}$, $R^{62}$ and $R^{63}$, are the same or different and represent hydrogen, C1–4 alkyl, phenyl or C1–4 alkyl substituted with phenyl, $R^9$ is hydrogen, C1–8 alkyl, phenyl or C1–8 alkyl substituted with phenyl or $R^9$ is taken together with $R^{7-1A}$ to form C2–6 alkylene, wherein one carbon atom may be replaced by oxygen, sulfur or —NR⁶⁰— and the alkylene may be substituted with —NR⁶¹R⁶² or —OR⁶³, q is an integer of 1–4,

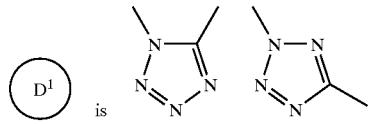

Z is a single bond, C1–6 alkylene, C2–6 alkenylene, C2–6 alkynylene, —O—, —S—; —CO—, —SO—, —SO₂, —NR¹⁰—, or C1–6 alkylene whose one carbon atom is replaced by —O—, —S—; —CO—, —SO—, —SO₂, or —NR¹⁰—, $R^{10}$ is hydrogen atom, C1–4 alkyl, phenyl, or C1–4 alkyl substituted with phenyl, E is hydrogen atom, halogen atom, CF₃, diphenyl(C1–4) alkyl, tri(C1–4 alkyl)silyl, C1–4 alkyl, —COOR¹⁸, —CONR¹⁹R²⁰, —NR¹⁹R²⁰, -G-(R³⁵)ᵣ, —CH₂—PO (OR³⁶)₂, or —CH(PO(OR³⁶)₂)₂, $R^{18}$ is hydrogen atom, C1–4 alkyl, phenyl or C1–4 alkyl substituted with phenyl, $R^{19}$ and $R^{20}$ are each independently, hydrogen atom, C1–4 alkyl, phenyl, or C1–4 alkyl substituted with phenyl, $R^{19}$ and $R^{20}$ are taken together with the nitrogen atom to which they are attached to form a 5–7 membered monocyclic heteroring containing 1–2 of nitrogen, 1 of nitrogen and oxygen atom or 1 of nitrogen or sulfur atom, G is C3–10 mono- or bi-cyclic carboring or 5–18 membered mono-, bi- or tri-cyclic heteroring containing 1–3 of nitrogen, 1 of oxygen and/or 1 of sulfur, r is an integer of 1–5, $R^{35}$ is (i) hydrogen, (ii) C1–8 alkyl, (iii) halogen, (iv) nitro, (v) CF₃, (vi) cyano, (vii) —OR³⁷, (viii) —NR³⁷R³⁸, (ix) —SR³⁷, (x) —COOR³⁷, (Xi) —COR³⁷, (xii) —CONR¹⁹R²⁰, (xiii) C3–10 mono- or bi-cyclic carboring, (xiv) 5–18 mono-, bi- or tri-cyclic heteroring containing 1–3 of nitrogen, 1 of oxygen and/or 1 of sulfur, (xv) C1–8 alkyl substituted with C3–10 mono- or bi-cyclic carboring or 5–18 mono-, bi- or tri-cyclic heteroring containing 1–3 of nitrogen, 1 of oxygen and/or 1 of sulfur (the above carboring or heteroring may be substituted with 1–5 of a group selected from the following groups: C1–8 alkyl, phenyl, C1–4 alkyl substituted with phenyl, halogen, nitro, CF₃, cyano, tetrazole, —OR³⁹, —NR³⁹R⁴⁰, —SR³⁹, COOR³⁹ and —COR³⁹, $R^{36}$ is hydrogen, C1–8 alkyl, cyano, phenyl, C1–8 alkyl substituted with phenyl or cyano, or C1–4 alkyl substituted with 1–3 of halogen, $R^{37}$ hydrogen, C1–4 alkyl, phenyl or C1–4 alkyl substituted with phenyl, $R^{38}$ is hydrogen, C1–4 alkyl, phenyl, C1–4 alkyl substituted with phenyl, C2–5 acyl or COCF₃, $R^{39}$ and $R^{40}$ are each independently, hydrogen, C1–4 alkyl, phenyl or C1–4 alkyl substituted with phenyl, with proviso that (i) when Z is —SO—, E is not hydrogen, and (ii) CycA in R, $R^1$, $R^2$, $R^4$, $R^5$, $R^{7-1A}$, $R^{8-1A}$ and $R^{16}$ are the same or different and CycA, CycB, CycC, CycD, CycE and CycF may each independently be substituted with 1–5 of $R^{27}$:

$R^{27}$ is
(1) C1–8 alkyl,
(2) halogen atom,
(3) —NR¹¹R¹²,
(4) —OR¹³,
(5) a C5–10 mono-or bi-cyclic carboring,
(6) nitro,
(7) CF₃,
(8) cyano,
(9) a 5–10 membered mono- or bi-cyclic heteroring,
(10) —SR¹⁴,
(11) —COR¹⁵,
(12) oxo,
(13) —SO₂R¹⁵,
(14) —OCF₃ or
(15) C1–8 alkyl substituted with 1–5 of a group selected from the following (a)–(m):
(a) halogen, (b) —NR¹¹R¹², (c) —OR¹³, (d) a C5–10 mono- or bi-cyclic carboring, (e) nitro, (f) CF₃, (g) cyano, (h) a 5–10 membered mono- or bi-cyclic heteroring, (j) —SR¹⁴, (k) —COR¹⁵, (l) —SO₂R¹⁵, (m) —OCF₃, wherein $R^{11}$ and $R^{12}$ are the same or different and represent hydrogen, C1–4 alkyl, —COO—(C1–4 alkyl), phenyl or C1–4 alkyl substituted with phenyl, $R^{13}$ and $R^{14}$ are the same or different and represent hydrogen, C1–4 alkyl, phenyl or C1–4 alkyl substituted with phenyl, $R^{15}$ is C1–4 alkyl, phenyl, —$NR^{11}R^{12}$, wherein all symbols have the same meanings as above, —$OR^{13}$, wherein $R^{13}$ has the same meaning as above, or C1–4 alkyl substituted with phenyl, or a non-toxic salt thereof.

2. The compound according to claim 1,
wherein R is
(i) hydrogen,
(ii) C1–8 alkyl,
(iii) CycA,
(iv) C1–8 alkyl substituted with a group selected from CycA or nitro,

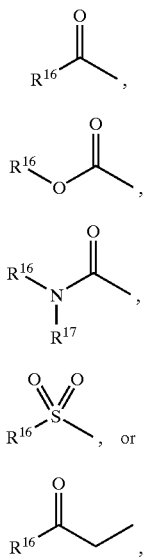

(v)

(vi)

(vii)

(viii)

, or (ix)

$R^{16}$ is
(1) C1–8 alkyl,
(2) C2–8 alkenyl,
(3) C2–8 alkynyl,
(4) CycA,
(5) C1–8 alkyl substituted with a group selected from CycA or —NHC(O)-CycA,
(6) C2–8 alkenyl substituted with CycA,
(7) C2–8 alkynyl substituted with CycA,
$AA^1$ is
(i) a single bond,

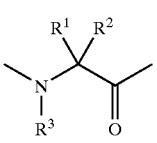

(ii)

or $AA^1$ may be taken together with R to represent

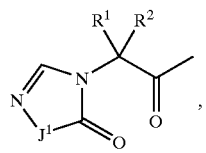

(i)

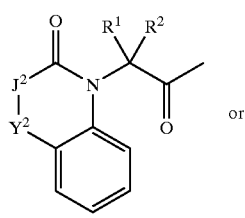

or (ii)

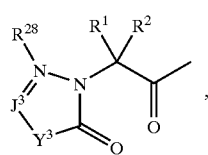

(iii)

wherein $J^1$ is oxygen, sulfur, —$NR^{29}$—, wherein $R^{29}$ is hydrogen, C1–4 alkyl, CycA or C1–4 alkyl substituted with CycA, C1–3 alkylene or C2–3 alkenylene, $J^2$ is a single bond or C1–2 alkylene, $Y^2$ is —N=CH—, —CH=N— or C1–2 alkylene, $j^3$ is carbonyl or C1–3 alkylene, $Y^3$ is C1–3 alkylene, oxygen or —$NR^{29}$—, wherein $R^{29}$ has the same meaning as above, $R^{28}$ is hydrogen, C1–4 alkyl, CycA or C1–4 alkyl substituted with CycA, or $R^{28}$ is taken together with $R^1$ to form C2–4 alkylene, and the other symbols have the same meanings as defined in claim 1and each ring may be substituted with 1–5 of $R^{27}$, $AA^2$ is
(i) a single bond,

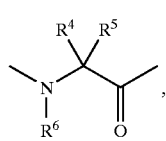

(ii)

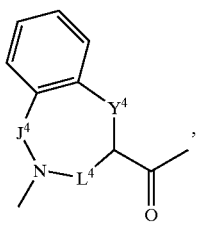

(iii)

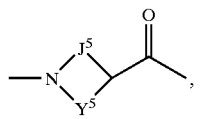

(iv)

187
-continued (v)

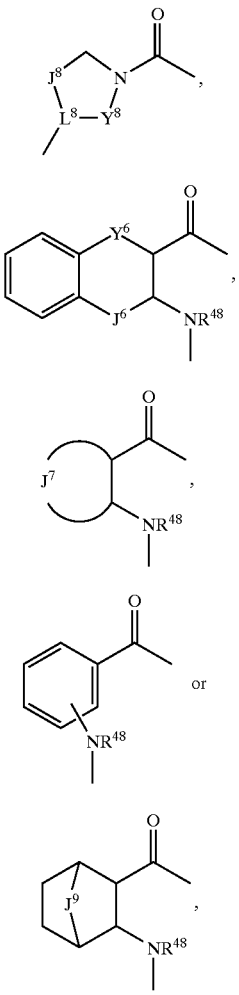

(vi)

(vii)

(viii)

or (ix)

wherein $J^4$, $Y^4$, $L^4$ are the same or different and represent a single bond or C1–3 alkylene (with the proviso that $J^4$, $Y^4$ and $L^4$ do not represent a single bond at the same time), $J^5$ is C1–6 alkylene, $Y^5$ is a single bond, C1–3 alkylene or —NR$^{67}$—, wherein R$^{67}$ is hydrogen, C1–4 alkyl, phenyl or C1–4 alkyl substituted with phenyl, $J^8$ is C1–5 alkylene, wherein one carbon atom may be replaced by oxygen, $Y^8$ is a single bond or C1–4 alkylene, $L^8$ is —N— or —CH—, $j^6$ and $Y^6$ are the same or different and represent a single bond or C1–3 alkylene, with the proviso that $J^6$ and $Y^6$ do not represent a single bond at the same time, $J^7$ is C1–6 alkylene, wherein one carbon atom may be replaced by oxygen, sulfur or —NR$^{67}$—, wherein R$^{67}$ has the same meaning as above, $J^9$ is C1–3 alkylene, oxygen, sulfur or —NR$^{67}$—, wherein R$^{67}$ has the same meaning as above, and each ring may be substituted with 1–5 of R$^{27}$, or

188

AA$^2$ and AA$^1$ are taken together to form

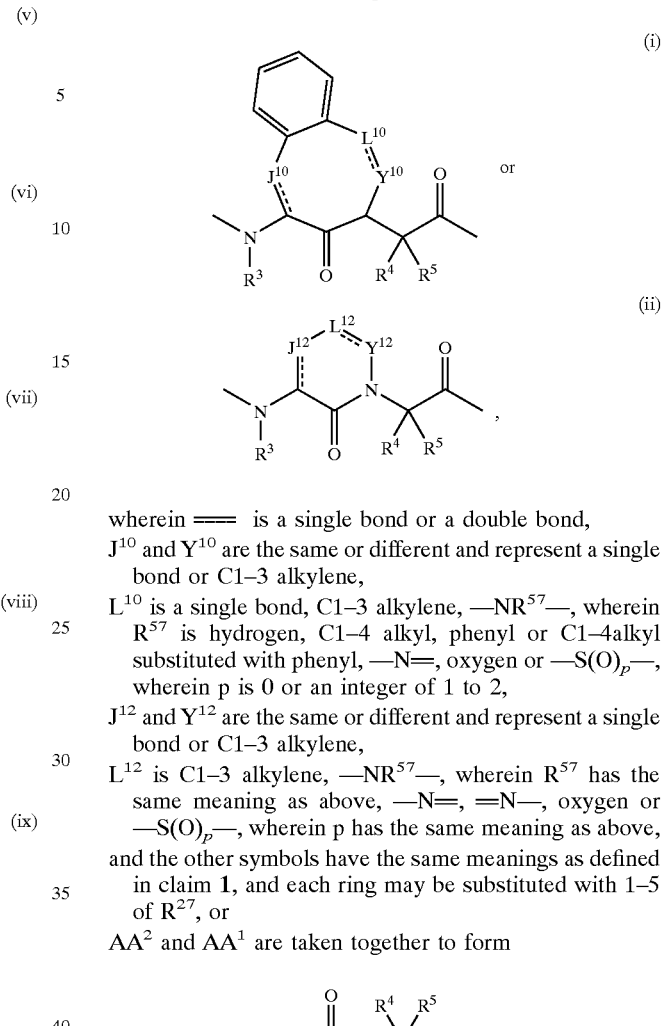

wherein === is a single bond or a double bond, $J^{10}$ and $Y^{10}$ are the same or different and represent a single bond or C1–3 alkylene, $L^{10}$ is a single bond, C1–3 alkylene, —NR$^{57}$—, wherein R$^{57}$ is hydrogen, C1–4 alkyl, phenyl or C1–4alkyl substituted with phenyl, —N=, oxygen or —S(O)$_p$—, wherein p is 0 or an integer of 1 to 2, $J^{12}$ and $Y^{12}$ are the same or different and represent a single bond or C1–3 alkylene, $L^{12}$ is C1–3 alkylene, —NR$^{57}$—, wherein R$^{57}$ has the same meaning as above, —N=, =N—, oxygen or —S(O)$_p$—, wherein p has the same meaning as above, and the other symbols have the same meanings as defined in claim 1, and each ring may be substituted with 1–5 of R$^{27}$, or AA$^2$ and AA$^1$ are taken together to form

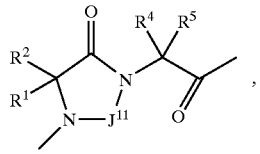

wherein $J^{11}$ is carbonyl or C2–4 alkylene and the other symbols have the same meanings as defined in claim 1, and R$^{27}$ in CycA is (1) C1–8 alkyl,
(2) halogen,
(3) —NR$^{11}$R$^{12}$,
(4) —OR$^{13}$,
(5) phenyl,
(6) nitro,
(7) CF$_3$,
(8) cyano,
(9) tetrazole,
(10) —SR$^{14}$,
(11) —COR$^{15}$,
(12) oxo, or
(13) C1–8 alkyl substituted with 1–5 group selected from the following (a)–(k):
(a) halogen, (b) —NR$^{11}$R$^{12}$, (c) —OR$^{13}$, (d) phenyl, (e) nitro, (f) CF$_3$, (g) cyano, (h) tetrazole, (j) —SR$^{14}$, or (k) —COR$^{15}$, wherein all symbols have the same meanings as above, or a non-toxic salt thereof.

3. The compound according to claim 2, wherein R is C1–8 alkyl, or C1–8 alkyl substituted with CycA or nitro,

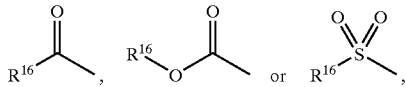

AA¹ is a single bond or

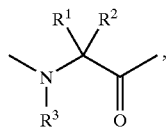

AA² is a single bond,

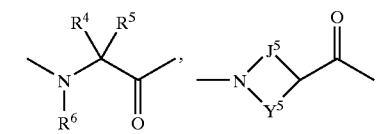

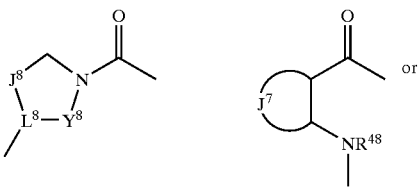

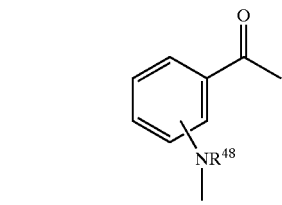

or a non-toxic salt thereof.

4. The compound according to claim 3, wherein R is C1–8 alkyl, C2–8 alkenyl, C2–8 alkynyl, CycA or C1–8 alkyl, C2–8 alkenyl or C2–8 alkynyl substituted with CycA, wherein CycA is mono- or bi-cyclic C5–10 carboaryl or partially or completely saturated form thereof, or mono- or bi-cyclic 5–10 membered heteroaryl containing 1–2 of nitrogen, 1–2 of oxygen and/or 1 of sulfur or partially or completely saturated one thereof, $R^1$ is hydrogen, C1–8 alkyl, phenyl, or C1–8 alkyl substituted with $NH_2$, C1–4 alkoxy, SH, $SCH_3$, phenyl, hydroxyphenyl, COOH, $CONH_2$, guanidino, imidazole or indole and $R^2$ is hydrogen or $R^1$ and $R^2$ are taken together to form C3–6 alkylene, $R^3$ is hydrogen or C1–4 alkyl or $R^3$ and $R^1$ are taken together to form C2–4 alkylene, AA² is a single bond,

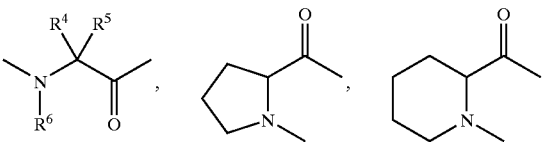

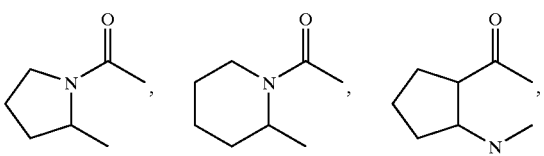

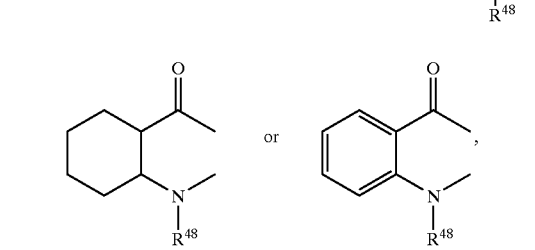

$R^4$ is hydrogen, C1–8 alkyl, phenyl, or C1–8 alkyl substituted with $NH_2$, C1–4 alkoxy, SH, $SCH_3$, phenyl, hydroxyphenyl, COOH, $CONH_2$, guanidino, imidazole or indole and $R^5$ is hydrogen or $R^4$ and $R^5$ are taken together to form C3–6 alkylene, $R^6$ is hydrogen or C1–4 alkyl or $R^6$ and $R^4$ are taken together to form C2–4 alkylene, $R^{48}$ is hydrogen or C1–4 alkyl, $R^{7-1A}$ is hydrogen, C1–8 alkyl, phenyl, or C1–8 alkyl substituted with $NH_2$, C1–4 alkoxy, SH, $SCH_3$, phenyl, hydroxyphenyl, COOH, $CONH_2$, guanidino, imidazole or indole and $R^8$ is hydrogen or $R^{7-1A}$ and $R^{8-1A}$ are taken together to form C3–6 alkylene, $R^9$ is hydrogen or C1–4 alkyl or $R^9$ and $R^{7-1A}$ are taken together to form C2–4 alkylene, or a non-toxic salt thereof.

5. The compound according to claim 1, wherein $R^{16}$ is C1–8 alkyl, C2–8 alkenyl or C2–8 alkynyl substituted with a group selected from halogen, nitro, $CF_3$, cyano or $NR^{18}R^{19}$.

6. The compound according to claim 1, wherein $R^{16}$ is (1) CycA containing 1–5 of substituent $R^{16}$ or (2) C1–8 alkyl, C2–8 alkenyl or C2–8 alkynyl substituted with CycA containing 1–5 of substituent $R^{27}$, wherein at least one of $R^{27}$ included in (1) and (2) is selected from (i) a C5–10 mono- or bi-cyclic carboring, (ii) a 5–10 membered mono- or bi-cyclic heteroring, (iii) —$SO_2R^{15}$, (iv) —$OCF_3$ and (v) C1–8 alkyl substituted with 1–5 of a group selected from (a) halogen, (b) —$NR^{11}R^{12}$, (c) —$OR^{13}$, (d) a C5–10 mono- or bi-cyclic carboring, (e) nitro, (f) $CF_3$, (g) cyano, (h) a 5–10 membered mono- or bi-cyclic heteroring, (j) —$SR^{14}$, (k) —$COR^{15}$, (l) —$SO_2R^{15}$ and (m) —$OCF_3$, wherein at least one substituent thereof is a C5–10 mono- or bi-cyclic carboring, a 5–10 membered mono- or bi-cyclic heteroring, —$SO_2R^{15}$ and —$OCF_3$, or a non-toxic salt thereof.

7. The compound according to claim 1, which is (1) 2(S)-N-(3(S)-1-(5-phenyltetrazol-2-yl)-2-oxo-5-methyl-3-hexyl)-2-benzyloxycarbonylamino-4-methylpentanamide, (2) 2(S)-N-(3(S)-1-(5-morpholinotetrazol-2-yl)-2-oxo-5-methyl-3-hexyl)-2-benzyloxycarbonylamino-4-methylpentanamide, (3) 2(S)-N-(3(S)-1-(tetrazol-2-yl)-2-oxo-5-methyl-3-hexyl)-2-benzyloxycarbonylamino-4-methylpentanamide, (4) 2(S)-N-(3(S)-1-(tetrazol-1-yl)-2-oxo-5-methyl-3-hexyl)-2-benzyloxycarbonylamino-4-methylpentanamide, (5) 2(S)-N-(3(S)-1-(5-(pyrrolidin-1-yl)tetrazol-2-yl)-2-oxo-5-methyl-3-hexyl)-2-benzyloxycarbonylamino-4-methylpentan amide, (6) 2(S)-N-(3(S)-1-(5-benzyltetrazol-2-yl)-2-oxo-5-methyl-3-hexyl)-2-benzyloxycarbonylamino-4-methylpentanamide, (7) 2(S)-N-(3(S)-1-(5-benzyltetrazol-1-yl)-2-oxo-5-methyl-3-hexyl)-2-benzyloxycarbonylamino-4-methylpentanamide, (8) 2(S)-N-(3(S)-1-(5-ethylthiotetrazol-2-yl)-2-oxo-5-methyl-3-hexyl)-2-benzyloxycarbonylamino-4-methylpentanamide, (9) 2(S)-N-(3(S)-1-(5-ethylthiotetrazol-1-yl)-2-oxo-5-methyl-3-hexyl)-2-benzyloxycarbonylamino-4-methylpentanamide,

(10) 2(S)-N-(1-(5-methyltetrazol-2-yl)-2-oxo-5-methyl-3-hexyl)-2-benzyloxycarbonylamino-4-methylpentanamide,

(11) 2(S)-N-(1-(5-methyltetrazol-1-yl)-2-oxo-5-methyl-3-hexyl)-2-benzyloxycarbonylamino-4-methylpentanamide,

(12) 2(S)-N-(3(S)-1-(5-piperidinotetrazol-2-yl)-2-oxo-5-methyl-3-hexyl)-2-benzyloxycarbonylamino-4-methylpentanamide,

(13) 2(S)-N-(3(S)-1-(5-(3-pyridyl)tetrazol-2-yl)-2-oxo-5-methyl-3-hexyl)-2-benzyloxycarbonylamino-4-methylpentanamide,

(14) 2(S)-N-(3(S)-1-(5-(2-pyridyl)tetrazol-2-yl)-2-oxo-5-methyl-3-hexyl)-2-benzyloxycarbonylamino-4-methylpentanamide,

(15) 2(S)-N-(3(S)-1-(5-(2-pyridyl)tetrazol-1-yl)-2-oxo-5-methyl-3-hexyl)-2-benzyloxycarbonylamino-4-methylpentanamide,

(16) 2(S)-N-(3(S)-1-(5-(4-pyridyl)tetrazol-2-yl)-2-oxo-5-methyl-3-hexyl)-2-benzyloxycarbonylamino-4-methylpentanamide,

(17) 2(S)-N-(3(S)-1-(5-(1,1'-biphenyl-4-yl)tetrazol-yl)-2-oxo-5-methyl-3-hexyl)-2-benzyloxycarbonylamino-4-methyl pentanamide,

(18) 2(S)-N-(3(S)-1-(5-(1,1'-biphenyl-4-yl)tetrazol-1-yl)-2-oxo-5-methyl-3-hexyl)-2-benzyloxycarbonylamino-4-methyl pentanamide,

(19) 2(S)-N-(3(S)-1-(5-(2-phenylethyl)tetrazol-2-yl)-2-oxo-5-methyl-3-hexyl)-2-benzyloxycarbonylamino-4-methylpentanamide,

(20) 2(S)-N-(3(S)-1-(5-(2-phenylethyl)tetrazol-1-yl)-2-oxo-5-methyl-3-hexyl)-2-benzyloxycarbonylamino-4-methylpentanamide,

(21) 2(S)-N-(3(S)-1-(5-(3-phenylpropyl)tetrazol-2-yl)-2-oxo-5-methyl-3-hexyl)-2-benzyloxycarbonylamino-4-methylpentan amide,

(22) 2(S)-N-(3(S)-1-(5-(3-phenylpropyl)tetrazol-1-yl)-2-oxo-5-methyl-3-hexyl)-2-benzyloxycarbonylamino-4-methylpentan amide,

(23) 2(S)-N-(3(S)-1-(5-(4-phenylbutyl)tetrazol-2-yl)-2-oxo-5-methyl-3-hexyl)-2-benzyloxycarbonylamino-4-mehylpentan amide,

(24) 2(S)-N-(3(S)-1-(5-(4-phenylbutyl)tetrazol-1-yl)-2-oxo-5-methyl-3-hexyl)-2-benzyloxycarbonylamino-4-methylpentanamide,

(25) 2(S)-N-(3(S)-1-(5-(1,1'-biphenyl-3-yl)tetrazol-2-yl)-2-oxo-5-methyl-3-hexyl)-2-benzyloxycarbonylamino-4-methyl pentanamide,

(26) 2(S)-N-(3(S)-1-(5-(1,1'-biphenyl-3-yl)tetrazol-1-yl)-2-oxo-5-methyl-3-hexyl)-2-benzyloxycarbonylamino-4-methyl pentanamide,

(27) 2(S)-N-(3(S)-1-(5-phenoxymethyltetrazol-2-yl)-2-oxo-5-methyl-3-hexyl)-2-benzyloxycarbonylamino-4-methylpentanamide,

(28) 2(S)-N-(3(S)-1-(5-phenoxymethyltetrazol-1-yl)-2-oxo-5-methyl-3-hexyl)-2-benzyloxycarbonylamino-4-methylpentan amide,

(29) 2(S)-N-(3(S)-1-(5-benzyloxymethyltetrazol-2-yl)-2-oxo-5-methyl-3-hexyl)-2-benzyloxycarbonylamino-4-methylpentan amide,

(30) 2(S)-N-(3(S)-1-(5-benzyloxymethyltetrazol-1-yl)-2-oxo-5-methyl-3-hexyl)-2-benzyloxycarbonylamino4-methylpentanamide,

(31) 2(S)-N-(3(S)-1-(5-(4-pyridylmethyl)tetrazol-2-yl)-2-oxo-5-methyl-3-hexyl)-2-benzyloxycarbonylamino-4-methylpentan amide,

(32) 2(S)-N-(3 (S)-1-(5-(4-pyridylmethyl)tetrazol-1-yl)-2-oxo-5-methyl-3-hexyl)-2-benzyloxycarbonylamino-4-methylpentan amide,

(33) 2(S)-N-(3(S)-1-(5-(2-(3-pyridyl)ethyl)tetrazol-2-yl)-2-oxo-5-methyl-3-hexyl)-2-benzyloxycarbonylamino-4-methyl pentanamide,

(34) 2(S)-N-(3(S)-1-(5-(2-(3-pyridyl)ethyl)tetrazol-1-yl)-2-oxo-5-methyl-3-hexyl)-2-benzyloxycarbonylamino-4-methyl pentanamide,

(35) 2(S)-N-(3(S)-1-(5-(2,6-difluorophenyl)tetrazol-2-yl)-2-oxo-5-methyl-3-hexyl)-2-benzyloxycarbonylamino-4-methyl pentanamide,

(36) 2(S)-N-(3(S)-1-(5-(2,6-difluorophenyl)tetrazol-1-yl)-2-oxo-5-methyl-3-hexyl)-2-benzyloxycarbonylamino-4-methyl pentanamide,

(37) 2(S)-N-(3(S)-1-(5-(4-trifluoromethylphenyl)tetrazol-2-yl)-2-oxo-5-methyl-3-hexyl)-2-benzyloxycarbonyl-amino-4-methyl pentanamide,

(38) 2(S)-N-(3(S)-1-(5-(3,5-difluoro-4-dimethylaminophenyl) tetrazol-2-yl)-2-oxo-5-methyl-3-hexyl)-2-benzyloxycarbonyl amino-4-methylpentanamide,

(39) 2(S)-N-(3(S)-1-(5-(4-fluorophenyl)tetrazol-2-yl)-2-oxo-5-methyl-3-hexyl)-2-benzyloxycarbonylamino-4-methylpentan amide,

(40) 2(S)-N-(3(S)-1-(5-(4-benzyloxyphenyl)tetrazol-2-yl)-2-oxo-5-methyl-3-hexyl)-2-benzyloxycarbonyl-amino-4-methyl pentanamide,

(41) 2(S)-N-(3(S)-1-(5-(perfluorophenyl)tetrazol-2-yl)-2-oxo-5-methyl-3-hexyl)-2-benzyloxycarbonylamino-4-methylpentan amide,

(42) 2(S)-N-(3(S)-1-(5-(perfluorophenyl)tetrazol-1-yl)-2-oxo-5-methyl-3-hexyl)-2-benzyloxycarbonylamino-4-methylpentan amide,

(43) 2(S)-N-(3(S)-1-(5-(2,6-bis(trifluoromethyl)phenyl)tetrazol-2-yl)-2-oxo-5-methyl-3-hexyl)-2-benzyloxycarbonyl amino-4-methylpentanamide,

(44) 2(S)-N43(S)-1-(S-(2,6-bis(trifluoromethyl)phenyl)tetrazol-1-yl)-2-oxo-5-methyl-3-hexyl)-2-benzyloxycarbonyl amino-4-methylpentanamide,

(45) 2(S)-N-(3(S)-1-(5-(4-nitrophenyl)tetrazol-2-yl)-2-oxo-5-methyl-3-hexyl)-2-benzyloxycarbonylamino-4-methylpentanamide,

(46) 2(S)-N-(3(S)-1-(5-(3-benzyloxyphenyl)tetrazol-2-yl)-2-oxo-5-methyl-3-hexyl)-2-benzyloxycarbonyl-amino4-methyl pentanamide,

(47) 2(S)-N-(3(S)-1-(5-(2-benzyloxyphenyl)tetrazol-2-yl)-2-oxo-5-methyl-3-hexyl)-2-benzyloxycarbonyl-amino-4-methyl pentanamide,

(48) 2(S)-N-(4-methyl-2-oxo-1-(tetrazol-2-yl)-3-pentyl)-1-benzyloxycarbonyl-2-pyrrolidinecarboxamide,

(49) 2(S)-N-(4-methyl-2-oxo-1-(tetrazol-1-yl)-3-pentyl)-1-benzyloxycarbonyl-2-pyrrolidinecarboxamide,

(50) N-(2-oxo-4-phenyl-1-(tetrazol-2-yl)-3-butyl)-2-benxyloxycarbonylaminoacetamide,

(51) N-(2-oxo-4-phenyl-1-(tetrazol-1-yl)-3-butyl)-2-benxyloxycarbonylaminoacetamide,

(52) 2(S)-N-(3(S)-4-methyl-2-oxo-1-(5-phenyltetrazol-2-yl)-3-pentyl)-1-(2(S)-2-methoxycarbonylamino-3-methylbutyryl)-2-pyrrolidinecarboxamide,

(53) 2(S)-N-(3(S)-4-methyl-2-oxo-1-(5-phenyltetrazol-1-yl)-3-pentyl)-1-(2(S)-2-methoxycarbonylamino-3-methylbutyryl)-2-pyrrolidinecarboxamide,

(54) 2(S)-N-(3(S)-4-methyl -2-oxo-1-(tetrazol-2-yl)-3-pentyl)-1-(2(S)-2-methoxycarbonylanino-3-methylbutyryl)-2-pyrrolidinecarboxamide,

(55) 2(S)-N-(3(S)-4-methyl-2-oxo-1-(tetrazol-1-yl)-3-pentyl)-1-(2(S)-2-methoxycarbonylamino-3-methylbutyryl)-2-pyrrolidinecarboxamide,

(56) 3-benzyloxycarbonylamino-1-(5-(2,6-dichlorophenylthio) tetrazol-2-yl)butan-2-one

(57) 3-benzyloxycarbonylamino-1-(5-(2,6-dichlorophenylthio) tetrazol-1-yl)butan-2-one,

(58) 7-amino-3-benzyloxycarbonylamino-1-(5-(2,6-dichloro phenylthio)tetrazol-2-yl)heptan-2-one,

(59) 7-amino-3-benzyloxycarbonylamino-1-(5-(2,6-dichloro phenylthio)tetrazol-1-yl)heptan-2-one,

(60) 3-benzyloxycarbonylamino-4-methyl-1-(tetrazol-2-yl) pentan-2-one,

(61) 3-benzyloxycarbonylamino-4-methyl-1-(tetrazol-1-yl) pentan-2-one,

(62) 3-benzyloxycarbonylamino-4-phenyl-1-(tetrazol-2-yl) butan-2-one,

(63) 3-benzyloxycarbonylamino-4-phenyl-1-(tetrazol-1-yl) butan-2-one,

(64) 3-benzyloxycarbonylamino-4-(4-hydroxyphenyl)-1-(5-(2,6-dichlorophenylthio)tetrazol-2-yl)butan-2-one,

(65) 3-benzyloxycarbonylamino-4-(4-hydroxyphenyl)-1-(5-(2,6-dichlorophenylthio)tetrazol-1-yl)butan-2-one,

(66) 2(S)-N-(4-methyl-oxo-1-(tetrazol-2-yl)-3-pentyl)-2-pyrrolidinecarboxamide,

(67) 2(S)-N-(4-methyl-2-oxo-1-(tetrazol-1-yl)-3-pentyl)-2-pyrrolidinecarboxamide,

(68) 2-amino-N-(2-oxo-4-phenyl-1-(tetrazol-2-yl)-3-butyl) acetamide,

(69) 2-amino-N-(2-oxo-4-phenyl-1-(tetrazol-1-yl)-3-butyl) acetamide,

(70) 3-amino-4-methyl-1-(tetrazol-2-yl)pentan-2-one,

(71) 3-amino-4-methyl-1-(tetrazol-1-yl)pentan-2-one,

(72) 3-amino-4-phenyl-1-(tetrazol-2-yl)butan-2-one,

(73) 3-amino-4-phenyl-1-(tetrazol-1-yl)butan-2-one,

(74) N-((3S)-1-(5-phenyltetrazol-2-yl)-2-oxo-5-methyl-3-hexyl)-t-butoxycarboxamide,

(75) 3(S)-3-amino-5-methyl-1-(5-phenyltetrazol-2-yl) hexan-2-one,

(76) (1R,2S)-2-benzoylamino-N-[3(S)-1-(5-phenyl-tetrazol-2-yl)-2-oxo-5-methyl-3-hexyl]cyclohexane-carboxamide,

(77) N-[3(S)-1-(5-phenyltetrazol-2-yl)-2-oxo-5-methyl-3-hexyl]benzamide,

(78) N-(3(S)-1-(5-phenyltetrazol-2-yl)-2-oxo-5-methyl-3-hexyl]cyclohexanecarboxamide,

(79) (1S,2R)-2-benzoylamino-N-[3(S)-1-(5-phenyl-tetrazol-2-yl)-2-oxo-5-methyl-3-hexyl]cyclohexane-carboxamide,

(80) N-[3(S)-1-(5-phenyltetrazol-2-yl]-2-oxo-5-methyl-3-hexyl]-4-benzyloxybenzamide,

(81) N-[3(S)-1-(5-phenyltetrazol-2-yl)-2-oxo-5-methyl-3-hexyl]-3-benzyloxybenzamide,

(82) N-[3(S)-1-(5-phenyltetrazol-2-yl)-2-oxo-5-methyl-3-hexyl]-3-phenylpropenamide,

(83) N-[3(S)-1-(5-phenyltetrazol-2-yl)-2-oxo-5-methyl-3-hexyl]-3-cyclopentylpropanamide,

(84) N-[3(S)-1-(5-phenyltetrazol-2-yl)-2-oxo-5-methyl-3-hexyl]benzenesulfonamide,

(85) N-[3(S)-1-(5-phenyltetrazol-2-yl)-2-oxo-5-methyl-3-hexyl]-3-benzoylaminopropanamide or

(86) N-[3(S)-1-(5-phenyltetrazol-2-yl)-2-oxo-5-methyl-3-hexyl]-2-benzyloxybenzamide, or a non-toxic salt thereof.

8. A composition comprising the compound of formula (I-1A) described in claim 1, or a non-toxic salt thereof and a pharmaceutically acceptable carrier.

9. A method for inhibiting cysteine protease comprising administering to a subject an effective amount of the compound of formula (I-1A) described in claim 1, or a non-toxic salt thereof.

10. The method according to claim 9, wherein said cysteine protease is cathepsin K, cathepsin S. cathepsin L, cathepsin B, cathepsin H, calpain or caspase-1.

11. The method according to claim 10, wherein said cysteine protease is cathepsin K.

12. The method according to claim 10, wherein said cysteine protease is cathepsin S.

13. A method for treatment of bone resorption diseases, comprising administering to a subject an effective amount of the compound of formula (I-1A), or a non-toxic salt thereof, described in claim 1.

* * * * *